US012729202B2

(12) United States Patent
Brandl et al.

(10) Patent No.: US 12,729,202 B2
(45) Date of Patent: Sep. 8, 2026

(54) COMPOUNDS AND COMPOSITIONS AS Sppl2a INHIBITORS

(71) Applicant: Novartis AG, Basel (CH)

(72) Inventors: Trixi Brandl, Basel (CH); Claus Ehrhardt, Basel (CH); Robert Epple, Solana Beach, CA (US); Christian Markert, Basel (CH); Pascal Rigollier, Basel (CH); Juraj Velcicky, Basel (CH)

(73) Assignee: NOVARTIS AG, Basel (CH)

( * ) Notice: Subject to any disclaimer, the term of this patent is extended or adjusted under 35 U.S.C. 154(b) by 658 days.

(21) Appl. No.: 18/044,455

(22) PCT Filed: Sep. 15, 2021

(86) PCT No.: PCT/IB2021/058398
§ 371 (c)(1),
(2) Date: Mar. 8, 2023

(87) PCT Pub. No.: WO2022/058902
PCT Pub. Date: Mar. 24, 2022

(65) Prior Publication Data
US 2023/0365571 A1 Nov. 16, 2023

Related U.S. Application Data

(60) Provisional application No. 63/079,604, filed on Sep. 17, 2020.

(51) Int. Cl.
*C07D 487/04* (2006.01)

(52) U.S. Cl.
CPC .................................. *C07D 487/04* (2013.01)

(58) Field of Classification Search
CPC ............................ C07D 487/04; A61K 31/551
See application file for complete search history.

(56) References Cited

PUBLICATIONS

Velcicky, et al.; Journal of Medicinal Chemistry, v61, pp. 865-880; 2018 (Year: 2018).*
Certal, et al.; Journal of Medicinal Chemistry, v55, pp. 4788-4805; 2012 (Year: 2012).*
Kumari, et al.; Journal of Medicinal Chemistry, v63, pp. 12290-12358; 2020 (Year: 2020).*
International Search Report and Written Opinion for International Application No. PCT/IB2021/058398, mailed Oct. 15, 2021, 9 pages.
Thompson et al., "Synthesis and evaluation of succinoyl-caprolactam γ-secretase inhibitors", *Bioorganic & Medicinal Chemistry Letters* 16(9):2357-2363 (2006).
Velcicky et al., "Discovery of the First Potent, Selective, and Orally Bioavailable Signal Peptide Peptidase-Like 2a (SPPL2a) Inhibitor Displaying Pronounced Immunomodulatory Effects In Vivo", *Journal of Medicinal Chemistry* 61(3):865-880 (2018).
Foster, "Deuterium Isotope Effects in the Metabolism of Drugs and Xenobiotics: Implications for Drug Design", *Advances in Drug Research* 14:1-40 (1985).

* cited by examiner

*Primary Examiner* — Jeffrey S Lundgren
*Assistant Examiner* — W. Justin Youngblood
(74) *Attorney, Agent, or Firm* — Brian C. Trinque; Nicole Sassu; Lathrop GPM LLP

(57) ABSTRACT

The present invention relates to tricyclic compounds comprising a diazepinone moiety which are effective in inhibiting Sppl2a (signal peptide peptidase like protease 2a), to pharmaceutical compositions containing such inhibitors, and to methods of using such inhibitors and compositions.

18 Claims, No Drawings

COMPOUNDS AND COMPOSITIONS AS Sppl2a INHIBITORS

FIELD OF THE INVENTION

The present invention relates to tricyclic compounds comprising a diazepinone moiety which are effective in inhibiting signal peptide peptidase like protease 2a (Sppl2a), to pharmaceutical compositions containing such inhibitors, to a method for synthesizing said novel derivatives and to methods of using such inhibitors and compositions.

BACKGROUND OF THE INVENTION

The protein Sppl2a appears to play a role in innate and adaptive immunity by cleaving different transmembrane anchored proteins and thereby affecting the function of a variety of immune cells.

Sppl2a was initially described as the protease cleaving the membrane spanning portion of TNF-α and thereby controlling the release of IL-12 from dendritic cells. Recent observations suggest that Sppl2a might be implicated in the processing of CD74, also known as the invariant chain, an important mediator of antigen presentation via class II molecules, which allows differentiation of foreign antigens from self antigens. Many autoimmune diseases may evolve when the immune system loses its capacity to discriminate "self" from "non-self". A recent publication from D. Beisner et al. "The intramembrane protease Sppl2a is required for B cell and DC development and survival via cleavage of the invariant chain", J. Exp. Med. 210, pp 23-39, 2013) describes that CD74 is cleaved by Sppl2a. Inhibition of this process in mice may result in a significant reduction of the number of mature B cells and myeloid dendritic cells. The scientific literature further suggests that inhibiting Sppl2a leads to the accumulation of the N-terminal fragment of CD74 (p8) in intracellular compartments, thereby inducing the death of B cells and myeloid dendritic cells. Although the molecular details of Sppl2a processing and disappearance of B cells/myeloid dendritic cells are still poorly understood, the accumulation of the unprocessed CD74 appears to impair T cell dependent antibody response in mice. Inhibition of this protease may be relevant for the repression of detrimental, uncontrolled immune responses e.g. pathological conditions where autoantibodies might be critical to autoimmune diseases. Sppl2a inhibition might also influence the proliferation of B-cell lymphomas, which seems to be associated with the expression of high levels of CD74.

Therefore potent and generally selective inhibitors of Sppl2a may represent a new and attractive mechanistic path to treat diseases and/or conditions especially of the immune system.

SUMMARY OF THE INVENTION

In one aspect the invention therefore provides a compound of the Formula (I), or a pharmaceutically acceptable salt thereof,

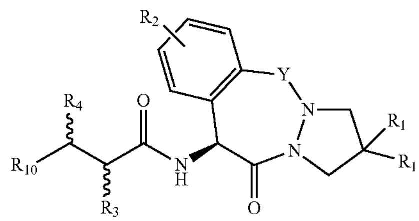

(I)

wherein:

Y is $CH_2$ or C═O;

Y is $CH_2$ or C═O;

$R_1$ is H, $C_1$-$C_6$alkyl or halogen;

$R_2$ is H or halogen;

$R_3$ is H, $C_1$-$C_6$alkyl, $C_1$-$C_6$haloalkyl, $C_3$-$C_6$cycloalkyl, $C_1$-$C_6$alkyl-phenyl or $C_1$-$C_6$alkyl substituted with $C_1$-$C_6$alkoxy;

$R_4$ is H, $C_1$-$C_6$alkyl or $C_1$-$C_6$alkyl-phenyl;

$R_{10}$ is —NHC(═O)$R_5$, —C(═O)NH$R_5$ or a 9 or 10 membered bicyclic heteroaryl having 1 to 4 heteroatoms as ring members each independently selected from N, O and S, wherein the bicyclic heteroaryl is unsubstituted or the bicyclic heteroaryl is substituted with one or more $R_6$;

$R_5$ is a 5-membered heteroaryl having 1, 2 or 3 heteroatoms as ring members each independently selected from N, O and S, wherein the 5-membered heteroaryl is unsubstituted or the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;

vi) $C_1$-$C_6$haloalkyl;

vii) —NHC(═O)$C_1$-$C_6$alkyl, wherein the $C_1$-$C_6$alkyl is optionally substituted by $C_1$-$C_6$alkoxy;

viii) —NHC(═O)—$C_1$-$C_6$haloalkyl;

ix) —NHC(═O)—$C_3$-$C_6$cycloalkyl;

x) —C(═O)NH—$C_1$-$C_6$alkyl, wherein the $C_1$-$C_6$alkyl is optionally substituted by $C_1$-$C_6$alkoxy;

xi) —C(═O)NH—$C_1$-$C_6$haloalkyl;

xii) —C(═O)NH—$C_3$-$C_6$cycloalkyl xiii) —NHC(═O)phenyl, wherein the phenyl is optionally substituted with one or more substituents independently selected from halogen and $C_1$-$C_6$alkyl;

xiv) —C(═O)NHphenyl, wherein the phenyl is optionally substituted with one or more substituents independently selected from halogen and $C_1$-$C_6$alkyl;

xv) $C_1$-$C_6$alkoxy or $C_1$-$C_6$haloalkoxy;

xvi) phenyloxy optionally substituted with one or more halogen;

xvii) phenyl optionally substituted by one or more substituents independently selected from halogen, —CN, $C_1$-$C_6$alkyl, $C_1$-$C_6$alkoxy, $C_1$-$C_6$haloakoxy and $C_1$-$C_6$haloalkyl;

xviii) a 4 to 6-member heterocyclyl optionally substituted with oxo, —C(═O)O$C_1$-$C_6$alkyl or —C(═O)O$C_1$-$C_6$cycloalkyl;

xix) a 5 or 6 membered heteroaryl having 1 or 2 heteroatoms as ring members each independently selected from N, O and S, wherein the heteroaryl is unsubstituted or the heteroaryl is substituted by one or more substitutents independently selected from $C_1$-$C_6$alkyl, halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and a $C_1$-$C_6$alkyl optionally substituted by —OH, $C_1$-$C_6$alkoxy or a 4 to 6-member heterocyclyl optionally substituted with oxo; and xx) a 9 or 10 membered bicyclic heteroaryl having 1 to 4 heteroatoms as ring members each independently selected from N, O and S, wherein the heteroaryl is unsubstituted or the heteroaryl is substituted by one or more substitutents independently selected from $C_1$-$C_6$alkyl, halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and a $C_1$-$C_6$alkyl optionally substituted by $C_1$-$C_6$alkoxy;

each $R_6$ is independently selected from $C_1$-$C_6$alkyl, $C_1$-$C_6$alkoxy, $C_1$-$C_6$haloalkyl, cyano and halogen;

$R_{11}$ is H, $C_1$-$C_6$alkyl or halogen;

or $R_1$ and $R_{11}$ together with the carbon atom to which they are attached, may form a 3 to 6 membered carbocyclic ring.

As used herein, the serpentine line in a compound of formula (I) characterizing the chemical bond leading to substituent $R_4$ indicates two (2) stereochemical options. In one embodiment the stereochemistry of the carbon atom to which $R_4$ is being attached is (S), in another embodiment said stereochemistry is (R), or in still another embodiment it is a mixture thereof.

As used herein, the serpentine line in a compound of formula (I) characterizing the chemical bond leading to substituent $R_3$ indicates two (2) stereochemical options. In one embodiment the stereochemistry of the carbon atom to which $R_3$ is being attached is (S), in another embodiment said stereochemistry is (R), or in still another embodiment it is a mixture thereof.

Another aspect of the present invention is a pharmaceutical composition comprising a therapeutically effective amount of a compound of the invention, or a pharmaceutically acceptable salt thereof, and one or more pharmaceutically acceptable carriers.

Another aspect of the present invention is a pharmaceutical composition comprising a compound of the invention, or a pharmaceutically acceptable salt, and one or more pharmaceutically acceptable carriers.

In another aspect, the invention provides a method of treating or preventing a disease or disorder mediated by the activity of signal peptide peptidase like protease 2a (Sppl2a), wherein the method comprises administering to a subject in need of such treatment a therapeutically effective amount of a compound of the invention, or a pharmaceutically acceptable salt.

In another aspect, the invention provides a method of treating or preventing a disease or disorder mediated by the activity of signal peptide peptidase like protease 2a (Sppl2a), wherein the method comprises administering to a subject in need of such treatment a compound of the invention, or a pharmaceutically acceptable salt.

In another aspect, the invention provides a method of treating an autoimmune disease in a subject in need thereof, wherein the method comprises administering to the subject a therapeutically effective amount of a compound of the invention, or a pharmaceutically acceptable salt thereof.

In another aspect, the invention provides a method of treating an autoimmune disease in a subject in need thereof, wherein the method comprises administering to the subject a compound of the invention, or a pharmaceutically acceptable salt thereof.

In another aspect, the invention provides a method of treating an autoimmune disease in a subject in need thereof, wherein the method comprises administering to the subject a therapeutically effective amount of a compound of the invention, or a pharmaceutically acceptable salt thereof, and wherein the autoimmune disease is Sjogren's disease, systemic lupus erythematosus (SLE), rheumatoid arthritis (RA), lupus nephritis, systemic sclerosis, multiple sclerosis (MS), autoimmune hepatitis, uveitis, pemphigus vulgaris, pemphigus foliaceus, myasthenia gravis, Hashimoto thyroiditis, thrombocytopenia purpura, myocarditis, atopic dermatitis, Goodpasture syndrome or type I diabetes.

In another aspect, the invention provides a method of treating an autoimmune disease in a subject in need thereof, wherein the method comprises administering to the subject a compound of the invention, or a pharmaceutically acceptable salt thereof, and wherein the autoimmune disease is Sjogren's disease, systemic lupus erythematosus (SLE), rheumatoid arthritis (RA), lupus nephritis, systemic sclerosis, multiple sclerosis (MS), autoimmune hepatitis, uveitis, pemphigus vulgaris, pemphigus foliaceus, myasthenia gravis, Hashimoto thyroiditis, thrombocytopenia purpura, myocarditis, atopic dermatitis, Goodpasture syndrome, or type I diabetes.

In another aspect, the invention provides a method of treating graft versus host disease (GvHD) in a subject, wherein the method comprises administering to the subject a therapeutically effective amount of a compound of the invention, or a pharmaceutically acceptable salt thereof. In certain embodiments the graft versus host disease (GvHD) is an acute graft versus host disease, while in other embodiments the graft versus host disease (GvHD) is a chronic graft versus host disease.

In another aspect, the invention provides a method of preventing graft versus host disease (GvHD) in a subject, wherein the method comprises administering to the subject a therapeutically effective amount of a compound of the invention, or a pharmaceutically acceptable salt thereof, prior to transplantation. In certain embodiments the graft versus host disease (GvHD) is an acute graft versus host disease, while in other embodiments the graft versus host disease (GvHD) is a chronic graft versus host disease.

In another aspect, the invention provides a method of treating graft versus host disease (GvHD) in a subject, wherein the method comprises administering to the subject a compound of the invention, or a pharmaceutically acceptable salt thereof. In certain embodiments the graft versus host disease (GvHD) is an acute graft versus host disease, while in other embodiments the graft versus host disease (GvHD) is a chronic graft versus host disease.

In another aspect, the invention provides a method of preventing graft versus host disease (GvHD) in a subject, wherein the method comprises administering to the subject a compound of the invention, or a pharmaceutically acceptable salt thereof, prior to transplantation. In certain embodiments the graft versus host disease (GvHD) is an acute graft versus host disease, while in other embodiments the graft versus host disease (GvHD) is a chronic graft versus host disease.

In another aspect, the invention provides use of a compound of of the invention, or a pharmaceutically acceptable salt thereof, in the manufacture of a medicament for the treatment of a disease or disorder associated with or mediated by the activity of signal peptide peptidase like protease 2a (Sppl2a).

In another aspect, the invention provides use of a compound of the invention, or a pharmaceutically acceptable salt thereof, in the manufacture of a medicament for the treatment of an autoimmune disease.

In another aspect, the invention provides use of a compound of the invention, or a pharmaceutically acceptable salt thereof, in the manufacture of a medicament for the treatment of an autoimmune disease, wherein the autoimmune disease is Sjogren's disease, systemic lupus erythematosus (SLE), rheumatoid arthritis (RA), lupus nephritis, systemic sclerosis, multiple sclerosis (MS), autoimmune hepatitis, uveitis, pemphigus vulgaris, pemphigus foliaceus, myasthenia gravis, Hashimoto thyroiditis, thrombocytopenia purpura, myocarditis, atopic dermatitis, Goodpasture syndrome, or type I diabetes.

In another aspect, the invention provides use of a compound of the invention, or a pharmaceutically acceptable salt thereof, in the manufacture of a medicament for the treatment or prevention of a graft versus host disease (GvHD). In certain embodiments the graft versus host disease (GvHD) is an acute graft versus host disease, while in other embodiments the graft versus host disease (GvHD) is a chronic graft versus host disease.

In another aspect, the invention provides the use of a compound of the invention, or a pharmaceutically acceptable salt thereof, in the treatment of a disease or disorder associated with or mediated by the activity of signal peptide peptidase like protease 2a (Sppl2a).

In another aspect, the invention provides the use of a compound of the invention, or a pharmaceutically acceptable salt thereof, in the treatment of an autoimmune disease.

In another aspect, the invention provides the use of a compound of the invention, or a pharmaceutically acceptable salt thereof, in the treatment of an autoimmune disease, wherein the autoimmune disease is Sjogren's disease, systemic lupus erythematosus (SLE), rheumatoid arthritis (RA), lupus nephritis, systemic sclerosis, multiple sclerosis (MS), autoimmune hepatitis, uveitis, pemphigus vulgaris, pemphigus foliaceus, myasthenia gravis, Hashimoto thyroiditis, thrombocytopenia purpura, myocarditis, atopic dermatitis, Goodpasture syndrome, or type I diabetes.

In another aspect, the invention provides the use of a compound of the invention, or a pharmaceutically acceptable salt thereof, in the treatment or prevention of a graft versus host disease (GvHD). In certain embodiments the graft versus host disease (GvHD) is an acute graft versus host disease, while in other embodiments the graft versus host disease (GvHD) is a chronic graft versus host disease.

In another aspect, the invention provides a compound of the invention, or a pharmaceutically acceptable salt thereof, for use in the treatment of a disease or disorder associated with of mediated by the activity of signal peptide peptidase like protease 2a (Sppl2a).

In another aspect, the invention provides a compound of the invention, or a pharmaceutically acceptable salt thereof, for use in the treatment of an autoimmune disease.

In another aspect, the invention provides a compound of the invention, or a pharmaceutically acceptable salt thereof, for use in the treatment of an autoimmune disease, wherein the autoimmune disease is Sjogren's disease, systemic lupus erythematosus (SLE), rheumatoid arthritis (RA), lupus nephritis, systemic sclerosis, multiple sclerosis (MS), autoimmune hepatitis, uveitis, pemphigus vulgaris, pemphigus foliaceus, myasthenia gravis, Hashimoto thyroiditis, thrombocytopenia purpura, myocarditis, atopic dermatitis, Goodpasture syndrome, or type I diabetes.

In another aspect, the invention provides a compound of the invention, or a pharmaceutically acceptable salt thereof, for use in the treatment or prevention of a graft versus host disease (GvHD). In certain embodiments the graft versus host disease (GvHD) is an acute graft versus host disease, while in other embodiments the graft versus host disease (GvHD) is a chronic graft versus host disease.

DETAILED DESCRIPTION

Definitions

The term "alkyl," as used herein, refers to a fully saturated branched or straight chain hydrocarbon having up to 20 carbon atoms. In certain embodiments an alkyl group is a "$C_1$-$C_2$alkyl", "$C_1$-$C_3$alkyl", "$C_1$-$C_4$alkyl", "$C_1$-$C_5$alkyl", "$C_1$-$C_6$alkyl", "$C_1$-$C_7$alkyl", "$C_1$-$C_8$alkyl", "$C_1$-$C_9$alkyl" or "$C_1$-$C_{10}$alkyl", wherein the terms "$C_1$-$C_2$alkyl", "$C_1$-$C_3$alkyl", "$C_1$-$C_4$alkyl", "$C_1$-$C_5$alkyl", "$C_1$-$C_6$alkyl", "$C_1$-$C_7$alkyl", "$C_1$-$C_8$alkyl", "$C_1$-$C_9$alkyl" and "$C_1$-$C_{10}$alkyl", as used herein, refer to an alkyl group containing at least 1, and at most 2, 3, 4, 5, 6, 7, 8, 9 or 10 carbon atoms, respectively. Non-limiting examples of alkyl groups include methyl, ethyl, n-propyl, isopropyl, n-butyl, isobutyl, sec-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkoxy", as used herein, refers to —O-alkyl or -alkyl-O—, wherein "alkyl" is as defined herein. In certain embodiments an alkoxy group is a "$C_1$-$C_2$alkoxy", "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" or "$C_1$-$C_{10}$alkoxy", wherein the terms "$C_1$-$C_3$alkoxy", "$C_1$-$C_4$alkoxy", "$C_1$-$C_5$alkoxy", "$C_1$-$C_6$alkoxy", "$C_1$-$C_7$alkoxy", "$C_1$-$C_8$alkoxy", "$C_1$-$C_9$alkoxy" and "$C_1$-$C_{10}$alkoxy", as used herein refer to —O—$C_1$-$C_2$alkyl, —O—$C_1$-$C_3$alkyl, —O—$C_1$-$C_4$alkyl, —O—$C_1$-$C_5$alkyl, —O—$C_1$-$C_6$alkyl, —O—$C_1$-$C_7$alkyl, —O—$C_1$-$C_8$alkyl, —O—$C_1$-$C_9$alkyl or —O—$C_1$-$C_{10}$alkyl, respectively. Non-limiting examples of "alkoxy" groups include methoxy, ethoxy, n-propoxy, isopropoxy, n-butoxy, isobutoxy, sec-butoxy, tert-butoxy, n-pentoxy, isopentoxy, hexoxy, heptoxy, octoxy, nonoxy and decoxy.

The term "$C_3$-$C_8$cycloalkyl" as used herein, refers to a fully saturated, monocyclic hydrocarbon ring system having 3 to 8 carbon atoms as ring members. Non-limiting examples of such "$C_3$-$C_8$cycloalkyl" groups include cyclopropyl, cyclobutyl, cyclopentyl, cyclohexyl, cycloheptyl and cyclooctyl. In certain embodiments, the term "$C_3$-$C_6$cycloalkyl" as used herein, refers to a fully saturated, monocyclic hydrocarbon ring system having 3 to 6 carbon atoms as ring members. Non-limiting examples of such "$C_3$-$C_8$cycloalkyl" groups include cyclopropyl, cyclobutyl, cyclopentyl and cyclohexyl.

The term "3 to 6 membered carbocyclic ring", as used herein, refers to a 3 to 6 membered, saturated or partially saturated hydrocarbon ring. Non-limiting examples of such carbocyclic ring groups include cyclopropyl, cyclobutyl, cyclopentyl, cyclohexyl, cycloheptyl, cyclooctyl, cyclopentenyl, cyclohexenyl, cycloheptenyl and cyclooctenyl.

The term "$C_3$-$C_6$cycloalkenyl" as used herein, refers to a partially saturated (but not aromatic), monocyclic hydrocarbon ring system having 3 to 6 carbon atoms as ring members.

The term "$C_1$-$C_6$alkyl-phenyl" as used herein, refer to a $C_1$-$C_6$alkyl as defined above which is substituted with a phenyl group. Non-limiting example of a $C_1$-$C_6$alkyl-phenyl is benzyl.

The term "haloalkyl" as used herein, refers to an alkyl group as defined herein, wherein at least one of the hydrogen atoms of the alkyl is replaced by a halo group (as defined herein). The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Dihaloalkyl and polyhaloalkyl groups can have two or more of the same halo atoms or a combination of different halo groups within the alkyl. Typically the polyhaloalkyl contains up to 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl. Preferred haloalkyl groups, unless specified otherwise, include monofluoro-, difluoro- and trifluoro-substituted methyl and ethyl groups, e.g. $CF_3$, $CHF_2$, $CH_2F$, $CH_2CHF_2$ and $CH_2CF_3$.

The term "$C_1$-$C_6$haloalkyl" as used herein, refers to the respective "$C_1$-$C_6$alkyl", as defined herein, wherein at least one of the hydrogen atoms of the "$C_1$-$C_6$alkyl" is replaced by a halo group (as defined herein). The $C_1$-$C_6$haloalkyl groups can be mono$C_1$-$C_6$haloalkyl, wherein such $C_1$-$C_6$haloalkyl groups have one iodo, one bromo, one chloro or one fluoro. Additionally, the $C_1$-$C_6$haloalkyl groups can be di$C_1$-$C_6$haloalkyl wherein such $C_1$-$C_6$haloalkyl groups can have two halo atoms independently selected from iodo, bromo, chloro or fluoro. Furthermore, the $C_1$-$C_6$haloalkyl groups can be poly$C_1$-$C_6$haloalkyl wherein such $C_1$-$C_6$haloalkyl groups can have two or more of the same halo atoms or a combination of two or more different halo atoms. Such poly$C_1$-$C_6$haloalkyl can be perhalo$C_1$-$C_6$haloalkyl where all the hydrogen atoms of the respective $C_1$-$C_6$alkyl have been replaced with halo atoms and the halo atoms can be the same or a combination of different halo atoms. Non-limiting examples of "$C_1$-$C_6$haloalkyl" groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, fluoroethyl, difluoroethyl, trifluoroethyl, difluoropropyl, dichloroethyl and dichloropropyl.

The term "haloalkoxy" as used herein, refers to the group —O-haloalkyl wherein at least one of the hydrogen atoms of the alkyl group of the alkoxy is replaced by a halo group (as defined herein). The haloalkoxy can be monohaloalkoxy, dihaloalkoxy, trihaloalkoxy, or polyhaloalkoxy including perhaloalkoxy. A monohaloalkoxy can have one iodo, bromo, chloro or fluoro within the alkyl group. Dihaloalkoxy and polyhaloalkoxy groups can have two or more of the same halo atoms or a combination of different halo groups within the alkyl. Typically the polyhaloalkoxy contains up to 6, or 4, or 3, or 2 halo groups. Non-limiting examples of haloalkoxy include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, difluoroethoxy, difluoropropoxy, dichloroethoxy and dichloropropoxy. A perhalo-alkoxy refers to an alkoxy having all hydrogen atoms replaced with halo atoms, e.g., trifluoromethoxy. Preferred haloalkoxy groups, unless specified otherwise, include monofluoro-, difluoro- and trifluoro-substituted methoxy and ethoxy groups, e.g. $—OCF_3$, $—OCHF_2$, $—OCH_2F$, $—OCH_2CHF_2$ and $—OCH_2CF_3$.

The term "$C_1$-$C_6$haloalkoxy" as used herein, refers to the group —O—$C_1$-$C_6$haloalkyl, wherein at least one of the hydrogen atoms of the "$C_1$-$C_6$alkyl" of the "$C_1$-$C_6$alkoxy" is replaced by a halo group (as defined herein). The $C_1$-$C_6$haloalkoxy groups can be mono$C_1$-$C_6$haloalkoxy, wherein such $C_1$-$C_6$haloalkoxy groups have one iodo, one bromo, one chloro or one fluoro. Additionally, the $C_1$-$C_6$haloalkoxy groups can be di$C_1$-$C_6$haloalkoxy wherein such $C_1$-$C_6$haloalkoxy groups can have two halo atoms independently selected from iodo, bromo, chloro or fluoro. Furthermore, the $C_1$-$C_6$haloalkoxy groups can be poly$C_1$-$C_6$haloalkoxy wherein such $C_1$-$C_6$haloalkoxy groups can have two or more of the same halo atoms or a combination of two or more different halo atoms. Such poly$C_1$-$C_6$haloalkoxy can be perhalo$C_1$-$C_6$haloalkoxy where all the hydrogen atoms of the respective $C_1$-$C_6$alkoxy have been replaced with halo atoms and the halo atoms can be the same or a combination of different halo atoms. Non-limiting examples of "$C_1$-$C_6$haloalkoxy" groups include fluoromethoxy, difluoromethoxy, trifluoromethoxy, chloromethoxy, dichloromethoxy, trichloromethoxy, pentafluoroethoxy, heptafluoropropoxy, difluorochloromethoxy, dichlorofluoromethoxy, fluoroethoxy, difluoroethoxy, trifluoroethoxy, difluoropropoxy, dichloroethoxy and dichloropropoxy.

The terms "halogen" or "halo" as used herein, refer to fluoro (F), chloro (Cl), bromo (Br) and iodo (I).

The term "heteroatoms" or "hetero atoms", as used herein, refers to nitrogen (N), oxygen (O) or sulfur (S) atoms.

The term "heteroaryl," as used herein, refers to an aromatic ring system containing one or more heteroatoms. Heteroaryl groups containing more than one heteroatom may contain different heteroatoms. Heteroaryl groups may be monocyclic ring systems or fused bicyclic ring systems. Monocyclic heteroaryl rings have from 5 to 6 ring atoms. Bicyclic heteroaryl rings have from 7 to 12 ring member atoms. Bicyclic heteroaryl rings include those ring systems wherein a heteroaryl ring is fused to a phenyl ring. Non-limiting examples of heteroaryl groups, as used herein, include benzofuranyl, benzo[c]thiophenyl, benzothiophenyl, benzoxazolyl, benzothiazolyl, benzimidazolyl, cinnolinyl, furazanyl, furyl, imidazolyl, indolyl, indolizinyl, indazolyl, isoindolyl, isoquinolinyl, isoxazolyl, isothiazolyl, oxazolyl, oxaindolyl, oxadiazolyl (including 1,3,4-oxadiazolyl and 1,2,4-oxadiazolyl), purinyl, pyrazolyl, pyrrolyl, phthalazinyl, pyridinyl (including 2-, 3-, and 4-pyridinyl), pyridazinyl, pyrazinyl, pyrimidinyl, quinoxalinyl, quinolinyl, quinazolinyl, tetrazinyl, tetrazolyl, tetrazolo[1,5-a]pyridinyl, thiazolyl, thiadiazolyl (including 1,3,4-thiadiazolyl), thienyl, triazinyl, and triazolyl.

The term "5-membered heteroaryl", as used herein, refers to an aromatic, 5 membered monocyclic ring system having 1, 2 or 3 heteroatoms as ring members, each of which is independently selected from N, O and S. Non-limiting examples of such 5 membered heteroaryl groups, as used herein, include furyl, imidazolyl, isoxazolyl, isothiazolyl, oxazolyl, pyrrolyl, pyrazolyl, thiadiazolyl, thiazolyl, thienyl and triazolyl. In certain embodiments the "5-membered heteroaryl", as used herein, refers to an aromatic, 5 membered monocyclic ring system having 1 or 2 heteroatoms as ring members, each of which is independently selected from N, O and S. Non-limiting examples of such 5 membered heteroaryl groups, as used herein, include furyl, imidazolyl, isoxazolyl, isothiazolyl, oxazolyl, pyrrolyl, pyrazolyl, thiadiazolyl, thiazolyl, thienyl and triazolyl.

The term "6-membered heteroaryl", as used herein, refers to an aromatic, 6 membered monocyclic ring system having 1, 2 or 3 heteroatoms as ring members, each of which is independently selected from N, O and S. Non-limiting examples of such 6 membered heteroaryl groups, as used herein, include pyridyl, pyridazinyl, pyrazinyl, pyrimidinyl and triazinyl. In certain embodiments the term "6-membered heteroaryl", as used herein, refers to an aromatic, 6 membered monocyclic ring system having 1 or 2 heteroatoms as ring members, each of which is independently selected from N, O and S. Non-limiting examples of such 6 membered heteroaryl groups, as used herein, include pyridyl, pyridazinyl, pyrazinyl, and pyrimidinyl.

The term "9 or 10 membered bicyclic heteroaryl", as used herein, refers to a 9 or 10 membered fused, bicyclic aromatic ring system having 1, 2, 3 or 4 heteroatoms as ring members, each of which is independently selected from N, O and S. Non-limiting examples of such bicyclic heteroaryl groups, as used herein, include indolyl, quinolinyl, isoquinolinyl, indazolyl, purinyl, phthalazinyl, naphthyridinyl, quinazolinyl, cinnolinyl, thieno[2,3-b]furanyl, 1H-pyrazolo[4,3-d]-oxazolyl, imidazo[2,1-b] thiazolyl, pyrazino[2,3-d]pyridazinyl, imidazo[1,2-b][1,2,4]triazinyl, benzoxazolyl, benzimidazolyl, imidazopyridinyl and benzothiazolyl. In certain embodiments such a bicyclic heteroaryl group is 1H-benzo[d]imidazolyl or 1H-imidazo[4,5-c]pyridinyl.

The term "4-6 membered heterocyclyl" as used herein, refers to 4 to 6 membered, saturated or partially saturated hydrocarbon ring containing 1 to 2 heteroatoms as ring members, each independently selected from N, NH, $NR^A$, O or S, where $R^A$ is H, $C_1$-$C_6$alkyl or $C_3$-$C_8$cycloalkyl. The heterocyclyl group can be attached to another group at a nitrogen or a carbon atom. Non-limiting examples of 4-6 membered heterocycloalkyl groups, as used herein, include azetadinyl, azetadin-1-yl, azetadin-2-yl, azetadin-3-yl, oxetanyl, oxetan-2-yl, oxetan-3-yl, oxetan-4-yl, thietanyl, thietan-2-yl, thietan-3-yl, thietan-4-yl, pyrrolidinyl, pyrrolidin-1-yl, pyrrolidin-2-yl, pyrrolidin-3-yl, pyrrolidin-4-yl, pyrrolidin-5-yl, tetrahydrofuranyl, tetrahydrofuran-2-yl, tetrahydrofuran-3-yl, tetrahydrofuran-4-yl, tetrahydrofuran-5-yl, tetrahydrothienyl, tetrahydrothien-2-yl, tetrahydrothien-3-yl, tetrahydrothien-4-yl, tetrahydrothien-5-yl, piperidinyl, piperidin-1-yl, piperidin-2-yl, piperidin-3-yl, piperidin-4-yl, piperidin-5-yl, piperidin-6-yl, tetrahydropyranyl, tetrahydropyran-2-yl, tetrahydropyran-3-yl, tetrahydropyran-4-yl, tetrahydropyran-5-yl, tetrahydropyran-6-yl, tetrahydrothiopyranyl, tetrahydrothiopyran-2-yl, tetrahydrothiopyran-3-yl, tetrahydrothiopyran-4-yl, tetrahydrothiopyran-5-yl, tetrahydrothiopyran-6-yl, piperazinyl, piperazin-1-yl, piperazin-2-yl, piperazin-3-yl, piperazin-4-yl, piperazin-5-yl, piperazin-6-yl, morpholinyl, morpholin-2-yl, morpholin-3-yl, morpholin-4-yl, morpholin-5-yl, morpholin-6-yl, thiomorpholinyl, thiomorpholin-2-yl, thiomorpholin-3-yl, thiomorpholin-4-yl, thiomorpholin-5-yl, thiomorpholin-6-yl, oxathianyl, oxathian-2-yl, oxathian-3-yl, oxathian-5-yl, oxathian-6-yl, dithianyl, dithian-2-yl, dithian-3-yl, dithian-5-yl, dithian-6-yl, dioxolanyl, dioxolan-2-yl, dioxolan-4-yl, dioxolan-5-yl, thioxanyl, thioxan-2-yl, thioxan-3-yl, thioxan-4-yl, thioxan-5-yl, dithiolanyl, dithiolan-2-yl, dithiolan-4-yl, dithiolan-5-yl, pyrazolidinyl, pyrazolidin-1-yl, pyrazolidin-2-yl, pyrazolidin-3-yl, pyrazolidin-4-yl, pyrazolidin-5-yl, 2-azabicyclo[4.2.0]octanyl, octahydro-1H-cyclopenta[b]pyridine and decahydroquinoline.

The term "isomers", as used herein, refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

The term "pharmaceutically acceptable carrier", as used herein, includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by Sppl2a, or (ii) associated with or mediated by Sppl2a activity, or (iii) characterized by activity (normal or abnormal) of Sppl2a; or (2) reducing or inhibiting the activity of Sppl2a; or (3) reducing or inhibiting the expression of Sppl2a. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Sppl2a; or at least partially reducing or inhibiting the expression of Sppl2a.

The term "subject" as used herein may refer to an animal. The animal may be a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

The terms "inhibit", "inhibition" or "inhibiting", as used herein, refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "preventing" refer to delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

Unless specified otherwise, the terms "compound of the invention", "compounds of the invention", "compound of the present invention" or "compounds of the present invention" refers to a compound or compounds of Formula (I), Formula (II), Formula (III), Formula (IV), and subformulae thereof (such as Formula (IIA), Formula (IIB), Formula (IIC), Formula (IID), Formula (IIIA), Formula (IIIB), Formula (IIIC) and Formula (IIID)) and exemplified compounds, and salts thereof, as well as all stereoisomers (including diastereoisomers and enantiomers) thereof.

Various enumerated embodiments of the present invention are described herein. It will be recognized that features specified in each embodiment may be combined with other specified features to provide further embodiments of the present invention.

Compounds of the Invention

The invention provides a compounds of Formula (I), or a pharmaceutical acceptable salt or stereoisomer thereof, (I)

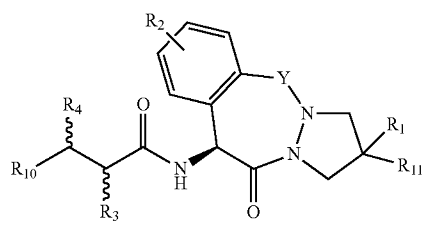

wherein:

Y is $CH_2$ or C═O;

$R_1$ is H, $C_1$-$C_6$alkyl or halogen;

$R_2$ is H or halogen;

$R_3$ is H, $C_1$-$C_6$alkyl, $C_1$-$C_6$haloalkyl, $C_3$-$C_6$cycloalkyl, $C_1$-$C_6$alkyl-phenyl or $C_1$-$C_6$alkyl substituted with $C_1$-$C_6$alkoxy;

$R_4$ is H, $C_1$-$C_6$alkyl or $C_1$-$C_6$alkyl-phenyl;

$R_{10}$ is —NHC(═O)$R_5$, —C(═O)NH$R_5$ or a bicyclic 7 to 12 membered heteroaryl ring having from 2 to 4 heteroatoms as ring members each independently selected from N, O and S, wherein the bicyclic heteroaryl is unsubstituted or the bicyclic heteroaryl is substituted with one or more $R_6$;

$R_5$ is a 5-membered heteroaryl having 1, 2 or 3 heteroatoms as ring members each independently selected from N, O and S, wherein the 5-membered heteroaryl is unsubstituted or the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;

vi) $C_1$-$C_6$haloalkyl;

vii) —NHC(═O)$C_1$-$C_6$alkyl, wherein the $C_1$-$C_6$alkyl is optionally substituted by $C_1$-$C_6$alkoxy;

viii) —NHC(═O)—$C_1$-$C_6$haloalkyl;

ix) —NHC(═O)—$C_3$-$C_6$cycloalkyl;

x) —C(═O)NH—$C_1$-$C_6$alkyl, wherein the $C_1$-$C_6$alkyl is optionally substituted by $C_1$-$C_6$alkoxy;

xi) —C(═O)NH—$C_1$-$C_6$haloalkyl;

xii) —C(═O)NH—$C_3$-$C_6$cycloalkyl xiii) —NHC(═O)phenyl, wherein the phenyl is optionally substituted with one or more substituents independently selected from halogen and $C_1$-$C_6$alkyl;

xiv) —C(═O)NHphenyl, wherein the phenyl is optionally substituted with one or more substituents independently selected from halogen and $C_1$-$C_6$alkyl;

xv) $C_1$-$C_6$alkoxy or $C_1$-$C_6$haloakoxy;

xvi) phenyloxy optionally substituted with one or more halogen;

xvii) phenyl optionally substituted by one or more substituents independently selected from halogen, —CN, $C_1$-$C_6$alkyl, $C_1$-$C_6$alkoxy, $C_1$-$C_6$haloakoxy and $C_1$-$C_6$haloalkyl;

xviii) a 4 to 6-member heterocyclyl optionally substituted with oxo, —C(═O)O$C_1$-$C_6$alkyl or —C(═O)O$C_1$-$C_6$cycloalkyl;

xix) a 5 or 6 membered heteroaryl having 1 or 2 heteroatoms as ring members each independently selected from N, O and S, wherein the heteroaryl is unsubstituted or the heteroaryl is substituted by one or more substitutents independently selected from $C_1$-$C_6$alkyl, halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and a $C_1$-$C_6$alkyl optionally substituted by —OH, $C_1$-$C_6$alkoxy or a 4 to 6-member heterocyclyl optionally substituted with oxo; and xx) a 9 or 10 membered bicyclic heteroaryl having 1 to 4 heteroatoms as ring members each independently selected from N, O and S, wherein the heteroaryl is unsubstituted or the heteroaryl is substituted by one or more substitutents independently selected from $C_1$-$C_6$alkyl, halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and a $C_1$-$C_6$alkyl optionally substituted by $C_1$-$C_6$alkoxy;

each $R_6$ is independently selected from $C_1$-$C_6$alkyl, $C_1$-$C_6$alkoxy, $C_1$-$C_6$haloalkyl, cyano and halogen;

$R_1$ is H, $C_1$-$C_6$alkyl or halogen;

or $R_1$ and $R_{11}$ together with the carbon atom to which they are attached, may form a 3 to 6 membered carbocyclic ring.

Various embodiments of the compounds of the invention are described herein. It will be recognized that features specified in each embodiment may be combined with other specified features to provide further embodiments. The following enumerated embodiments are representative of the compounds of Formula (I) of the invention.

Embodiment 1. A compound of Formula (I), or a pharmaceutically acceptable salt or stereoisomer thereof,

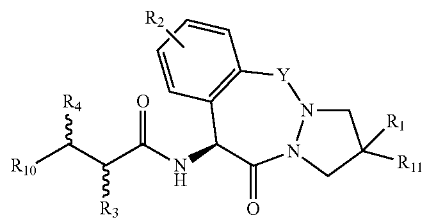

(I)

wherein:

Y is $CH_2$ or C═O;

$R_1$ is H, $C_1$-$C_6$alkyl or halogen;

$R_2$ is H or halogen;

$R_3$ is H, $C_1$-$C_6$alkyl, $C_1$-$C_6$haloalkyl, $C_3$-$C_6$cycloalkyl, $C_1$-$C_6$alkyl-phenyl or $C_1$-$C_6$alkyl substituted with $C_1$-$C_6$alkoxy;

$R_4$ is H, $C_1$-$C_6$alkyl or $C_1$-$C_6$alkyl-phenyl;

$R_{10}$ is —NHC(═O)$R_5$, —C(═O)NH$R_5$ or a 9 or 10 membered bicyclic heteroaryl having 1 to 4 heteroatoms as ring members each independently selected from N, O and S, wherein the bicyclic heteroaryl is unsubstituted or the bicyclic heteroaryl is substituted with one or more $R_6$;

$R_5$ is a 5-membered heteroaryl having 1, 2 or 3 heteroatoms as ring members each independently selected from N, O and S, wherein the 5-membered heteroaryl is unsubstituted or the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;

vi) $C_1$-$C_6$haloalkyl;

vii) —NHC(═O)$C_1$-$C_6$alkyl, wherein the $C_1$-$C_6$alkyl is optionally substituted by $C_1$-$C_6$alkoxy;

viii) —NHC(═O)—$C_1$-$C_6$haloalkyl;

ix) —NHC(═O)—$C_3$-$C_6$cycloalkyl;

x) —C(═O)NH—$C_1$-$C_6$alkyl, wherein the $C_1$-$C_6$alkyl is optionally substituted by $C_1$-$C_6$alkoxy;

xi) —C(═O)NH—$C_1$-$C_6$haloalkyl;

xii) —C(═O)NH—$C_3$-$C_6$cycloalkyl xiii) —NHC(═O)phenyl, wherein the phenyl is optionally substituted with one or more substituents independently selected from halogen and $C_1$-$C_6$alkyl;

xiv) —C(═O)NHphenyl, wherein the phenyl is optionally substituted with one or more substituents independently selected from halogen and $C_1$-$C_6$alkyl;

xv) $C_1$-$C_6$alkoxy or $C_1$-$C_6$haloalkoxy;

xvi) phenyloxy optionally substituted with one or more halogen;

xvii) phenyl optionally substituted by one or more substituents independently selected from halogen, —CN, $C_1$-$C_6$alkyl, $C_1$-$C_6$alkoxy and $C_1$-$C_6$haloalkyl;

xviii) a 4 to 6-member heterocyclyl optionally substituted with oxo, —C(═O)O$C_1$-$C_6$alkyl or —C(═O)O$C_1$-$C_6$cycloalkyl;

xix) a 5 or 6 membered heteroaryl having 1 or 2 heteroatoms as ring members each independently selected from N, O and S, wherein the heteroaryl is unsubstituted or the heteroaryl is substituted by one or more substitutents independently selected from $C_1$-$C_6$alkyl, halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and a $C_1$-$C_6$alkyl optionally substituted by —OH, $C_1$-$C_6$alkoxy or a 4 to 6-member heterocyclyl optionally substituted with oxo; and xx) a 9 or 10 membered bicyclic heteroaryl having 1 to 4 heteroatoms as ring members each independently selected from N, O and S, wherein the heteroaryl is unsubstituted or the heteroaryl is substituted by one or more substitutents independently selected from $C_1$-$C_6$alkyl, halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and a $C_1$-$C_6$alkyl optionally substituted by $C_1$-$C_6$alkoxy;

each $R_6$ is independently selected from $C_1$-$C_6$alkyl, $C_1$-$C_6$alkoxy, $C_1$-$C_6$haloalkyl, cyano and halogen;

$R_1$ is H, $C_1$-$C_6$alkyl or halogen;

or $R_1$ and $R_{11}$ together with the carbon atom to which they are attached, may form a 3 to 6 membered carbocyclic ring.

Embodiment 2. The compound of Embodiment 1, or a pharmaceutically acceptable salt or stereoisomer thereof, wherein $R_{10}$ is —NHC(═O)$R_5$.

Embodiment 3. The compound of Embodiment 1, or a pharmaceutically acceptable salt or stereoisomer thereof, wherein $R_{10}$ is —C(═O)NH$R_5$.

Embodiment 4. The compound of Embodiment 1, or a pharmaceutically acceptable salt or stereoisomer thereof, wherein $R_{10}$ is a 9 or 10 membered bicyclic heteroaryl having 1 to 4 heteroatoms as ring members each independently selected from N, O and S, wherein the bicyclic heteroaryl is unsubstituted or the bicyclic heteroaryl is substituted with one or more $R_6$.

Embodiment 5. The compound of Embodiment 1, or a pharmaceutically acceptable salt or stereoisomer thereof, wherein $R^{10}$ is

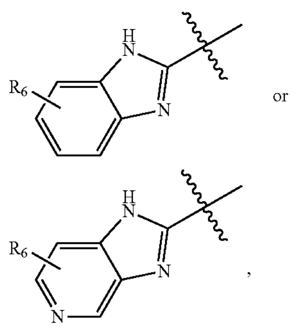

wherein $R_6$ is H, $C_1$-$C_6$alkyl, $C_1$-$C_6$alkoxy, $C_1$-$C_6$haloalkyl, cyano or halogen.

Embodiment 6. The compound of any one of Embodiments 1 to 4, or a pharmaceutically acceptable salt or stereoisomer thereof, wherein $R_4$ is H.

Embodiment 7. The compound of any one of Embodiments 1 to 4, or a pharmaceutically acceptable salt or stereoisomer thereof, wherein $R_4$ is $C_1$-$C_6$alkyl.

Embodiment 8. The compound of any one of Embodiments 1 to 4, or a pharmaceutically acceptable salt or stereoisomer thereof, wherein $R_4$ is $C_1$-$C_6$alkyl-phenyl.

Embodiment 9. The compound of Embodiment 1, or a pharmaceutically acceptable salt or stereoisomer thereof, having a structure of Formula (II)

(II)

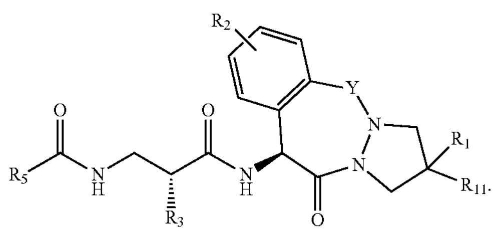

Embodiment 10. The compound of Embodiment 1, or a pharmaceutically acceptable salt or stereoisomer thereof, having a structure of Formula (III)

(III)

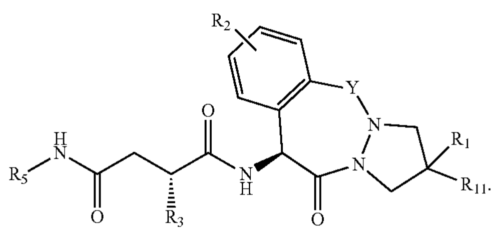

Embodiment 11. The compound of Embodiment 1, or a pharmaceutically acceptable salt or stereoisomer thereof, having a structure of Formula (IV):

(IV)

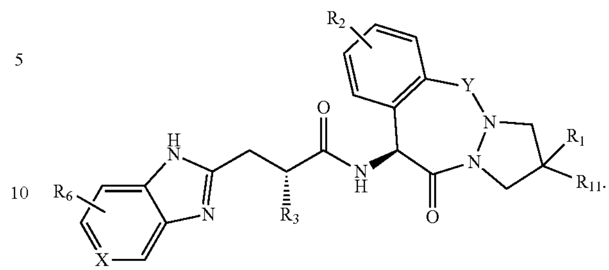

Embodiment 12. The compound of any one of Embodiments 1 to 11, or a pharmaceutically acceptable salt or stereoisomer thereof, wherein $R_1$ is H.

Embodiment 13. The compound of any one of Embodiments 1 to 11, or a pharmaceutically acceptable salt or stereoisomer thereof, wherein $R_1$ is $C_1$-$C_6$alkyl.

Embodiment 14. The compound of any one of Embodiments 1 to 11, or a pharmaceutically acceptable salt or stereoisomer thereof, wherein $R_1$ is halogen.

Embodiment 15. The compound of any one of Embodiments 1 to 11, or a pharmaceutically acceptable salt or stereoisomer thereof, wherein $R_{11}$ is H.

Embodiment 16. The compound of any one of Embodiments 1 to 11, or a pharmaceutically acceptable salt or stereoisomer thereof, wherein $R_{11}$ is $C_1$-$C_6$alkyl.

Embodiment 17. The compound of any one of Embodiments 1 to 11, or a pharmaceutically acceptable salt or stereoisomer thereof, wherein $R_{11}$ is halogen.

Embodiment 18. The compound of any one of Embodiments 1 to 11, or a pharmaceutically acceptable salt or stereoisomer thereof, wherein $R_1$ and $R_{11}$ together with the carbon atom to which they are attached, form a 3 to 6 membered carbocyclic ring.

Embodiment 19. The compound of any one of Embodiments 1 to 11, or a pharmaceutically acceptable salt or stereoisomer thereof, wherein $R_1$ and $R_{11}$ together with the carbon atom to which they are attached, form a cyclopropyl ring.

Embodiment 20. The compound of any one of Embodiments 1 to 19, or a pharmaceutically acceptable salt or stereoisomer thereof, wherein $R_2$ is H.

Embodiment 21. The compound of any one of Embodiments 1 to 19, or a pharmaceutically acceptable salt or stereoisomer thereof, wherein $R_2$ is halogen.

Embodiment 22. The compound of any one of Embodiments 1 to 19, or a pharmaceutically acceptable salt or stereoisomer thereof, wherein $R_2$ is F.

Embodiment 23. The compound of Embodiment 1 or Embodiment 9, or a pharmaceutically acceptable salt or stereoisomer thereof, having a structure of Formula (IIA):

(IIA)

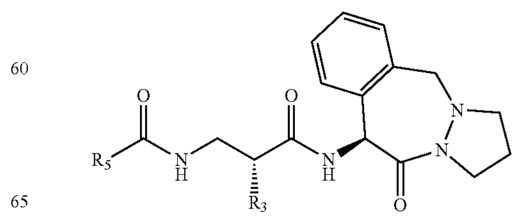

Embodiment 24. The compound of Embodiment 1 or Embodiment 9, or a pharmaceutically acceptable salt or stereoisomer thereof, having a structure of Formula (IIB):

(IIB)

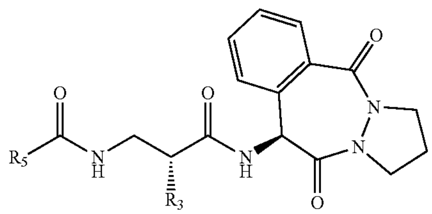

Embodiment 25. The compound of Embodiment 1 or Embodiment 9, or a pharmaceutically acceptable salt or stereoisomer thereof, having a structure of Formula (IIC):

(IIC)

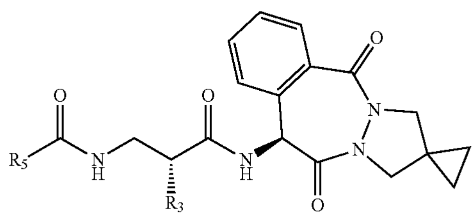

Embodiment 26. The compound of Embodiment 1 or Embodiment 9, or a pharmaceutically acceptable salt or stereoisomer thereof, having a structure of Formula (IID):

(IID)

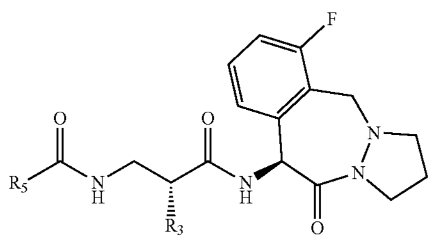

Embodiment 27. The compound of Embodiment 1 or Embodiment 9, or a pharmaceutically acceptable salt or stereoisomer thereof, having a structure of Formula (IIA), Formula (IIB), Formula (IIC) or Formula (IID):

(IIA)

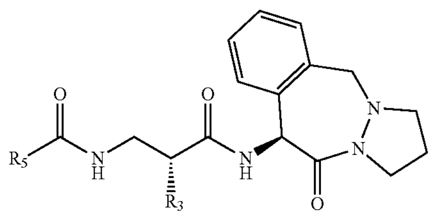

-continued (IIB)

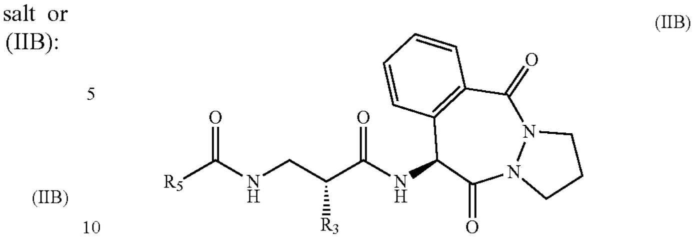

(IIC)

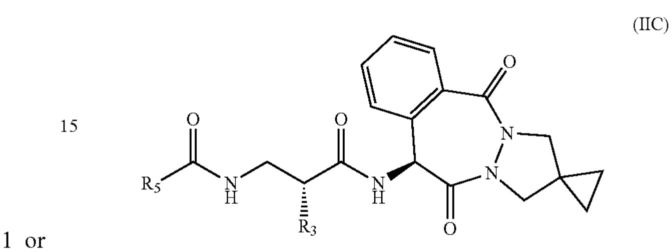

(IID)

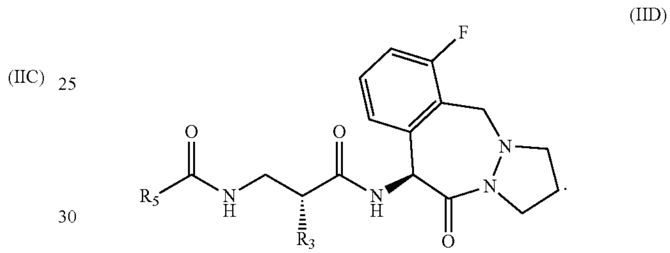

Embodiment 28. The compound of Embodiment 1 or Embodiment 10, or a pharmaceutically acceptable salt or stereoisomer thereof, having a structure of Formula (IIIA):

(IIIA)

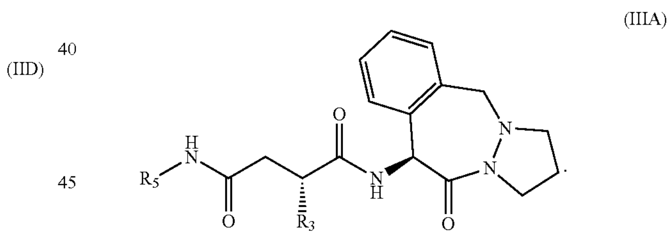

Embodiment 29. The compound of Embodiment 1 or Embodiment 10, or a pharmaceutically acceptable salt or stereoisomer thereof, having a structure of Formula (IIIB):

(IIIB)

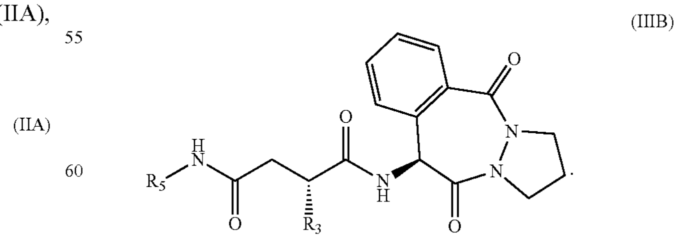

Embodiment 30. The compound of Embodiment 1 or Embodiment 10, or a pharmaceutically acceptable salt or stereoisomer thereof, having a structure of Formula (IIIC):

(IIIC)

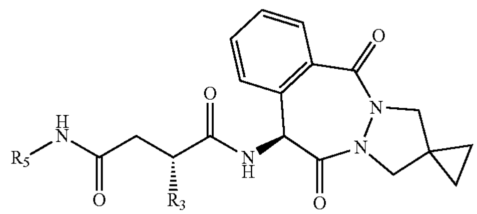

Embodiment 31. The compound of Embodiment 1 or Embodiment 10, or a pharmaceutically acceptable salt or stereoisomer thereof, having a structure of Formula (IIID):

(IIID)

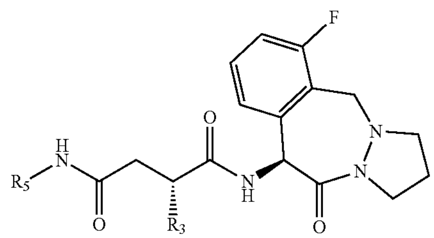

Embodiment 32. The compound of Embodiment 1 or Embodiment 10, or a pharmaceutically acceptable salt or stereoisomer thereof, having a structure of Formula (IIIA), Formula (IIIB), Formula (IIIC) or Formula (IIID):

(IIIA)

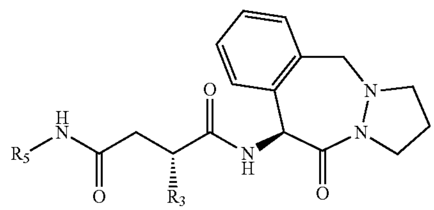

(IIIB)

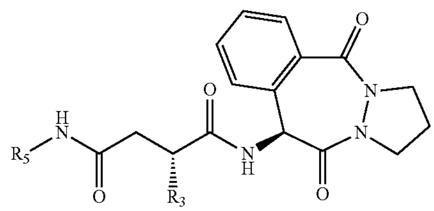

(IIIC)

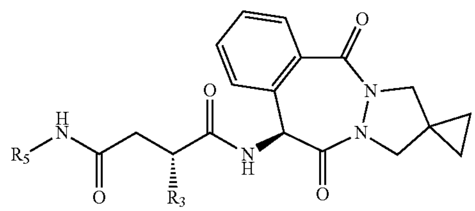

-continued (IIID)

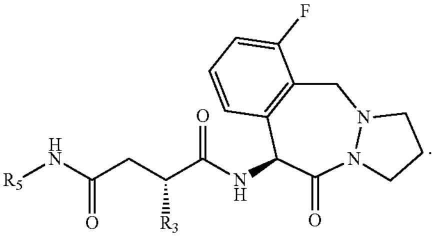

Embodiment 33. The compound of any one of Embodiments 1 to 32, or a pharmaceutically acceptable salt or stereoisomer thereof, wherein $R_3$ is H.

Embodiment 34. The compound of any one of Embodiments 1 to 32, or a pharmaceutically acceptable salt or stereoisomer thereof, wherein $R_3$ is $C_1$-$C_6$alkyl.

Embodiment 35. The compound of any one of Embodiments 1 to 32, or a pharmaceutically acceptable salt or stereoisomer thereof, wherein $R_3$ is methyl, ethyl, propyl or iso-propyl.

Embodiment 36. The compound of any one of Embodiments 1 to 32, or a pharmaceutically acceptable salt or stereoisomer thereof, wherein $R_3$ is $C_1$-$C_6$halolkyl.

Embodiment 37. The compound of any one of Embodiments 1 to 32, or a pharmaceutically acceptable salt or stereoisomer thereof, wherein $R_3$ is $CF_3$.

Embodiment 38. The compound of any one of Embodiments 1 to 32, or a pharmaceutically acceptable salt or stereoisomer thereof, wherein $R_3$ is $C_1$-$C_6$alkyl-phenyl.

Embodiment 39. The compound of any one of Embodiments 1 to 32, or a pharmaceutically acceptable salt or stereoisomer thereof, wherein $R_3$ is $-CH_2$-phenyl.

Embodiment 40. The compound of any one of Embodiments 1 to 32, or a pharmaceutically acceptable salt or stereoisomer thereof, wherein $R_3$ is $C_3$-$C_6$cycloalkyl.

Embodiment 41. The compound of any one of Embodiments 1 to 32, or a pharmaceutically acceptable salt or stereoisomer thereof, wherein $R_3$ is cyclopropyl or cyclobutyl.

Embodiment 42. The compound of any one of Embodiments 1 to 32, or a pharmaceutically acceptable salt or stereoisomer thereof, wherein $R_3$ is $C_1$-$C_6$alkyl substituted with $C_1$-$C_6$alkoxy.

Embodiment 43. The compound of any one of Embodiments 1 to 32, or a pharmaceutically acceptable salt or stereoisomer thereof, wherein $R_3$ is $-CH_2CH_2OCH_3$.

Embodiment 44. The compound of any one of Embodiments 1 to 43, or a pharmaceutically acceptable salt or stereoisomer thereof, wherein $R_5$ is a 5-membered heteroaryl having 1, 2 or 3 heteroatoms as ring members each independently selected from N, O and S, wherein the 5-membered heteroaryl is unsubstituted Embodiment 45. The compound of any one of Embodiments 1 to 43, or a pharmaceutically acceptable salt or stereoisomer thereof, wherein $R_5$ is a 5-membered heteroaryl having 1, 2 or 3 heteroatoms as ring members each independently selected from N, O and S, wherein the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;
vi) $C_1$-$C_6$haloalkyl;
vii) —NHC(═O)$C_1$-$C_6$alkyl, wherein the $C_1$-$C_6$alkyl is optionally substituted by $C_1$-$C_6$alkoxy;
viii) —NHC(═O)—$C_1$-$C_6$haloalkyl;
ix) —NHC(═O)—$C_3$-$C_6$cycloalkyl;
x) —C(═O)NH—$C_1$-$C_6$alkyl, wherein the $C_1$-$C_6$alkyl is optionally substituted by $C_1$-$C_6$alkoxy;
xi) —C(═O)NH—$C_1$-$C_6$haloalkyl;
xii) —C(═O)NH—$C_3$-$C_6$cycloalkyl
xiii) —NHC(═O)phenyl, wherein the phenyl is optionally substituted with one or more substituents independently selected from halogen and $C_1$-$C_6$alkyl;
xiv) —C(═O)NHphenyl, wherein the phenyl is optionally substituted with one or more substituents independently selected from halogen and $C_1$-$C_6$alkyl;
xv) $C_1$-$C_6$alkoxy or $C_1$-$C_6$haloalkoxy;
xvi) phenyloxy optionally substituted with one or more halogen;
xvii) phenyl optionally substituted by one or more substituents independently selected from halogen, —CN, $C_1$-$C_6$alkyl, $C_1$-$C_6$alkoxy, $C_1$-$C_6$haloalkoxy and $C_1$-$C_6$haloalkyl;
xviii) a 4 to 6-member heterocyclyl optionally substituted with oxo, —C(═O)O$C_1$-$C_6$alkyl or —C(═O)O$C_1$-$C_6$cycloalkyl; and
xix) a 5 or 6 membered heteroaryl having 1 or 2 heteroatoms as ring members each independently selected from N, O and S, wherein the heteroaryl is unsubstituted or the heteroaryl is substituted by one or more substitutents independently selected from $C_1$-$C_6$alkyl, halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and a $C_1$-$C_6$alkyl optionally substituted by —OH, $C_1$-$C_6$alkoxy or a 4 to 6-member heterocyclyl optionally substituted with oxo; and
xx) a 9 or 10 membered bicyclic heteroaryl having 1 to 4 heteroatoms as ring members each independently selected from N, O and S, wherein the heteroaryl is unsubstituted or the heteroaryl is substituted by one or more substitutents independently selected from $C_1$-$C_6$alkyl, halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and a $C_1$-$C_6$alkyl optionally substituted by $C_1$-$C_6$alkoxy.

Embodiment 46. The compounds of any one of Embodiments 1 to 43, or a pharmaceutically acceptable salt thereof, wherein $R_5$ is:

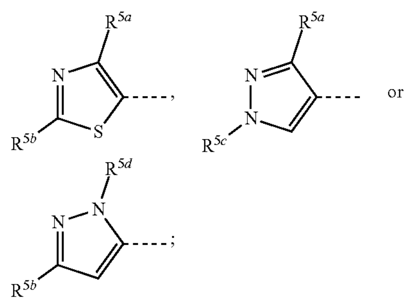

wherein $R^{5a}$ is $C_1$-$C_6$alkyl, $C_1$-$C_6$haloalkyl or halogen;

$R^{5b}$ is —C(O)—NH—$C_1$-$C_6$alkyl, —C(O)NH—$C_1$-$C_6$haloalkyl, —C(O)NHphenyl, $C_1$-$C_6$alkoxy, $C_1$-$C_6$haloalkoxy, $C_3$-$C_6$cycloalkyl, $C_3$-$C_6$cycloalkenyl, 4- to 6-membered heterocyclyl, 5- or 6-membered ring heteroaryl; wherein heteroaryl is optionally substituted with halogen, $C_1$-$C_6$alkyl, $C_1$-$C_6$haloalkyl, $C_1$-$C_6$alkoxy, $C_1$-$C_6$haloakoxy or $C_3$-$C_6$cycloalkyl; and wherein heterocyclyl is optionally substituted with oxo, —C(O)O—$C_1$-$C_6$alkyl or —C(O)O—$C_3$-$C_6$cycloalkyl; and wherein —C(O)NHphenyl is optionally substituted with halogen or $C_1$-$C_6$alkyl;

$R^{5c}$ is 5- or 6-membered ring heteroaryl optionally substituted with halogen, $C_1$-$C_6$alkyl, $C_1$-$C_6$haloalkyl, $C_1$-$C_6$alkoxy, $C_1$-$C_6$haloakoxy or $C_3$-$C_6$cycloalkyl; and $R^{5d}$ is $C_1$-$C_6$alkyl or $C_1$-$C_6$haloalkyl.

Embodiment 47. The compound of any one of Embodiments 1 to 43, or a pharmaceutically acceptable salt or stereoisomer thereof, wherein $R_5$ is

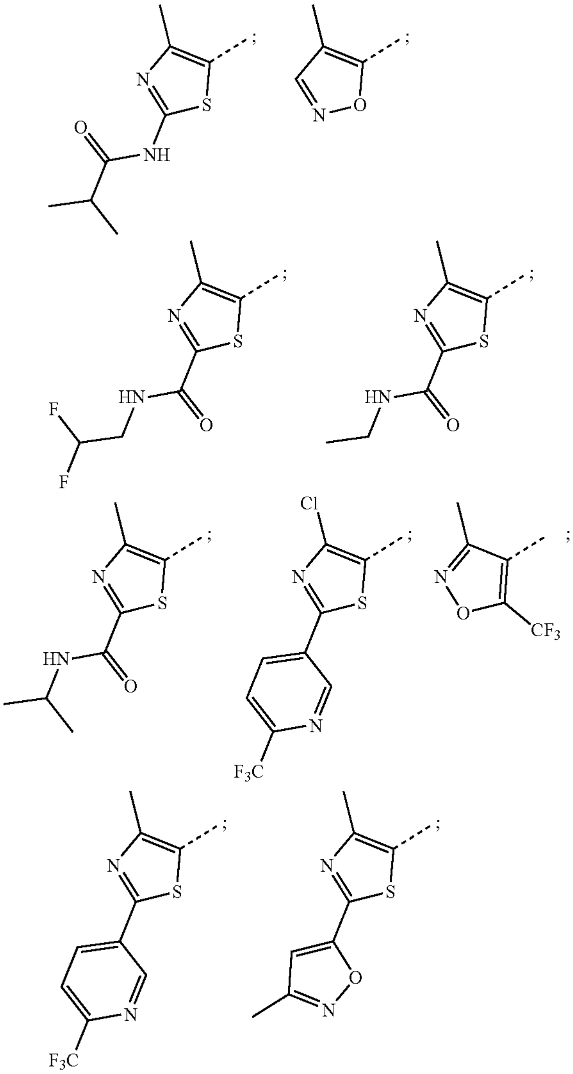

-continued
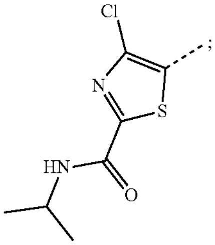
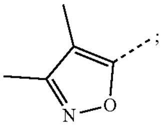
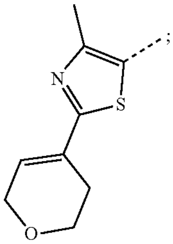
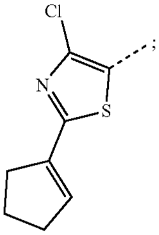
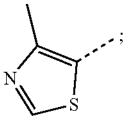
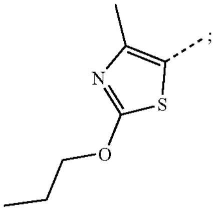
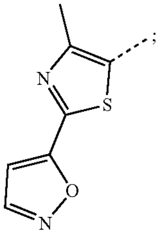
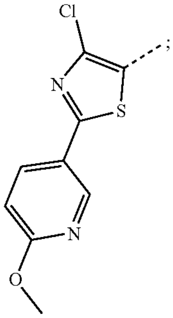
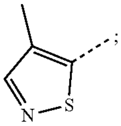
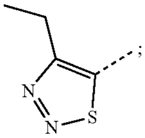
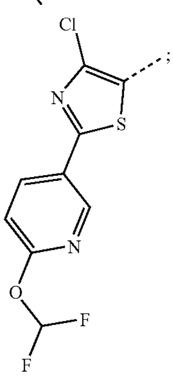
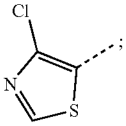
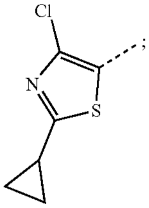
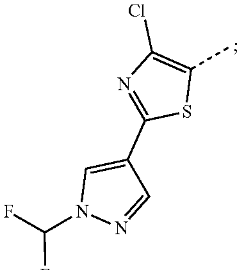
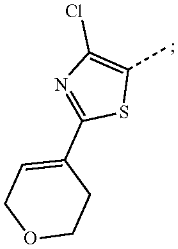
-continued
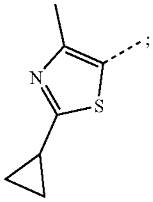
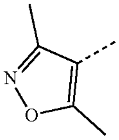
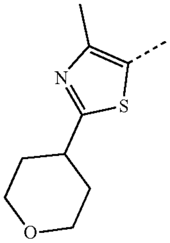
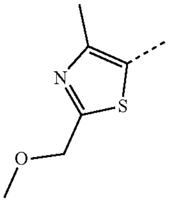
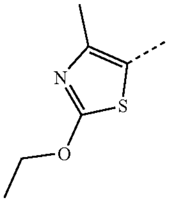
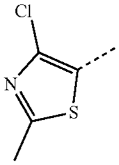
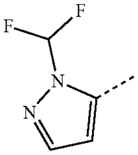
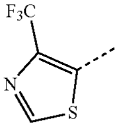
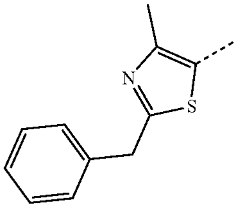
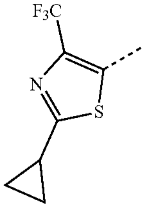
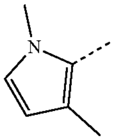
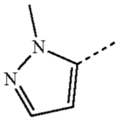
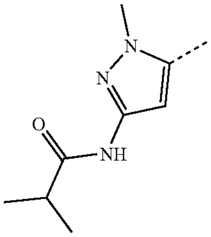
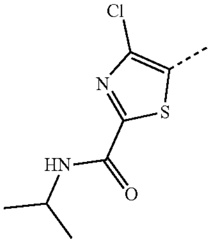
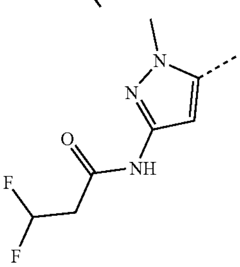
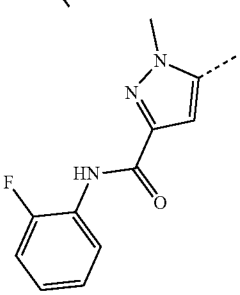
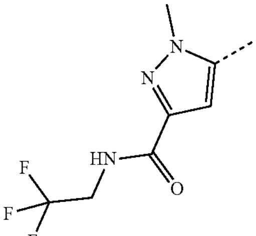
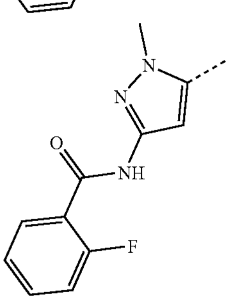

-continued
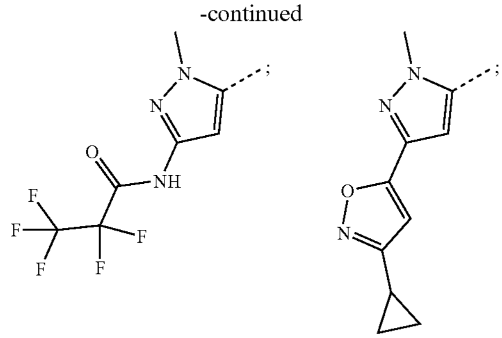
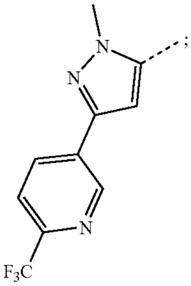
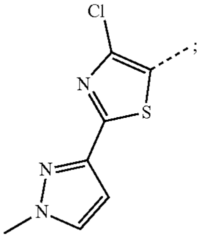
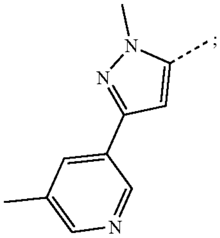
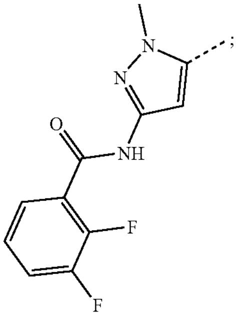
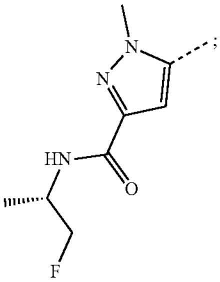
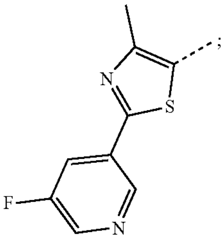
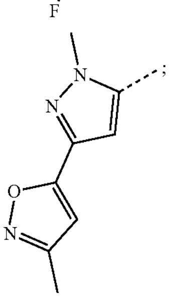
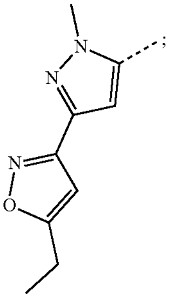
-continued
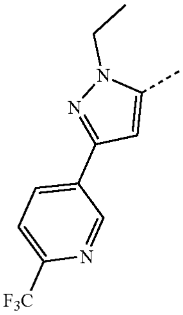
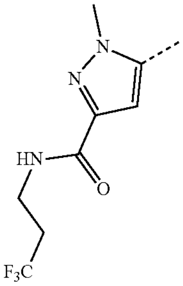
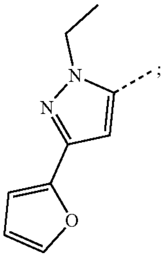
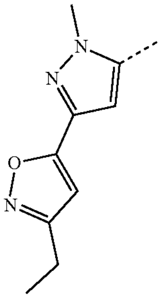
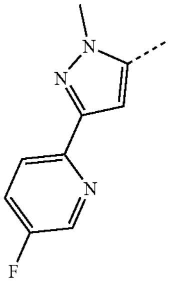
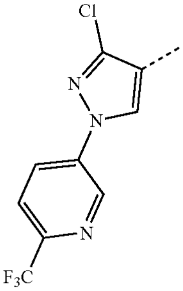
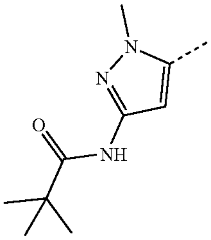
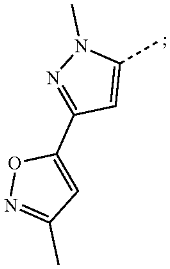
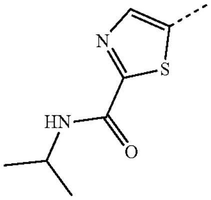
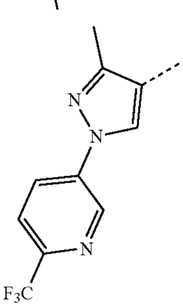
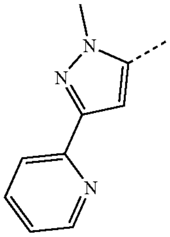

-continued
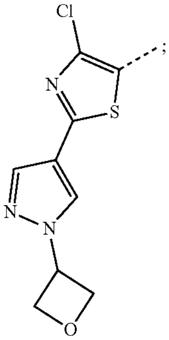
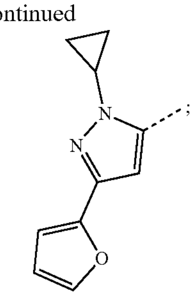
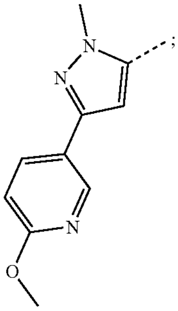
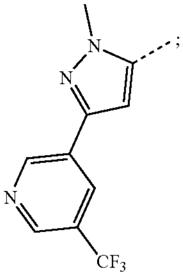
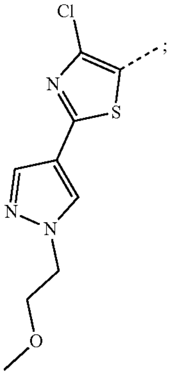
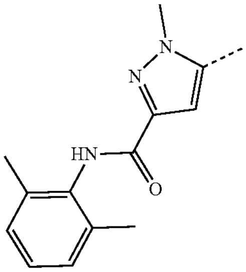
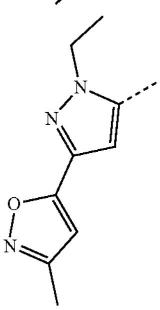
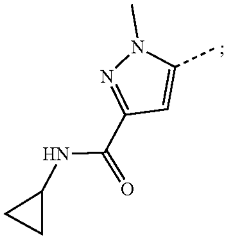
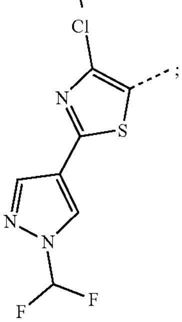
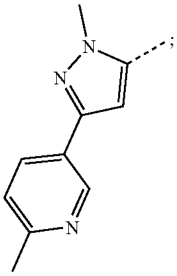
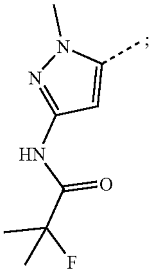
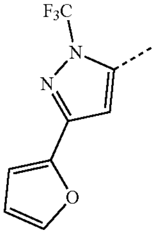
-continued
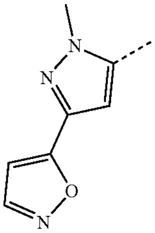
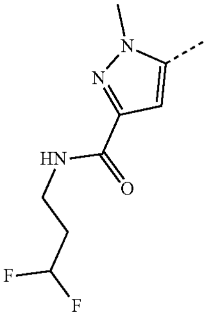
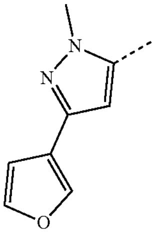
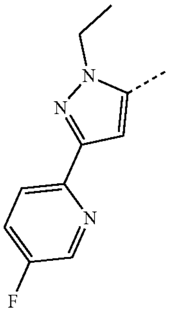
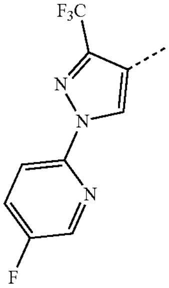
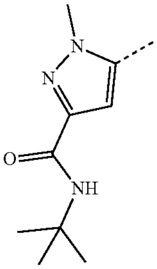
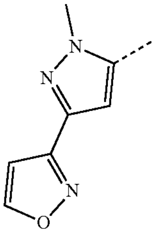
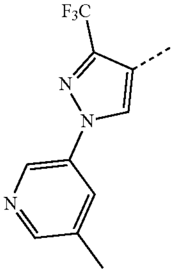
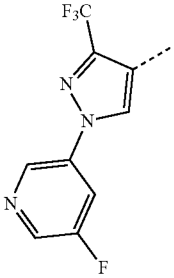
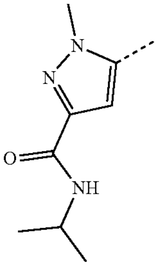
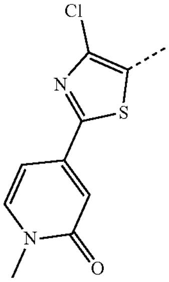
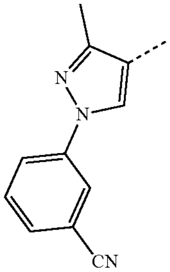
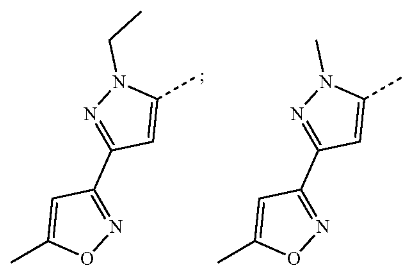

-continued
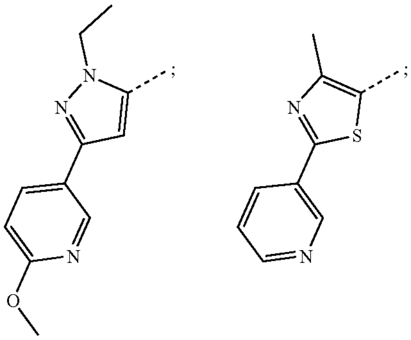
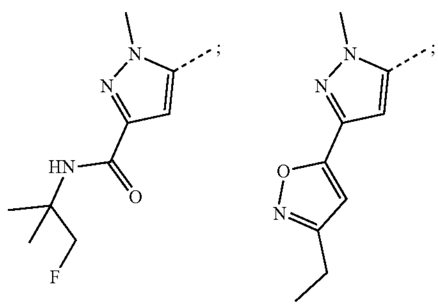
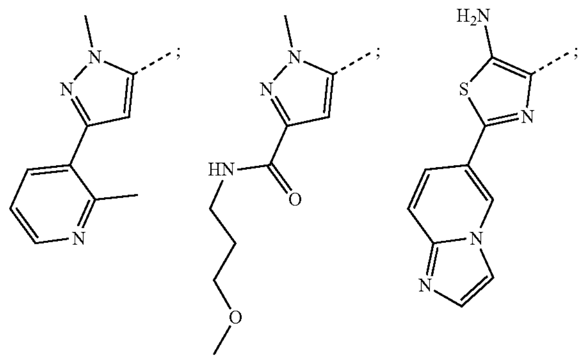
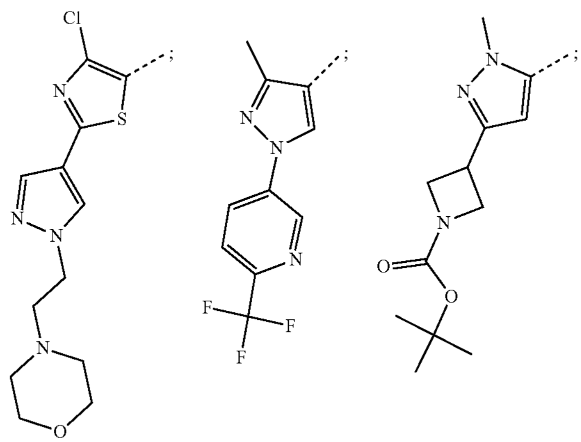
-continued
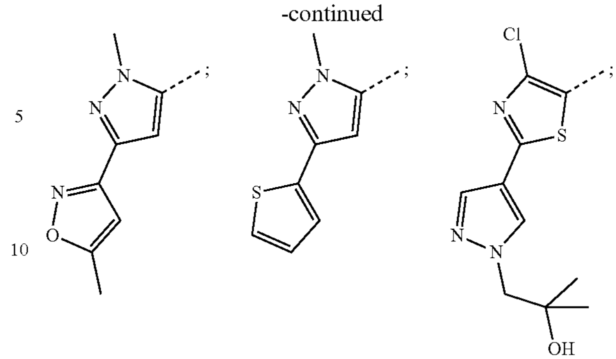
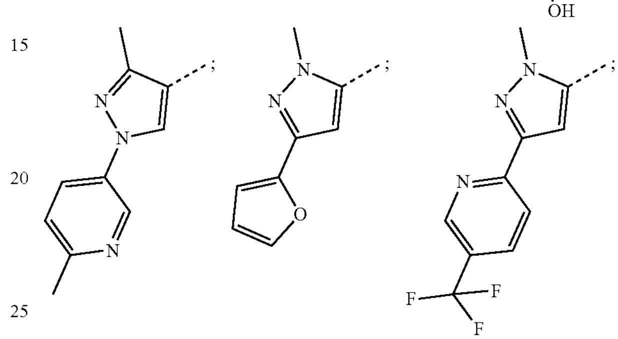
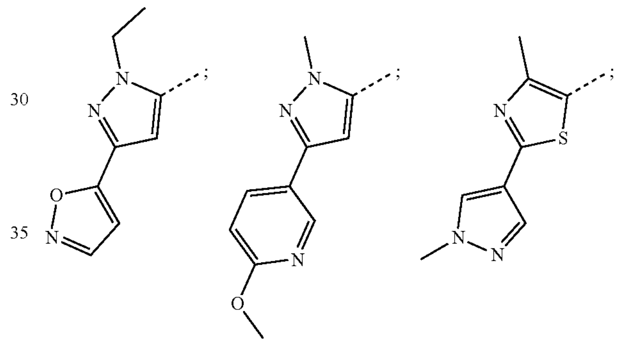
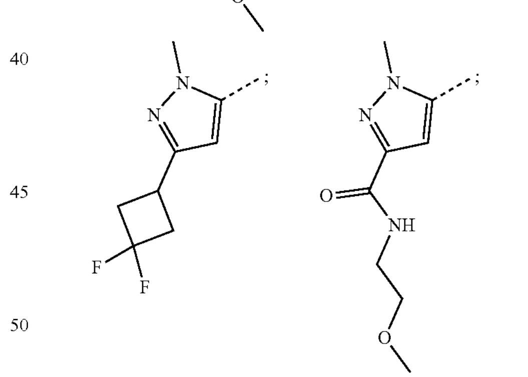
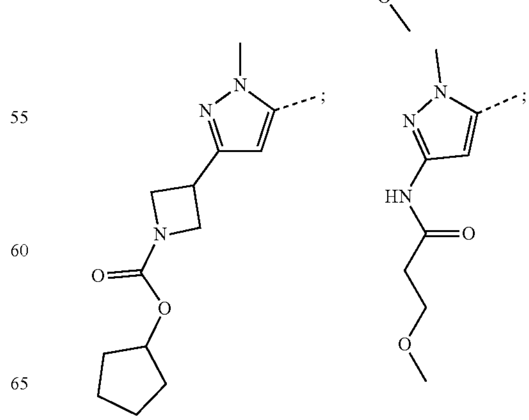

-continued
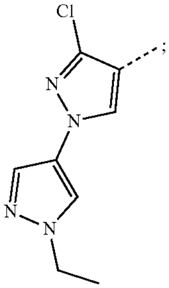
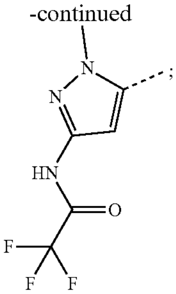
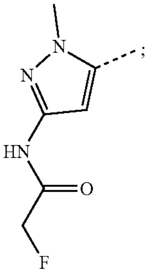
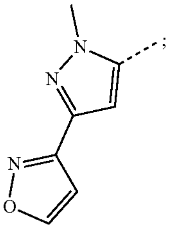
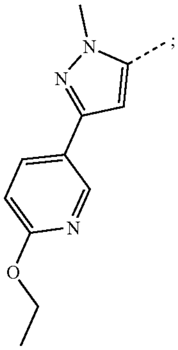
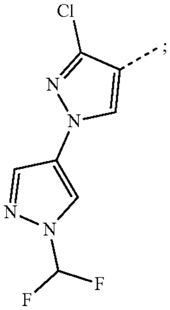
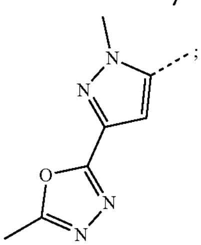
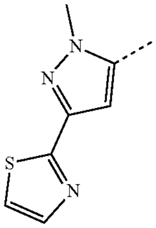
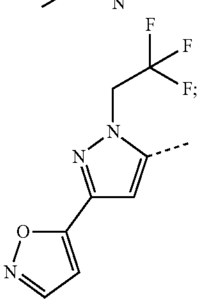
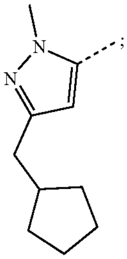
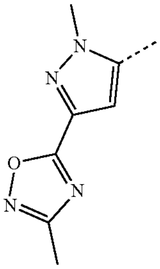
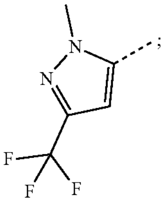
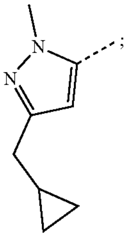
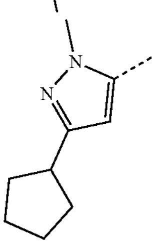
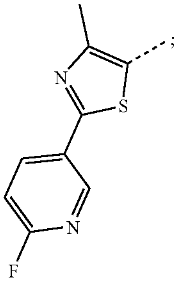
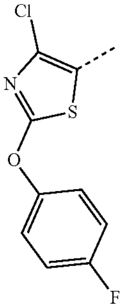
or
-continued
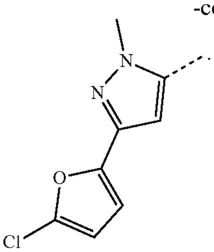
Embodiment 48. The compound of any one of Embodiments 1 to 43, or a pharmaceutically acceptable salt or stereoisomer thereof, wherein $R_5$ is,
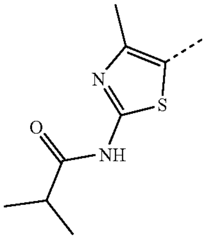
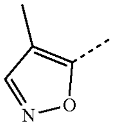
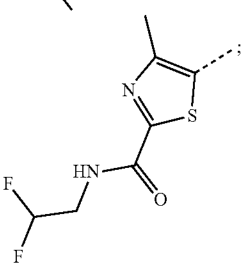
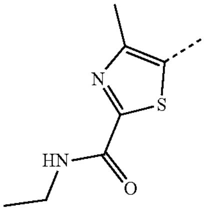
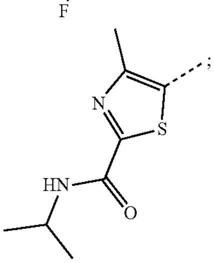
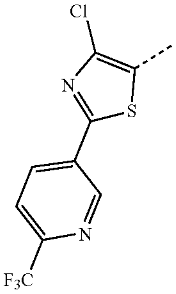
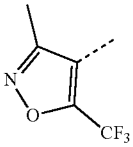
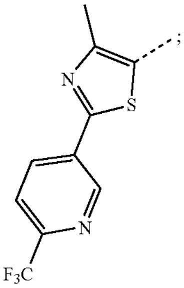
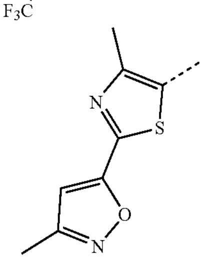
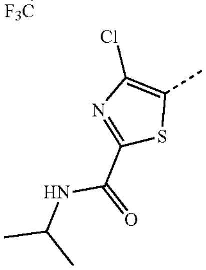
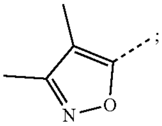

-continued
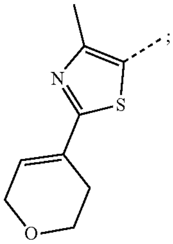
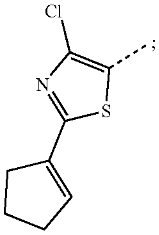
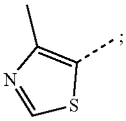
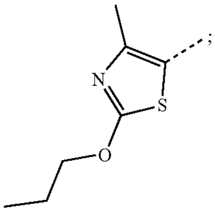
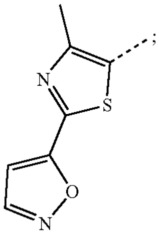
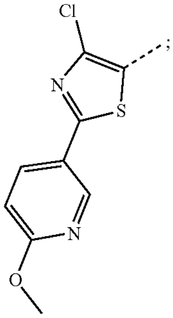
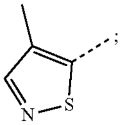
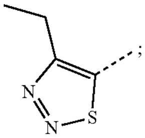
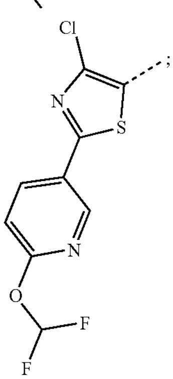
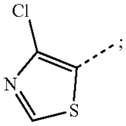
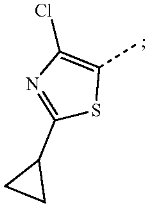
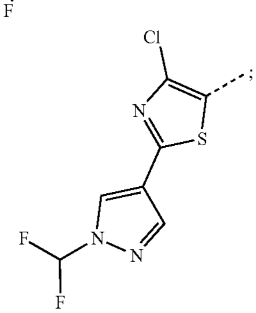
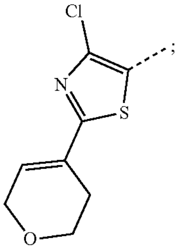
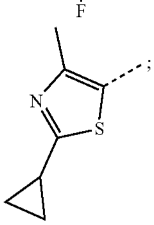
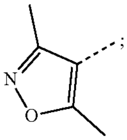
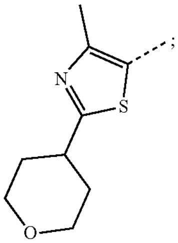
-continued
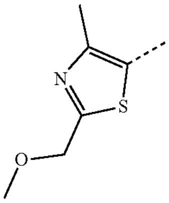
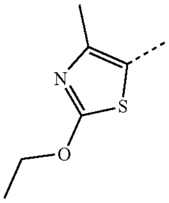
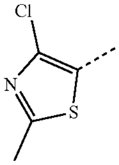
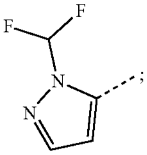
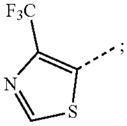
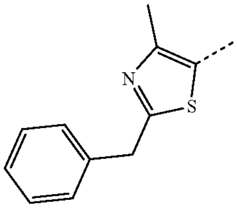
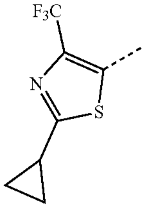
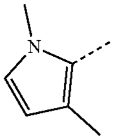
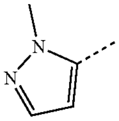
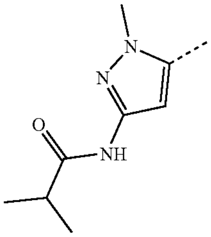
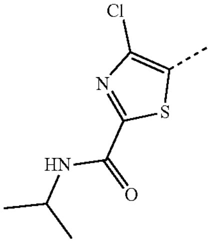
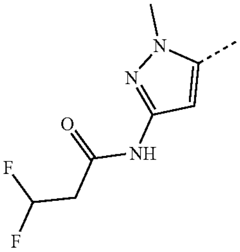
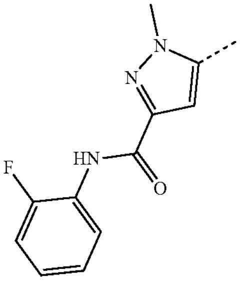
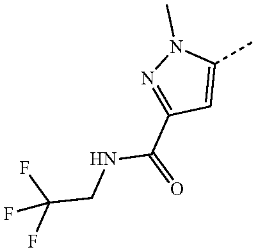
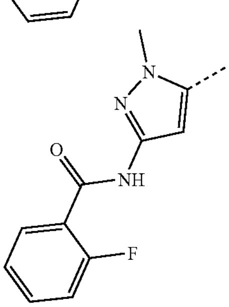

-continued
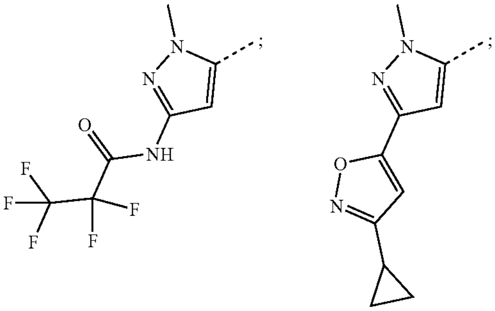
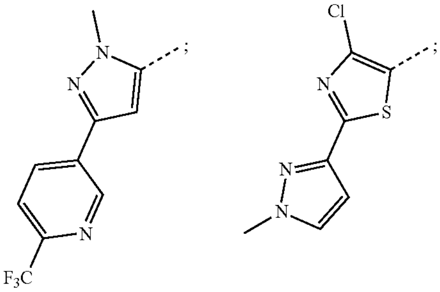
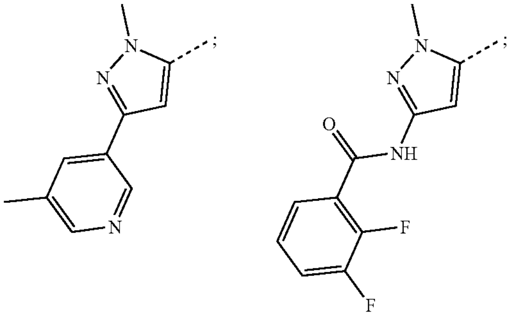
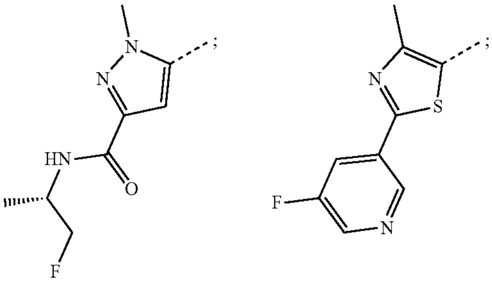
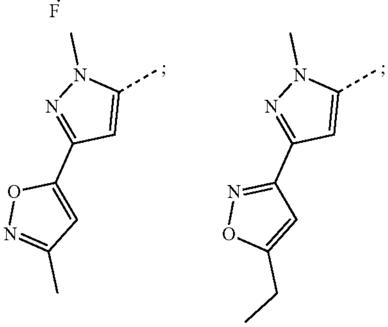
-continued
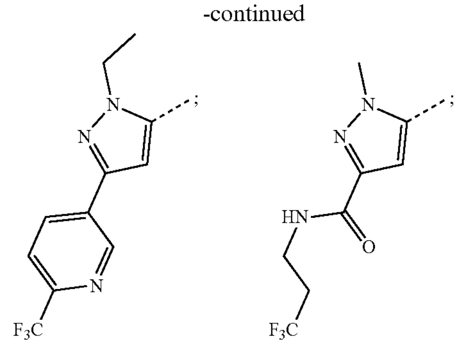
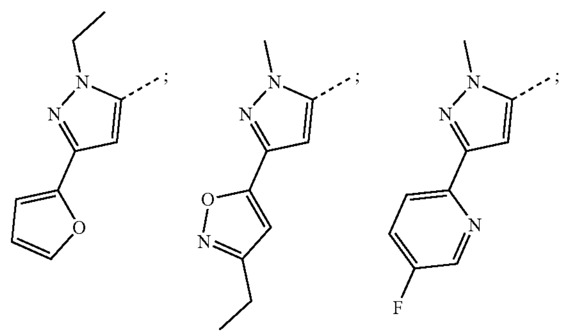
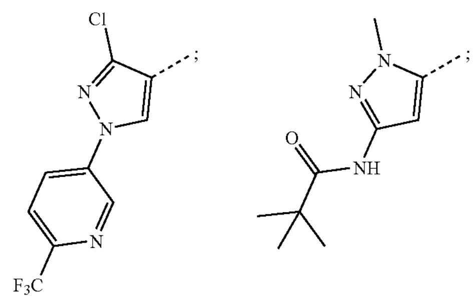
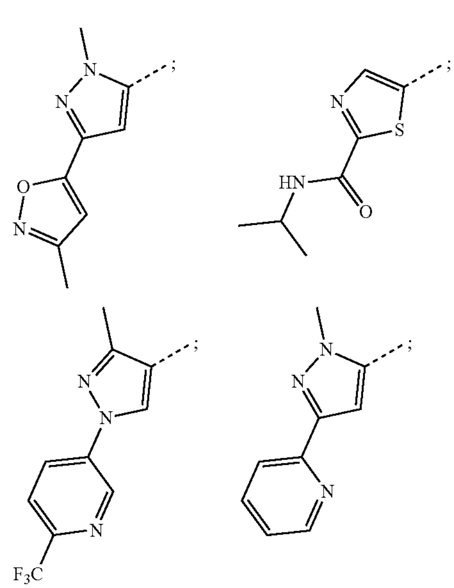

-continued

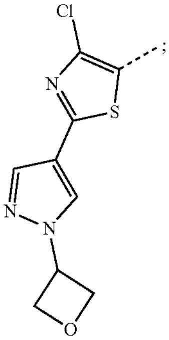

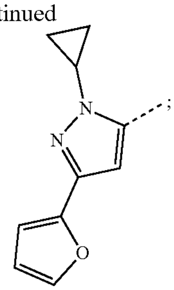

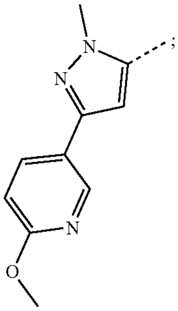

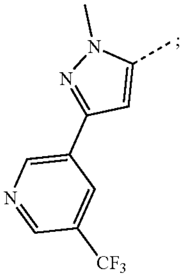

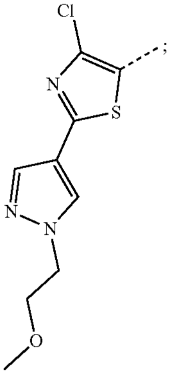

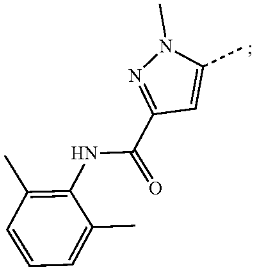

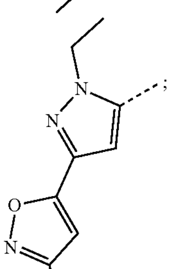

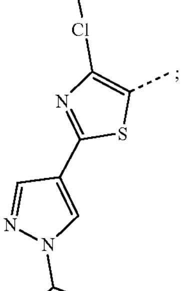

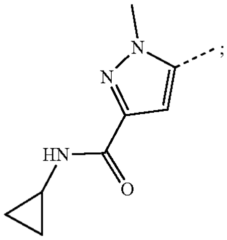

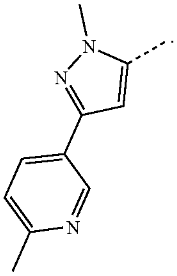

Embodiment 49. The compound of Embodiment 1, or a pharmaceutically acceptable salt or stereoisomer thereof, wherein the compound is $N^2$,4-dimethyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-4-methylisoxazole-5-carboxamide;

2-isobutyramido-4-methyl-N—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide;

2-isobutyramido-4-methyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-5-carboxamide;

$N^2$-(2,2-difluoroethyl)-4-methyl-$N^5$—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide;

$N^5$—((R)-2-cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-(2,2-difluoroethyl)-4-methylthiazole-2,5-dicarboxamide;

$N^2$-ethyl-4-methyl-$N^5$—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide;

$N^2$-(2,2-difluoroethyl)-4-methyl-$N^5$—((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide;

$N^5$—((R)-2-cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$,4-dimethylthiazole-2,5-dicarboxamide;

$N^2$-ethyl-4-methyl-$N^5$—((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide;

$N^2$,4-dimethyl-$N^5$—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide;

$N^5$—((R)-2-cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-ethyl-4-methylthiazole-2,5-dicarboxamide:

$N^2$,4-dimethyl-$N^5$—((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide;

$N^2$-isopropyl-4-methyl-$N^5$—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide;

4-chloro-N—((R)-2-(((S)-11-oxo-2,3,10,11-tetrahydro-1H,5H-benzo[d]pyrazolo[1,2-a][1,2]diazepin-10-yl)carbamoyl)butyl)-2-(6-(trifluoromethyl) pyridin-3-yl)thiazole-5-carboxamide;

$N^2$-ethyl-4-methyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

3-methyl-N—((R)-2-(((S)-11-oxo-2,3,10,11-tetrahydro-1H,5H-benzo[d]pyrazolo[1,2-a][1,2]diazepin-10-yl)carbamoyl)butyl)-5-(trifluoromethyl)isoxazole-4-carboxamide;

4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)-2-(6-(trifluoromethyl) pyridin-3-yl)thiazole-5-carboxamide;

$N^2$-isopropyl-4-methyl-$N^5$—((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide;

4-methyl-2-(3-methylisoxazol-5-yl)-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

$N^2$-(2,2-difluoroethyl)-4-methyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

4-chloro-$N^2$-isopropyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

4-methyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)-2-(3-methylisoxazol-5-yl)thiazole-5-carboxamide;

$N^2$-isopropyl-4-methyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

3,4-dimethyl-N—((R)-2-(((S)-11-oxo-2,3,10,11-tetrahydro-1H,5H-benzo[d]pyrazolo[1,2-a][1,2]diazepin-10-yl)carbamoyl)butyl)isoxazole-5-carboxamide;

2-(3,6-dihydro-2H-pyran-4-yl)-4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

$N^5$—((R)-2-cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-isopropyl-4-methylthiazole-2,5-dicarboxamide;

4-chloro-2-(cyclopent-1-en-1-yl)-N—((R)-2-(((S)-5,11-dioxo-2,3,10,11-tetrahydro-1H,5H-benzo[d]pyrazolo[1,2-a][1,2]diazepin-10-yl)carbamoyl)butyl)thiazole-5-carboxamide;

4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)-2-propoxythiazole-5-carboxamide;

N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-3-methyl-5-(trifluoromethyl)isoxazole-4-carboxamide;

2-(isoxazol-5-yl)-4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

3,4-dimethyl-N—((R)-2-(((S)-11-oxo-2,3,10,11-tetrahydro-1H,5H-benzo[d]pyrazolo[1,2-a][1,2]diazepin-10-yl)carbamoyl)pentyl)isoxazole-5-carboxamide;

4-chloro-N—((R)-2-(((S)-5,11-dioxo-2,3,10,11-tetrahydro-1H,5H-benzo[d]pyrazolo[1,2-a][1,2]diazepin-10-yl)carbamoyl)butyl)-2-(6-methoxypyridin-3-yl)thiazole-5-carboxamide;

N—((R)-2-(((S)-5,11-dioxo-2,3,10,11-tetrahydro-1H,5H-benzo[d]pyrazolo[1,2-a][1,2]diazepin-10-yl)carbamoyl)butyl)-4-methylisothiazole-5-carboxamide;

N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-4-ethyl-1,2,3-thiadiazole-5-carboxamide;

4-chloro-2-(6-(difluoromethoxy)pyridin-3-yl)-N—((R)-2-(((S)-5,11-dioxo-2,3,10,11-tetrahydro-1H,5H-benzo[d]pyrazolo[1,2-a][1,2]diazepin-10-yl)carbamoyl)butyl)thiazole-5-carboxamide;

N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-4-methyl-2-(6-(trifluoromethyl)pyridin-3-yl)thiazole-5-carboxamide;

4-chloro-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

4-chloro-N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-2-(6-(trifluoromethyl)pyridin-3-yl)thiazole-5-carboxamide;

N—((R)-2-cyclopropyl-3-(((S)-5,11-dioxo-2,3,10,11-tetrahydro-1H,5H-benzo[d]pyrazolo[1,2-a][1,2]diazepin-10-yl)amino)-3-oxopropyl)-4-methyl-2-(3-methylisoxazol-5-yl)thiazole-5-carboxamide;

N—((R)-4-methoxy-2-(((S)-11-oxo-2,3,10,11-tetrahydro-1H,5H-benzo[d]pyrazolo[1,2-a][1,2]diazepin-10-yl)carbamoyl)butyl)-4-methyl-2-(3-methylisoxazol-5-yl)thiazole-5-carboxamide;

4-chloro-2-cyclopropyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-5-carboxamide;

2-(3,6-dihydro-2H-pyran-4-yl)-4-methyl-N—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide;

4-chloro-2-(1-(difluoromethyl)-1H-pyrazol-4-yl)-N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)thiazole-5-carboxamide;

4-chloro-2-(3,6-dihydro-2H-pyran-4-yl)-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

2-cyclopropyl-4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-3,5-dimethylisoxazole-4-carboxamide;

4-chloro-N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)thiazole-5-carboxamide;

4-methyl-2-(tetrahydro-2H-pyran-4-yl)-N—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide;

4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)isoxazole-5-carboxamide;

2-(methoxymethyl)-4-methyl-N—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide;

2-ethoxy-4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

4-chloro-2-cyclopropyl-N—((R)-2-cyclopropyl-3-(((S)-6-fluoro-11-oxo-2,3,10,11-tetrahydro-1H,5H-benzo[d]pyrazolo[1,2-a][1,2]diazepin-10-yl)amino)-3-oxopropyl)thiazole-5-carboxamide;

4-chloro-N—((R)-2-cyclopropyl-3-(((S)-6-fluoro-11-oxo-2,3,10,11-tetrahydro-1H,5H-benzo[d]pyrazolo[1,2-a][1,2]diazepin-10-yl)amino)-3-oxopropyl)-2-methylthiazole-5-carboxamide;

1-(difluoromethyl)-N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-1H-pyrazole-5-carboxamide;

N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-4-(trifluoromethyl)thiazole-5-carboxamide;

2-benzyl-4-methyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-5-carboxamide;

2-cyclopropyl-N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-4-(trifluoromethyl)thiazole-5-carboxamide;

1,3-dimethyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)-1H-pyrrole-2-carboxamide;

1-methyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)-1H-pyrazole-5-carboxamide;

(R)—$N^4$-(3-isobutyramido-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclobutyl-$N^4$-(3-isobutyramido-1-methyl-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(4-chloro-2-(isopropylcarbamoyl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-((2,2-difluoroethyl)carbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(2-(isopropylcarbamoyl)-4-methylthiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^4$-(3-(isopropylcarbamoyl)-1-methyl-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-((2,2,2-trifluoroethyl)carbamoyl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(2-fluorobenzamido)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(2,2,3,3,3-pentafluoropropanamido)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(3-cyclopropylisoxazol-5-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(6-(trifluoromethyl)pyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(4-chloro-2-(1-methyl-1H-pyrazol-3-yl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(5-methylpyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^4$-(1-methyl-3-(5-methylpyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(2,3-difluorobenzamido)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^1$—((S)-6-fluoro-11-oxo-2,3,10,11-tetrahydro-1H,5H-benzo[d]pyrazolo[1,2-a][1,2]diazepin-10-yl)-$N^4$-(3-(isopropylcarbamoyl)-1-methyl-1H-pyrazol-5-yl)succinamide;

(S)-2-cyclopropyl-$N^4$-(3-(((S)-1-fluoropropan-2-yl)carbamoyl)-1-methyl-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(2-(5-fluoropyridin-3-yl)-4-methylthiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(5-methylisoxazol-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(5-ethylisoxazol-3-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclobutyl-$N^1$—((S)-5,11-dioxo-10,11-dihydro-1H,3H,5H-spiro[benzo[d]pyrazolo[1,2-a][1,2]diazepine-2,1'-cyclopropan]-10-yl)-$N^4$-(3-isobutyramido-1-methyl-1H-pyrazol-5-yl)succinamide;

(R)—$N^4$-(1-ethyl-3-(6-(trifluoromethyl) pyridin-3-yl)-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-((3,3,3-trifluoropropyl)carbamoyl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(1-ethyl-3-(furan-2-yl)-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(3-ethylisoxazol-5-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(5-fluoropyridin-2-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-chloro-1-(6-(trifluoromethyl)pyridin-3-yl)-1H-pyrazol-4-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-pivalamido-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(3-methylisoxazol-5-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(2-(isopropylcarbamoyl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(3-methyl-1-(6-(trifluoromethyl)pyridin-3-yl)-1H-pyrazol-4-yl)-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^1$—((S)-5,11-dioxo-10,11-dihydro-1H,3H,5H-spiro[benzo[d]pyrazolo[1,2-a][1,2]diazepine-2,1'-cyclopropan]-10-yl)-$N^4$-(3-isobutyramido-1-methyl-1H-pyrazol-5-yl)succinamide;

(R)-2-methyl-$N^4$-(1-methyl-3-(pyridin-2-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(4-chloro-2-(1-(oxetan-3-yl)-1H-pyrazol-4-yl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(1-cyclopropyl-3-(furan-2-yl)-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(6-methoxypyridin-3-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(5-(trifluoromethyl)pyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(4-chloro-2-(1-(2-methoxyethyl)-1H-pyrazol-4-yl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^1$—((S)-6-fluoro-11-oxo-2,3,10,11-tetrahydro-1H,5H-benzo[d]pyrazolo[1,2-a][1,2]diazepin-10-yl)-$N^4$-(3-(((S)-1-fluoropropan-2-yl)carbamoyl)-1-methyl-1H-pyrazol-5-yl)succinamide;

(R)—$N^4$-(1-ethyl-3-(3-methylisoxazol-5-yl)-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(cyclopropylcarbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^4$-(3-(3-cyclopropylisoxazol-5-yl)-1-methyl-1H-pyrazol-5-yl)-$N^1$—((S)-5,11-dioxo-10,11-dihydro-1H,3H,5H-spiro[benzo[d]pyrazolo[1,2-a][1,2]diazepine-2,1'-cyclopropan]-10-yl)succinamide;

(S)—$N^4$-(4-chloro-2-(1-(difluoromethyl)-1H-pyrazol-4-yl)thiazol-5-yl)-2-cyclopropyl-$N^1$—((S)-5,11-dioxo-2,3,10,11-tetrahydro-1H,5H-benzo[d]pyrazolo[1,2-a][1,2]diazepin-10-yl)succinamide;

(R)-2-methyl-$N^4$-(1-methyl-3-(6-methylpyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(S)—$N^4$-(4-chloro-2-(6-(trifluoromethyl)pyridin-3-yl)thiazol-5-yl)-2-cyclopropyl-$N^1$—((S)-5,11-dioxo-10,11-dihydro-1H,3H,5H-spiro[benzo[d]pyrazolo[1,2-a][1,2]diazepine-2,1'-cyclopropan]-10-yl)succinamide;

(S)—$N^4$-(4-chloro-2-(6-(trifluoromethyl)pyridin-3-yl)thiazol-5-yl)-2-cyclopropyl-$N^1$—((S)-5,11-dioxo-2,3,10,11-tetrahydro-1H,5H-benzo[d]pyrazolo[1,2-a][1,2]diazepin-10-yl)succinamide;

(R)—$N^4$-(4-chloro-2-(6-(trifluoromethyl)pyridin-3-yl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-((2-fluorophenyl)carbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-((2,6-dimethylphenyl)carbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide (R)-3-(1H-benzo[d]imidazol-2-yl)-2-methyl-N—((S)-11-oxo-2,3,10,11-tetrahydro-1H,5H-benzo[d]pyrazolo[1,2-a][1,2]diazepin-10-yl)propanamide;

(R)-2-methyl-3-(7-methyl-1H-benzo[d]imidazol-2-yl)-N—((S)-11-oxo-2,3,10,11-tetrahydro-1H,5H-benzo[d]pyrazolo[1,2-a][1,2]diazepin-10-yl)propanamide;

(R)-3-(7-bromo-1H-benzo[d]imidazol-2-yl)-2-methyl-N—((S)-11-oxo-2,3,10,11-tetrahydro-1H,5H-benzo[d]pyrazolo[1,2-a][1,2]diazepin-10-yl)propanamide;

(R)-2-methyl-N—((S)-11-oxo-2,3,10,11-tetrahydro-1H,5H-benzo[d]pyrazolo[1,2-a][1,2]diazepin-10-yl)-3-(7-(trifluoromethyl)-1H-benzo[d]imidazol-2-yl)propanamide;

(R)-3-(4-chloro-1H-benzo[d]imidazol-2-yl)-2-methyl-N—((S)-11-oxo-2,3,10,11-tetrahydro-1H,5H-benzo[d]pyrazolo[1,2-a][1,2]diazepin-10-yl)propanamide;

(R)-3-(6-fluoro-7-methyl-1H-benzo[d]imidazol-2-yl)-2-methyl-N—((S)-11-oxo-2,3,10,11-tetrahydro-1H,5H-benzo[d]pyrazolo[1,2-a][1,2]diazepin-10-yl)propanamide;

(R)-3-(5-fluoro-7-methyl-1H-benzo[d]imidazol-2-yl)-2-methyl-N—((S)-11-oxo-2,3,10,11-tetrahydro-1H,5H-benzo[d]pyrazolo[1,2-a][1,2]diazepin-10-yl)propanamide;

(R)—N—((S)-6-fluoro-11-oxo-2,3,10,11-tetrahydro-1H,5H-benzo[d]pyrazolo[1,2-a][1,2]diazepin-10-yl)-3-(5-fluoro-7-methyl-1H-benzo[d]imidazol-2-yl)-2-methylpropanamide, or (R)-2-((5-fluoro-7-methyl-1H-benzo[d]imidazol-2-yl)methyl)-N—((S)-11-oxo-2,3,10,11-tetrahydro-1H,5H-benzo[d]pyrazolo[1,2-a][1,2]diazepin-10-yl)pentanamide.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The terms "pharmaceutically acceptable salt" or "pharmaceutically acceptable salts", as used herein, refers to a salt or salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. The organic acid or inorganic acids used to form pharmaceutically acceptable acid addition salts of compounds of the present invention include, but are not limited to, acetic acid, adipic acid, ascorbic acid, aspartic acid, benzoic acid, benzenesulfonic acid, carbonic acid, camphor sulfonic acid, capric acid, chlorotheophyllinate, citric acid, ethanedisulfonic acid, fumaric acid, D-glycero-D-gulo-Heptonicacid, galactaric aid, galactaric acid/mucic acid, gluceptic acid, glucoheptonoic acid, gluconic acid, glucuronic acid, glutamatic acid, glutaric acid, glycolic acid, hippuric acid, hydrobromic acid, hydrochloric acid, hydroiodic acid, isethionic acid, lactic acid, lactobionic acid, lauryl sulfuric acid, malic acid, maleic acid, malonic acid, mandelic acid, mesylic acid, methanesulfonic acid, mucic acid, naphthoic acid, 1-hydroxy-2-naphthoic acid, naphthalenesulfonic acid, 2-naphthalenesulfonic acid, nicotinic acid, nitric acid, octadecanoic acid, oleaic acid, oxalic acid, palmitic acid, pamoic acid, phosphoric acid, polygalacturonic acid, propionic acid, sebacic acid, stearic acid, succinic acid, sulfosalicylic acid, sulfuric acid, tartaric acid, p-toluenesulfonic acid, trifluoroacetic acid and triphenylacetic acid.

Salt forms of the compounds of the present invention can be converted into the free compounds by treatment with a suitable basic agent.

Pharmaceutically acceptable acid addition salts of compounds of the present invention include, but are not limited to, a acetate, adipate, ascorbate, aspartate, benzoate, besylatye, benzenesulfonate, bicarbonate/carbonate, bisulfate/sulfate, bromide/hydrobromide, camphor sulfonate, camsylate, caprate, chloride/hydrochloride, chlorotheophyllinate, citrate, edisylate, ethanedisulfonate, fumarate, gluceptate, glucoheptonate, gluconate, glucuronate, glutamate, glutarate, glycolate, hippurate, hydroiodide/iodide, isethionate, lactate, lactobionate, laurylsulphate, malate, maleate, malonate, mandelate, mesylate, methanesulfonate, methylsulfate, mucate, naphthoate, napsylate, 2-napsylate, naphthalenesulfonate, 2-naphthalenesulfonate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, p-toluenesulfonate, trifluoroacetate, trifenatate, triphenylacetete and xinafoate salt forms.

Pharmaceutically acceptable base addition salts can be formed with inorganic and organic bases. Organic bases used to form pharmaceutically acceptable base addition salts of compounds of the present invention include, but are not limited to, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine. Inorganic bases used to form pharmaceutically acceptable base addition salts of compounds of the present invention include, but are not limited to, sodium hydroxide, potassium hydroxide, ammonium hydroxide, ammonium salts and metals from columns I to XII of the periodic table. Pharmaceutically acceptable base addition salts of compounds of the present invention include, but are not limited to, sodium, potassium, ammonium, calcium, magnesium, iron, silver, zinc, and copper salts; particularly suitable salts include ammonium, potassium, sodium, calcium and magnesium salts.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds of the present invention include, for example, isotopes of hydrogen.

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the present invention. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the present invention include isotopes of hydrogen, carbon, nitrogen, oxygen, phosphorous, fluorine, and chlorine, such as $^3H$, $^{11}C$, $^{13}C$, $^{14}C$, $^{15}N$, $^{18}F$ $^{31}P$, $^{32}P$, $^{35}S$, $^{36}Cl$, $^{123}I$, $^{124}I$, $^{125}I$ respectively. Accordingly it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.).

By way of example, compounds of the present invention can exist in a deuterated form as shown below:

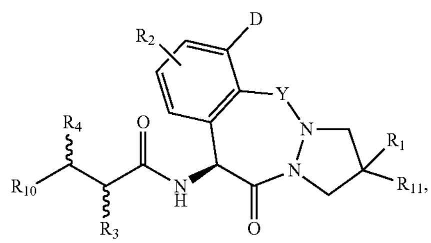

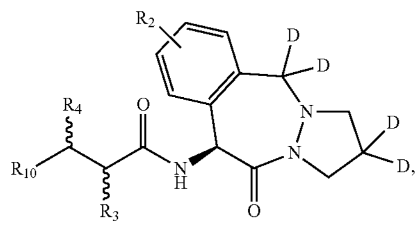

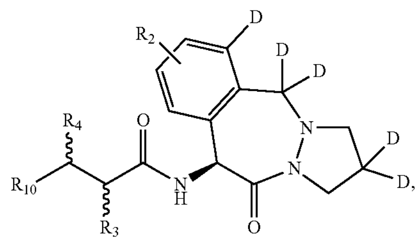

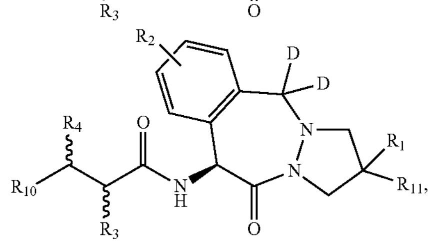

-continued

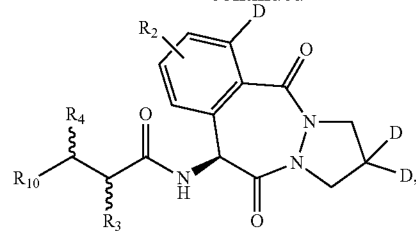

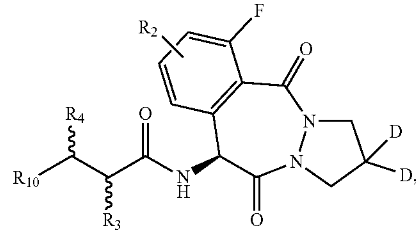

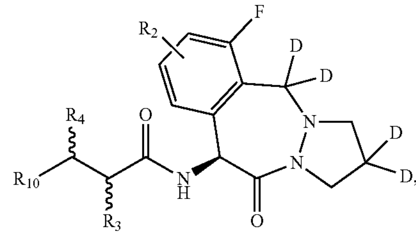

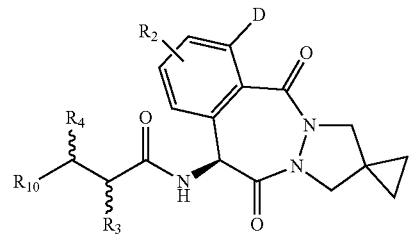

and

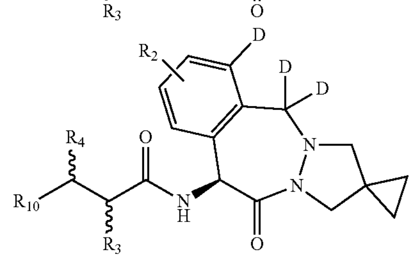

Pharmaceutically acceptable solvates in accordance with the invention include those wherein the solvent of crystallization may be isotopically substituted, e.g. $D_2O$, d6-acetone, DMSO.

Compounds of the invention that contain groups capable of acting as donors and/or acceptors for hydrogen bonds may be capable of forming co-crystals with suitable co-crystal formers. These co-crystals may be prepared from compounds of the invention by known co-crystal forming procedures. Such procedures include grinding, heating, co-subliming, co-melting, or contacting in solution compounds of the invention with the co-crystal former under crystallization conditions and isolating co-crystals thereby formed. Suitable co-crystal formers include those described in WO 2004/078163. Hence the invention further provides co-crystals comprising a compound of the invention.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the present invention, including salts, hydrates and solvates thereof, may inherently or by design form polymorphs.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Processes for Making Compounds of Invention

General procedures for preparing compounds of the present invention are described herein. In the reactions described, reactive functional groups, for example hydroxy, amino, imino or carboxy groups, where these are desired in the final product, may be protected to avoid their unwanted participation in the reactions. Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Methods of Synthesizing Compounds of the Invention

Agents of the invention may be prepared by a reaction sequence shown in the reaction schemes of the experimental part (see hereinbelow).

Typically, the compounds of the invention may be prepared according to the Schemes 1-4 provided infra. Compounds of the present invention were made by processes described herein and as illustrated in the Examples. The combination of various building blocks and intermediates described herein can be applied to yield compounds of the invention. Non-limiting examples of synthetic schemes used to make compounds of the present invention is illustrated in Schemes 1 to 4. Further guidance can be found in the examples section.

Compounds of Formula (II) can be prepared as outlined in Scheme 1.

Scheme 1

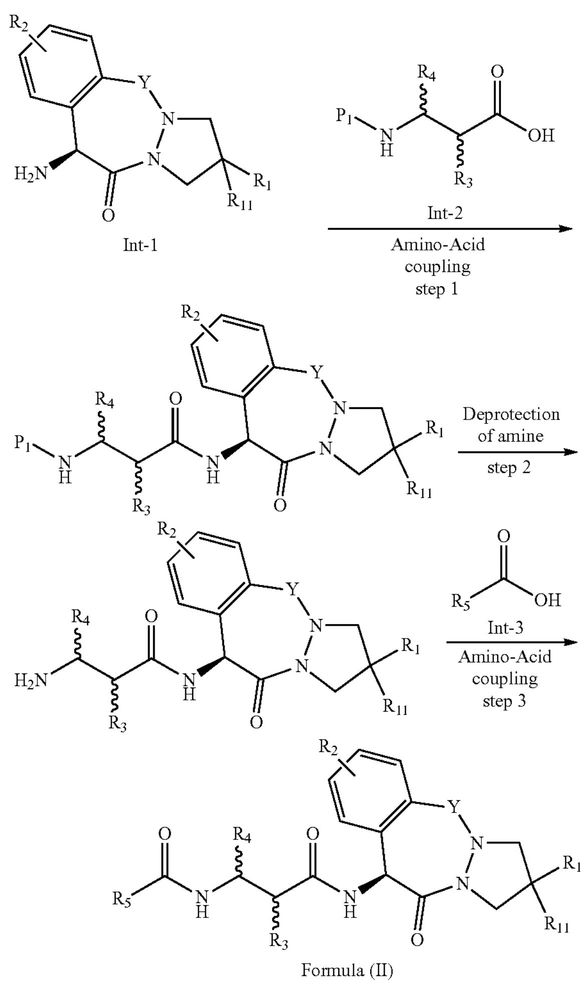

Formula (II)

An amide of Int-1 with the corresponding N-protected p-amino acids (Int-2) can be achieved using various coupling reagents or conditions (E. Valeur, M. Bradley, *Chem. Soc. Rev.* 2009, 38, 606-631; A. El-Faham, F. Albericio, *Chem. Rev.* 2011, 111, 6557-6602). After removal of the protecting group (T. W. Greene and P. G. M. Wuts, "Protective Groups in Organic Synthesis", Third edition, Wiley, New York 1999) such as Boc or Cbz in the formed amides, the released amine intermediate can be coupled with various acid building blocks (Int-3) to provide the final compounds of Formula (II).

Similarly, compounds of Formula (III) can be prepared as outlined in Scheme 2.

Scheme 2

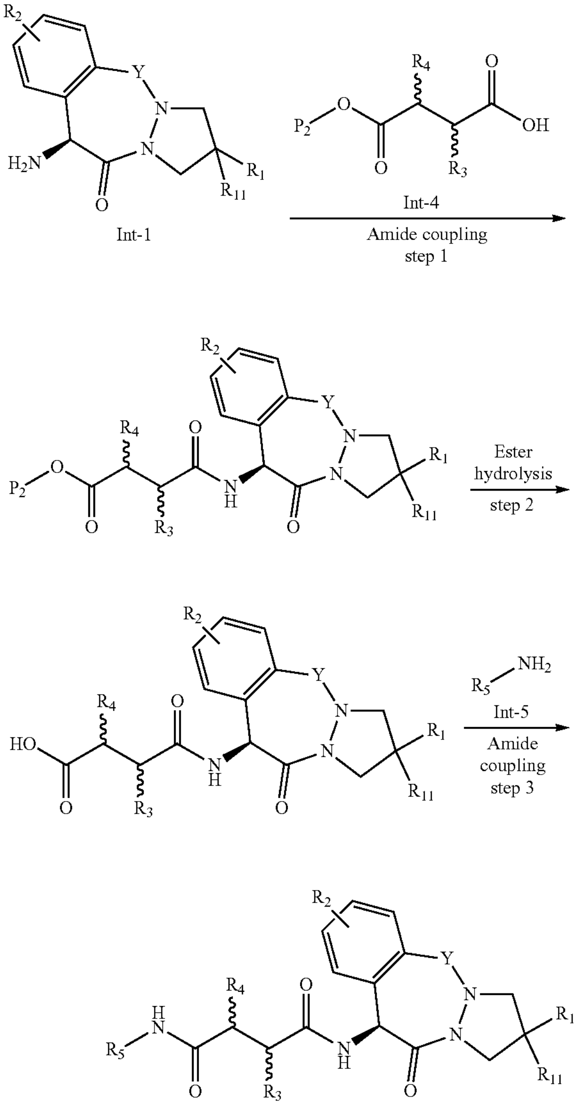

Formula (III)

Similar to the preparation of the compounds of Formula (II), the compounds of Formula (III) can be achieved by amide coupling between amines (Int-1), but in this case various mono-protected succinates (Int-4) are used as acid partners. The chiral succinates intermediates (Int-4) can be prepared in enantiopure form by various methods including asymmetric hydrogenation of α-substituted acrylic acids using chiral catalysts (e.g. P. M. Donate, D. Frederico, R. daSilva, M. G. Constantino, G. Del Ponte, P. S. Bonatto, *Tetrahedron:Asymmetry* 2003, 14, 3253-3256) or by Evans method utilizing chiral oxazolidine auxiliary (D. A. Evans, L. D. Wu, J. J. M. Wiener, J. S. Johnson, D. H. B. Ripin, J. S. Tedrow, *J. Org. Chem.* 1999, 64, 6411-6417). Alternatively, such chiral acids can be prepared also by chiral resolution (J. M. Keith, J. F. Larrow, E. N. Jacobsen, *Adv. Synth. Catal.* 2001, 343, 5-26) using chiral amines or enzymes, by dynamic kinetic resolution or chiral separation using preparative chiral chromatography methods. The formed amide ester intermediates then undergo ester hydrolysis and the obtained acid intermediates can be coupled with aliphatic or aromatic amines to provide the final products of Formula (III).

The required chiral amine intermediates Int-1 wherein Y is CH2 can be prepared as outlined in Scheme 3.

Scheme 3

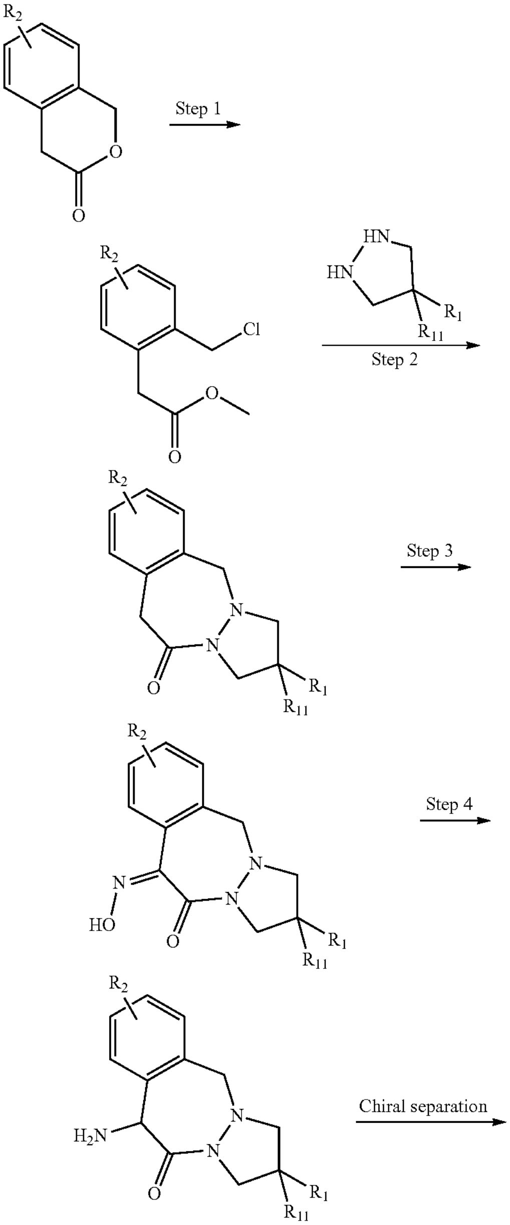

-continued

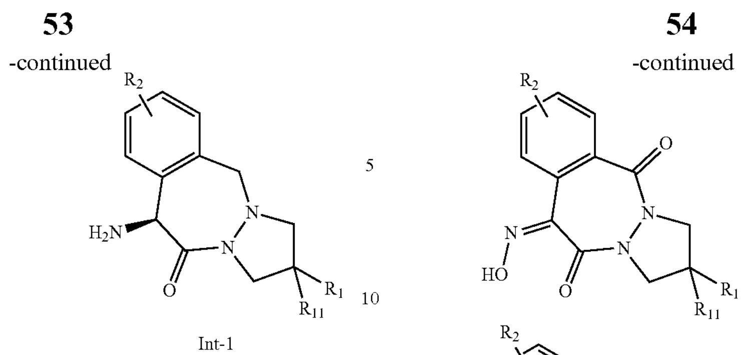

Int-1

The tricyclic core is prepared by cyclization of 2-(2-(halomethyl)phenyl)acetates (prepared from the corresponding isochroman-3-ones—D. J. Ritchie, H. S. R. McCann, M. C. H. Standen, R. V. H. Jones, U.S. Pat. No. 6,048,998, 2000; CAN128:75194) with pyrazolidines (E. E. Boros, F. Bouvier, S. Randhawa, M. H. Rabinowitz, *J. Heterocycl. Chem.* 2001, 38, 613-616). The required primary amine can be introduced to such compounds by several ways. Such molecules can be transformed into α-bromo-derivatives that undergo a nucleophilic substitution with an azide which can then be reduced into the primary amine (e.g. ZHANG, Xuqing; WALL, Mark; SUI, Zhihua WO2015/160772, 2015, A1). Other possibility to introduce the azide is to employ a one-step sequence utilizing the azidation of the corresponding enolate with 2,4,6-triisopropylbenzenesulfonyl azide (e.g. C. V. C. Prasad et al. *Bioorg. Med. Chem. Lett.* 2007, 17, 4006-4011) or a copper-catalyzed azidation (S.-E. Suh, S.-J. Chen, M. Mandal, I. A. Guzei, C. J. Cramer, S. S. Stahl, *J. Am. Chem. Soc.* 2020, 142, 11388-11393). Alternatively, as shown in scheme 3, the amine can also be introduced by the formation of an oxime and its reduction (F. Hoffmann-Emery, R. Jakob-Roetne, A. Flohr, F. Bliss, R. Reents, *Tet. Lett.* 2009, 50, 6380-6382). The enantiomerically pure amine can be obtained either by chiral resolution, by formation of separable and cleavable diastereomeric mixture (F. Hoffmann-Emery, R. Jakob-Roetne, A. Flohr, F. Bliss, R. Reents, *Tet. Lett.* 2009, 50, 6380-6382) or preparative chiral chromatography method.

Intermediate 1 (Int-1) wherein Y is C(O) can be prepared according to Scheme 4:

Scheme 4

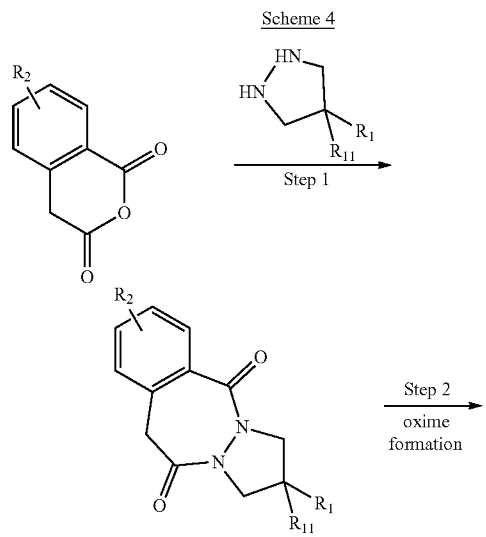

-continued

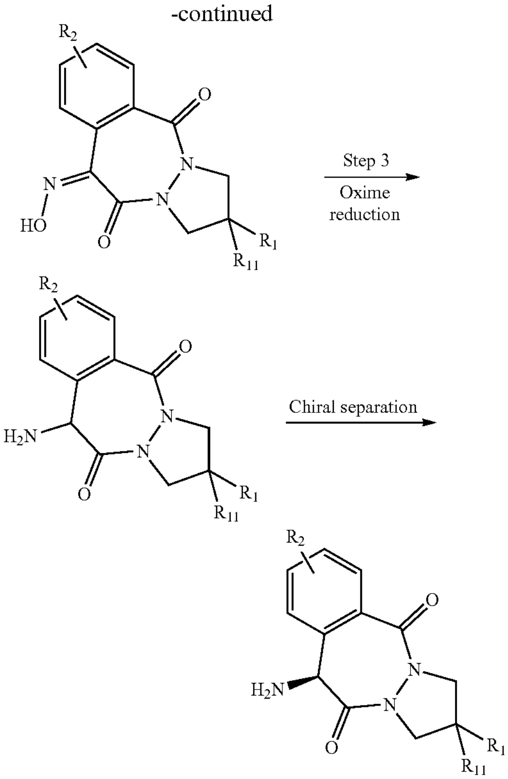

Int-1

The oxo-trycicles can be made analogous to the synthesis of tricycles described in Scheme 3 if isochromane-1,3-diones instead of 2-(2-(halomethyl)phenyl)acetates are used in the cyclization with pyrazolidines. Alternatively, the Int-1 from Scheme 3 can be oxidazed with $RuO_2$ (A. G. Schultz, T. J. Guzi, E. Larsson, R. Rahm, K. Thakkar, J. M. Bidlack, *J. Org. Chem.* 1998, 63, 7795-7804) to directly provide the Int-1 wherein Y is C(O). Chiral separation can also be performed as described in Scheme 3

Administration and Pharmaceutical Compositions

For the therapeutic uses of compounds of the present invention, such compounds are administered either alone or as part of a pharmaceutical composition. Accordingly, in another aspect of the present invention provides a pharmaceutical composition, which comprises a compound of the present invention, or pharmaceutically acceptable salt or stereoisomer thereof, and one or more pharmaceutically acceptable carriers. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. In certain embodiments, the pharmaceutical composition comprising a compound of the present invention can be formulated for intramuscularly, intravenously, subcutaneously, orally, pulmonary, intrathecally, topically or intranasally administration.

The pharmaceutical compositions of the present invention can be made up in a solid form (including without limitation capsules, tablets, pills, granules, powders or suppositories), or in a liquid form (including without limitation solutions, suspensions or emulsions). Tablets may be either film coated or enteric coated according to methods known in the art.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Suitable compositions for oral administration include a compound of the present invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable carriers/excipients which are suitable for the manufacture of tablets. These carriers/excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

The parenteral compositions (e.g, intravenous (IV) formulation) are aqueous isotonic solutions or suspensions. The parenteral compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are generally prepared according to conventional mixing, granulating or coating methods, respectively, and contain about 0.1-75%, or contain about 1-50%, of the active ingredient.

The compound of the present invention or pharmaceutical composition thereof for use in a subject (e.g., human) is typically administered orally or parenterally at a therapeutic dose of less than or equal to about 100 mg/kg. When administered intravenously via infusion, the dosage may depend upon the infusion rate at which an iv formulation is administered. In general, the therapeutically effective dosage of a compound, the pharmaceutical composition, or the combinations thereof, is dependent on the species of the subject, the body weight, age and individual condition, the disorder or disease or the severity thereof being treated.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

Certain aspects and examples of the pharmaceutical compositions of the present invention are provided in the following listing of enumerated embodiments. It will be recognized that features specified in each embodiment may be combined with other specified features to provide further embodiments of the present invention.

Embodiment 50. A pharmaceutical composition comprising a compound of Formula (I) or any one of Embodiments 1 to 49, or a pharmaceutically acceptable salt or stereoisomer thereof, and one or more pharmaceutically acceptable carriers.

Embodiment 51. A pharmaceutical composition comprising a compound of Embodiment 49, or a pharmaceutically acceptable salt or stereoisomer thereof, and one or more pharmaceutically acceptable carriers.

Embodiment 52. The pharmaceutical composition of Embodiment 50 or Embodiment 51 comprising one or more additional therapeutic agents.

Pharmacology and Utility

The compounds of the invention, in free form or in pharmaceutically acceptable salt form, exhibit valuable pharmacological properties, e.g. inhibition of cellular levels of Sppl2a, as indicated by the in vitro tests provided herein, and are therefore indicated for therapy or for use as research chemicals, e.g. as tool compounds.

Accordingly, the compounds of the invention may generally be useful in the treatment of an indication involving for example cells expressing high level of CD74 and/or cells involved in class 11 dependent antigen presentation. In addition, the compounds of the invention may be useful in treating autoimmune diseases and/or disorders. In particular, the compounds of the invention may be useful in the treatment and/or prevention of pemphigus vulgaris, pemphigus foliaceus, Sjogren's disease, systemic lupus erythematosus (SLE), rheumatoid arthritis (RA), myasthenia gravis, Hashimoto thyroiditis, thrombocytopenia purpura, myocarditis, atopic dermatitis, Goodpasture syndrome, multiple sclerosis (MS) or type I diabetes.

Furthermore, the compounds of the invention may be useful in the prevention of rejection in clinical/surgical transplantation procedures of solid organs, tissues or cell populations such as stem cells. Moreover, compounds of the invention might be useful in treating and/or preventing both acute and chronic graft versus host disease (GvHD) associated with transplantation of solid organs, tissues or cell populations. Compounds of the invention might further be used prophylactically, e.g. as induction therapy, to prepare the host prior to transplantation of solid organs, tissues or cell populations; or compounds of the invention might further be used therapeutically after transplantation of solid organs, tissues or cell populations. Non-limiting examples of transplantations are kidney transplantation, heart transplantation (acute or chronic), and bone narrow transplantation. Moreover, compounds of this invention might be useful in the treatment of a donor prior to the donation of organs, tissues or cells.

Additionally, compounds of the invention might be useful in the treatment of lymphomas in particular arising from modified B cells expressing high levels of CD74, such as non-Hodgkin's lymphoma (NHL), Burkitt Lymphoma (BL) and multiple myeloma (MM).

Certain aspects and examples of the use of compounds of the present invention and pharmaceutical compositions of the present invention are provided in the following listing of enumerated embodiments. It will be recognized that features specified in each embodiment may be combined with other specified features to provide further embodiments of the present invention.

Embodiment 53. A method of treating a disease or disorder associated with the activity of signal peptide peptidase like protease 2a (Sppl2a), wherein the method comprises administering to a subject in need of such treatment a therapeutically effective amount of a compound of any one of Embodiments 1 to 49, or a pharmaceutically acceptable salt.

Embodiment 54. A method of treating a disease or disorder associated with the activity of signal peptide peptidase like protease 2a (Sppl2a), wherein the method comprises administering to a subject in need of such treatment a compound of any one of Embodiments 1 to 49, or a pharmaceutically acceptable salt.

Embodiment 55. Use of a compound of any one of Embodiments 1 to 49, or a pharmaceutically acceptable salt thereof, in the manufacture of a medicament for the treatment of a disease or disorder associated with the activity of signal peptide peptidase like protease 2a (Sppl2a).

Embodiment 56. Use of a compound of any one of Embodiments 1 to 49, or a pharmaceutically acceptable salt thereof, in the treatment of a disease or disorder associated with the activity of signal peptide peptidase like protease 2a (Sppl2a).

Embodiment 57. A compound of any one of Embodiments 1 to 49, or a pharmaceutically acceptable salt thereof, for use in the treatment of a disease or disorder associated with the activity of signal peptide peptidase like protease 2a (Sppl2a).

Embodiment 58. A method of treating an autoimmune disease in a subject in need thereof, wherein the method comprises administering to the subject a therapeutically effective amount of a compound of any one of Embodiments 1 to 49, or a pharmaceutically acceptable salt thereof.

Embodiment 59. A method of treating an autoimmune disease in a subject in need thereof, wherein the method comprises administering to the subject a compound of any one of Embodiments 1 to 49, or a pharmaceutically acceptable salt thereof.

Embodiment 60. Use of a compound of any one of Embodiments 1 to 49, or a pharmaceutically acceptable salt thereof, in the manufacture of a medicament for the treatment of an autoimmune disease.

Embodiment 61. Use of a compound of any one of Embodiments 1 to 49, or a pharmaceutically acceptable salt thereof, in the treatment of an autoimmune disease.

Embodiment 62. A compound of any one of Embodiments 1 to 49, or a pharmaceutically acceptable salt thereof, for use in the treatment of an autoimmune disease.

Embodiment 63. The method of any one of Embodiments 53, 54, 58 or 59, the use of a compound in any one of Embodiments 55, 56, 60 or 61, or the compound for the use of Embodiments 57 or 62, wherein the autoimmune disease is Sjogren's disease, systemic lupus erythematosus (SLE), rheumatoid arthritis (RA), lupus nephritis, systemic sclerosis, multiple sclerosis (MS), autoimmune hepatitis, uveitis, pemphigus vulgaris, pemphigus foliaceus, myasthenia gravis, Hashimoto thyroiditis, thrombocytopenia purpura, myocarditis, atopic dermatitis, Goodpasture syndrome, or type I diabetes.

Embodiment 64. The method of any one of Embodiments 53, 54, 58 or 59, the use of a compound in any one of Embodiments 55, 56, 60 or 61, or the compound for the use of Embodiments 57 or 62, wherein the autoimmune disease is multiple sclerosis (MS), Sjogren's disease, systemic rheumatoid arthritis (RA), lupus nephritis or systemic sclerosis.

Embodiment 65. The method of any one of Embodiments 53, 54, 58 or 59, the use of a compound in any one of Embodiments 55, 56, 60 or 61, or the compound for the use of Embodiments 57 or 62, wherein the autoimmune disease is multiple sclerosis (MS).

Embodiment 66. A method of treating a disease associated with the expression of high levels of CD74 in B cells in a subject, wherein the method comprises administering to the subject a therapeutically effective amount of a compound of any one of Embodiments 1 to 49, or a pharmaceutically acceptable salt thereof.

Embodiment 67. A method of treating a disease associated with the expression of high levels of CD74 in B cells in a subject, wherein the method comprises administering to the subject a compound of any one of Embodiments 1 to 49, or a pharmaceutically acceptable salt thereof.

Embodiment 68. Use of a compound of any one of Embodiments 1 to 49, or a pharmaceutically acceptable salt thereof, in the manufacture of a medicament for the treatment of a disease associated with the expression of high levels of CD74 in B cells in a subject.

Embodiment 69. Use of a compound of any one of Embodiments 1 to 49, or a pharmaceutically acceptable salt thereof, in the treatment of a disease associated with the expression of high levels of CD74 in B cells in a subject.

Embodiment 70. A compound of any one of Embodiments 1 to 49, or a pharmaceutically acceptable salt thereof, for use in the treatment of a disease associated with the expression of high levels of CD74 in B cells in a subject.

Embodiment 71. The method of any one of Embodiments 66 or 67, the use of a compound in any one of Embodiments 68 or 69, or the compound for the use of Embodiment 70, wherein the a B-cell lymphoma is non-Hodgkin's lymphoma (NHL), Burkitt Lymphoma (BL) and multiple myeloma (MM).

Embodiment 72. A method of treating a B-cell lymphoma in a subject in need thereof, wherein the method comprises administering to the subject a therapeutically effective amount of a compound of any one of Embodiments 1 to 49, or a pharmaceutically acceptable salt thereof.

Embodiment 73. A method of treating a B-cell lymphoma in a subject in need thereof, wherein the method comprises administering to the subject a compound of any one of Embodiments 1 to 49, or a pharmaceutically acceptable salt thereof.

Embodiment 74. Use of a compound of any one of Embodiments 1 to 49, or a pharmaceutically acceptable salt thereof, in the manufacture of a medicament for the treatment of a B-cell lymphoma.

Embodiment 75. Use of a compound of any one of Embodiments 1 to 49, or a pharmaceutically acceptable salt thereof, in the treatment of a B-cell lymphoma.

Embodiment 76. A compound of any one of Embodiments 1 to 49, or a pharmaceutically acceptable salt thereof, for use in the treatment of a B-cell lymphoma.

Embodiment 77. The method of any one of Embodiments 72 or 73, the use of a compound in any one of Embodiments 74 or 75, or the compound for the use of Embodiment 76, wherein the a B-cell lymphoma is non-Hodgkin's lymphoma (NHL), Burkitt Lymphoma (BL) and multiple myeloma (MM).

Embodiment 78. A method for treating graft versus host disease (GvHD) in a subject after transplantation, wherein the method comprises administering to the subject a therapeutically effective amount of a compound of any one of Embodiments 1 to 49, or a pharmaceutically acceptable salt thereof, wherein the transplantation is the transplantation of a solid organ, a tissue or a cell population.

Embodiment 79. A method for treating graft versus host disease (GvHD) in a subject after transplantation, wherein the method comprises administering to the subject a compound of any one of Embodiments 1 to 49, or a pharmaceutically acceptable salt thereof, wherein the transplantation is the transplantation of a solid organ, a tissue or a cell population.

Embodiment 80. A method for preventing graft versus host disease (GvHD) in a subject after transplantation, wherein the method comprises administering to the subject prior to transplantation a therapeutically effective amount of a compound of any one of Embodiments 1 to 49, or a pharmaceutically acceptable salt thereof, wherein the transplantation is the transplantation of a solid organ, a tissue or a cell population.

Embodiment 81. A method for preventing graft versus host disease (GvHD) in a subject after transplantation, wherein the method comprises administering to the subject prior to transplantation a compound of any one of Embodiments 1 to 49, or a pharmaceutically acceptable salt thereof, wherein the transplantation is the transplantation of a solid organ, a tissue or a cell population.

Embodiment 82. Use a compound of any one of Embodiments 1 to 49 for treating graft versus host disease (GvHD) in a subject after transplantation, wherein the transplantation is the transplantation of a solid organ, a tissue or a cell population.

Embodiment 83. Use a compound of any one of Embodiments 1 to 49 in the manufacture of a medicament for treating graft versus host disease (GvHD) in a subject after transplantation, wherein the transplantation is the transplantation of a solid organ, a tissue or a cell population.

Embodiment 84. A compound of any one of Embodiments 1 to 49 for the use in treating graft versus host disease (GvHD) in a subject after transplantation, wherein the transplantation is the transplantation of a solid organ, a tissue or a cell population.

Embodiment 85. The method of any one of Embodiments 78 to 81, the use of a compound in any one of Embodiments 82 or 83, or the compound for the use of Embodiment 84, wherein the transplantation is transplantation of a solid organ.

Embodiment 86. The method of any one of Embodiments 78 to 81, the use of a compound in any one of Embodiments 82 or 83, or the compound for the use of Embodiment 84, wherein the transplantation is bone marrow transplantation.

Embodiment 87. The method of any one of Embodiments 78 to 81, the use of a compound in any one of Embodiments 82 or 83, or the compound for the use of Embodiment 84, wherein the transplantation is stem cell transplantation.

Embodiment 88. The method of any one of Embodiments 78 to 81, the use of a compound in any one of Embodiments 82 or 83, or the compound for the use of Embodiment 84, wherein the transplantation is hematopoietic stem cell transplantation.

Embodiment 89. The method of any one of Embodiments 78 to 81, the use of a compound in any one of Embodiments 82 or 83, or the compound for the use of Embodiment 84, wherein the transplantation is transplantation of a tissue.

Embodiment 90. The method of any one of Embodiments 78 to 81 or 85 to 89, the use of a compound in any one of Embodiments 82, 83 or 85 to 89, or the compound for the use of Embodiment 84 to 89, wherein the graft versus host disease (GvHD) is an acute graft versus host disease.

Embodiment 91. The method of any one of Embodiments 78 to 81 or 85 to 89, the use of a compound in any one of Embodiments 82, 83 or 85 to 89, or the compound for the use of Embodiment 84 to 89, wherein the graft versus host disease (GvHD) is a chronic graft versus host disease.

Combination Therapy

In certain instances, it may be advantageous to administer a compound of the present invention in combination with one or more additional therapeutic agents. A therapeutic agent is, for example, a chemical compound, peptide, antibody, antibody fragment or nucleic acid, which is therapeutically active or enhances the therapeutic activity when administered to a patient in combination with a compound of the present invention.

Compounds of the invention may be administered as the sole active ingredient or together with other drugs useful against neoplastic diseases, inflammatory disorders, in immunomodulating regimens or in induction therapy to prevent GvHD and transplant rejection. For example, the compounds of the invention may be used in combination e.g. with cyclosporins, rapamycins or ascomycins, or their immunosuppressive analogs or derivatives, e.g. cyclosporin A, cyclosporin G, Isa tx247, FK-506, sirolimus or everolimus; with corticosteroids e.g. prednisone; cyclophosphamide; azathioprene; methotrexate; gold salts; sulfasalazine, antimalarials; leflunomide; mizoribine; mycophenolic acid; mycophenolate mofetil; 15-deoxyspergualine; with a S1P receptor agonist e.g FTY720 or an analogue thereof; with immuno-suppressive monoclonal antibodies, e.g. monoclonal antibodies to leukocyte receptors, e.g. MHC, or other immunomodulatory compounds, e.g. CTLA4Ig.

A compound of formula I may also be used in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, antiandrogens, bengamides, bisphosphonates, antiproliferative antibodies and temozolomide (TEMODAL).

EXAMPLES

The compounds of the present invention can be produced as shown in the following examples. The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art or can be produced by organic synthesis methods as described herein.

For illustrative purposes, the general reaction schemes depicted herein provide potential routes for synthesizing the compounds of the present invention as well as key intermediates. For a more detailed description of the individual reaction steps, see the Examples section below. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Abbreviations

ACN acetonitrile
abs absolute
AcOH acetic acid
aq. aqueous
br. s broad singlet
$Boc_2O$ di-tert-butyl bicarbonate
BuLi n-Butyl lithium
$CaCO_3$ calcium carbonate
$Cs_2CO_3$ cesium carbonate
CO carbon monoxide
COMU (1-cyano-2-ethoxy-2-oxoethylideneaminooxy)-dimethylamino-morpholinocarbenium hexafluoro-phosphate
CuBr copper(I) bromide
CuCl copper(I) chloride
d doublet
DAST (diethylamino)sulfur trifluoride
DBU 1,8-diazabicyclo[5.4.0]undec-7-ene
DCM dichloromethane
de diastereomeric excess
DIPEA N,N-diisopropylethylamine
DMA dimethylacetamide
DMAP 4-(dimethylamino)pyridine
DME dimethoxyethane
DMF dimethylformamide
DMSO dimethylsulfoxide
DPPA biphenyl phosphorazidate
EDC 1-ethyl-3-(3-dimethylaminopropyl)carbodiimid
ee enantiomeric excess
$Et_3N$ triethylamine
$Et_2O$ diethylether
EtOAc ethyl acetate
EtOH ethanol
Flow flow rate
h hour(s)
Hex hexane, mixture of isomers
HATU O-(7-azabenzotriazol-1-yl)-N,N,N',N'-tetramethyluroniumhexafluorophosphonate
HBTU 2-(1H-benzotriazol-1-yl)-1,1,3,3-tetramethyluronium tetrafluoroborate
HCl hydrochloric acid
HPLC High Performance Liquid Chromatography
HV High Vacuum
IPA isopropylalcohol
i-PrOH isopropanol
KHMDS potassium hexamethyldisilazane
$KHSO_4$ potassium hydrogensulfate
L liter(s)
LCMS Liquid Chromatography/Mass Spectrometry
LDA lithium diisopropylamine
$LiAlH_4$ lithium aluminium hydride
LiHMDS lithium hexamethyldisilazane
LiOH lithium hydroxide
M molar (mol/L)
Me methyl
Mel methyl iodide
MeOH methanol
$MnO_2$ manganese dioxide
MsCl mesyl chloride
min minute(s)
mL milliliter
mm millimeter
MHz megaHertz
MS Mass Spectrometry
MTBE methyl tert-butyl ether
μm micrometer
$NaBH_4$ sodium borohydride
$NaBH_3CN$ sodium cyanoborohydride
NaCl sodium chloride
NaH sodium hydride
$NaHCO_3$ sodium bicarbonate
NaHMDS sodium hexamethyldisilazane
NaI sodium iodide
NaOAc sodium acetate
NaOH sodium hydroxide
$Na_2SO_3$ sodium sulfite
$Na_2SO_4$ sodium sulfate
NBS N-Bromo succinimide
$NH_3$ ammonia
$NH_4Cl$ ammonium chloride
Ni Nickel
NMM 4-methylmorpholine
NMR Nuclear Magnetic Resonance
o/n overnight
Pd/C palladium on charcoal
$Pd(dppf)Cl_2 \cdot CH_2Cl_2$ 1,1'-bis(diphenylphosphino)ferrocenedichloro palladium(II) dichloromethane complex
PhMe toluene
Prep Preparative
PyBOP (benzotriazol-1-yloxy)-tripyrrolidinophosphonium-Hexafluorophosphate
q Quartet
rt room temperature
$t_R$ retention time
s singlet
sat. saturated
$scCO_2$ super critical carbone dioxide
SEM-Cl 2-(Trimethylsilyl)ethoxymethyl chloride
SFC Supercritical Fluid Chromatography
t triplet
T3P 1-Propanephosphonic anhydride
TEA triethylamine
TFA trifluoroacetic acid
THF tetrahydrofuran
TLC Thin Layer Chromatography
TMSCI trimethylsilyl chloride
TMSCN trimethylsilanecarbonitrile
TOTU O-[(Ethoxycarbonyl)cyanomethylenamino]-N,N,N',N'-tetramethyluronium tetrafluoroborate
TsOH para-toluene sulfonic acid
UPLC Ultra Performance Liquid Chromatography Trademarks Celite=Celite® (The Celite Corporation)=filtering aid based on diatomaceous earth PL Thiol Cartridge=Stratosphere® SPE, PL-Thiol MP SPE+, 500 mg per 6 mL tube, 1.5 mmol (nominal)

$NH_2$ Isolute (=Isolute® $NH_2$, Isolute® is registered for Argonaut Technologies, Inc.)=ion exchange with amino groups based on silica gel Nucleosil=Nucleosil®, trademark of Machery & Nagel, DQren, FRG for HPLC materials PTFE membrane=Chromafil O-45/15MS Polytetrafluoroethylene Machereynagel)

Temperatures are measured in degrees Celsius. Unless otherwise indicated, the reactions take place at rt.

Phase separator: Biotage—Isolute Phase separator (Part Nr: 120-1908-F for 70 mL and Part Nr: 120-1909-J for 150 mL)

TLC conditions: $R_f$ values for TLC are measured on 5×10 cm TLC plates, silica gel $F_{254}$, Merck, Darmstadt, Germany.

Analytical Methods

HPLC Conditions:

Method a: HPLC Instrument: Agilent 1100 series; Column: Waters X-Bridge C18 2.5 μm 3*30 mm, Eluent A: water+0.1% TFA, B: ACN+0.1% TFA, Gradient 10 to 98% B in 3 min, Flow: 1.4 mL/min Method b: HPLC Instrument: Agilent 1100 series; Column: Waters X-Bridge C18 2.5 μm 3*50 mm, Eluent A: water+0.1% TFA, B: ACN+0.1% TFA, Gradient 10 to 98% B in 8.6 min, Flow: 1.4 mL/min Method c: HPLC Instrument: Agilent 1200 series; Column: Waters Eclipse XDB-C18 1.8 μm 2.1*30 mm, Eluent A: water+0.1% TFA, B: ACN+0.1% TFA, Gradient 5 to 100% B in 3 min, Flow: 1.4 mL/min Method d: HPLC Instrument: Agilent 1200 series; Waters X-Bridge C18, 2.5 μm, 3*30 mm, Eluent A: water+7.3 mM $NH_4OH$; B: ACN+7.3 mM $NH_4OH$. Gradient 10 to 98% B in 8.6 min, Flow: 1 mL/min UPLC Conditions:

LCMS method a: UPLC/MS Instrument: Waters UPLC Acquity; column: Acquity HSS T3 1.8 μm 2.1*50 mm at 50° C., Eluent A: water+0.05% HCOOH+3.75 mM ammonium acetate, B: ACN+0.04% HCOOH, Gradient: 2 to 98% B in 1.4 min, Flow: 1.2 mL/min (2 min)

LCMS method b: UPLC/MS Instrument: Waters UPLC Acquity; column: Acquity HSS T3 1.8 μm 2.1*50 mm at 60° C., Eluent A: water+0.05% HCOOH+3.75 mM ammonium acetate, B: ACN+0.04% HCOOH, Gradient: 5 to 98% B in 1.4 min, Flow: 1 mL/min (2 min)

LCMS method c: Agilent HPLC-MS; column: Ascentis Expresse 2.7 m 2.1*30 mm at 60° C., Eluent A: water+0.05% HCOOH+3.75 mM ammonium acetate, B: ACN+0.04% HCOOH, Gradient: 2 to 98% B in 1.4 min, Flow: 1 mL/min (2 min)

LCMS method d: Agilent LCMS: Waters SunFire C18, 2.5 m, 3*30 mm, Eluent A: water+0.1% HCOOH; B: ACN+0.1% HCOOH. Gradient 10 to 98% B in 2.5 min, Flow: 1.4 mL/min LCMS method e: Waters UPLC Acquity; column: Acquity HSS T3 1.8 μm, 2.1×50 mm at 60° C., Eluent A: water+0.05% HCOOH+3.75 mM ammonium acetate, B: MeCN+0.04% HCOOH, Gradient: 10 to 95% B in 1.5 min, Flow: 1.0 mL/min LCMS method f: Waters UPLC Acquity; column: Acquity HSS T3, 1.8 μm, 2.1×50 mm, at 60° C., Eluent A: water+0.05% HCOOH+3.75 mM ammonium acetate, B: MeCN+0.04% HCOOH, Gradient: 5 to 98% B in 9.4 min hold 0.4 min, Flow: 0.8 mL/min LCMS method g: Agilent LCMS; column: Waters Acquity HSS T3, 1.8 μm, 2.1×50 mm, at 60° C., Eluent A: $H_2O$+0.05% TFA; B: MeCN+0.035% TFA. Gradient: 10 to 100% B in 1.35 min, Flow: 0.9 mL/min.

Synthesis of Intermediates

Type A Intermediates

Synthesis of (S)-10-amino-2,3,5,10-tetrahydro-1H,11H-benzo[d]pyrazolo[1,2-a][1,2]diazepin-11-one (int-A1)

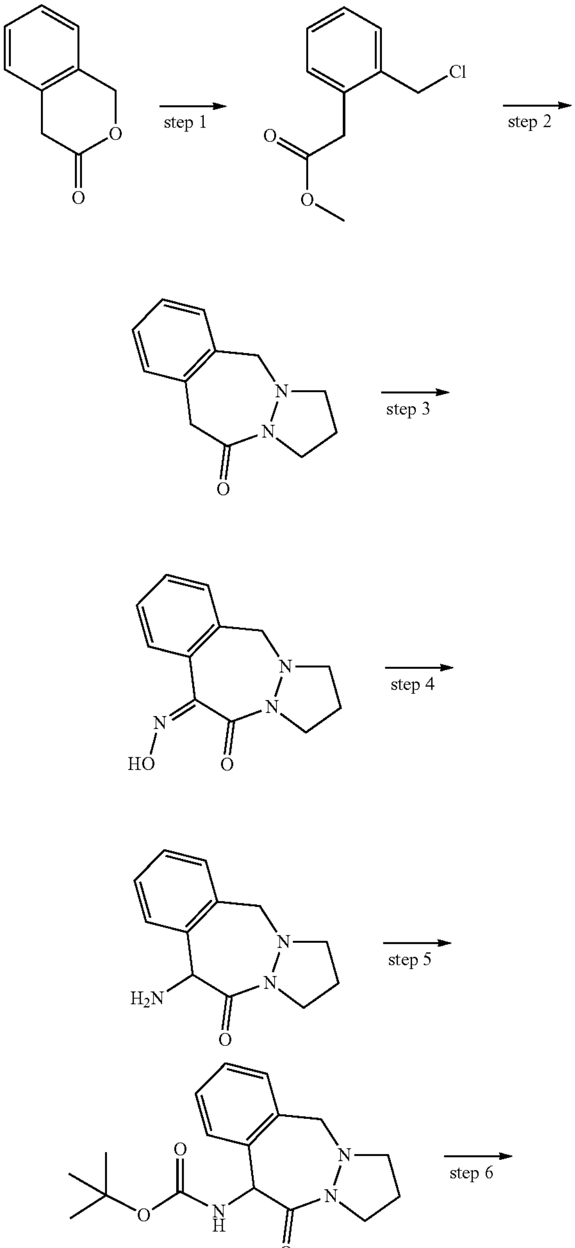

-continued

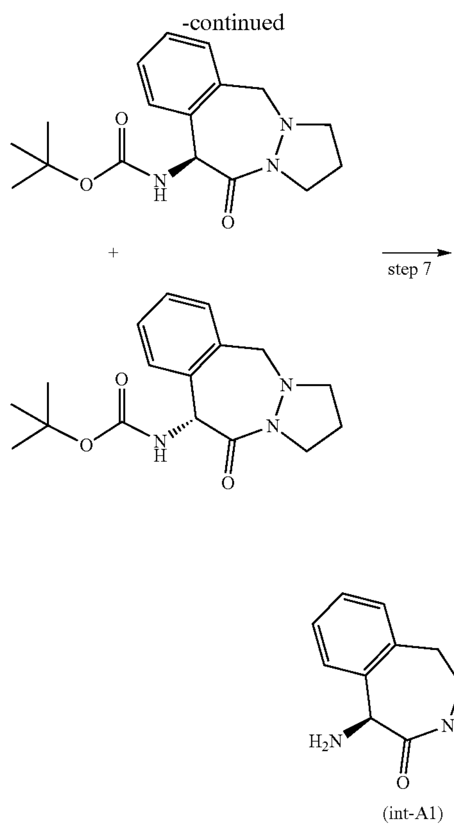

(int-A1)

Step 1: Thionyl chloride (14.8 mL, 202 mmol) was added dropwise at 0° C. to a suspension of isochroman-3-one (15 g, 101 mmol) in methanol (150 mL). The resulting solution was stirred at 0° C. for 2 h followed by stirring at rt for 16 h. The reaction mixture was concentrated, the crude material was dissolved in Ethyl acetate and washed with sat. aq. $NaHCO_3$ solution. The organic layer was dried ($Na_2SO_4$) and concentrated to give methyl 2-(2-(chloromethyl)phenyl) acetate. $^1H$ NMR (DMSO-$d_6$, 400 MHz): δ 7.44-7.47 (m, 1H), 7.27-7.36 (m, 3H), 4.80 (s, 2H), 3.85 (s, 2H), 3.63 (s, 3H).

Step 2: Pyrazolidine dihydrochloride (14.2 g, 98 mmol) was added at rt to a solution of methyl 2-(2-(chloromethyl) phenyl)acetate (19.4 g, 98 mmol) in DMF (500 mL) followed by DIPEA (85 mL, 488 mmol), sodium iodide (14.6 g, 98 mmol) and sodium acetate (32.0 g, 391 mmol). The suspension was stirred at rt for 16 h. The reaction mixture was concentrated, the crude material was dissolved in ethyl acetate and washed with sat. $NaHCO_3$ solution. The organic phase was dried ($Na_2SO_4$), concentrated and purified by column chromatography (10-20% ethyl acetate in toluene) to give 2,3,5,10-tetrahydrobenzo[d]pyrazolo[1,2-a][1,2]diazepin-11(1H)-one. LCMS (method d) m/z 203.1 $[M+H]^+$, $t_R$=1.35 min. $^1H$ NMR (DMSO-$d_6$, 400 MHz): δ 7.14-7.26 (m, 3H), 7.03 (d, J=7.3 Hz, 1H), 4.15 (s, 2H), 3.84 (br s, 2H), 3.48 (t, J=7.2 Hz, 2H), 3.19 (t, J=6.7 Hz, 2H), 2.19 (quin, J=7.0 Hz, 2H).

Step 3: 1M LiHMDS solution in THF (93 mL, 93 mmol) was added dropwise at 0° C. to a solution of 2,3,5,10-tetrahydrobenzo[d]pyrazolo[1,2-a][1,2]diazepin-11(1H)-one (14.0 g, 62 mmol) and isopentyl nitrite (10.8 mL, 81 mmol) in THF (750 mL), and the solution was stirred at 0° C. for 2 h. The reaction mixture was concentrated and dissolved in ethyl acetate, washed with sat. $NaHCO_3$ solution, dried ($Na_2SO_4$), concentrated and purified by column chromatography (10-90% ethyl acetate in toluene with 0.1% $Et_3N$) to provide a mixture of (Z) and (E)-10-(hydroxyimino)-2,3,5,10-tetrahydrobenzo[d]pyrazolo[1,2-a][1,2]diazepin-11(1H)-one. LCMS (method d) m/z 232.0 $[M+H]^+$, $t_R$=0.90 & 1.06 min.

Step 4: Zinc dust (10.9 g, 166 mmol) was added at rt to a solution of (Z) and (E)-10-(hydroxyimino)-2,3,5,10-tetrahydrobenzo[d]pyrazolo[1,2-a][1,2]diazepin-11(1H)-one (9.6 g, 42 mmol) in AcOH (300 mL) and a 10% HCl aq. solution (300 mL) and the reaction mixture was stirred at rt for 2 h. The reaction mixture was filtered and the filtrate was concentrated under vacuum to give 10-amino-2,3,5,10-tetrahydrobenzo[d]pyrazolo[1,2-a][1,2]diazepin-11(1H)-one which was used in the next step without further purification.

Step 5: $Boc_2O$ (9.0 g, 41 mmol) and $Na_2CO_3$ (13.0 g, 124 mmol) were added at rt to a solution of 10-amino-2,3,5,10-tetrahydrobenzo[d]pyrazolo[1,2-a][1,2]diazepin-11(1H)-one (29.2 g, 41 mmol) in dioxane (400 mL) and water (200 mL), and the resulting mixture was stirred at rt for 16 h. The mixture was concentrated and treated with ethyl acetate and sat. $NaHCO_3$ solution. The organic layer was dried ($MgSO_4$) and concentrated to give the crude product which was purified by column chromatography (0-80% ethyl acetate in cyclohexane) to yield racemic tert-butyl 11-oxo-1,2,3,5,10,11-hexahydrobenzo[d]pyrazolo[1,2-a][1,2]diazepin-10-ylcarbamate.

Step 6 (chiral separation); The two enantiomers of tert-butyl 11-oxo-1,2,3,5,10,11-hexahydrobenzo[d]pyrazolo[1,2-a][1,2]diazepin-10-ylcarbamate were separated by chiral HPLC (Thar SFC-200 instrument, mobile phase: $scCO_2$/EtOH 85:15, column: Chiralcel OD-H, 30×250 mm) to provide tert-butyl (S)-(11-oxo-2,3,10,11-tetrahydro-1H,5H-benzo[d]pyrazolo[1,2-a][1,2]diazepin-10-yl)carbamate (enantiomeric excess ≥99.5%) and tert-butyl (R)-(11-oxo-2,3,10,11-tetrahydro-1H,5H-benzo[d]pyrazolo[1,2-a][1,2] diazepin-10-yl)carbamate (enantiomeric excess ≥99.5%). Analytical data for tert-butyl (S)-(11-oxo-2,3,10,11-tetrahydro-1H,5H-benzo[d]pyrazolo[1,2-a][1,2]diazepin-10-yl) carbamate: LCMS (method b) m/z 318.3 $[M+H]^+$, $t_R$=1.03 min. $^1H$ NMR (400 MHz, DMSO-$d_6$) δ ppm 7.31 (d, J=7.3 Hz, 1H), 7.15-7.27 (m, 2H), 7.05 (d, J=6.7 Hz, 1H), 7.00 (d, J=9.1 Hz, 1H), 6.42 (d, J=9.1 Hz, 1H), 4.22 (s, 2H), 3.42-3.60 (m, 2H), 3.22-3.30 (m, 1H), 3.13-3.21 (m, 1H), 2.27-2.41 (m, 1H), 2.04-2.16 (m, 1H), 1.43 (s, 9H).

Step 7: tert-butyl (S)-(11-oxo-2,3,10,11-tetrahydro-1H,5H-benzo[d]pyrazolo[1,2-a][1,2]diazepin-10-yl)carbamate (17.7 g, 56 mmol) was treated with 4M HCl in dioxane (250 mL) and the mixture was stirred at rt for 1 h. The reaction mixture was concentrated to yield (S)-10-amino-2,3,5,10-tetrahydro-1H,11H-benzo[d]pyrazolo[1,2-a][1,2]diazepin-11-one (int-A1) as an HCl salt. LCMS (method b) m/z 218.3 $[M+H]^+$, $t_R$=0.40 min. Stereochemistry confirmed by X-ray analysis: $[\alpha]^{23}_D$ −105.7 (c=1.0, MeOH). $^1H$ NMR (400 MHz, DMSO-$d_6$) δ ppm 8.89 (br s, 3H), 7.29-7.39 (m, 2H), 7.24 (d, J=7.6 Hz, 1H), 7.16 (d, J=7.1 Hz, 1H), 5.98 (s, 1H), 4.28 (s, 2H), 3.55-3.62 (m, 2H), 3.18-3.29 (m, 2H), 2.29-2.44 (m, 1H), 2.12-2.19 (m, 1H).

Synthesis of (S)-10-amino-6-fluoro-2,3,5,10-tetrahydro-1H,11H-benzo[d]pyrazolo[1,2-a][1,2]diazepin-11-one (int-A2)

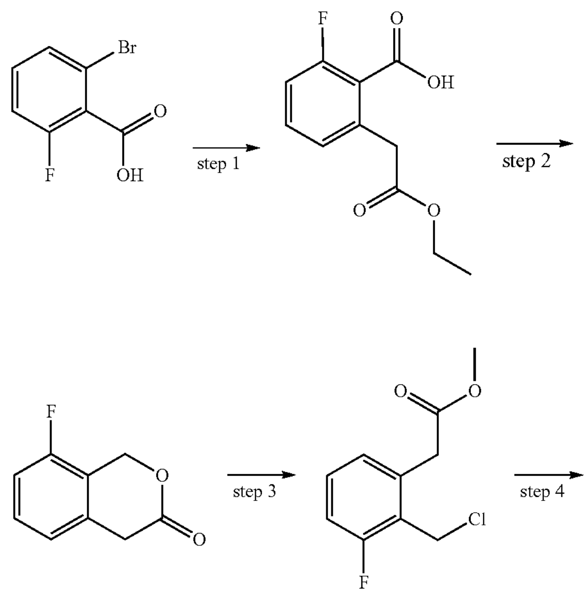

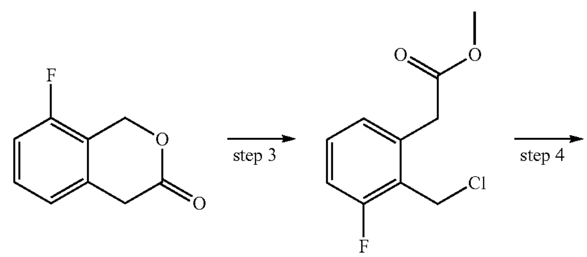

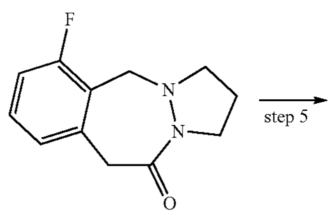

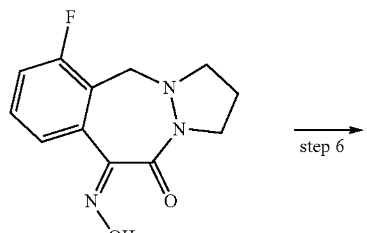

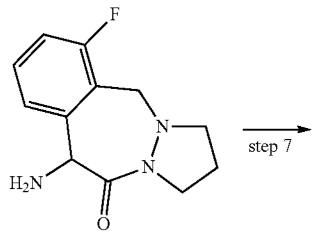

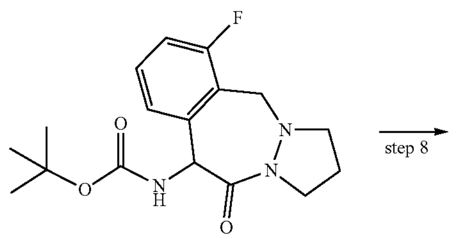

-continued

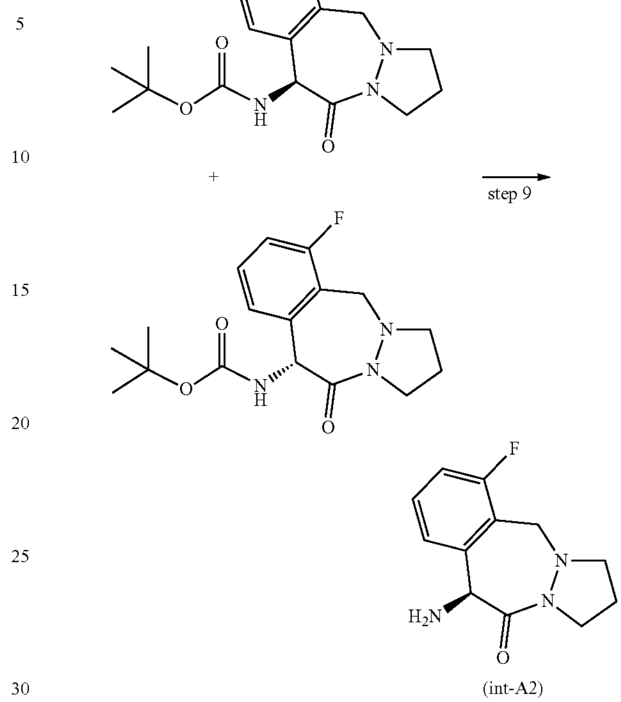

(int-A2)

Step 1: Ethyl acetoacetate (17.7 mL, 140 mmol) followed by 2-bromo-6-fluorobenzoic acid (15.3 g, 70 mmol) and CuBr (10.0 g, 70 mmol) were added at rt to a solution of NaOEt in EtOH (prepared by dissolving Na metal (4.83 g, 210 mmol) in abs. EtOH (400 mL)). The reaction mixture was stirred at reflux for 2 h and, after cooling to room temperature, was filtered over a pad of Celite©. Solvent was removed in vacuo and the residue partitioned between 2N HCl and $CH_2Cl_2$. The organic layer was then treated with sat. $NaHCO_3$ until basic pH was reached. The water layer was washed with $CH_2Cl_2$, acidified with 2N HCl to pH 1 and extracted with $CH_2Cl_2$. The organic layer was washed with brine, dried ($Na_2SO_4$) and concentrated to give 2-(2-ethoxy-2-oxoethyl)-6-fluorobenzoic acid. LCMS (method b) m/z 226.5 $[M+H]^+$, $t_R$=0.65 min. $^1H$ NMR (400 MHz, DMSO-$d_6$) δ ppm 13.40 (br s, 1H), 7.42-7.52 (m, 1H), 7.17-7.26 (m, 2H), 4.06 (q, J=7.1 Hz, 2H), 3.84 (s, 2H), 1.17 (t, J=7.1 Hz, 3H).

Step 2. Ethyl chlorocarbonate (4.4 mL, 46 mmol) was added at 0° C. to a solution of 2-(2-ethoxy-2-oxoethyl)-6-fluorobenzoic acid (9.5 g, 42 mmol) and $Et_3N$ (6.4 mL, 46 mmol) in $CH_2Cl_2$ (84 mL). After stirring at rt for 2 h, the mixture was quenched by addition of 1N HCl and the mixture was extracted with $CH_2Cl_2$. Organic layers were washed with brine, dried ($Na_2SO_4$) and concentrated. The crude intermediate was dissolved in THF (100 mL) and cold (0° C.) $NaBH_4$ (3.2 g, 84 mmol) in $H_2O$ (34 mL) was added at −15° C. After stirring at −15° C. for 1 h, the mixture was quenched by addition of 1N HCl and extracted with $Et_2O$. Organic layers were washed with sat. $NaHCO_3$, water and brine, dried ($Na_2SO_4$) and concentrated. The crude intermediate was heated together with TsOH·$H_2O$ (399 mg, 2.1 mmol) in PhMe (100 mL) at 80° C. for 1 h. After cooling to rt, the mixture was concentrated, diluted with $Et_2O$ and washed with sat. $NaHCO_3$, water and brine, dried ($Na_2SO_4$)

and concentrated to give 8-fluoroisochroman-3-one. LCMS (method b) m/z 167.1 $[M+H]^+$, $t_R$=0.71 min. $^1$H NMR (400 MHz, DMSO-$d_6$) δ ppm 7.33-7.46 (m, 1H), 7.10-7.23 (m, 2H), 5.43 (s, 2H), 3.87 (s, 2H).

Step 3: Thionyl chloride (0.88 mL, 12.0 mmol) was added dropwise at 0° C. to a suspension of 8-fluoroisochroman-3-one (1.0 g, 6.0 mmol) in MeOH (10 mL). The solution was stirred at 0° C. for 1 h, then at rt for 16 h. The reaction mixture was treated with toluene, washed with water followed by a sat. $NaHCO_3$ until pH 6-7. The combined organic layers were washed with brine, dried ($Na_2SO_4$) and concentrated to give methyl 2-(2-(chloromethyl)-3-fluorophenyl) acetate which was used directly for the next step. LCMS (method b) m/z 240.1 $[M+Na]^+$, $t_R$=1.01 min. $^1$H NMR ((400 MHz, DMSO-$d_6$) δ ppm 7.33-7.50 (m, 1H), 7.10-7.27 (m, 2H), 4.79 (s, 2H), 3.89 (s, 2H), 3.63 (s, 3H).

Step 4: A mixture of methyl 2-(2-(chloromethyl)-3-fluorophenyl)acetate (1.0 g, 4.6 mmol), pyrazolidine dihydrochloride (0.67 g, 4.6 mmol), DIPEA (4.0 mL, 23 mmol), NaI (0.69 g, 4.6 mmol) and NaOAc (1.52 g, 18.5 mmol) in DMF (45 mL) was stirred in a microwave oven at 200° C. for 10 min. After cooling to rt, the reaction mixture was treated with ethyl acetate and extracted with sat. $NaHCO_3$. The organic layer was washed with brine, dried ($Na_2SO_4$), concentrated and purified by column chromatography (25-50% ethyl acetate in cyclohexane) to give 6-fluoro-2,3,5,10-tetrahydrobenzo[d]pyrazolo[1,2-a][1,2]diazepin-11(1H)-one. LCMS (method b) m/z 221.2 $[M+H]^+$, $t_R$=0.78 min. $^1$H NMR (400 MHz, DMSO-$d_6$) δ ppm 7.20 (dd, J=7.3, 6.6 Hz, 1H), 7.02-7.09 (m, 2H), 4.10 (s, 2H), 3.49 (t, J=7.3 Hz, 2H), 3.32 (s, 2H), 3.24 (t, J=6.7 Hz, 2H), 2.18-2.22 (m, 2H).

Step 5: 1M LiHMDS in THF (3.4 mL, 3.4 mmol) was added dropwise at 0° C. to a mixture of 6-fluoro-2,3,5,10-tetrahydrobenzo[d]pyrazolo[1,2-a][1,2]diazepin-11(1H)-one (300 mg, 1.4 mmol) and isopentylnitrite (330 μL, 2.5 mmol) in THF (10 mL). The reaction was stirred at 0° C. for 2 h, before it was treated with sat. $NaHCO_3$ solution and extracted with ethyl acetate. The organic layer was dried ($Na_2SO_4$) and evaporated to give (E/Z)-6-fluoro-10-(hydroxyimino)-2,3,5,10-tetrahydrobenzo[d]pyrazolo[1,2-a][1,2]diazepin-11(1H)-one which was used without further purification in the next step. LCMS (method b) m/z 250.2 $[M+H]^+$, $t_R$=0.66 min.

Step 6: A mixture of (E/Z)-6-fluoro-10-(hydroxyimino)-2,3,5,10-tetrahydrobenzo[d]pyrazolo[1,2-a][1,2]diazepin-11(1H)-one (141 g, 566 mmol) was hydrogenated (4 bar) over 10% Pd/C (16 g) in a mixture of ethanol (3.3 L) and 1M HCl (0.9 L) at rt for 16 h. The reaction mixture was concentrated to provide 10-amino-6-fluoro-2,3,5,10-tetrahydro-1H,11H-benzo[d]pyrazolo[1,2-a][1,2]diazepin-11-one as an HCl salt which was used in the next step without further purification. LCMS (method b) m/z 236.2 $[M+H]^+$, $t_R$=0.43 min. $^1$H NMR (400 MHz, DMSO-$d_6$) δ ppm 9.03 (s, 3H), 7.42 (q, J=8.0 Hz, 1H), 7.26-7.29 (m, 1H), 7.13 (d, J=7.9 Hz, 1H), 6.04 (s, 1H), 4.22 (s, 2H), 3.56-3.64 (m, 2H), 3.23-3.32 (m, 2H), 2.34-2.44 (m, 1H), 2.11-2.19 (m, 1H).

Step 7: A solution of $Boc_2O$ (151 g, 680 mmol) in $CH_2Cl_2$ (300 mL) was added at rt to a solution of 10-amino-6-fluoro-2,3,5,10-tetrahydro-1H,11H-benzo[d]pyrazolo[1,2-a][1,2] diazepin-11-one (HCl salt, 154 g, 567 mmol) and DIPEA (352 mL, 1984 mmol) in $CH_2Cl_2$ (3.4 L). The mixture was stirred at rt for 16 h. It was then treated with water, the aqueous phase was extracted with $CH_2Cl_2$ and the combined organic phases were dried ($Na_2SO_4$) and concentrated. The crude product was purified by column chromatography (25% EtOH in heptanes) to yield racemic tert-butyl (6-fluoro-11-oxo-2,3,10,11-tetrahydro-1H,5H-benzo[d] pyrazolo[1,2-a][1,2]diazepin-10-yl)carbamate.

Step 8 (chiral separation); The two enantiomers of tert-butyl (6-fluoro-11-oxo-2,3,10,11-tetrahydro-1H,5H-benzo [d]pyrazolo[1,2-a][1,2]diazepin-10-yl)carbamate were separated by chiral HPLC (Bayer CC50 SMB unit, mobile phase: acetonitrile/methanol 1:1, column: Chiralpak AD, 8×(10×100 mm)) to provide tert-butyl (S)-(6-fluoro-11-oxo-2,3,10,11-tetrahydro-1H,5H-benzo[d]pyrazolo[1,2-a][1,2]diazepin-10-yl)carbamate (enantiomeric excess >99.5%) and tert-butyl (R)-(6-fluoro-11-oxo-2,3,10,11-tetrahydro-1H,5H-benzo[d]pyrazolo[1,2-a][1,2]diazepin-10-yl)carbamate (enantiomeric excess >99.5%). Analytical data for tert-butyl (S)-(6-fluoro-11-oxo-2,3,10,11-tetrahydro-1H,5H-benzo[d] pyrazolo[1,2-a][1,2]diazepin-10-yl)carbamate: LCMS (method b) m/z 336.2 $[M+H]^+$, $t_R$=1.04 min. $[\alpha]^{23}_D$ −57.2 (c=1.0, MeOH). $^1$H NMR (400 MHz, DMSO-$d_6$) δ ppm 7.25-7.30 (m, 1H), 7.19 (d, J=8.0 Hz, 1H), 7.09-7.15 (m, 2H), 6.45 (d, J=9.2 Hz, 1H), 4.12 (s, 2H), 3.51-3.56 (m, 2H), 3.25-3.30 (m, 2H), 2.33-2.42 (m, 1H), 2.07-2.14 (m, 1H), 1.43 (s, 9H).

Step 9: A mixture of tert-butyl (S)-(6-fluoro-11-oxo-2,3,10,11-tetrahydro-1H,5H-benzo[d]pyrazolo[1,2-a][1,2]diazepin-10-yl)carbamate (1.3 g, 4.0 mmol) in $CH_2Cl_2$ (20 mL) was treated at 0° C. with 4M HCl in dioxane (20 mL, 80 mmol) and the reaction mixture was stirred at 0° C. for 2 h. $Et_2O$ was added, the resulting precipitate was filtered off and dried in vacuum to yield (S)-10-amino-6-fluoro-2,3,5,10-tetrahydro-1H,11H-benzo[d]pyrazolo[1,2-a][1,2]diazepin-11-one (int-A2) as an HCl salt. LCMS (method b) m/z 236.2 $[M+H]^+$, $t_R$=0.44 min. $[\alpha]_{23}^D$ −99.0 (c=1.0, MeOH). $^1$H NMR (400 MHz, DMSO-$d_6$) δ ppm 9.03 (s, 3H), 7.42 (q, J=8.0 Hz, 1H), 7.26-7.29 (m, 1H), 7.13 (d, J=7.9 Hz, 1H), 6.04 (s, 1H), 4.22 (s, 2H), 3.56-3.64 (m, 2H), 3.23-3.32 (m, 2H), 2.34-2.44 (m, 1H), 2.11-2.19 (m, 1H).

Type B Intermediates

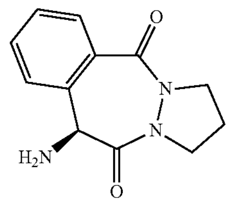 [SMILES: N[C@@H]1C(=O)N2CCCN2C(=O)c2ccccc21]

Synthesis of (S)-10-amino-2,3-dihydro-1H,5H-benzo[d]pyrazolo[1,2-a][1,2]diazepine-5,11(10H)-dione (int-B1)

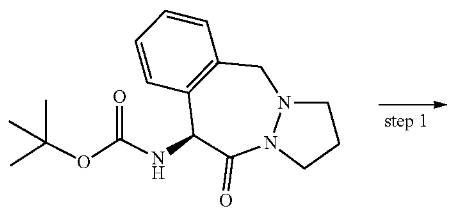

-continued

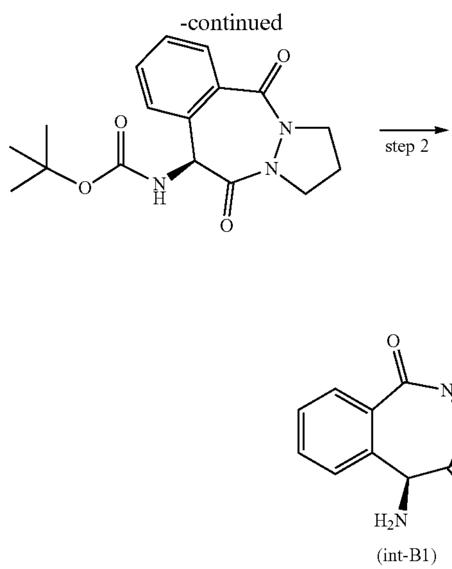

(int-B1)

Step 1: Sodium periodate (36.8 g, 172 mmol) in water (380 mL) was added at rt over 15 min to a mixture of tert-butyl (S)-(11-oxo-2,3,10,11-tetrahydro-1H,5H-benzo[d]pyrazolo[1,2-a][1,2]diazepin-10-yl)carbamate (13.6 g, 43 mmol) and ruthenium (IV) oxide hydrate (650 mg, 4.3 mmol) in ethyl acetate (430 mL). After the addition, the resulting mixture was stirred at rt for 15 min before it was treated with water and $CH_2Cl_2$. The water phase was extracted with $CH_2Cl_2$ and the combined organic layers were then treated with charcoal and filtered through a plug of Celite. The filtrate was washed with water and brine, dried ($Na_2SO_4$) and concentrated to give tert-butyl (S)-(5,11-dioxo-2,3,10,11-tetrahydro-1H,5H-benzo[d]pyrazolo[1,2-a][1,2]diazepin-10-yl)carbamate. LCMS (method b) m/z 332.3 $[M+H]^+$, $t_R$=0.90 min. $[\alpha]^{23}_D$ −102.3 (c=1.0, MeOH). $^1H$ NMR (400 MHz, DMSO-$d_6$) δ ppm 7.78 (d, J=7.6 Hz, 1H), 7.54-7.68 (m, 2H), 7.40-7.52 (m, 2H), 5.67 (d, J=8.6 Hz, 1H), 4.27 (dt, J=10.8, 7.2 Hz, 1H), 3.99-4.09 (m, 1H), 3.61 (dt, J=10.4, 7.3 Hz, 1H), 3.12-3.27 (m, 1H), 2.08-2.18 (m, 2H), 1.42 (s, 9H).

Step 2: 4M HCl in dioxane (151 mL, 604 mmol) was added to a solution of tert-butyl (S)-(5,11-dioxo-2,3,10,11-tetrahydro-1H,5H-benzo[d]pyrazolo[1,2-a][1,2]diazepin-10-yl)carbamate (10 g, mmol) in $CH_2Cl_2$ (151 mL) and the mixture was stirred at rt for 2 h. The reaction mixture was then concentrated and suspended in $Et_2O$ followed by evaporation to remove residual HCl. Finally, the crude was triturated with $Et_2O$, filtered and the obtained solid was dried in vacuum to yield (S)-10-amino-2,3-dihydro-1H,5H-benzo[d]pyrazolo[1,2-a][1,2]diazepine-5,11(10H)-dione (int-B1) as an HCl salt. LCMS (method b) m/z 232.2 $[M+H]^+$, $t_R$=0.32 min. $[\alpha]^{23}_D$ −145.0 (c=1.0, MeOH). $^1H$ NMR (400 MHz, DMSO-$d_6$) δ ppm 9.24 (s, 3H), 7.87 (dd, J=7.7, 1.2 Hz, 1H), 7.75 (t, J=7.7 Hz, 1H), 7.58 (t, J=7.6 Hz, 1H), 7.43 (d, J=7.8 Hz, 1H), 5.74 (s, 1H), 4.30 (dt, J=11.0, 7.5 Hz, 1H), 4.09 (ddd, J=10.9, 7.9, 4.8 Hz, 1H), 3.55-3.61 (m, 1H), 3.28-3.33 (m, 1H), 2.01-2.26 (m, 2H).

Type C Intermediates

Synthesis of (S)-10-amino-1H,3H,5H-spiro[benzo[d]pyrazolo[1,2-a][1,2]diazepine-2,1'-cyclopropane]-5,11(10H)-dione (int-C1)

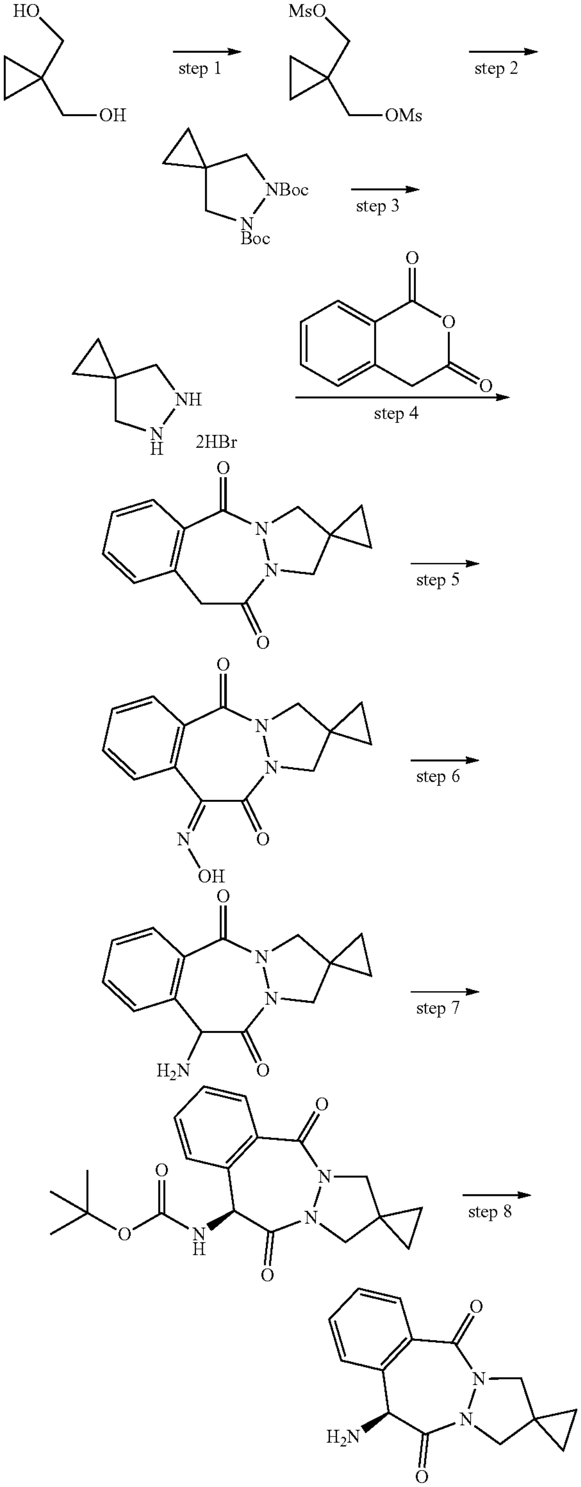

(int-C1)

Step 1: A solution of MsCl (57.2 mL, 734 mmol) in $CH_2Cl_2$ (160 mL) was added dropwise at 0° C. to a solution of cyclopropane-1,1-diyldimethanol (25.0 g, 245 mmol) and $Et_3N$ (136 mL, 979 mmol) in $CH_2Cl_2$ (250 mL). The reaction mixture was stirred at rt for 16 h. 1M HCl (900 mL) was then added and the mixture was extracted with $CH_2Cl_2$. The combined organic layers were washed with brine, dried ($Na_2SO_4$) and concentrated to a volume of 100-150 mL. Hexane was added and the resulting precipitate was filtered off, washed with hexane and dried in vacuum to give cyclopropane-1,1-diylbis(methylene) dimethanesulfonate. $^1H$ NMR (400 MHz, DMSO-$d_6$) δ ppm 4.14 (s, 4H), 3.19 (s, 6H), 0.77 (s, 4H).

Step 2: A solution of di-tert-butyl hydrazine-1,2-dicarboxylate (18.6 g, 80 mmol) in dry DMF (65 mL) was added dropwise at 0° C. to a suspension of NaH (60% dispersion in oil, 6.7 g, 168 mmol) in dry DMF (40 mL) and the suspension was stirred at rt for 1 h. After addition of cyclopropane-1,1-diylbis(methylene) dimethanesulfonate (20.7 g, 80 mmol) the reaction mixture was stirred at rt for 16 h. It was then poured onto ice and water (1.3 L). The formed precipitate was filtered off, washed with water and dried in vacuum to give di-tert-butyl 5,6-diazaspiro[2.4]heptane-5,6-dicarboxylate. LCMS (method g) m/z 619.4 $[2M+Na]^+$, $t_R$=1.57 min. $^1H$ NMR (400 MHz, DMSO-$d_6$) δ ppm 3.56 (d, J=10.6 Hz, 2H), 3.17 (d, J=10.6 Hz, 2H), 1.41 (s, 18H), 0.63-0.68 (m, 4H).

Step 3: Hydrobromic acid solution (33 wt % in AcOH, 38.5 mL, 0.22 mol) was added slowly at 0° C. to a solution of di-tert-butyl 5,6-diazaspiro[2.4]heptane-5,6-dicarboxylate (12 g, 40 mmol) in $Et_2O$ (200 mL) and the mixture was stirred at rt for 16 h. After cooling to 0° C., the solid was filtered off, washed with $Et_2O$ and dried in vacuum to give 5,6-diazaspiro[2.4]heptane dihydrobromide. LCMS (method g) m/z 99.2 $[M+H]^+$, $t_R$=0.26 min. $^1H$ NMR (400 MHz, DMSO-$d_6$) δ ppm 7.80 (br s, 4H), 3.06 (s, 4H), 0.76 (s, 4H).

Step 4: 5,6-Diazaspiro[2.4]heptane dihydrobromide (5.2 g, 20 mmol) was added at rt to a solution of homophthalic anhydride (3.3 g, 20 mmol) in AcOH (35 mL) and pyridine (18 mL). The solution was then stirred at 130° C. for 20 h. After cooling to rt, the mixture was diluted with water and extracted with $CH_2Cl_2$. The combined organic layers were washed with 10% HCl, 5% $NaHCO_3$, water and brine, dried ($Na_2SO_4$) and concentrated. The crude product was purified by column chromatography (20-50% ethyl acetate in hexane) to give 1H-spiro[benzo[d]pyrazolo[1,2-a][1,2]diazepine-2,1'-cyclopropane]-5,11(3H,10H)-dione. LCMS (method g) m/z 243.2 $[M+H]^+$, $t_R$=1.11 min. $^1H$ NMR (400 MHz, DMSO-$d_6$) δ ppm 7.79 (dd, J=7.7 Hz, 1.4, 1H), 7.54-7.58 (m, 1H), 7.41-7.47 (m, 2H), 4.20 (d, J=11.0 Hz, 1H), 4.14 (d, J=13.4 Hz, 1H), 3.88 (d, J=10.6 Hz, 1H), 3.46-3.57 (m, 2H), 3.23 (d, J=10.5 Hz, 1H), 0.75-0.79 (m, 4H).

Step 5: 1M LiHMDS in THF (26 mL, 26 mmol) was added dropwise at 0° C. to a suspension of 1H-spiro[benzo[d]pyrazolo[1,2-a][1,2]diazepine-2,1'-cyclopropane]-5,11(3H,10H)-dione (4.1 g, 17 mmol) and isopentyl nitrite (3.4 mL, 26 mmol) in THF (34 mL). The reaction mixture was stirred at rt for 2 h. AcOH was added and the mixture was evaporated twice in vacuum to yield a mixture of (Z) and (E)-10-(hydroxyimino)-1H-spiro[benzo[d]pyrazolo[1,2-a][1,2]diazepine-2,1'-cyclopropane]-5,11(3H,10H)-dione which was used in the next step without further purification. LCMS (method g) m/z 272.2 $[M+H]^+$, $t_R$=1.10 and 1.13 min.

Step 6: 4M HCl (4.3 mL, 17 mmol) was added at rt to a mixture of crude (Z,E)-10-(hydroxyimino)-1H-spiro[benzo[d]pyrazolo[1,2-a][1,2]diazepine-2,1'-cyclo-propane]-5,11(3H,10H)-dione (4.6 g, 17.0 mmol) in AcOH (92 mL). The mixture was then cooled to 0° C. and Zn powder (4.5 g, 68 mmol) was added slowly. After the addition, the reaction mixture was stirred at rt for 1.5 h. The inorganic zinc residues were filtered off and washed with $CH_2Cl_2$. The filtrate was concentrated, redissolved in $CH_2Cl_2$, washed with 10% NaOH, brine, dried ($Na_2SO_4$) and concentrated. The residue was purified by column chromatography (0-4% MeOH in $CH_2Cl_2$ ($NH_3$)) to yield rac. 10-amino-1H,3H,5H-spiro[benzo[d]pyrazolo[1,2-a][1,2]diazepine-2,1'-cyclopropane]-5,11(10H)-dione. LCMS (method g) m/z 258.2 $[M+H]^+$, $t_R$=0.79 min. $^1H$ NMR (400 MHz, DMSO-$d_6$) δ ppm 7.73-7.78 (m, 2H), 7.62 (td, J=7.6, 1.4, 1H), 7.40-7.45 (m, 1H), 4.97 (s, 1H), 4.21 (d, J=11.2 Hz, 1H), 3.88 (d, J=10.8 Hz, 1H), 3.54 (d, J=11.2 Hz, 1H), 3.27 (d, J=10.8 Hz, 1H), 2.28 (s, 2H), 0.70-0.85 (m, 4H).

Step 7. $Boc_2O$ (76 g, 347 mmol) was added at room temperature to rac. 10-amino-1H,3H,5H-spiro[benzo[d]pyrazolo[1,2-a][1,2]diazepine-2,1'-cyclopropane]-5,11(10H)-dione (68 g, 231 mmol) and $Na_2CO_3$ (110 g, 1.04 mol) in dioxane/water (1:1 mixture, 1.4 L) and the resulting mixture was stirred at rt for 2 h. The formed precipitate was filtered off, washed twice with water and dried under vacuum. The solid was dissolved in dioxane containing 3% formic acid and the enantiomers were separated by preparative chiral HPLC (Thar SFC-200 instrument, mobile phase: $scCO_2$/EtOH 70:30, column: Chiralpak IC, 5 uM, 250×30 mm) to provide the (S)-enantiomer (>99.5% ee) and the (R)-enantiomer (>99.5% ee). Analytical data for tert-butyl (S)-(5,11-dioxo-10,11-dihydro-1H,3H,5H-spiro[benzo[d]pyrazolo[1,2-a][1,2]diazepine-2,1'-cyclopropan]-10-yl)carbamate. LCMS (method e) m/z 358.2 $[M+H]^+$, $t_R$=1.05 min. $[\alpha]^{23}_D$ −125.0 (c=1.0, MeOH). $^1H$ NMR (400 MHz, DMSO-$d_6$) δ ppm 7.81 (d, J=7.5 Hz, 1H), 7.61-7.71 (m, 2H), 7.45-7.51 (m, 2H), 5.74 (d, J=8.9 Hz, 1H), 4.21 (d, J=11.1 Hz, 1H), 3.90 (d, J=10.7 Hz, 1H), 3.62 (d, J=11.1 Hz, 1H), 3.27 (d, J=10.7 Hz, 1H), 1.42 (s, 9H), 0.71-0.82 (m, 4H).

Step 8. tert-Butyl (S)-(5,11-dioxo-10,11-dihydro-1H,3H,5H-spiro[benzo[d]pyrazolo[1,2-a][1,2]diazepine-2,1'-cyclopropan]-10-yl)carbamate (2.0 g, 5.6 mmol) was dissolved in $CH_2Cl_2$ (28 mL) and treated at 0° C. with 4M HCl in dioxane (28 mL, 112 mmol). After stirring at 0° C. for 1 h, the reaction mixture was concentrated. The residue was treated with CH2Cl2 and evaporated. It was then triturated with $Et_2O$, the formed precipitate was filtered off and dried in vacuum to yield (S)-10-amino-1H,3H,5H-spiro[benzo[d]pyrazolo[1,2-a][1,2]diazepine-2,1'-cyclopropane]-5,11(10H)-dione (int-C1) as an HCl salt. LCMS (method b) m/z 258.2 $[M+H]^+$, $t_R$=0.46 min. $[\alpha]^{23}_D$ −160.4 (c=1.0, MeOH). $^1H$ NMR (400 MHz, DMSO-$d_6$) δ ppm 9.33 (br s, 3H), 7.89 (d, J=7.4 Hz, 1H), 7.75 (t, J=7.2 Hz, 1H), 7.60 (t, J=7.3 Hz, 1H), 7.46 (d, J=7.9 Hz, 1H), 5.83 (s, 1H), 4.26 (d, J=11.1 Hz, 1H), 3.91 (d, J=10.9 Hz, 1H), 3.53 (d, J=11.1 Hz, 1H), 3.42 (d, J=10.3 Hz, 1H), 0.74-0.89 (m, 4H).

Type D Intermediates

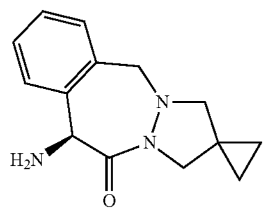 [SMILES: N[C@@H]1C(=O)N2CC3(CC3)CN2Cc2ccccc21]

Synthesis of 10-Amino-5,10-dihydro-1H-spiro [benzo[d]pyrazolo[1,2-a][1,2]diazepine-2,1'-cyclopropan]-11(3H)-one (int-C1)

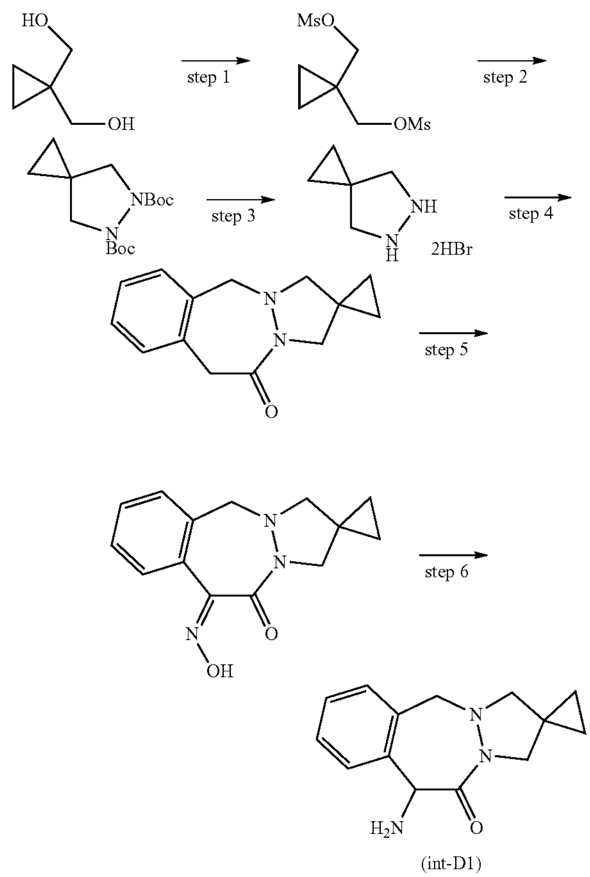

(int-D1)

Step 1: To a solution of cyclopropane-1,1-diyldimethanol (25.0 g, 245 mmol) in $CH_2Cl_2$ (250 mL) was added $Et_3N$ (136 mL, 979 mmol) and the reaction mixture was cooled to 0° C. A solution of MsCl (57.2 mL, 734 mmol) in $CH_2Cl_2$ (160 mL) was added dropwise and the cooling bath was removed. After stirring at rt for 16 h, 1N HCl (900 mL) was added and the mixture was extracted with $CH_2Cl_2$, the combined organic layers were washed with brine, and dried ($Na_2SO_4$). The solution was then concentrated to 100-150 mL volume and hexane was added. Brownish crystals were filtered off, washed with $CH_2Cl_2$-hexane, hexane and dried in high vacuum to give cyclopropane-1,1-diylbis(methylene) dimethanesulfonate. $^1$H NMR (400 MHz, DMSO-$d_6$) δ ppm 4.14 (s, 4H), 3.19 (s, 6H), 0.77 (s, 4H).

Step 2: A solution of di-tert-butyl hydrazine-1,2-dicarboxylate (18.6 g, 80 mmol) in anhydrous DMF (65 mL) was added at 0° C. to a suspension of NaH (6.72 g, 168 mmol) in anhydrous DMF (40 mL). The suspension was stirred at rt for 1 h before solid cyclopropane-1,1-diylbis(methylene) dimethanesulfonate (20.7 g, 80 mmol) was added and the resulting mixture was stirred at rt for 16 h. The reaction mixture was poured into ice and water (1.3 L), the solid was filtered off, washed with water and dried in high vacuum to give di-tert-butyl 5,6-diazaspiro[2.4]heptane-5,6-dicarboxylate. m/z 619 $[2M+Na]^+$, $^1$H NMR (400 MHz, DMSO-$d_6$) δ ppm 3.56 (d, 2H), 3.17 (d, 2H), 1.41 (s, 18H), 0.66 (m, 4H).

Step 3: Hydrobromic acid solution (33 wt % in AcOH, 38.5 mL) was slowly added at 0° C. to a solution of di-tert-butyl 5,6-diazaspiro[2.4]heptane-5,6-dicarboxylate (11.9 g, 40 mmol) in $Et_2O$ (200 mL) and the mixture was stirred at rt for 16 h. The reaction mixture was then cooled to 0° C. and filtered off. The solid was washed with $Et_2O$ and dried in high vacuum to give 5,6-diazaspiro[2.4]heptane dihydrobromide. m/z 99 $[M+H]^+$, $^1$H NMR (400 MHz, DMSO-$d_6$) δ ppm 7.80 (bs, 4H), 3.06 (s, 4H), 0.76 (s, 4H).

Step 4: A mixture of methyl 2-(2-(chloromethyl)phenyl) acetate (2.38 g, 12 mmol), 5,6-diazaspiro[2.4]heptane dihydrobromide (3.74 g, 14.4 mmol), anhydrous MeOH (30 mL) and DIPEA (10.5 mL, 60 mmol) was heated at 150° C. for 5 h in a microwave oven. After cooling to rt, the reaction mixture was concentrated, treated with water and extracted with $CH_2Cl_2$. The collected organic phases were dried ($Na_2SO_4$) and concentrated. The residue was purified by column chromatography (0-70% Ethyl acetate in hexane) to afford 5,10-dihydro-1H-spiro[benzo[d]pyrazolo[1,2-a][1,2]diazepine-2,1'-cyclopropan]-11(3H)-one. m/z 229 $[M+H]^+$, $t_R$=1.26 min (LCMS condition a), $^1$H NMR (600 MHz, DMSO-$d_6$) δ ppm 7.20 (m, 1H), 7.18 (m, 2H), 7.07 (m, 1H), 4.35 (s, 2H), 3.86 (bs, 2H), 3.47 (s, 2H), 3.23 (bs, 2H), 0.76 (m, 4H).

Step 5: Isoamyl nitrite (0.646 mL, 4.80 mmol) was added at 0° C. to a solution of 5,10-dihydro-1H-spiro[benzo[d]pyrazolo[1,2-a][1,2]diazepine-2,1'-cyclopropan]-11(3H)-one (913 mg, 4 mmol) in THF (10 mL) followed by addition of LiHMDS (1M in THF, 5.60 mL, 5.60 mmol). After stirring the reaction mixture at 0° C. for 2 h, the reaction was quenched by addition of water and the mixture was concentrated. The crude product was triturated with $Et_2O$, the solid was filtered off and washed with $Et_2O$. It was then dissolved in ethyl acetate and washed with sat. $NaHCO_3$ solution. The aqueous phase was extracted with ethyl acetate, the collected organic layers were dried ($Na_2SO_4$), and concentrated to provide the crude title compound as a mixture of (Z, E) isomers: (Z,E)-10-(hydroxyimino)-5,10-dihydro-1H-spiro[benzo[d]pyrazolo[1,2-a][1,2]diazepine-2,1'-cyclopropan]-11(3H)-one. m/z 258 $[M+H]^+$, $t_R$=1.14 min (LCMS condition a), $^1$H NMR (400 MHz, DMSO-$d_6$) δ ppm 11.49+11.46 (s, 1H), 7.64 and 7.30 (m, 4H), 4.34 (bs, 2H), 3.52 (s, 2H), 3.14 (bs, 2H), 0.78 (m, 4H).

Step 6: Zinc powder (1.0 g, 15.9 mmol) was slowly added at 0° C. to a mixture of 4N HCl (1 mL) and (Z,E)-10-(hydroxyimino)-5,10-dihydro-1H-spiro[benzo[d]pyrazolo[1,2-a][1,2]diazepine-2,1'-cyclopropan]-11(3H)-one (1.03 g, 3.98 mmol) in AcOH (20 mL) and the reaction mixture was stirred at rt for 2.5 h. The mixture was then filtered to remove zinc and the solids were washed with $CH_2Cl_2$. The filtrate was treated with 1N NaOH and the aqueous phase was extracted with $CH_2Cl_2$. The combined organic phases were dried and concentrated. The residue was purified by column chromatography (0-10% MeOH in (1% $NH_4OH$ in $CH_2Cl_2$)) to give 10-amino-5,10-dihydro-1H-spiro[benzo[d]pyrazolo[1,2-a][1,2]diazepine-2,1'-cyclopropan]-11(3H)-one. m/z 244 $[M+H]^+$, $t_R$=0.90 min (LCMS condition a), $^1$H NMR (400 MHz, DMSO-$d_6$) δ ppm 7.80 (m, 1H), 7.19 (m, 2H), 7.03 (m, 1H), 5.53 (s, 1H), 4.50 (d, 1H), 4.30 (d, 1H), 3.64 (d, 1H), 3.42 (d, 1H), 3.36 (d, 1H), 2.86 (d, 1H), 2.05 (s, 2H), 0.85 (m, 2H), 0.74 (m, 1H), 0.66 (m, 1H).

Chiral separation as described for type A and type C intermediates (via BOC protection, chiral separation and BOC deprotection) allows isolation of type D intermediate.

Type L Intermediates

Synthesis of 2-(((tert-butoxycarbonyl)amino) methyl)-3,3,3-trifluoropropanoic acid (int-L1)

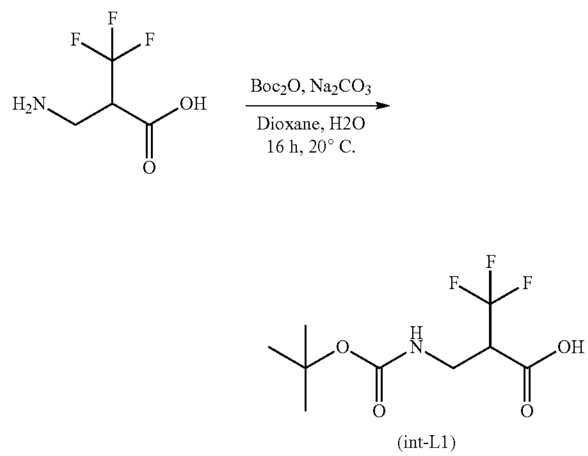

(int-L1)

To a mixture of 2-(aminomethyl)-3,3,3-trifluoropropanoic acid (15 g, 95 mmol) in dioxane (300 mL) was added water (300 mL), $Na_2CO_3$ (45.5 g, 430 mmol) and $Boc_2O$ (33.3 mL, 143 mmol). The reaction was stirred at rt for 16 h, then $CH_2Cl_2$ was added and the mixture was acidified with 1N HCl. The aqueous layer was extracted with ethyl acetate and the combined organic layers were dried ($MgSO_4$) and concentrated. The crude product was used without further purification. LCMS (method e) M/z 256 $[M-H]^-$; $t_R$=2.70 min. $^1H$ NMR (400 MHz, DMSO-$d_6$) δ ppm 13.5 (s, 1H), 7.17 (m, 1H), 3.49 (m, 1H), 3.37 (m, 2H), 1.38 (s, 9H).

Synthesis of (R)-3-((tert-butoxycarbonyl)amino)-2-cyclopropylpropanoic acid (int-L2)

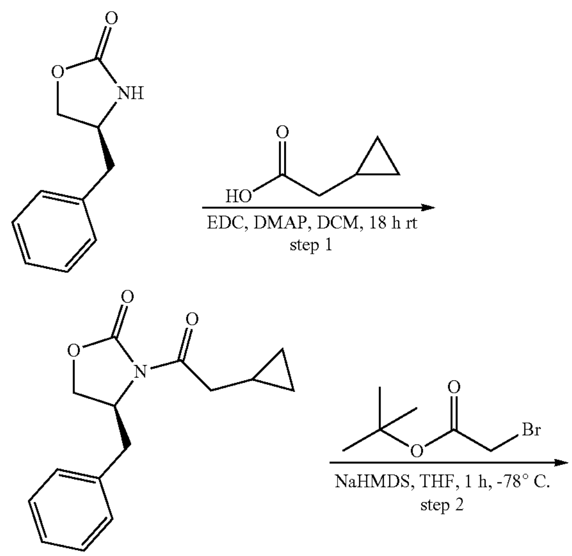

-continued

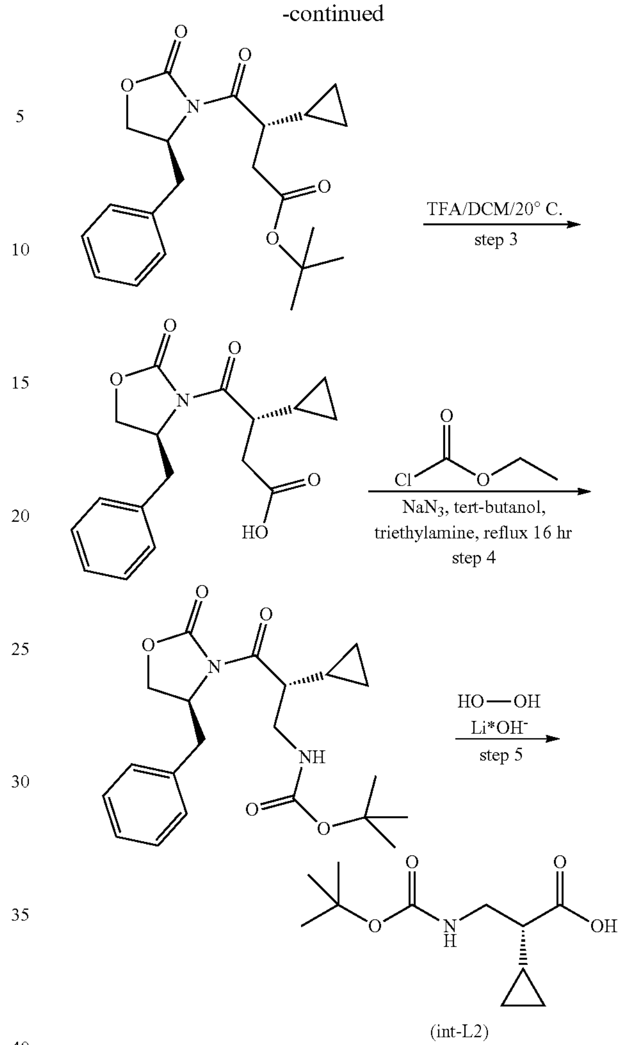

(int-L2)

Step 1: EDC (6.5 g, 33.9 mmol) was then added at rt to a mixture of (S)-4-benzyloxazolidin-2-one (3.0 g, 5.64 mmol), DMAP (3.1 g, 25.4 mmol) and 2-cyclopropylacetic acid (2.36 mL, 25.4 mmol) in $CH_2Cl_2$ (20 mL) and the mixture was stirred at rt for 16 h. The reaction mixture was then diluted with $CH_2Cl_2$, washed with water, 1N HCl, 1N NaOH and brine, dried ($Na_2SO_4$) and concentrated to give (S)-4-benzyl-3-(2-cyclopropylacetyl)oxazolidin-2-one, which was used in the next step without further purification. LCMS (method b) m/z 260.2 $[M+H]^+$, $t_R$=1.05 min. $[\alpha]^{23}_D$ +90.6 (c=1.0, MeOH); $^1H$ NMR (400 MHz, $CDCl_3$) δ ppm 7.38-7.32 (m, 2H), 7.32-7.28 (m, 1H), 7.25-7.23 (m, 2H), 4.78-4.70 (m, 1H), 4.28-4.19 (m, 2H), 3.36 (dd, J=13.4, 3.2 Hz, 1H), 2.97 (dd, J=17.0, 6.7 Hz, 1H), 2.89-2.75 (m, 2H), 1.31-1.14 (m, 1H), 0.69-0.59 (m, 2H), 0.31-0.22 (m, 2H).

Step 2: 1M NaHMDS in THF (8.68 mL, 8.68 mmol) was added dropwise at −78° C. to a solution of (S)-4-benzyl-3-(2-cyclopropylacetyl)oxazolidin-2-one (1.5 g, 5.78 mmol) in THF (8 mL). After stirring at −78° C. for 1 h, tert-butyl 2-bromoacetate (1.55 mL, 10.41 mmol) was added and the mixture was stirred at −78° C. for 1 h. It was then quenched by addition of sat. $NH_4Cl$ and allowed to warm to rt. The mixture was extracted with ethyl acetate, the organic layers were washed with water and brine, dried ($Na_2SO_4$) and concentrated to give crude product which was purified by chromatography (5-20% ethyl acetate in cyclohexane) to give tert-butyl (S)-4-((S)-4-benzyl-2-oxooxazolidin-3-yl)-3-cyclopropyl-4-oxobutanoate. LCMS (method b) m/z 374.3 $[M+H]^+$, $t_R$=1.29 min. $^1$H NMR (400 MHz, $CDCl_3$) δ ppm 7.38-7.27 (m, 5H), 4.71 (td, J=6.7, 3.3 Hz, 1H), 4.22-4.13 (m, 2H), 3.79-3.70 (m, 1H), 3.39 (dd, J=13.4, 3.2 Hz, 1H), 2.97 (dd, J=16.8, 10.8 Hz, 1H), 2.73 (dd, J=13.4, 10.3 Hz, 1H), 2.59 (dd, J=16.8, 4.3 Hz, 1H), 1.43 (s, 9H), 1.01-0.89 (m, 1H), 0.61-0.48 (m, 2H), 0.48-0.40 (m, 1H), 0.35-0.18 (m, 1H).

Step 3: TFA (4.54 ul, 58.9 mmol) was added at rt to a solution of tert-butyl (S)-4-((S)-4-benzyl-2-oxooxazolidin-3-yl)-3-cyclopropyl-4-oxobutanoate (1.1 g, 2.95 mmol) in $CH_2Cl_2$ (25 mL) and the solution was stirred at rt for 1 h. The reaction mixture was then concentrated, the residue dissolved in $CH_2Cl_2$ and concentrated again. This was repeated using $Et_2O$ to remove the remaining TFA and yield (S)-4-((S)-4-benzyl-2-oxooxazolidin-3-yl)-3-cyclopropyl-4-oxobutanoic acid. LCMS (method b) m/z 318.2 $[M+H]^+$, $t_R$=0.90 min. $^1$H NMR (400 MHz, DMSO-$d_6$) δ ppm 12.31 (s, 1H), 7.34-7.29 (m, 4H), 7.29-7.22 (m, 1H), 4.75-4.64 (m, 1H), 4.34 (t, J=8.4 Hz, 1H), 4.15 (dd, J=8.9, 2.3 Hz, 1H), 3.70 (ddd, J=10.2, 8.9, 4.6 Hz, 1H), 2.99 (dd, J=13.6, 3.3 Hz, 1H), 2.90-2.73 (m, 2H), 2.55 (dd, J=16.9, 4.7 Hz, 1H), 0.95-0.84 (m, 1H), 0.51-0.41 (m, 1H), 0.41-0.31 (m, 2H), 0.26-0.16 (m, 1H).

Step 4: Ethyl chloroformate (480 mg, 4.42 mmol) was added at 0° C. to a solution of (S)-4-((S)-4-benzyl-2-oxooxazolidin-3-yl)-3-cyclopropyl-4-oxobutanoic acid (1.275 mg, 4.02 mmol) and triethylamine (672 μL, 4.82 mmol) in acetone (40 mL) and the reaction mixture was stirred at 0° C. for 1 h. Then a solution of $NaN_3$ (522 mg in 10 mL $H_2O$) was added to the reaction mixture at 0° C. and the mixture was stirred at 0° C. for 1 h. The solvent was removed and the residue extracted with $Et_2O$. The organic phased were dried ($Na_2SO_4$) and concentrated. Toluene (80 mL) was added to the residue and 40 mL of the solvent was distilled off to azeotropically remove residual water. tert-Butanol (20 mL) was added to the reaction mixture before stirring at reflux for 16 h. After cooling to rt, the solvent was removed and the residue was dissolved in $CH_2Cl_2$, washed with 2N HCl, water and brine, dried ($Na_2SO_4$) and concentrated to give tert-butyl ((R)-3-((S)-4-benzyl-2-oxooxazolidin-3-yl)-2-cyclopropyl-3-oxopropyl)carbamate. LCMS (method b) m/z 389.3 $[M+H]^+$, $t_R$=1.16 min. $^1$H NMR (400 MHz, DMSO-$d_6$) δ ppm 7.36-7.28 (m, 2H), 7.28-7.19 (m, 3H), 6.95 (t, J=5.5 Hz, 1H), 4.72-4.60 (m, 1H), 4.36-4.27 (m, 1H), 4.19-4.11 (m, 1H), 3.46-3.36 (m, 1H), 3.30-3.18 (m, 2H), 3.14-3.05 (m, 1H), 2.86-2.76 (m, 1H), 1.35 (s, 9H), 1.10-0.93 (m, 1H), 0.56-0.44 (m, 1H), 0.42-0.31 (m, 1H), 0.26-0.11 (m, 2H).

Step 5: Hydrogen peroxide (1.1 mL, 10.81 mmol) was added at 0° C. to a mixture of tert-butyl ((R)-3-((S)-4-benzyl-2-oxooxazolidin-3-yl)-2-cyclopropyl-3-oxopropyl) carbamate (1.4 g, 3.60 mmol) in THF (8 mL), followed by LiOH (302 mg, 7.21 mmol) and water (0.7 mL) and the reaction mixture was stirred at 0° C. for 2.5 h. The reaction mixture was then treated at 0° C. with sat. $NaHSO_3$ (4 mL) and sat. $NaHCO_3$ (10 mL). THF was removed under reduced pressure and the aqueous layer (pH 10) was washed with $CH_2Cl_2$. The aqueous layer was then cooled to 0° C. and acidified with 4N HCl and 10% $KHSO_4$ to pH 2. It was extracted with ethyl acetate, the combined organic phases were washed with water and brine, dried ($Na_2SO_4$) and concentrated to yield an oil which crystallized overnight. Recrystallization from hexane gave (R)-3-((tert-butoxycarbonyl)amino)-2-cyclopropylpropanoic acid (int-L2). $^1$H NMR (400 MHz, DMSO-$d_6$) δ ppm 12.12 (s, 1H), 6.78 (t, J=6.0 Hz, 1H), 3.21-2.96 (m, 2H), 1.81-1.62 (m, 1H), 1.36 (s, 9H), 0.89-0.69 (m, 1H), 0.55-0.31 (m, 2H), 0.26-0.08 (m, 2H).

Synthesis of (R)-2-(((tert-butoxycarbonyl)amino)methyl)butanoic acid (int-L3)

(int-L3)

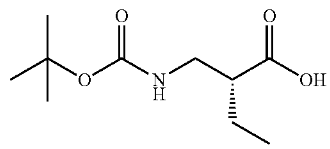

(R)-2-(((tert-Butoxycarbonyl)amino)methyl)butanoic acid (int-L3) was obtained using a method analogous to that described for the synthesis of ((tert-butoxycarbonyl)amino)-2-cyclopropylpropanoic acid (int-L2), except 2-cyclopropylacetic acid was replaced with butyric acid. $^1$H NMR (400 MHz, DMSO-$d_6$) δ ppm 12.12 (s, 1H), 6.80 (t, J=4.7 Hz, 1H), 3.15-3.04 (m, 1H), 3.04-2.92 (m, 1H), 2.39-2.28 (m, 1H), 1.54-1.40 (m, 2H), 1.37 (s, 9H), 0.84 (t, J=7.4 Hz, 3H).

Synthesis of (R)-2-(((tert-butoxycarbonyl)amino)methyl)pentanoic acid (int-L4)

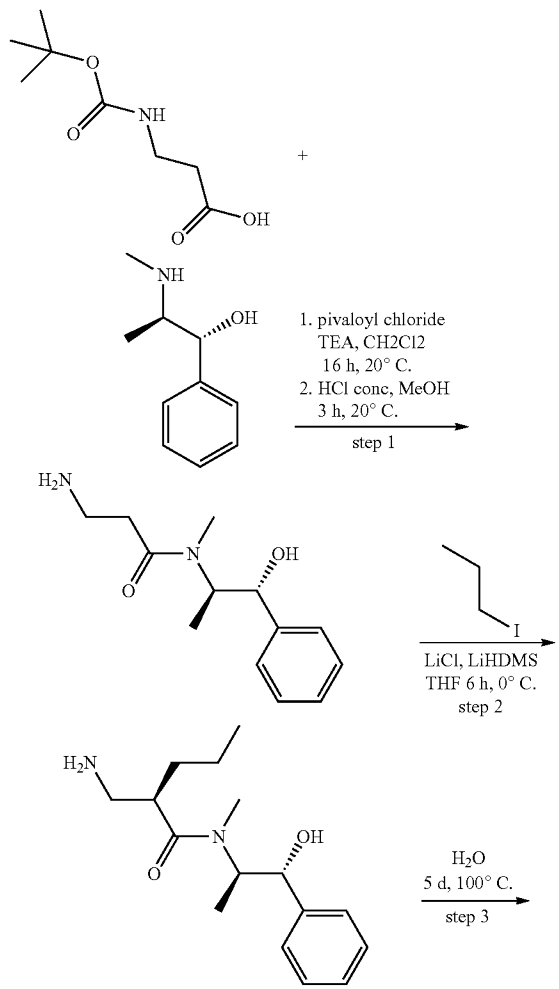

-continued

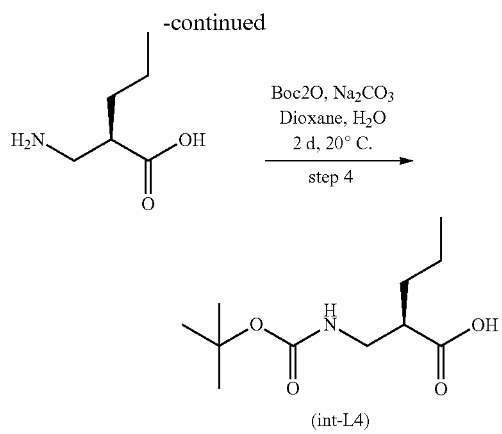

(int-L4)

Step 1: Pivaloyl chloride (3.25 mL, 26.4 mmol) was added to the solution of Boc-betaalanine (5 g, 26.4 mmol) in $CH_2Cl_2$ (50 mL) and TEA (3.87 mL, 27.7 mmol) at 0° C. and the mixture was stirred at 0° C. for 1 h. TEA (5.52 mL, 39.6 mmol) was then added, followed by a solution of (1R, 2R)-pseudoephedrine (4.37 g, 26.4 mmol) in $CH_2Cl_2$ (5 mL) and the mixture was stirred at 20° C. for 16 h. The reaction mixture was concentrated and the residue dissolved in 1:1 mixture of MeOH/$H_2O$ (30 mL). HCl conc. (22.5 mL) was added to the solution at 0° C. and the mixture stirred at 20° C. for 3 h. The reaction mixture was concentrated, dissolved in water and washed with ethyl acetate/cyclohexane (1/1). The water phase was made basic (pH 12) with 50% NaOH and extracted with $CH_2Cl_2$. The combined organic phases were dried ($Na_2SO_4$) and concentrated. The colorless oil was crystalized from toluene to give 3-amino-N-((1R,2R)-1-hydroxy-1-phenylpropan-2-yl)-N-methylpropanamide. LCMS (method e) m/z 237.0 $[M+H]^+$, $t_R$=0.40 min. $^1H$ NMR (400 MHz, DMSO-$d_6$): δ ppm 7.41-7.20 (m, 5H), 4.55-4.40 (m, 1H), 4.03-3.85 (m, 1H), 2.83+2.75 (s, 3H), 2.73-2.61 (m, 2H), 2.46-2.25 (m, 2H), 1.49 (s, 1H), 0.88+0.82 (d, J=6.7 Hz, 3H) ($NH_3^+$ not seen).

Step 2: LiHMDS (29.8 mL, 29.8 mmol) was added dropwise at 0° C. to a mixture of 3-amino-N-((1R,2R)-1-hydroxy-1-phenylpropan-2-yl)-N-methylpropanamide (2.2 g, 9.31 mmol) and LiCl (1.579 g, 37.2 mmol) in THF (44 mL). After 1 h stirring at 0° C., 1-iodopropane (1.364 mL, 13.96 mmol) was added slowly and the mixture was stirred at 0° C. for 6 h. Reaction was quenched by addition of water, followed by 6N HCl (until pH 3 was reached), and the aqueous phase was then washed with ethyl acetate/cyclohexane (1/1), made basic (pH 12) at 0° C. with 50% NaOH and extracted with $CH_2Cl_2$. The organic phase was dried ($MgSO_4$) and concentrated. The crude was purified by prep-HPLC (Macherey-Nagel Nucleosil 100-10 C18, Flow 40 mL/min, ACN: 5 min to 5%, 20 min to 100%). The product fractions were treated with sat. $NaHCO_3$ and extracted with $CH_2Cl_2$. The combined organic phases were dried ($MgSO_4$) and concentrated to give (R)-2-(aminomethyl)-N-((1R,2R)-1-hydroxy-1-phenylpropan-2-yl)-N-methylpentanamide. LCMS (method e) m/z 279.4 $[M+H]^+$, $t_R$=0.59 min. $^1H$ NMR (400 MHz, DMSO-$d_6$): δ ppm 7.39-7.19 (m, 5H), 4.85-4.72+4.17-4.06 (m, 1H), 4.55-4.47 (m, 1H), 3.00-2.55 (m, 4H), 2.49-2.42 (m, 2H), 1.73-1.11 (m, 5H), 1.03-0.59 (m, 6H). ($NH_3^+$ not seen).

Step 3: A mixture of (R)-2-(aminomethyl)-N-((1R,2R)-1-hydroxy-1-phenylpropan-2-yl)-N-methylpentanamide in water (10 mL) was stirred at 100° C. for 5 days. After cooling to rt, the reaction mixture was washed with $CH_2Cl_2$ and concentrated. The residue was crystalized from MeOH to give (R)-2-(aminomethyl)pentanoic acid. LCMS (method b) m/z 132.2 $[M+H]^+$, $t_R$=0.17 min. $^1H$ NMR (400 MHz, DMSO-$d_6$): δ ppm 2.80 (dd, J=12.2, 4.4 Hz, 1H), 2.69-2.56 (m, 1H), 2.08-1.94 (m, 1H), 1.65-1.48 (m, 1H), 1.39-1.16 (m, 3H), 0.85 (t, J=7.0 Hz, 3H). (NH3+ and COOH not seen)

Step 4: $Na_2CO_3$ (415 mg, 3.91 mmol) and $Boc_2O$ (0.30 mL, 1.30 mmol) were added to a solution of (R)-2-(aminomethyl)pentanoic acid in dioxane (2 mL) and water (1 mL) and the reaction mixture stirred at rt for 2 days. The reaction mixture was then washed with $CH_2Cl_2$, acidified with 1N HCl and extracted with ethyl acetate. The organic layers were dried ($MgSO_4$) and concentrated to give (R)-2-(((tert-butoxycarbonyl)amino)methyl)pentanoic acid (int-L4). LCMS (method b) m/z 232.2 $[M+H]^+$, $t_R$=1.22 min. $^1H$ NMR (400 MHz, DMSO-$d_6$): δ ppm 12.15 (s, 1H), 6.86 (t, J=5.9 Hz, 1H), 3.14-3.04 (m, 1H), 3.02-2.90 (m, 1H), 2.46-2.34 (m, 1H), 1.46-1.39 (m, 1H), 1.36 (s, 9H), 1.34-1.14 (m, 3H), 0.85 (t, J=7.1 Hz, 3H).

Synthesis of (R)-2-(((tert-butoxycarbonyl)amino)methyl)-4-methoxybutanoic acid (int-L5)

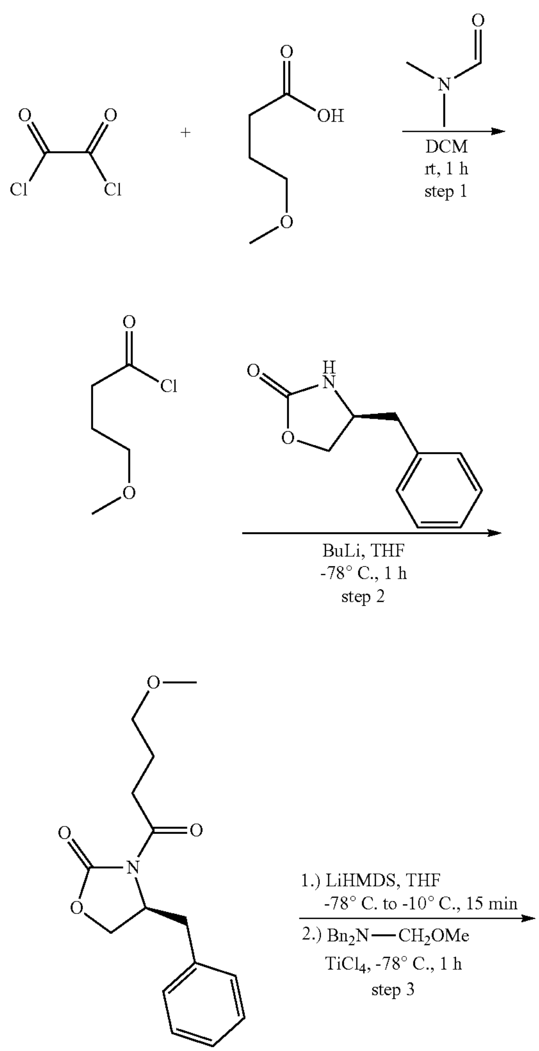

-continued

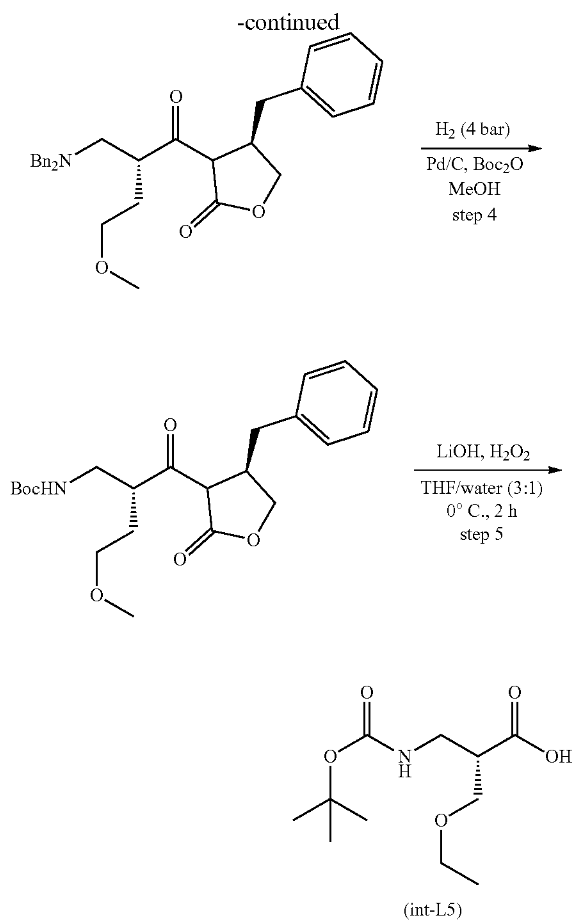

(int-L5)

Step 1: Oxalyl chloride (1.844 mL, 21.07 mmol) was added dropwise at rt to a stirred solution of 4-methoxybutanoic acid (2.37 g, 20.06 mmol) in $CH_2Cl_2$ (100 mL), followed by addition of a drop of DMF. The resulting solution was stirred at rt for 1 h. The reaction mixture was concentrated to provide 4-methoxybutanoyl chloride which was used directly in the next step.

Step 2: n-Butyllithium (1.6 M in hexanes) (12.54 mL, 20.06 mmol) was added dropwise at −78° C. to a stirred solution of (S)-4-benzyloxazolidin-2-one (3.55 g, 20.06 mmol) in THF (201 mL) and the resulting solution was stirred at −78° C. for 15 min. 4-Methoxybutanoyl chloride (2.74 g, 20.06 mmol) in THF (5 mL) was then added dropwise at −78° C. and the reaction mixture stirred for 1 h at −78° C. before it was quenched with sat. $NaHCO_3$ solution (100 mL). The aqueous phase was separated and extracted with $CH_2Cl_2$ and the combined organic fractions were dried ($MgSO_4$) and concentrated to afford the crude product which was purified by column chromatography (0-40% ethyl acetate in cyclohexane) to give (S)-4-benzyl-3-(4-methoxybutanoyl)oxazolidin-2-one. LCMS (method b) m/z 278.4 $[M+H]^+$; $t_R$=1.01 min. $^1H$ NMR (400 MHz, DMSO-$d_6$): δ ppm 7.44-7.04 (m, 5H), 4.75-4.57 (m, 1H), 4.31 (t, J=8.5 Hz, 1H), 4.17 (dd, J=8.8, 2.8 Hz, 1H), 3.36 (t, J=6.3 Hz, 2H), 3.23 (s, 3H), 3.00 (dd, J=13.5, 3.4 Hz, 1H), 2.95-2.75 (m, 3H), 1.88-1.72 (m, 2H).

Step 3: LiHMDS (1M in PhMe) (3.97 mL, 3.97 mmol) was added at −78° C. to a stirred solution of (S)-4-benzyl-3-(4-methoxybutanoyl)oxazolidin-2-one (1 g, 3.61 mmol) in THE (36.1 mL) and the resulting solution was warmed to −10° C. and stirred for 15 minutes. After cooling to −78° C., N,N-dibenzyl-1-methoxymethanamine (1.74 g, 7.21 mmol) was added, followed by addition of titanium(IV) chloride (0.080 mL, 0.721 mmol). The resulting solution was stirred at −78° C. for 1 h. The reaction mixture was quenched via the addition of sat. $NaHCO_3$ solution (50 mL). The aqueous phase was separated and extracted with $CH_2Cl_2$ and the combined organic fractions were dried ($MgSO_4$) and concentrated. The crude product was purified by column chromatography (0-25% ethyl acetate in cyclohexane) to give (S)-4-benzyl-3-((R)-2-((dibenzylamino)methyl)-4-methoxybutanoyl)oxazolidin-2-one. LCMS (method b) m/z 487.4 $[M+H]^+$; $t_R$=1.48 min.

Step 4: (S)-4-benzyl-3-((R)-2-((dibenzylamino)methyl)-4-methoxybutanoyl)oxazolidin-2-one (1.26 g, 2.59 mmol) in MeOH (25 mL) was hydrogenated using H2 (4 bar) and Pd/C (10 mol %) for 2 h at room temperature (0.18 g). The reaction mixture was then treated with $Boc_2O$ (0.9 g, 4.1 mmol) to give tert-butyl ((R)-2-((S)-4-benzyl-2 oxooxazolidine-3-carbonyl)-4-methoxybutyl)carbamate. LCMS (method b) m/z 407.2 $[M+H]^+$; $t_R$=1.13 min.

Step 5: 30% Hydrogen peroxide in water (399 mg, 3.52 mmol) followed by LiOH (73.9 mg, 1.761 mmol) in water (2.2 mL) were added at 0° C. to a solution of tert-butyl ((R)-2-((S)-4-benzyl-2-oxooxazolidine-3-carbonyl)-4-methoxybutyl)carbamate (358 mg, 0.881 mmol) in THF (6.6 mL) and the reaction mixture was stirred at 0° C. for 2 h. It was then treated with sat. $Na_2SO_3$ and sat. $NaHCO_3$. THF was distilled off under reduced pressure and the aqueous layer was washed with $CH_2Cl_2$. The aqueous layer was acidified with 2M HCl to pH 2 and extracted with $CH_2Cl_2$. The organic layers were dried ($Na_2SO_4$) and concentrated to yield (R)-2-(((tert-butoxycarbonyl)amino)methyl)-4-methoxybutanoic acid (int-L5). $^1H$ NMR (DMSO-$d_6$, 400 MHz): δ ppm 12.19 (s, 1H), 6.85 (t, J=5.9 Hz, 1H), 3.31-3.22 (m, 2H), 3.19 (s, 3H), 3.16-3.06 (m, 1H), 3.05-2.95 (m, 1H), 2.49-2.42 (m, 1H), 1.72-1.58 (m, 2H), 1.37 (s, 9H).

Note: N,N-Dibenzyl-1-methoxymethanamine ($Bn_2NCH_2OMe$) was obtained using the following procedure

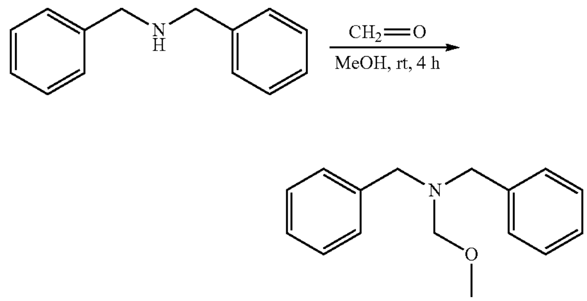

Potassium carbonate (21.0 g, 152 mmol) and formaldehyde (3.81 g, 127 mmol) were added to a solution of dibenzylamine (10.0 g, 50.7 mmol) in MeOH (10 mL) and the reaction mixture was stirred at rt for 4 h. $K_2CO_3$ (21.0 g, 152 mmol) was then added and the mixture was stirred at rt for 16 h. After filtration and concentration, the reaction mixture was purified by Kugelrohr distillation (100° C., 0.3 mbar) to give N,N-dibenzyl-1-methoxymethanamine.

Synthesis of (R)-4-(tert-butoxy)-2-methyl-4-oxobutanoic acid (int-L6)

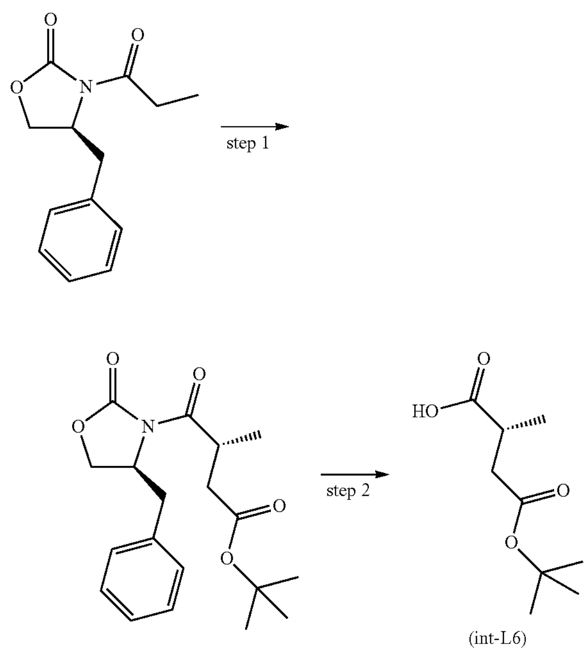

(int-L6)

Step 1: 1M NaHMDS in THF (37.7 mL, 37.7 mmol) was added dropwise at −78° C. to a solution of (S)-4-benzyl-3-propionyloxazolidin-2-one (8 g, 34.3 mmol) in THF (200 mL). After stirring for 1 h at −78° C., tert-butyl 2-bromoacetate (15.5 mL, 103 mmol) was added and the solution was stirred at −78° C. for 2.5 h. The reaction mixture was treated with sat. aq. $NH_4Cl$ and THF was removed under reduced pressure. The residue was extracted with ethyl acetate, the combined organic layers were dried ($MgSO_4$) and concentrated. Crystallization from $Et_2O$ yielded tert-butyl (R)-4-((S)-4-benzyl-2-oxooxazolidin-3-yl)-3-methyl-4-oxobutanoate. H NMR (400 MHz, $CDCl_3$): δ ppm 7.24-7.36 (m, 5H), 4.66 (td, J=6.7, 3.5 Hz, 1H), 4.11-4.21 (m, 3H), 3.34 (dd, J=13.4, 3.3 Hz, 1H), 2.85 (dd, J=16.8, 10.0 Hz, 1H), 2.75 (dd, J=13.4, 9.9 Hz, 1H), 2.38 (dd, J=16.8, 4.8 Hz, 1H), 1.43 (s, 9H), 1.20 (d, J=7.0 Hz, 3H). LCMS (method b) m/z 348.1 $[M+H]^+$; $t_R$=1.21 min. $[\alpha]^{23}$+78.9 (c=1.0, MeOH)

Step 2: 30% Hydrogen peroxide in water (2.7 mL, 26.5 mmol) followed by 0.5M aq. LiOH (26.5 mL, 13.2 mmol) were added at 0° C. to a solution of tert-butyl (R)-4-((S)-4-benzyl-2-oxooxazolidin-3-yl)-3-methyl-4-oxobutanoate (2.3 g, 6.6 mmol) in THF (66 mL) and the reaction mixture was stirred at 0° C. for 2 h. It was then treated with sat. aq. $Na_2SO_3$ and sat. aq. $NaHCO_3$. THF was distilled off under reduced pressure and the aqueous layer was extracted with $CH_2Cl_2$. The aqueous layer was acidified with 2M HCl to pH 2 and extracted with $CH_2Cl_2$. The organic layers were dried ($Na_2SO_4$) and concentrated to yield (R)-4-(tert-butoxy)-2-methyl-4-oxobutanoic acid (int-L6). $^1$H NMR (400 MHz, $CDCl_3$): δ ppm 2.90 (dq, J=14.1, 7.2 Hz, 1H), 2.65 (dd, J=16.4, 8.1 Hz, 1H), 2.37 (dd, J=16.4, 5.9 Hz, 1H), 1.45 (s, 9H), 1.25 (d, J=7.2 Hz, 3H), no signal was observed for the acidic proton. $[\alpha]^{23}_D$ +2.6 (c=1.0, MeOH).

Synthesis of (S)-4-(tert-Butoxy)-2-cyclopropyl-4-oxobutanoic acid (int-L7)

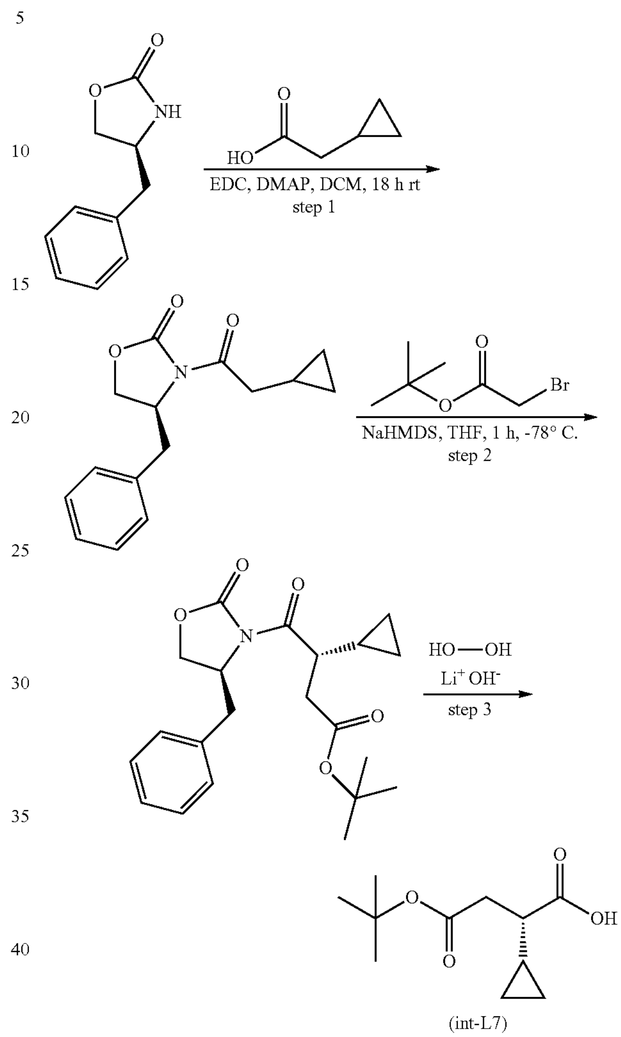

(int-L7)

Step 1: EDC (1.7 g, 8.9 mmol) was added at rt to a mixture of (S)-4-benzyloxazolidin-2-one (800 mg, 4.5 mmol), 2-cyclopropylacetic acid (600 mg, 6.0 mmol) and DMAP (565 mg, 4.6 mmol) in $CH_2Cl_2$ (5 mL) and the mixture was stirred at rt for 16 h. The mixture was diluted with $CH_2Cl_2$ and washed with water, 1M HCl, sat. aq. $NaHCO_3$, sat. aq. $NH_4Cl$, water and brine, dried ($Na_2SO_4$) and concentrated to give (S)-4-benzyl-3-(2-cyclopropylacetyl)oxazolidin-2-one. LCMS (method b) m/z 260.2 $[M+H]^+$, $t_R$=1.05 min. $[\alpha]^{23}_D$ +90.6 (c=1.0, MeOH); $^1$H NMR (400 MHz, $CDCl_3$) δ ppm 7.38-7.32 (m, 2H), 7.32-7.28 (m, 1H), 7.25-7.23 (m, 2H), 4.78-4.70 (m, 1H), 4.28-4.19 (m, 2H), 3.36 (dd, J=13.4, 3.2 Hz, 1H), 2.97 (dd, J=17.0, 6.7 Hz, 1H), 2.89-2.75 (m, 2H), 1.31-1.14 (m, 1H), 0.69-0.59 (m, 2H), 0.31-0.22 (m, 2H).

Step 2: 1M NaHMDS in THF (5.9 mL, 5.9 mmol) was added dropwise at −78° C. to a solution of (S)-4-benzyl-3-(2-cyclopropylacetyl)oxazolidin-2-one (1.0 g, 3.9 mmol) in THF (30 mL). After stirring at −78° C. for 1 h, tert-butyl 2-bromoacetate (1.2 mL, 7.8 mmol) was added and the solution was stirred for additional 1 h at −78° C. The reaction mixture was treated with sat. aq. $NH_4Cl$ (2 mL) and allowed to warm to rt, before it was dried ($Na_2SO_4$) and concentrated. The crude product was purified by column chromatography (0-50% ethyl acetate in hexane) to give tert-butyl (S)-4-((S)-4-benzyl-2-oxooxazolidin-3-yl)-3-cyclopropyl-4-oxobutanoate. LCMS (method b) m/z 374.3 $[M+H]^+$, $t_R$=1.29 min. $[\alpha]^{23}_D$ +69.0 (c=1.0, MeOH); $^1$H NMR (400 MHz, $CDCl_3$): δ ppm 7.38-7.27 (m, 5H), 4.71 (td, J=6.7, 3.3 Hz, 1H), 4.22-4.13 (m, 2H), 3.79-3.70 (m, 1H), 3.39 (dd, J=13.4, 3.2 Hz, 1H), 2.97 (dd, J=16.8, 10.8 Hz, 1H), 2.73 (dd, J=13.4, 10.3 Hz, 1H), 2.59 (dd, J=16.8, 4.3 Hz, 1H), 1.43 (s, 9H), 1.01-0.89 (m, 1H), 0.61-0.48 (m, 2H), 0.48-0.40 (m, 1H), 0.35-0.18 (m, 1H).

Step 3: Hydrogen peroxide (30% in water; 0.88 mL, 8.6 mmol) followed by LiOH (0.18 g, 4.3 mmol) in water (1 mL) were added at 0° C. to a solution of tert-butyl (S)-4-((S)-4-benzyl-2-oxooxazolidin-3-yl)-3-cyclopropyl-4-oxobutanoate (0.8 g, 2.1 mmol) in THF (20 mL) and the reaction mixture was stirred at 0° C. for 2 h. It was then treated with sat. aq. $NaHSO_3$ (20 mL) and sat. aq. $NaHCO_3$ (50 mL) at 0° C. THF was distilled off under reduced pressure and the aqueous layer was washed with $CH_2Cl_2$, then cooled to 0° C., acidified with 4M HCl to pH 2 and extracted with $CH_2Cl_2$. Combined organic extracts were dried ($Na_2SO_4$) and concentrated to give (S)-4-(tert-butoxy)-2-cyclopropyl-4-oxobutanoic acid (int-L7). LCMS (method b) m/z 213.2 $[M-H]^-$; $t_R$=0.90 min. $[\alpha]^{23}_D$ +51.2 (c=1.0, MeOH); $^1$H NMR (400 MHz, DMSO-$d_6$): δ ppm 12.12 (s, 1H), 2.53 (dd, J=16.3, 9.8 Hz, 1H), 2.40 (dd, J=16.0, 5.3 Hz, 1H), 1.87-1.95 (m, 1H), 1.37 (s, 9H), 0.75-0.87 (m, 1H), 0.38-0.49 (m, 2H), 0.29-0.36 (m, 1H), 0.12-0.21 (m, 1H).

Synthesis of (S)-4-(tert-butoxy)-2-cyclobutyl-4-oxobutanoic acid (int-L8)

(int-L8)

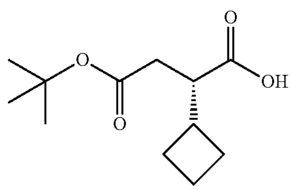

(S)-4-(tert-butoxy)-2-cyclobutyl-4-oxobutanoic acid (int-L8) was obtained was obtained using an analogous method as that described for the synthesis of (S)-4-(tert-butoxy)-2-cyclopropyl-4-oxobutanoic acid (int-L7) except 2-cyclopropylacetic acid was replaced with 2-cyclobutylacetic acid, LCMS (method b) m/z 229.3 $[M+H]^+$ $t_R$=0.99 min. $^1$H NMR (400 MHz, DMSO-$d_6$): δ ppm 12.07 (s, 1H), 2.59-2.51 (m, 1H), 2.39-2.15 (m, 3H), 2.00-1.62 (m, 6H), 1.37 (s, 9H).

The table below lists the L intermediates which were purchased.

| Intermediate Code | Compound Structure | Compound Name | Source |
|---|---|---|---|
| Int-L9 | 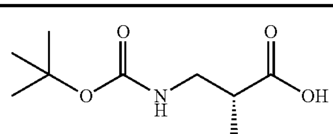 | (R)-3-((tert-butoxycarbonyl)amino-2-methylpropanoic acid | CAS: 132696-45-8 |

Type EC Intermediates

Synthesis of 2-isobutyramido-4-methylthiazole-5-carboxylic acid (int-EC1)

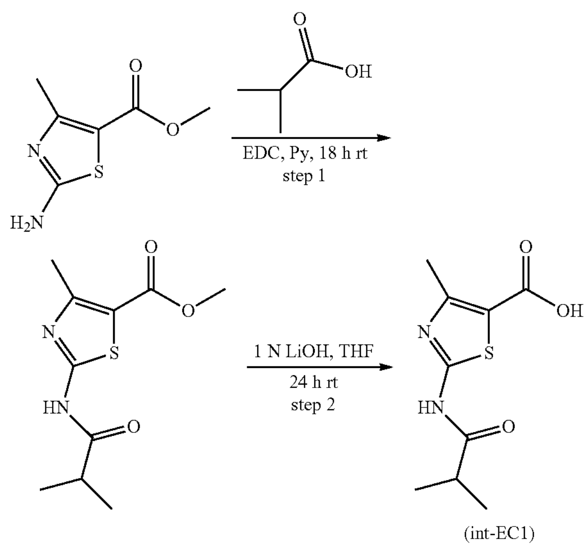

(int-EC1)

Step 1: Methyl 2-amino-4-methylthiazole-5-carboxylate (Combi blocks, CAS: 3829.80-9) (500 mg, 2.90 mmol) and isobutyric acid (285 μL, 3.05 mmol), pyridine (1.2 mL, 14.5 mmol) were dissolved in acetonitrile (29 mL) and EDC (1.1 g, 5.8 mmol) was added and the mixture (white suspension) was stirred overnight at room temperature. Dry DMF (10 mL), isobutyric acid (50 μL, 0.581 mmol) and HOBt (736 mg, 4.36 mmol) were added and the fine suspension was continued to stir at rt for an addition 22 hrs. The reaction mixture was concentrated, quenched with $H_2O$ and extracted twice with ethyl acetate. The organic layers were combined and washed with water, brine, dried with $Na_2SO_4$, filtered, and the filtrate concentrated to give crude solid. The crude product was dissolved in $CH_2Cl_2$/MeOH (9/1), charged on a precolumn with isolute and purified by column chromatography (10-30% ethyl acetate in cyclohexane) to give methyl 2-isobutyramido-4-methylthiazole-5-carboxylate. LCMS (method b) m/z 243.1 $[M+H]^+$, $t_R$=0.86 min. $^1$H NMR (400 MHz, DMSO-$d_6$) δ ppm 12.42 (s, 1H), 3.78 (s, 3H), 2.74 (h, J=6.9 Hz, 1H), 2.54 (s, 3H), 1.12 (d, J=6.3 Hz, 6H).

Step 2: 1M LiOH aq. solution (16.5 mL, 16.5 mmol) was added to a solution of methyl 2-isobutyramido-4-methylthiazole-5-carboxylate (400 mg, 1.65 mmol) in THF (16 mL). The mixture mixture was stirred for 16 h at rt. THF was removed under reduced pressure and the residue was washed with $Et_2O$. The aqueous phase was acidified with HCl, and the resulting white suspension was stirred for 30 min. and then filtered cold and dried on HV to give 2-isobutyramido-4-methylthiazole-5-carboxylic acid (int-EC1). LCMS (method b) m/z 229.2 $[M+H]^+$, $t_R$=0.62 min. $^1H$ NMR (400 MHz, DMSO-$d_6$) δ ppm 12.79 (s 1H), 12.31 (s, 1H), 2.72 (h, J=7.0 Hz, 1H), 2.52 (s, 3H), 1.11 (d, J=6.8 Hz, 6H).

Synthesis of 2-(ethylcarbamoyl)-4-methylthiazole-5-carboxylic acid (int-EC2)

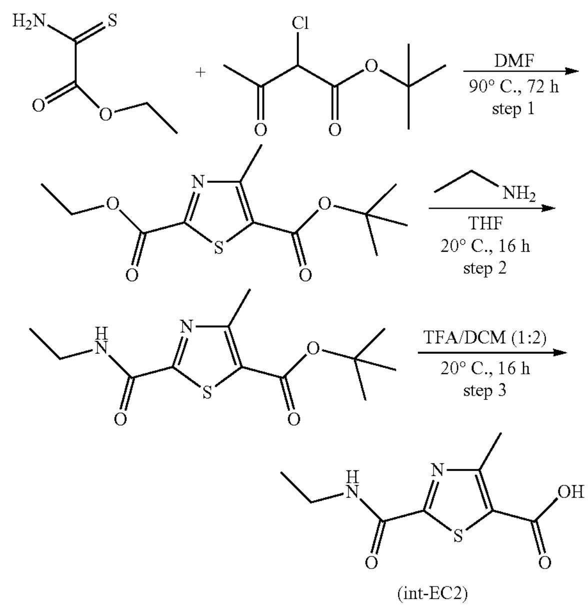

(int-EC2)

Step 1: Ethyl 2-amino-2-thioxoacetate (1.7 g, 12.8 mmol) was added to a solution of tert-butyl 2-chloro-3-oxobutanoate (2.46 g, 12.8 mmol) in DMF (10 mL), and the solution stirred 3 days at 90° C. After cooling to rt, the reaction mixture was concentrated and the residue purified by column chromatography (0-50% ethyl acetate in cyclohexane) to give 5-(tert-butyl) 2-ethyl 4-methylthiazole-2,5-dicarboxylate. LCMS (method e) m/z 272.1 $[M+H]^+$, $t_R$=1.23 min. $^1H$ NMR (400 MHz, DMSO-$d_6$) δ ppm 4.38 (d, J=7.1 Hz, 2H), 2.67 (s, 3H), 1.54 (s, 9H), 1.33 (t, J=7.0 Hz, 3H).

Step 2: A solution of 5-(tert-butyl) 2-ethyl 4-methylthiazole-2,5-dicarboxylate (500 mg, 1.84 mmol) in 2M solution of ethanamine in EtOH (27.6 mL, 55.2 mmol) was stirred at room temperature for 16 h. The reaction mixture was treated with ethyl acetate and washed with sat. $NaHCO_3$ and 1N HCl. The organic phase was dried ($MgSO_4$) and concentrated to give tert-butyl 2-(ethylcarbamoyl)-4-methylthiazole-5-carboxylate. LCMS (method b) m/z 271.1 $[M+H]^+$, $t_R$=1.14 min. $^1H$ NMR (400 MHz, DMSO-$d_6$) δ ppm 8.97 (t, J=6.1 Hz, 1H), 3.30-3.23 (m, 2H), 2.66 (s, 3H), 1.53 (s, 9H), 1.11 (t, J=7.3 Hz, 3H).

Step 3: A solution of tert-butyl 2-(ethylcarbamoyl)-4-methylthiazole-5-carboxylate (540 mg, 1.8 mmol) in TFA (15 mL) and $CH_2Cl_2$ (30 mL) was stirred at rt for 16 h. The reaction mixture was concentrated and treated with $Et_2O$. The precipitate was filtered off, washed with cold $Et_2O$ and dried in vacuum to give 2-(ethylcarbamoyl)-4-methylthiazole-5-carboxylic acid (int-EC2). LCMS (method b) m/z 215.1 $[M+H]^+$, $t_R$=0.54 min. $^1H$ NMR (400 MHz, DMSO-d6) δ ppm 8.97 (t, J=6.0 Hz, 1H), 3.30-3.26 (m, 2H), 2.67 (s, 3H), 1.12 (q, J=7.4 Hz, 3H) (acid proton not seen).

Synthesis of 2-((2,2-difluoroethyl)carbamoyl)-4-methylthiazole-5-carboxylic acid (int-EC3)

(int-EC3)

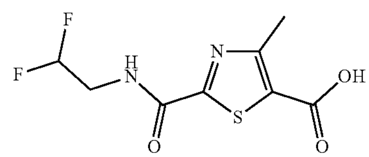

2-((2,2-Difluoroethyl)carbamoyl)-4-methylthiazole-5-carboxylic acid (int-EC3) was obtained using an analogous method as that described for the synthesis of 2-(ethylcarbamoyl)-4-methylthiazole-5-carboxylic acid (int-EC2), except in step 2 where ethanamine in THF was replaced with 2,2-difluoroethan-1-amine in ethanol. LCMS (method b) m/z 251.1 $[M+H]^+$, $t_R$=0.55 min. $^1H$ NMR (400 MHz, DMSO-$d_6$) δ ppm 9.24 (t, J=6.3 Hz, 1H), 6.14 (tt, J=55.8, 4.0 Hz, 1H), 3.66 (tdd, J=15.3, 6.2, 4.0 Hz, 2H), 2.69 (s, 3H) (acid proton not seen).

Synthesis of 4-methyl-2-methylcarbamoyl)thiazole-5-carboxylic acid (int-EC4)

(int-EC4)

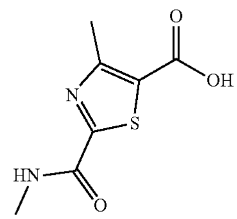

4-Methyl-2-(methylcarbamoyl)thiazole-5-carboxylic acid (int-EC4) was obtained using an analogous method as that described for the synthesis of 2-(ethylcarbamoyl)-4-methylthiazole-5-carboxylic acid (int-EC2), except in step 2 where ethanamine in THF was replaced with methamine in ethanol. LCMS (method a) m/z 201.1 $M+H]^+$, $t_R$=0.45 min.

Synthesis of 2-(isopropylcarbamoyl)-4-methylthiazole-5-carboxylic acid (int-EC5)

(int-EC5)

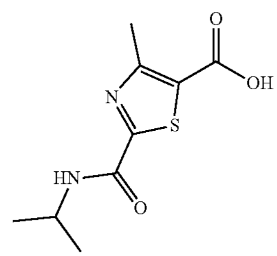

2-(Isopropylcarbamoyl)-4-methylthiazole-5-carboxylic acid (int-EC5) was obtained using an analogous method as that described for the synthesis of 2-(ethylcarbamoyl)-4- methylthiazole-5-carboxylic acid (int-EC2), except in step 2 where ethanamine in THF was replaced with propane-2-amine in ethanol. LCMS (method b) m/z 229.2 $[M+H]^+$, $t_R$=0.61 min. H NMR (400 MHz, DMSO-$d_6$) δ ppm 8.73 (d, J=8.5 Hz, 1H), 4.20-3.96 (m, 1H), 2.68 (s, 3H), 1.18 (d, J=6.6 Hz, 6H).

Synthesis of 4-chloro-2-(6-(trifluoromethyl)pyridin-3-yl)thiazole-5-carboxylic acid (int-EC6)

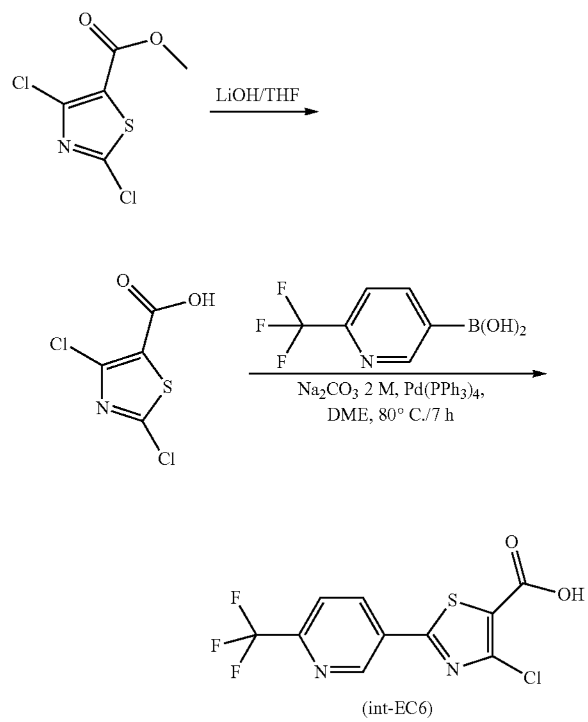

(int-EC6)

Step 1: To a solution of methyl 2,4-dichlorothiazole-5-carboxylate (10 g, 47.2 mmol) in THF (150 mL) was added 1N LiOH aq. solution (235 mL, 235 mmol). The reaction mixture was stirred at rt for 1 h. 0.1M NaOH aq. solution was added to the reaction mixture which was extracted with $Et_2O$. The aqueous phase was acidified with HCl, concentrated and extracted with $Et_2O$. The organic layer was washed with brine, dried ($Na_2SO_4$) and concentrated to give 2,4-dichlorothiazole-5-carboxylic acid. LCMS (method b) m/z 195.9+197.9 $[M-H]^-$, $t_R$=0.46 min.

Step 2: (6-(Trifluoromethyl)pyridin-3-yl)boronic acid (4.24 g, 22.2 mmol), $Pd(PPh_3)_4$ (1.17 g, 1.0 mmol) and 2M $Na_2CO_3$ aq. solution (25 mL, 1.88 mmol) were added to a mixture of 2,4-dichlorothiazole-5-carboxylic acid (4 g, 20.20 mmol) and DME (150 mL). The reaction mixture was stirred at 80° C. for 7 h in microwave oven. The reaction mixture was quenched with water and extracted with ethyl acetate. The aqueous phase was acidified with concentrated HCl and extracted with ethyl acetate. The combined organic layers were washed with brine, dried ($Na_2SO_4$) and concentrated. The crude was triturated with water/i-propanol (3/1) on ultrasound bath and the solid was filtered and dried on HV to give 4-chloro-2-(6-(trifluoromethyl)pyridin-3-yl)thiazole-5-carboxylic acid (int-EC6). LCMS (method b) m/z 309.0+311.0 $[M+H]^+$, $t_R$=0.76 min. $^1$H NMR (400 MHz, DMSO-$d_6$) δ ppm: 14.13 (s, 1H), 9.36 (s, 1H), 8.66 (d, J=8.5 Hz, 1H), 8.09 (d, J=8.3 Hz, 1H).

Synthesis of 4-methyl-2-(6-(trifluoromethyl)pyridin-3-yl)thiazole-5-carboxylic acid (int-EC7)

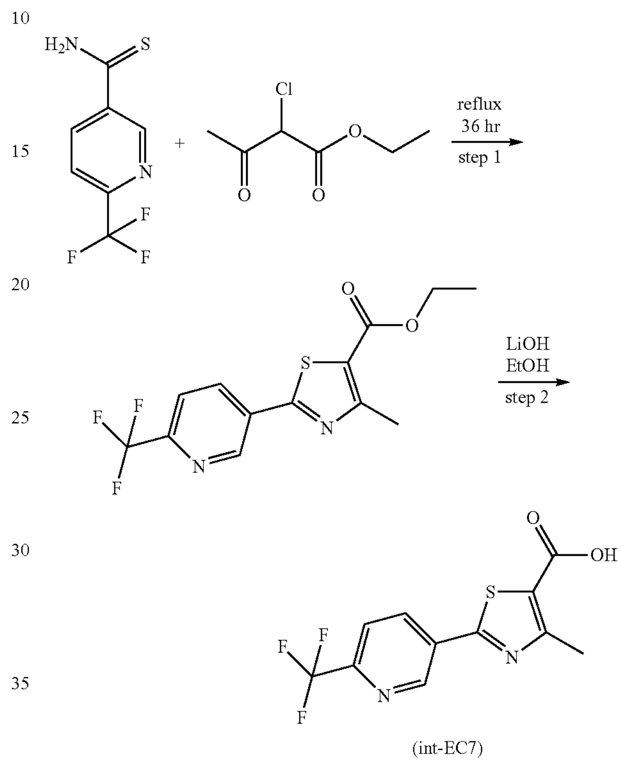

(int-EC7)

Step 1: Ethyl 2-chloroacetate (4.77 mL, 32.7 mmol) was added to a solution of 6-(trifluoromethyl)pyridine-3-carbothioamide (5.0 g, 24.25 mmol) in ethanol (80 mL) and the mixture was heated to reflux at 95° C. for 36 h. After cooling to rt, the resulting suspension was filtered off and dried in vacuum give ethyl 4-methyl-2-(6-(trifluoromethyl)pyridin-3-yl)thiazole-5-carboxylate. The filtrate was concentrated and then triturated with a small amount of EtOH, filtered off cold and dried in vacuo to give more ethyl 4-methyl-2-(6-(trifluoromethyl)pyridin-3-yl)thiazole-5-carboxylate. LCMS (method b) m/z 317.1 $[M+H]^+$, $t_R$=1.25 min. $^1$H NMR (400 MHz, DMSO-$d_6$) δ ppm 9.35 (s, 1H), 8.64 (d, J=7.4 Hz, 1H), 8.06 (d, J=8.3 Hz, 1H), 4.33 (q, J=7.2 Hz, 2H), 2.74 (s, 3H), 1.32 (t, J=7.1 Hz, 3H).

Step 2: LiOH in $H_2O$ (24.66 mL, 24.66 mmol) was added at rt to a mixture of ethyl 4-methyl-2-(6-(trifluoromethyl)pyridin-3-yl)thiazole-5-carboxylate (5.2 g, 16.44 mmol) in ethanol (110 mL) and the mixture was stirred at rt for 1.5 h. The solvent was removed, the residue was then treated with water and the solution was then acidified with 2N HCl. The resulting suspension was filtered off and the solid was dried in vacuum to give 4-methyl-2-(6-(trifluoromethyl)pyridin-3-yl)thiazole-5-carboxylic acid (int-EC7). LCMS (method b) m/z 289.1 $[M+H]^+$, $t_R$=0.86 min. $^1$H NMR (400 MHz, DMSO-$d_6$) δ ppm 13.67 (s, 1H), 9.31 (s, 1H), 8.60 (d, J=8.3 Hz, 1H), 8.04 (d, J=8.3 Hz, 1H), 2.71 (s, 3H).

Synthesis of 4-methyl-2-(3-methylisoxazol-5-yl) thiazole-5-carboxylic acid (int-EC8)

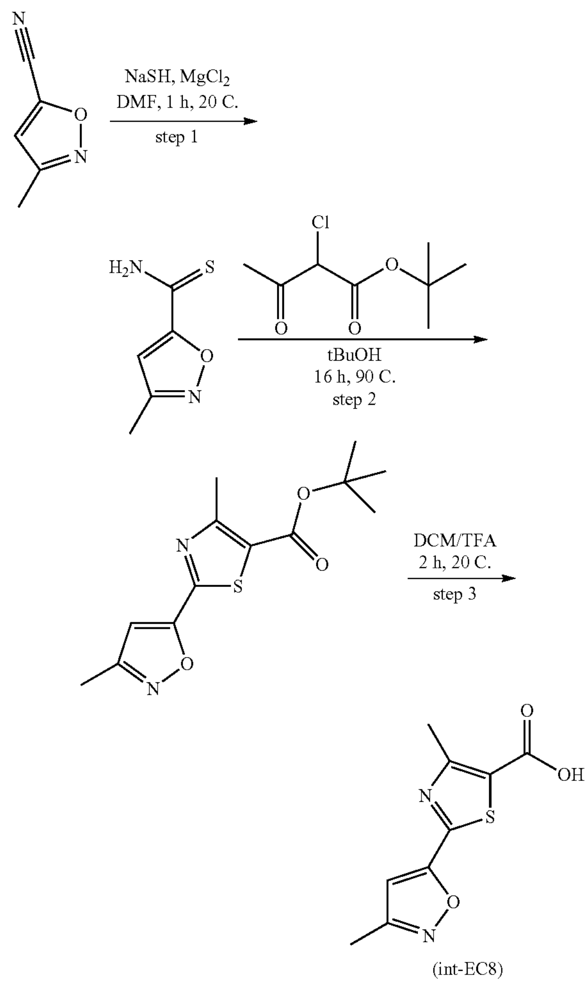

(int-EC8)

Step 1: 3-methylisoxazole-5-carbonitrile (1 g, 9.25 mmol) was added to a solution of sodium hydrogen sulfide (70% in $H_2O$) (1.48 g, 18.50 mmol) and $MgCl_2$ (0.88 g, 9.25 mmol) in DMF (10 mL) and the solution was then stirred at 20° C. for 1 h. Ethyl acetate and water were added to the reaction mixture, and the water phase was then washed with ethyl acetate. The organic layers were dried ($MgSO_4$) and concentrated to give 3-methylisoxazole-5-carbothioamide. LCMS (method e) m/z 143.1 $[M+H]^+$, $t_R$=0.52 min. $^1H$ NMR (400 MHz, DMSO-$d_6$) δ ppm 10.21 (s, 1H), 9.83 (s, 1H), 6.95 (s, 1H), 2.27 (s, 3H).

Step 2: 3-Methylisoxazole-5-carbothioamide (0.858 g, 5.19 mmol) was added to a solution of tert-butyl 2-chloro-3-oxobutanoate (1 g, 5.19 mmol) in t-BuOH (20 mL) and the reaction mixture was stirred at 90° C. for 16 h. After cooling to rt, the reaction mixture was concentrated and the crude product was purified by column chromatography (0-40% ethyl acetate in cyclohexane) to give tert-butyl 4-methyl-2-(3-methylisoxazol-5-yl)thiazole-5-carboxylate. LCMS (method e) m/z 281.2 $[M+H]^+$, $t_R$=1.35 min. $^1H$ NMR (400 MHz, DMSO-$d_6$) δ ppm 7.15 (s, 1H), 2.68 (s, 3H), 2.33 (s, 3H), 1.55 (s, 9H).

Step 3: TFA (5 mL) was added to a solution of tert-butyl 4-methyl-2-(3-methylisoxazol-5-yl)thiazole-5-carboxylate (440 mg, 1.57 mmol) in $CH_2Cl_2$ (10 mL). The solution was then stirred at rt for 2 h. The reaction mixture was concentrated to give 4-methyl-2-(3-methylisoxazol-5-yl)thiazole-5-carboxylic acid (int-EC8). LCMS (method e) m/z 225.1 $[M+H]^+$, $t_R$=0.62 min. $^1H$ NMR (400 MHz, DMSO-$d_6$) δ ppm 13.76 (s, 1H), 7.14 (s, 1H), 2.69 (s, 3H), 2.33 (s, 3H).

Synthesis of 4-chloro-2-(isopropylcarbamoyl)thiazole-5-carboxylic acid (int-EC9)

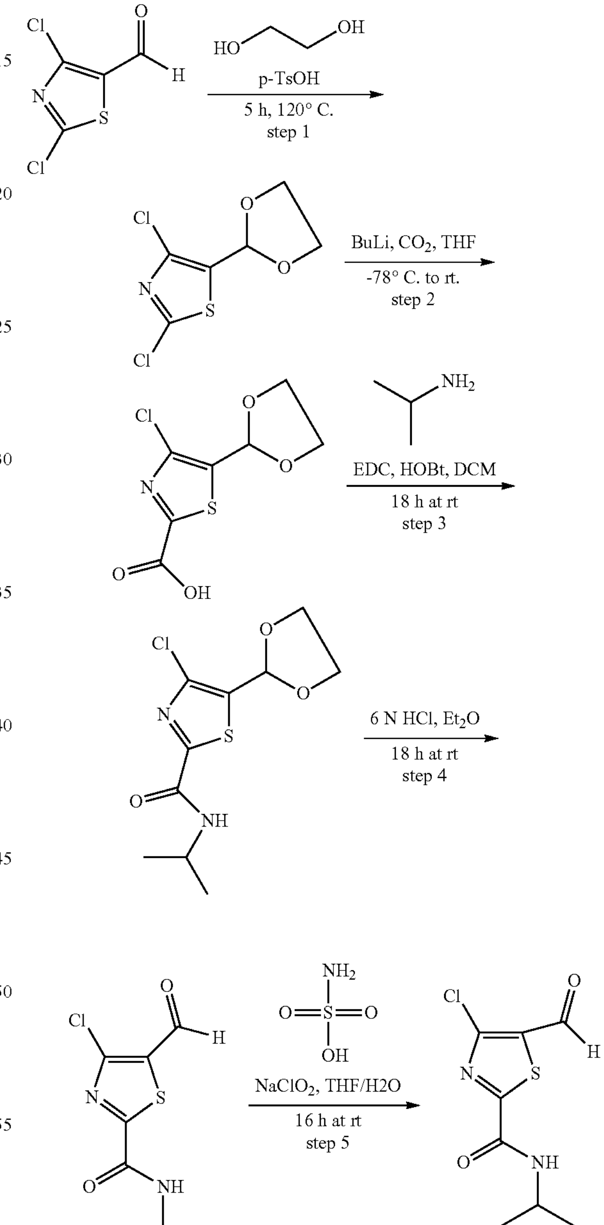

(int-EC9)

Step 1: Ethyleneglycol (4.6 mL, 82 mmol) and p-TsOH (260 mg, 1.37 mmol) were added to a solution of 2,4-dichlorothiazole-5-carbaldehyde (5.0 g, 27.5 mmol) in toluene (60 mL) and the mixture was stirred at reflux for 5 h. The reaction was cooled to rt, poured into 20% $Na_2CO_3$ (120 mL) and the solution was extracted twice with ethyl acetate. The combined organic phase was washed with $H_2O$ and brine, dried ($Na_2SO_4$) and concentrated. The residue was purified by column chromatography (10% ethyl acetate in cyclohexane) to give 2,4-dichloro-5-(1,3-dioxolan-2-yl)thiazole. LCMS (method b) m/z 228.0 $[M+H]^+$, $t_R$=0.96 min. $^1H$ NMR (400 MHz, DMSO-$d_6$) δ ppm 6.05 (s, 1H), 4.08-4.01 (m, 2H), 4.00-3.93 (m, 2H).

Step 2: n-Butyllithium (1.6M hexane solution, 87 mL, 13.9 mmol) was added at −78° C. to a solution of 2,4-dichloro-5-(1,3-dioxolan-2-yl)thiazole (3.0 g, 13.27 mmol) in THF (20 mL) and the mixture was stirred at −78° C. for 20 min. Solid carbon dioxide (20 g) was then introduced and the reaction mixture was gradually warmed to rt and stirred at rt for 16 h. The resulting suspension was concentrated and the crude product was suspended in ethyl acetate and the solid was collected by filtration to obtain 4-chloro-5-(1,3-dioxolan-2-yl)thiazole-2-carboxylic acid. LCMS (method b) m/z=236.2 $[M+H]^+$, $t_R$=0.39 min. $^1H$ NMR (400 MHz, DMSO-$d_6$) δ ppm 5.98 (s, 1H), 4.09-4.00 (m, 2H), 4.00-3.90 (m, 2H) (COOH proton not seen).

Step 3: Propan-2-amine (1.2 mL, 14.0 mmol) and EDC (3.65 g, 19.10 mmol) were added to a mixture of 4-chloro-5-(1,3-dioxolan-2-yl)thiazole-2-carboxylic acid (3.0 g, 12.73 mmol), HOBt (2.43 mg, 15.28 mmol) and $Et_3N$ (2.3 mL, 16.55 mmol) in $CH_2Cl_2$ (120 mL) and the suspension was stirred overnight at rt. The reaction mixture was concentrated and treated with ethyl acetate and 1N HCl. The combined organic layer was washed with sat. $NaHCO_3$, brine, dried ($Na_2SO_4$) and concentrated to give 4-chloro-5-(1,3-dioxolan-2-yl)-N-isopropylthiazole-2-carboxamide. LCMS (method b) m/z 277.1 $[M+H]^+$, $t_R$=0.94 min. $^1H$ NMR (400 MHz, DMSO-$d_6$) δ ppm 8.84 (d, J=8.3 Hz, 1H), 6.12 (s, 1H), 4.15-3.94 (m, 5H), 1.17 (d, J=6.6 Hz, 6H).

Step 4: 6M HCl (3.0 mL, 18.07 mmol) was added at rt to a solution of 4-chloro-5-(1,3-dioxolan-2-yl)-N-isopropylthiazole-2-carboxamide (1.0 g, 3.61 mmol) in $Et_2O$ (36.0 mL) and the solution was stirred for 16 h at rt. Then the pH of the mixture was adjusted to 7-8 with sat. $NaHCO_3$ and the organic layer was separated. The aqueous layer was extracted with $Et_2O$ and combined organic extracts were washed with brine, dried ($Na_2SO_4$) and concentrated to give 4-chloro-5-formyl-N-isopropylthiazole-2-carboxamide. LCMS (method b) m/z=233.2 $[M+H]^+$, $t_R$=0.86 min. $^1H$ NMR (400 MHz, DMSO-$d_6$) δ ppm 10.01 (s, 1H), 9.09 (d, J=8.4 Hz, 1H), 4.24-3.94 (m, 1H), 1.19 (d, J=6.6 Hz, 6H).

Step 5: A mixture of sulfamic acid (815 mg, 8.38 mmol) and $NaClO_2$ (947 mg, 8.38 mmol) in water (5 mL) was added to a solution of 4-chloro-5-formyl-N-isopropylthiazole-2-carboxamide (1.3 g, 2.15 mmol) in THF (33 mL) and water (18 mL) and the mixture was stirred for 16 h at rt. The reaction was quenched with $H_2O$ and the mixture was extracted twice with $Et_2O$. The organic layers were combined and washed with 0.5M NaOH. The water phase containing the product was acidified with conc. HCl and the resulting fine suspension was stirred in an ice bath for 30 min before the solid was filtered off and dried in high vacuum to provide 4-chloro-2-(isopropylcarbamoyl)thiazole-5-carboxylic acid (int-EC9). LCMS (method b) m/z=249.1 $[M+H]^+$, $t_R$=0.52 min. $^1H$ NMR (400 MHz, DMSO-$d_6$) δ ppm 14.14 (s, 1H), 8.97 (d, J=8.3 Hz, 1H), 4.28-3.95 (m, 1H), 1.18 (d, J=6.6 Hz, 6H)

Synthesis of 2-(3,6-dihydro-2H-pyran-4-yl)-4-methylthiazole-5-carboxylic acid (int-EC10)

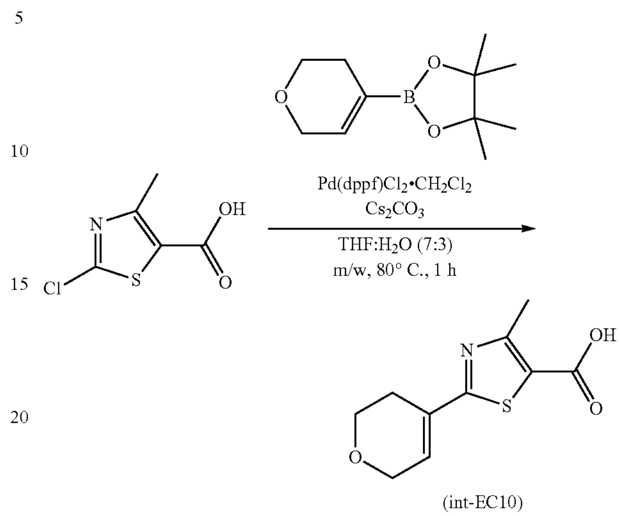

(int-EC10)

A mixture of cesium carbonate (550 mg, 1.689 mmol), 2-(3,6-dihydro-2H-pyran-4-yl)-4,4,5,5-tetramethyl-1,3,2-dioxaborolane (130 mg, 0.619 mmol) and 2-chloro-4-methylthiazole-5-carboxylic acid (100 mg, 0.563 mmol) in THF (2.6 mL) and water (1.1 mL) was purged with argon for 5 min. $Pd(dppf)Cl_2 \cdot CH_2Cl_2$ (46.0 mg, 0.056 mmol) was added and the resulting solution was heated in a microwave oven at 80° C. for 1 h. After cooling to rt, the reaction mixture was concentrated and the residue purified using preparative HPLC to provide a solid that was dissolved in $CH_2Cl_2$ (10 mL) and treated with sat. $NaHCO_3$ (10 mL). The aqueous phase was extracted with $CH_2Cl_2$ and the combined organic phases were dried ($MgSO_4$) and concentrated to give 2-(3,6-dihydro-2H-pyran-4-yl)-4-methylthiazole-5-carboxylic acid (int-EC10). LCMS (method b) m/z 226.1 $[M+H]^+$; $t_R$=0.63 mins, $^1H$ NMR (400 MHz, DMSO-$d_6$) δ ppm 13.29 (s, 1H), 6.84-6.77 (m, 1H), 4.25 (d, J=2.9 Hz, 2H), 3.80 (t, J=5.4 Hz, 2H), 2.60 (s, 3H), 2.59-2.55 (m, 2H).

Synthesis of 4-chloro-2-(cyclopent-1-en-1-yl)thiazole-5-carboxylic acid (int-EC11)

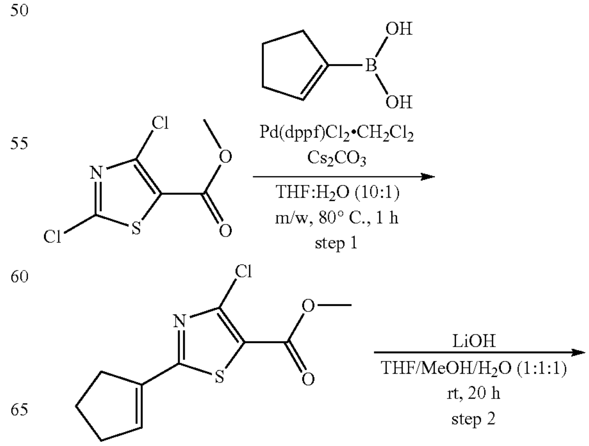

-continued

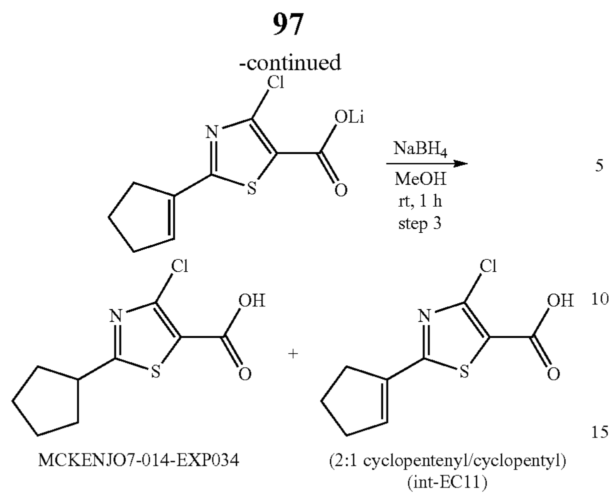

MCKENJO7-014-EXP034

(2:1 cyclopentenyl/cyclopentyl)
(int-EC11)

Step 1: A mixture of cesium carbonate (615 mg, 1.89 mmol), cyclopent-1-en-1-ylboronic acid (116 mg, 1.04 mmol) and methyl 2,4-dichlorothiazole-5-carboxylate (200 mg, 0.94 mmol) in THF (2.4 mL) and water (2.4 mL) was purged with argon for 5 min. before $Pd(dppf)Cl_2{\cdot}CH_2Cl_2$ (77 mg, 0.094 mmol) was added and the resulting mixture was heated in a microwave at 80° C. for 1 h. After cooling to rt, the reaction mixture was concentrated and the residue was purified using preparative HPLC. The obtained solid was dissolved in $CH_2Cl_2$ (10 mL) and treated with saturated aqueous sodium bicarbonate solution (10 mL). The aqueous phase was extracted with $CH_2Cl_2$ and the combined organic phases were dried ($MgSO_4$) and concentrated to give methyl 4-chloro-2-(cyclopent-1-en-1-yl)thiazole-5-carboxylate. M/z 244.1 $[M+H]^+$; $t_R$=1.23 mins (LCMS condition b), $^1H$ NMR (400 MHz, DMSO-$d_6$) δ ppm 6.91-6.82 (m, 1H), 3.83 (s, 3H), 2.77-2.68 (m, 2H), 2.62-2.54 (m, 2H), 2.06-1.94 (m, 2H).

Step 2: 2M LiOH (aq.) (0.42 mL, 0.84 mmol) was added to a mixture of methyl 4-chloro-2-(cyclopent-1-en-1-yl) thiazole-5-carboxylate (195 mg, 0.80 mmol) in a 1:1:1 mixture of MeOH/THF/$H_2O$ (8 mL) and the mixture was stirred at rt for 20 h. The mixture was then concentrated and used in the next step without further purification.

Step 3: To a stirred solution of lithium 4-chloro-2-(cyclopent-1-en-1-yl)thiazole-5-carboxylate (190 mg, 0.81 mmol) in MeOH (8.064 m) was added $NaBH_4$ (153 mg, 4.03 mmol) in one portion at rt and the resulting solution was stirred at rt for 1 h. The reaction mixture was concentrated, the residue dissolved in $CH_2Cl_2$ (20 mL) and treated with 1N HCl (10 mL). The aqueous phase was extracted with $CH_2Cl_2$ and the combined organic phases were dried ($MgSO_4$) and concentrated to give an inseparable 2:1 mixture of cyclopentenyl and cyclopentyl compound. Cyclopentenyl: M/z 230.1 $[M+H]^+$; $t_R$=0.81 mins LCMS (method b), cyclopentyl: M/z 232.1 $[M+H]^+$; $t_R$=0.83 mins. LCMS (method b).

Synthesis of 2-(isoxazol-5-yl)-4-methylthiazole-5-carboxylic acid (int-EC12)

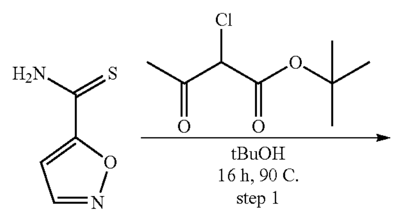

-continued

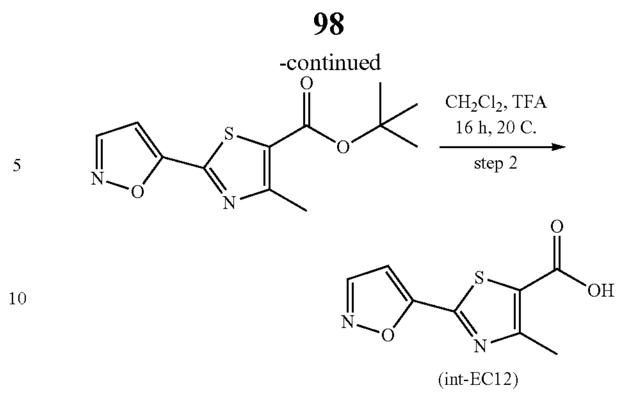

(int-EC12)

Step 1: Isoxazole-5-carbothioamide (0.665 g, 5.19 mmol) was added to a solution of tert-butyl 2-chloro-3-oxobutanoate (1 g, 5.19 mmol) in t-BuOH (10 mL) and the mixture was stirred at 90° C. for 16 h. After cooling to rt, the reaction mixture was concentrated and the crude was purified by column chromatography (0-50% ethyl acetate in cyclohexane) to give tert-butyl 2-(isoxazol-5-yl)-4-methylthiazole-5-carboxylate. LCMS (method a) m/z 267.3 $[M+H]^+$, $t_R$=1.28 min. $^1H$ NMR (400 MHz, DMSO-$d_6$): δ ppm 8.85 (d, J=2.0 Hz, 1H), 7.29 (d, J=2.0 Hz, 1H), 2.69 (s, 3H), 1.55 (s, 9H).

Step 2: TFA (3 mL) was added to a solution of tert-butyl 2-(isoxazol-5-yl)-4-methylthiazole-5-carboxylate (300 mg, 1.126 mmol) in $CH_2Cl_2$ (6 mL) and the solution was stirred at rt for 16 h. Then, the reaction mixture was concentrated to give 2-(isoxazol-5-yl)-4-methylthiazole-5-carboxylic acid (int-EC12). LCMS (method a) m/z 211.2 $[M+H]^+$, $t_R$=0.52 min. $^1H$ NMR (400 MHz, DMSO-$d_6$): δ ppm 13.78 (s, 1H), 8.85 (d, J=2.0 Hz, 1H), 7.28 (d, J=2.0 Hz, 1H), 2.70 (s, 3H).

Synthesis of 4-chloro-2-(6-methoxypyridin-3-yl) thiazole-5-carboxylic acid (int-EC13)

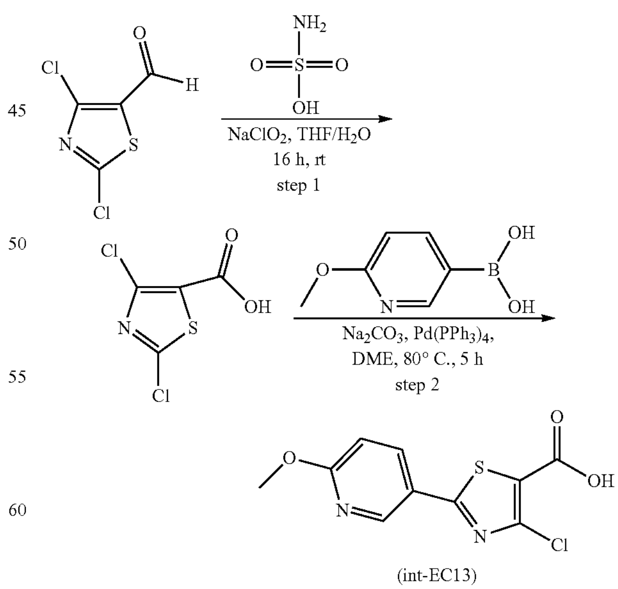

(int-EC13)

Step 1: A mixture of sulfamic acid (4.0 g, 41.2 mmol) and $NaClO_2$ (4.66 g, 4.66 mmol) in water (2 mL) was added to a solution of 2,4-dichlorothiazole-5-carbaldehyde (5 g, 27.5 mmol) in THF (150 mL) and water (100 mL) and the mixture was stirred at rt for 16 h. The reaction was quenched with $H_2O$ and extracted with $Et_2O$. The combined organic layers were washed with 0.5 M NaOH. The water phase was then acidified with conc. HCl and the solution was extracted with $Et_2O$, washed with brine, dried ($Na_2SO_4$) and concentrated. The residue was dried on high vacuum to provide 2,4-dichlorothiazole-5-carboxylic acid which was used in the next step without further purification. LCMS (method b) m/z 196.0 $[M+H]^+$, $t_R$=0.46 min. $^1H$ NMR (400 MHz, DMSO-$d_6$): δ ppm 14.20 (s, 1H).

Step 2: $Pd(PPh_3)_4$ (146 mg, 0.126 mmol) was added at rt to degassed mixture of (6-methoxypyridin-3-yl)boronic acid (427 mg, 2.65 mmol), 2M $Na_2CO_3$ (4.4 mL, 8.8 mmol) and 2,4-dichlorothiazole-5-carboxylic acid (500 mg, 2.52 mmol) in DME (13 mL) and the mixture heated at 80° C. for 5 h. After cooling, the reaction mixture was treated with water and washed with ethyl acetate. The water phase was acidified with conc. HCl and the white precipitate was filtered off cold to give 4-chloro-2-(6-methoxypyridin-3-yl)thiazole-5-carboxylic acid (int-EC13). LCMS (method b) m/z 271.2 $[M+H]^+$, $t_R$=0.71 min. $^1H$ NMR (400 MHz, DMSO-$d_6$): δ ppm 13.88 (s, 1H), 8.83 (d, J=2.5 Hz, 1H), 8.26 (dd, J=8.7, 2.6 Hz, 1H), 6.99 (d, J=8.8 Hz, 1H), 3.95 (s, 3H).

Synthesis of 4-chloro-2-(6-(difluoromethoxy)pyridin-3-yl)thiazole-5-carboxylic acid (int-EC14)

(int-EC14)

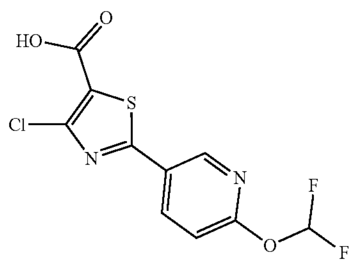

4-chloro-2-(6-(difluoromethoxy)pyridin-3-yl)thiazole-5-carboxylic acid (int-EC14) was obtained using an analogous method as that described for the synthesis of 4-chloro-2-(6-methoxypyridin-3-yl)thiazole-5-carboxylic acid (int-EC13) except (6-methoxypyridin-3-yl)boronic acid was replaced with 2-(difluoromethoxy)-5-(4,4,5,5-tetramethyl-1,3,2-dioxaborolan-2-yl)pyridine. LCMS (method b) m/z 307.0 $[M+H]^+$, $t_R$=0.77 min. $^1H$ NMR (400 MHz, DMSO-$d_6$) δ ppm 14.02 (s, 1H), 8.90 (d, J=2.5 Hz, 1H), 8.49 (dd, J=8.6, 2.5 Hz, 1H), 7.79 (t, J=72.2 Hz, 1H), 7.27 (d, J=8.7 Hz, 1H).

Synthesis of 4-chloro-2-cyclopropylthiazole-5-carboxylic acid (int-EC15)

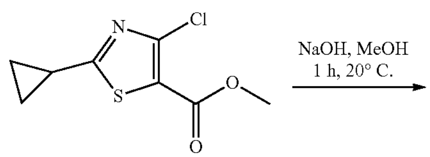

-continued

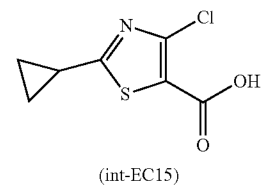

(int-EC15)

NaOH (13.78 mL, 13.78 mmol) was added to a solution of methyl 4-chloro-2-cyclopropylthiazole-5-carboxylate (1 g, 4.59 mmol) in MeOH (20 mL) and the solution was stirred at rt for 1 h. MeOH was removed under reduced pressure and the remaining solution was washed with $CH_2Cl_2$. The water phase was acidified with 1N HC and extracted with ethyl acetate. The combined organic layers were dried ($MgSO_4$) and concentrated to provide 4-chloro-2-cyclopropylthiazole-5-carboxylic acid (int-EC15). LCMS (method e) m/z 204.0 $[M+H]^+$, $t_R$=0.57 min. $^1H$ NMR (400 MHz, DMSO-$d_6$): δ ppm 13.62 (s, 1H), 2.49-2.40 (m, 1H), 1.28-1.15 (m, 2H), 1.11-0.97 (m, 2H).

Synthesis of 4-chloro-2-(1-(difluoromethyl)-1H-pyrazol-4-yl)thiazole-5-carboxylic acid (int-EC16)

(int-EC16)

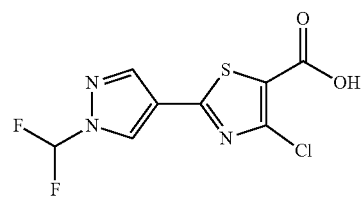

4-Chloro-2-(1-(difluoromethyl)-1H-pyrazol-4-yl)thiazole-5-carboxylic acid (int-EC16) was obtained using an analogous method as that described for the synthesis of 4-chloro-2-(6-methoxypyridin-3-yl)thiazole-5-carboxylic acid (int-EC13) except (6-methoxypyridin-3-yl)boronic acid was replaced with 1-(difluoromethyl)-4-(4,4,5,5-tetramethyl-1,3,2-dioxaborolan-2-yl)-1H-pyrazole. LCMS (method b) m/z 279.9 $[M+H]^+$, $t_R$=0.61 min. TH NMR (400 MHz, DMSO-$d_6$): δ ppm 8.87 (s, 1H), 8.26 (s, 1H), 7.85 (t, J=58.8 Hz, 1H).

Synthesis of 4-chloro-2-(3,6-dihydro-2H-pyran-4-yl)thiazole-5-carboxylic acid (int-EC17)

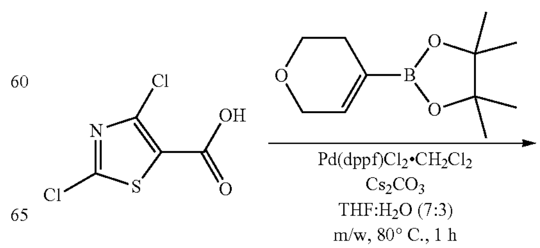

-continued

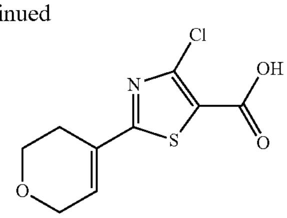

(int-EC17)

Pd(dppf)$Cl_2$·$CH_2Cl_2$ (124 mg, 0.151 mmol) was added at rt to a degassed mixture of cesium carbonate (1.48 g, 4.54 mmol), 2-(3,6-dihydro-2H-pyran-4-yl)-4,4,5,5-tetramethyl-1,3,2-dioxaborolane (350 mg, 1.666 mmol) and 2,4-dichlorothiazole-5-carboxylic acid (300 mg, 1.515 mmol) in THF (7.07 mL) and water (3.03 mL) and the resulting suspension was then heated in a microwave oven at 80° C. for 1 h. After cooling to rt, the reaction mixture was concentrated and the crude product was purified using preparative HPLC. The HPLC fractions were concentrated under reduced pressure to afford a white solid which was dissolved in $CH_2Cl_2$ (10 mL) and diluted with sat. $NaHCO_3$ solution (10 mL). The aqueous phase was separated and extracted with $CH_2Cl_2$ and the combined organic fractions were dried ($MgSO_4$) and then concentrated under reduced pressure to give 4-chloro-2-(3,6-dihydro-2H-pyran-4-yl)thiazole-5-carboxylic acid (int-EC17). LCMS (method b) m/z 246.1 $[M+H]^+$, $t_R$=0.59 min.

Synthesis of 4-methyl-2-(tetrahydro-2H-pyran-4-yl) thiazole-5-carboxylic acid (int-EC18)

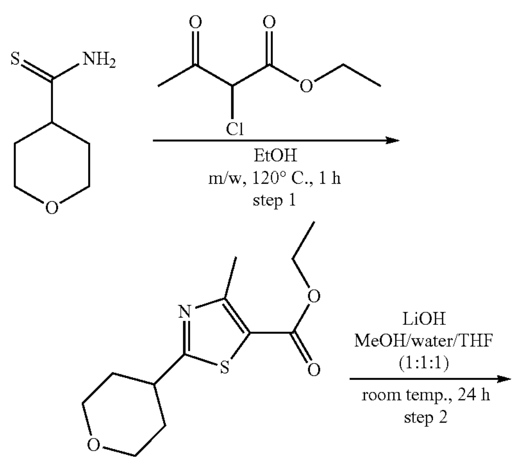

-continued

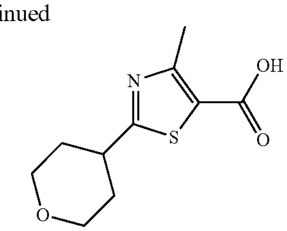

(int-EC18)

4-Methyl-2-(tetrahydro-2H-pyran-4-yl)thiazole-5-carboxylic acid (int-EC18) was obtained using a method analogous to that described for the synthesis of 4-methyl-2-(6-(trifluoromethyl)pyridin-3-yl)thiazole-5-carboxylic acid (int-EC7), except 6-(trifluoromethyl)pyridine-3-carbothioamide was replaced with tetrahydro-2H-pyran-4-carbothioamide. LCMS (method b) m/z 228.1 $[M+H]^+$, $t_R$=0.60 min.

Synthesis of 4-chloro-2-methylthiazole-5-carboxylic acid (int-EC19)

(int-EC19)

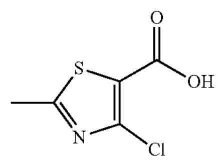

4-Chloro-2-methylthiazole-5-carboxylic acid (int-EC19) was obtained using an analogous method as that described in step 2 for the synthesis of 4-chloro-2-(6-methoxypyridin-3-yl)thiazole-5-carboxylic acid (int-EC13) except (6-methoxypyridin-3-yl)boronic acid was replaced with 2,4,6-trimethyl-1,3,5,2,4,6-trioxatriborinane, Pd($PPh_3$) was replaced with Pd(dppf)$Cl_2$·$CH_2Cl_2$ and dioxane was used as solvent. LCMS (method e) m/z 177.9 $[M+H]^+$, $t_R$=0.38 min. $^1$H NMR (DMSO-$d_6$, 400 MHz): δ ppm 13.69 (s, 1H), 2.67 (s, 3H).

The table below lists the carboxylic acid type EC intermediates which were purchased.

| Intermediate Code | Compound Structure | Compound Name | Source |
|---|---|---|---|
| Int-EC20 | 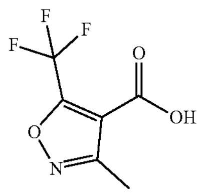 | 3-methyl-5-(trifluoromethyl)isoxazole-4-carboxylic acid | ABCR (AB231552) |

-continued

| Intermediate Code | Compound Structure | Compound Name | Source |
|---|---|---|---|
| Int-EC21 | 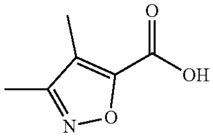 | 3,4-dimethylisoxazole-5-carboxylic acid | ChemCollect (KL004599) |
| Int-EC22 | 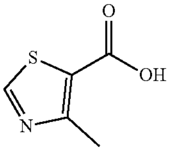 | 4-methylthiazole-5-carboxylic acid | Enamine (EN300-29658) |
| Int-EC23 | 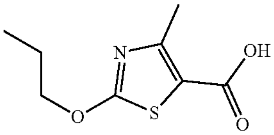 | 4-methyl-2-propoxythiazole-5-carboxylic acid | ABCR (AB413629) |
| Int-EC24 | 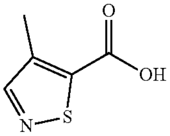 | 4-methylisothiazole-5-carboxylic acid | Fluorochem (317769) |
| Int-EC25 | 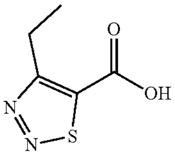 | 4-ethyl-1,2,3-thiadiazole-5-carboxylic acid | Enamine (EN300-13869) |
| Int-EC26 | 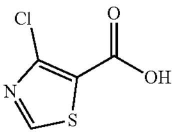 | 4-chlorothiazole-5-carboxylic acid | Enamine (EN300-43224) |
| Int-EC27 | 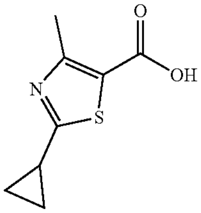 | 2-cyclopropyl-4-methylthiazole-5-carboxylic acid | UkrOrgSynthesis (BBV-5106372) |
| Int-EC28 | 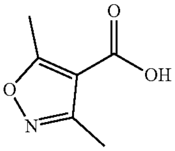 | 3,5-dimethylisoxazole-4-carboxylic acid | Lancaster (7399) |
| Int-EC29 | 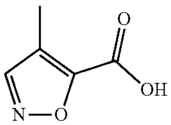 | 4-methylisoxazole-5-carboxylic acid | Atlantic (CA00708) |

-continued

| Intermediate Code | Compound Structure | Compound Name | Source |
|---|---|---|---|
| Int-EC30 | 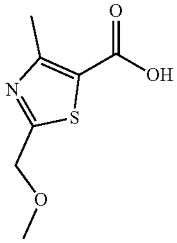 | 2-(methoxymethyl)-4-methylthiazole-5-carboxylic acid | Enamine (EN300-119790) |
| Int-EC31 | 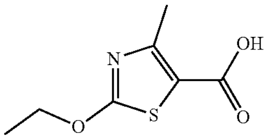 | 2-ethoxy-4-methylthiazole-5-carboxylic acid | ABCR (AB416692) |
| Int-EC32 | 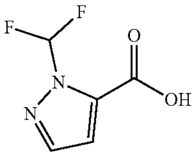 [SMILES: O=C(O)c1ccnn1C(F)F] | 1-(difluoromethyl)-1H-pyrazole-5-carboxylic acid | Enamine (EN300-83620) |
| Int-EC33 | 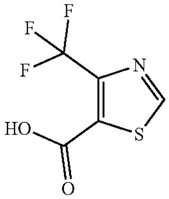 [SMILES: O=C(O)c1scnc1C(F)(F)F] | 4-(trifluoromethyl)thiazole-5-carboxylic acid | ABCR (AB455230) |
| Int-EC34 | 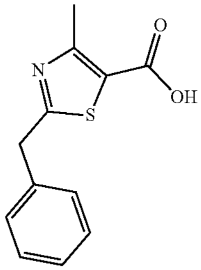 [SMILES: Cc1nc(Cc2ccccc2)sc1C(=O)O] | 2-benzyl-4-methylthiazole-5-carboxylic acid | ABCR (AB303090) |
| Int-EC35 | 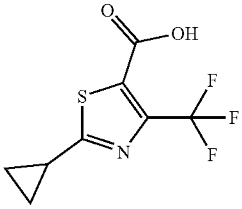 [SMILES: O=C(O)c1sc(C2CC2)nc1C(F)(F)F] | 2-cyclopropyl-4-(trifluoromethyl)thiazole-5-carboxylic acid | Aldrich (ENA388191868) |
| Int-EC36 | 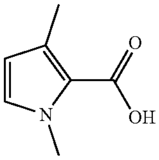 | 1,3-dimethyl-1H-pyrrole-2-carboxylic acid | Princeton BioMolecular Resarch Inc. |

-continued

| Intermediate Code | Compound Structure | Compound Name | Source |
|---|---|---|---|
| Int-EC37 | 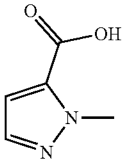 | 1-methyl-1H-pyrazole-5-carboxylic acid | ABCR (AB352395) |

Synthesis of N-(5-amino-1-methyl-1H-pyrazol-3-yl) isobutyramide (int-EC38)

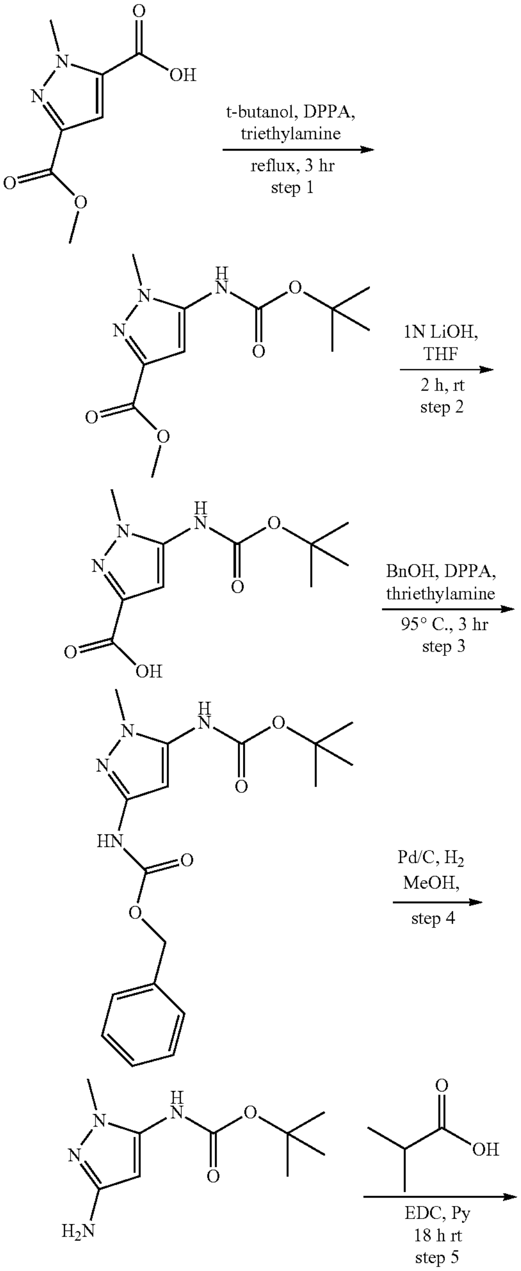

-continued

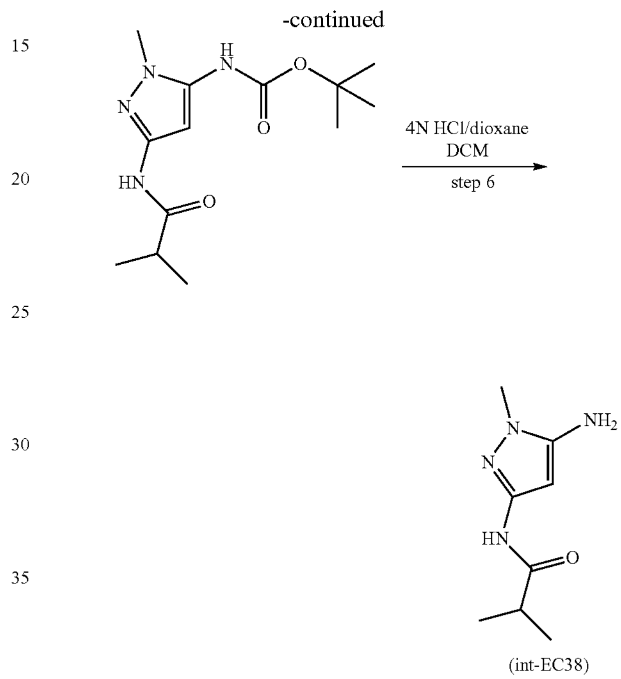

(int-EC38)

Step 1: Diphenyl phosphoryl azidate (DPPA) (9.0 mL, 407 mmol) and $Et_3N$ (4.2 mL, 30.0 mmol) were added to a solution of 3-(ethoxycarbonyl)-1-methyl-1H-pyrazole-5-carboxylic acid (5.0 g, 27.2 mmol) in tert-butanol (90 mL) and the reaction mixture stirred at 95° C. for 3 h. After cooling, the reaction Mixture was concentrated and the residue was treated with water and ethyl acetate. The water phase was extracted with ethyl acetate. The combined organic phases were washed with brine, dried ($Na_2SO_4$) and concentrated to give crude product which was purified by column chromatography (20-70% ethyl acetate in cyclohexane) to give methyl 5-((tert-butoxycarbonyl)amino)-1-methyl-1H-pyrazole-3-carboxylate. LCMS (method b) m/z 256.2 $[M+H]^+$, $t_R$=0.78 min. $^1H$ NMR (400 MHz, DMSO-$d_6$) δ ppm 9.51 (s, 1H), 6.53 (s, 1H), 3.77 (s, 3H), 3.73 (s, 3H), 1.46 (s, 9H).

Step 2: 1 M LiOH in $H_2O$ (25 mL, 24.14 mmol) was added to a suspension of methyl 5-((tert-butoxycarbonyl) amino)-1-methyl-1H-pyrazole-3-carboxylate (3.0 g, 11.75 mmol) in THF (45 mL) and the mixture was stirred at rt for 2 h. The THF was evaporated and the residue was treated with water and ethyl acetate. The water phase was acidified with conc. HCl and the resulting white suspension was stirred for 30 min., then filtered off cold and dried under high vacuum to give 5-((tert-butoxycarbonyl)amino)-1-methyl-1H-pyrazole-3-carboxylic acid. LCMS (method b) m/z 242.2 $[M+H]^+$, $t_R$=0.61 min. $^1H$ NMR (400 MHz, DMSO-$d_6$) δ ppm 12.50 (s, 1H), 9.43 (s, 1H), 6.45 (s, 1H), 3.70 (s, 3H), 1.46 (s, 9H).

Step 3: DPPA (0.95 mL, 4.29 mmol) and $Et_3N$ (0.44 mL, 3.15 mmol) were added to a solution 5-((tert-butoxycarbonyl)amino)-1-methyl-1H-pyrazole-3-carboxylic acid (690 mg, 2.86 mmol) in benzylacohol (9.0 mL) and the reaction mixture was stirred at 95° C. for 3 h. After cooling to rt, the reaction mixture was treated with water and ethyl acetate and the water phase was extracted with ethyl acetate. The combined organic layers were washed with brine, dried ($Na_2SO_4$) and concentrated to give crude product which was purified by column chromatography (10-50% ethyl acetate in cyclohexane) to give benzyl tert-butyl (1-methyl-1H-pyrazole-3,5-diyl)dicarbamate. LCMS (method b) m/z 347.3 $[M+H]^+$, $t_R$=0.98 min. $^1H$ NMR (400 MHz, DMSO-$d_6$) δ ppm 9.83 (s, 1H), 9.25 (s, 1H), 7.43-7.37 (m, 4H), 7.36-7.27 (m, 1H), 6.14 (s, 1H), 5.11 (s, 2H), 3.50 (s, 3H), 1.45 (s, 9H).

Step 4: Benzyl tert-butyl (1-methyl-1H-pyrazole-3,5-diyl) dicarbamate (480 mg, 1.39 mmol) in MeOH (25 mL) was hydrogenated using H cube (full $H_2$, Pd/C cartridge, 30° C., 1 h). The solution was then concentrated to give a crude product which was treated with 0.5 M HCl and ethyl acetate. The water phase was made basic with conc. NaOH and extracted with ethyl acetate. The organic layers were washed with brine, dried ($Na_2SO_4$) and concentrated to give tert-butyl (3-amino-1-methyl-1H-pyrazol-5-yl)carbamate. LCMS (method b) m/z 213.4 $[M+H]^+$, $t_R$=0.55 min. $^1H$ NMR (400 MHz, DMSO-$d_6$) δ ppm 9.00 (s, 1H), 5.28 (s, 1H), 4.39 (s, 2H), 3.36 (s, 3H), 1.44 (s, 9H).

Step 5: Pyridine (171 μl, 2.12 mmol) and EDC (162 mg, 0.848 mmol) were added at rt to a solution of tert-butyl (3-amino-1-methyl-1H-pyrazol-5-yl)carbamate (90 mg, 0.424 mmol) and isobutyric acid (44 μl, 0.466 mmol) in acetonitrile (4 mL). After stirring at rt for 18 h, the reaction mixture was treated with water and the mixture was concentrated and extracted with ethyl acetate. The combined organic layers were washed with water and brine, dried ($Na_2SO_4$) and concentrated to give tert-butyl (3-isobutyramido-1-methyl-1H-pyrazol-5-yl)carbamate. LCMS (method b) m/z 283.5 $[M+H]^+$, $t_R$=0.77 min. $^1H$ NMR (400 MHz, DMSO-da) δ ppm 10.10 (s, 1H), 9.23 (s, 1H), 6.32 (s, 1H), 3.52 (s, 3H), 2.62-2.52 (m, 1H), 1.46 (s, 9H), 1.04 (d, J=6.8 Hz, 6H).

Step 6: 4M HCl in dioxane (1.24 mL, 4.96 mmol) was added to a solution of tert-butyl (3-isobutyramido-1-methyl-1H-pyrazol-5-yl)carbamate (70 mg, 0.248 mmol) in $CH_2Cl_2$ (2.5 mL) and the mixture was stirred at rt for 1 h. The reaction mixture was then concentrated and the oily residue was dissolved in $CH_2Cl_2$ and concentrated, dissolved in $Et_2O$ and concentrated to give N-(5-amino-1-methyl-1H-pyrazol-3-yl)isobutyramide (int-EC38). LCMS (method b) m/z 183.2 $[M+H]^+$, $t_R$=0.39 min. $^1H$ NMR (400 MHz, DMSO-$d_6$) δ ppm 11.25 (s, 1H), 5.50 (s, 1H), 3.93 (s, 3H), 2.69-2.57 (m, 1H), 1.10 (d, J=6.8 Hz, 6H).

Synthesis of 5-amino-4-chloro-N-isopropylthiazole-2-carboxamide (int-EC39)

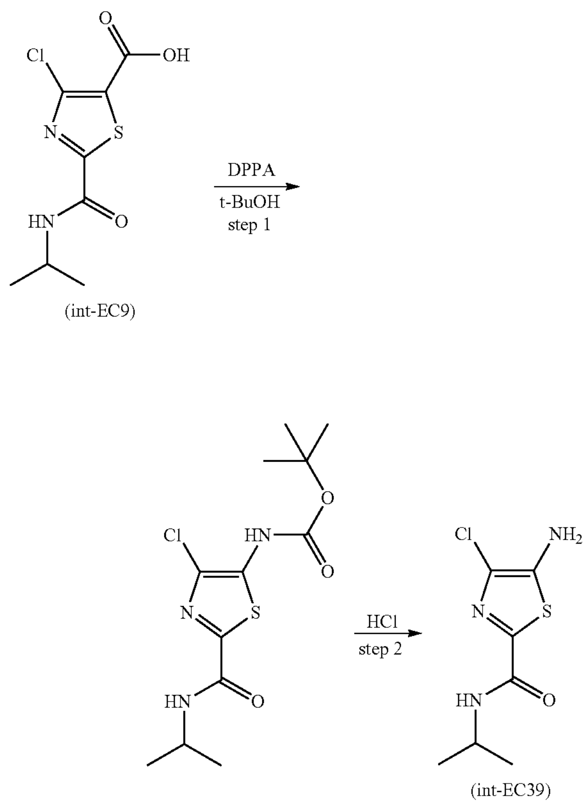

(int-EC9)

(int-EC39)

Step 1: Diphenyl phosphoryl azid (1.75 mL, 7.84 mmol) and $Et_3N$ (0.80 mL, 5.75 mmol) were added at rt to a solution of 4-chloro-2-(isopropylcarbamoyl)thiazole-5-carboxylic acid (int-EC9, 1.30 g, 5.23 mmol) in tert-butanol (17 mL) and the reaction mixture was stirred at 95° C. for 3 h. After cooling to rt, the solvent was evaporated and the reaction mixture was treated with water and ethyl acetate. The water phase was extracted with ethyl acetate and the organic phases were washed with brine, dried ($Na_2SO_4$) and concentrated. The crude product was purified by column chromatography (10-20% ethyl acetate in cyclohexane) to give tert-butyl (4-chloro-2-(isopropylcarbamoyl)thiazol-5-yl)carbamate. LCMS (method b) m/z 320.2 $[M+H]^+$, $t_R$=1.09 min. $^1H$ NMR (400 MHz, DMSO-$d_6$) δ ppm 10.60 (s, 1H), 8.51 (d, J=8.4 Hz, 1H), 4.31-3.92 (m, 1H), 1.50 (s, 9H), 1.16 (d, J=6.6 Hz, 6H).

Step 2: 4M HCl in dioxane (19 mL, 78 mmol) was added at rt to a solution of tert-butyl (4-chloro-2-(isopropylcarbamoyl)thiazol-5-yl)carbamate (1.25 g, 3.91 mmol) in $CH_2Cl_2$ (39 mL) and the solution stirred at rt for 16 h. The reaction mixture was concentrated and the oily residue was then dissolved in $CH_2Cl_2$ and concentrated, dissolved in $Et_2O$ and concentrated to give 5-amino-4-chloro-N-isopropylthiazole-2-carboxamide (int-EC39). LCMS (method b)

m/z 220.2 $[M+H]^+$, $t_R$=0.73 min. $^1H$ NMR (400 MHz, DMSO-$d_6$) δ ppm 8.16 (d, J=8.4 Hz, 1H), 6.48 (s, 2H), 4.10-3.90 (m, 1H), 1.13 (d, J=6.6 Hz, 6H).

Synthesis of 5-amino-N-(2,2-difluoroethyl)-1-methyl-1H-pyrazole-3-carboxamide (int-EC40)

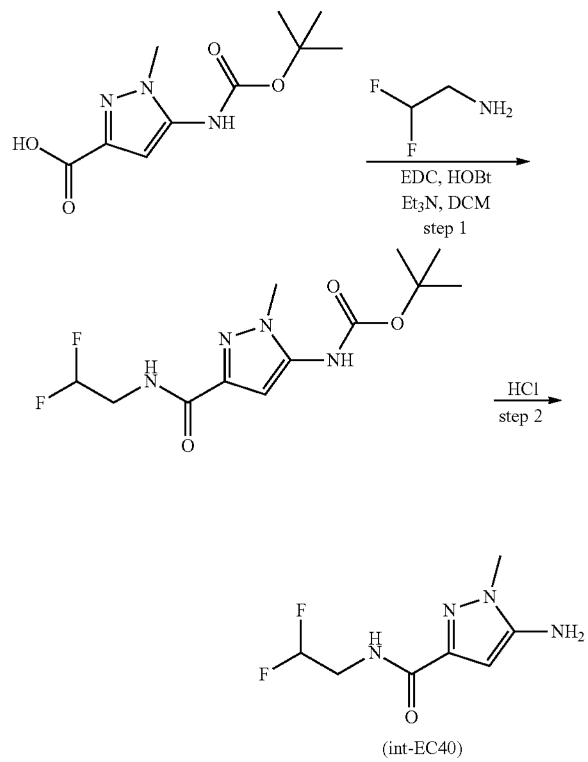

(int-EC40)

Step 1: EDC (574 mg, 3 mmol) was added at rt to a solution of 5-((tert-butoxycarbonyl)amino)-1-methyl-1H-pyrazole-3-carboxylic acid (see step 2 in the synthesis of int-EC38) (121 mg, 0.5 mmol), 2,2-difluoroethanamine (0.042 mL, 0.6 mmol), $Et_3N$ (0.090 mL, 0.65 mmol) and HOBT (81 mg, 0.6 mmol) in $CH_2Cl_2$ (4 mL) and the reaction mixture was stirred at rt for 48 h. The mixture was then washed with sat. $NaHCO_3$ and water, dried ($Na_2SO_4$) and concentrated. The crude product was purified by column chromatography (10-50% ethyl acetate in cyclohexane) to give tert-butyl (3-((2,2-difluoroethyl)carbamoyl)-1-methyl-1H-pyrazol-5-yl)carbamate. LCMS (method b) m/z 305.3 $[M+H]^+$, $t_R$=0.78 min. $^1H$ NMR (400 MHz, DMSO-$d_6$) δ ppm 7.03 (t, J=6.0 Hz, 1H), 6.64 (s, 1H), 6.15 (s, 1H), 5.91 (tt, J=56.1, 4.2 Hz, 1H), 3.85-3.70 (m, 5H), 1.50 (s, 9H).

Step 2: 4 M HCl in dioxane (1.3 mL, 5.2 mmol) was added at rt to a solution of tert-butyl (3-((2,2-difluoroethyl) carbamoyl)-1-methyl-1H-pyrazol-5-yl)carbamate (79 mg 0.26 mmol) in $CH_2Cl_2$ (2.6 mmol) and the reaction mixture was stirred at rt for 2 h. The suspension was concentrated give 5-amino-N-(2,2-difluoroethyl)-1-methyl-1H-pyrazole-3-carboxamide (int-EC40). LCMS (method b) m/z 205.2 $[M+H]^+$, $t_R$=0.39 min. $^1H$ NMR (400 MHz, DMSO-$d_6$) δ ppm 8.23 (t, J=6.2 Hz, 1H), 6.05 (t, J=56.3 Hz, 1H), 5.78 (s, 1H), 3.60-3.56 (m, 8H).

Synthesis of 5-amino-N-isopropyl-4-methylthiazole-2-carboxamide (int-EC41)

(int-EC41)

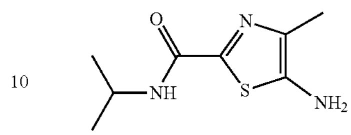

5-amino-N-isopropyl-4-methylthiazole-2-carboxamide (int-EC41) was obtained using an analogous method as that described for the synthesis of 5-amino-N-(2,2-difluoroethyl)-1-methyl-1H-pyrazole-3-carboxamide (int-EC40), except 5-((tert-butoxycarbonyl)amino)-1-methyl-1H-pyrazole-3-carboxylic acid was replaced with 5-((tert-butoxycarbonyl)amino)-4-methylthiazole-2-carboxylic acid and 2,2-difluoroethanamine was replaced with propan-2-amine. LCMS (method b) m/z 200.2 $[M+H]^+$, $t_R$=0.62 min. $^1H$ NMR (400 MHz, DMSO-$d_6$) δ ppm 7.81 (d, J=8.4 Hz, 1H), 6.51 (s, 3H), 4.10-3.92 (m, 1H), 2.16 (s, 3H), 1.13 (d, J=6.6 Hz, 6H).

Note: 5-((tert-butoxycarbonyl)amino)-4-methylthiazole-2-carboxylic acid was obtained using the following procedure:

Step 1: TFA (5.1 mL, 66.3 mmol) was added at rt to a solution of 5-(tert-butyl) 2-ethyl 4-methylthiazole-2,5-dicarboxylate (see step 1 in the synthesis of int-EC2) (0.9 g, 332 mmol) in $CH_2Cl_2$ (33 mL) and the mixture stirred at rt for 2 h. The reaction solution was then concentrated and the oily residue was dissolved in $CH_2Cl_2$, concentrated, dissolved with $Et_2O$ and concentrated under high vacuum to give 2-(ethoxycarbonyl)-4-methylthiazole-5-carboxylic acid. LCMS (method b) m/z 216.1 $[M+H]^+$, $t_R$=0.55 min. $^1H$ NMR (400 MHz, DMSO-$d_3$) δ ppm 13.87 (s, 1H), 4.38 (q, J=7.1 Hz, 2H), 2.68 (s, 3H), 1.33 (t, J=71 Hz, 3H).

Step 2: DPPA (1.10 mL, 5.02 mmol) and triethylamine (513 μl, 3.68 mmol) were added to a solution of 2-(ethoxycarbonyl)-4-methylthiazole-5-carboxylic acid (0.72 g, 3.35 mmol) in tert butanol (12 mL) and the reaction mixture stirred at 95° C. for 3 h. After cooling to rt, the solvent was removed, the residue was treated with water and extracted with ethyl acetate. The combined organic phases were washed with brine, dried ($Na_2SO_4$) and concentrated. The crude product was purified by column chromatography (20-40% ethyl acetate in cyclohexane) to give ethyl 5-((tert-butoxycarbonyl)amino)-4-methylthiazole-2-carboxylate. LCMS (method b) m/z 287.2 $[M+H]^+$, $t_R$=1.00 min. $^1H$ NMR (400 MHz, DMSO-$d_6$) δ ppm 10.49 (s, 1H), 4.30 (q, J=7.1 Hz, 2H), 2.36 (s, 3H), 1.50 (s, 9H), 1.30 (t, J=7.1 Hz, 3H).

Step 3: 1M LiOH in $H_2O$ (10 mL, 10 mmol) was added to a suspension of ethyl 5-((tert-butoxycarbonyl)amino)-4-methylthiazole-2-carboxylate (0.60 g, 2.1 mmol) in THF (20 mL) and the mixture was stirred at rt for 7 h. The THF was then removed and the residue was treated with water and washed with ethyl acetate. The water phase was acidified with conc. HCl and the resulting white suspension was stirred for 30 min before being filtered off cold and dried under high vacuum to give 5-((tert-butoxycarbonyl)amino)-4-methylthiazole-2-carboxylic acid. LCMS (method b) m/z 259.2 $[M+H]^+$, $t_R$=0.62 min. $^1H$ NMR (400 MHz, DMSO-$d_3$) δ ppm 13.37 (s, 1H), 1035 (s, 1H), 2.34 (s, 3H), 1.50 (s, 9H).

Synthesis of 5-amino-N-isopropyl-1-methyl-1H-pyrazole-3-carboxamide (int-EC42)

(int-EC42)

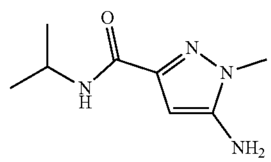

5-Amino-N-isopropyl-1-methyl-1H-pyrazole-3-carboxamide (int-EC42) was obtained using an analogous method as that described for the synthesis of 5-amino-N-(2,2-difluoroethyl)-1-methyl-1H-pyrazole-3-carboxamide (int-EC40), except 2,2-difluoroethanamine was replaced with propan-2-amine. LCMS (method b) m/z 183.1 $[M+H]^+$, $t_R$=0.46 min. $^1H$ NMR (400 MHz, DMSO-$d_6$) δ ppm 7.77 (d, J=8.2 Hz, 1H), 6.55 (s, 3H), 5.85 (s, 1H), 4.09-3.93 (m, 1H), 3.60 (s, 3H), 1.12 (d, J=6.6 Hz, 6H).

Synthesis of 5-amino-N-isopropyl-1-methyl-1H-pyrazole-3-carboxamide (int-EC43)

(int-EC43)

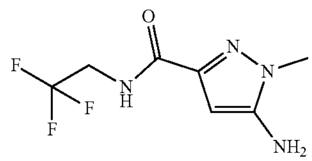

5-Amino-N-isopropyl-1-methyl-1H-pyrazole-3-carboxamide (int-EC43) was obtained using an analogous method as that described for the synthesis of 5-amino-N-(2,2-difluoroethyl)-1-methyl-1H-pyrazole-3-carboxamide (int-EC40), except 2,2-difluoroethanamine was replaced with 2,2,2-trifluoroethanamine. LCMS (method b) m/z 223.2 $[M+H]^+$, $t_R$=0.48 min. $^1H$ NMR (400 MHz, DMSO-$d_6$) δ ppm 8.38 (t, J=6.7 Hz, 1H), 5.72 (s, 1H), 3.94-3.91 (m, 5H), 3.59 (s, 3H).

Synthesis of N-(5-amino-1-methyl-1H-pyrazol-3-yl)-2-fluorobenzamide (int-EC44)

(int-EC44)

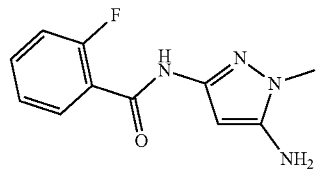

N-(5-Amino-1-methyl-1H-pyrazol-3-yl)-2-fluorobenzamide (int-EC44) was obtained using an analogous method as that described for the synthesis of N-(5-amino-1-methyl-1H-pyrazol-3-yl)isobutyramide (int-EC38), except isobutyric acid (step 5) was replaced with 2-fluorobenzoic acid, LCMS (method b) m/z 235.2 $[M+H]^+$, $t_R$=0.54 min. $^1H$ NMR (400 MHz, DMSO-$d_6$) δ ppm 11.54 (s, 1H), 8.92 (d, J=5.6 Hz, 1H), 8.10-8.02 (m, 1H), 7.73 (t, J=7.2 Hz, 1H), 7.69-7.59 (m, 1H), 5.70 (s, 1H), 3.59 (s, 3H), 3.57 (s, 3H).

Synthesis of N-(5-amino-1-methyl-1H-pyrazol-3-yl)-2,2,3,3,3-pentafluoropropanamide (int-EC45)

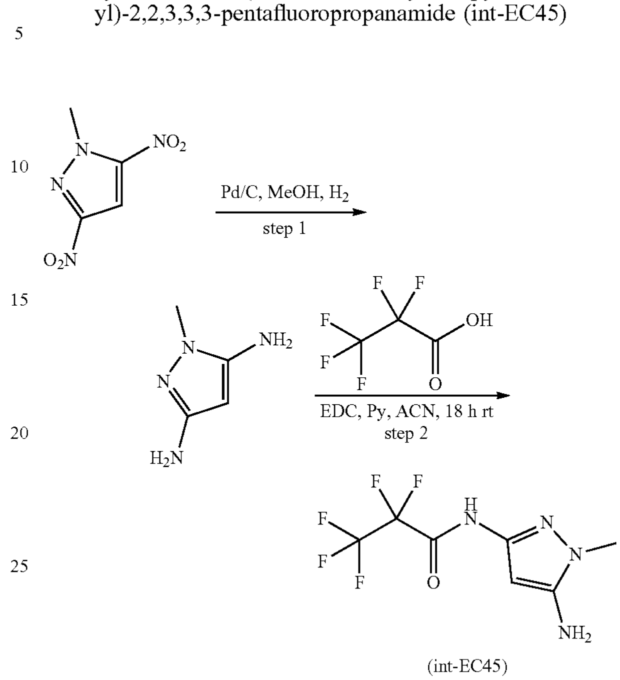

(int-EC45)

Step 1: A solution of 1-methyl-3,5-dinitro-1H-pyrazole (1.0 g, 5.81 mmol) in MeOH (110 mL) was hydrogenated using H cube (10% Pd/C, full $H_2$ conditions, 30° C.). The solution was then concentrated to give 1-methyl-1H-pyrazole-3,5-diamine which was used in the next step without further purification, LCMS (method b) m/z 113.1 $[M+H]^+$, $t_R$=0.68 min. $^1H$ NMR (400 MHz, DMSO-$d_6$) δ ppm 4.86 (s, 2H), 4.57 (s, 1H), 4.11 (s, 2H), 3.25 (s, 3H).

Step 2: EDC (512 mg, 2.68 mmol) was added at rt to a solution of 1-methyl-1H-pyrazole-3,5-diamine (150 mg, 1.338 mmol), 2,2,3,3,3-pentafluoropropanoic acid (139 μL, 1.34 mmol) and pyridine (539 μL, 6.69 mmol) in acetonitrile (10 mL) and the mixture was stirred at rt for 18 h. The reaction was then treated with water and extracted with ethyl acetate. The combined organic layers were washed with water and brine, dried ($Na_2SO_4$) and concentrated. The crude product was purified by column chromatography (40-80% ethyl acetate in cyclohexane) to give N-(5-amino-1-methyl-1H-pyrazol-3-yl)-2,2,3,3,3-pentafluoropropanamide (int-EC45). LCMS (method b) m/z 259.1 $[M+H]^+$, $t_R$=0.64 min. $^1H$ NMR (400 MHz, DMSO-$d_6$) δ ppm 11.66 (s, 1H), 5.64 (s, 1H), 5.35 (s, 2H), 3.47 (s, 3H).

Synthesis of 3-(3-cyclopropylisoxazol-5-yl)-1-methyl-1H-pyrazol-5-amine (int-EC46)

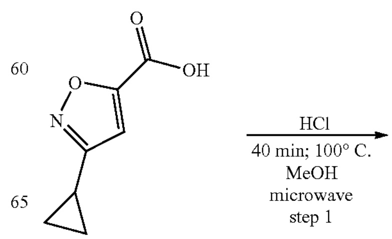

-continued

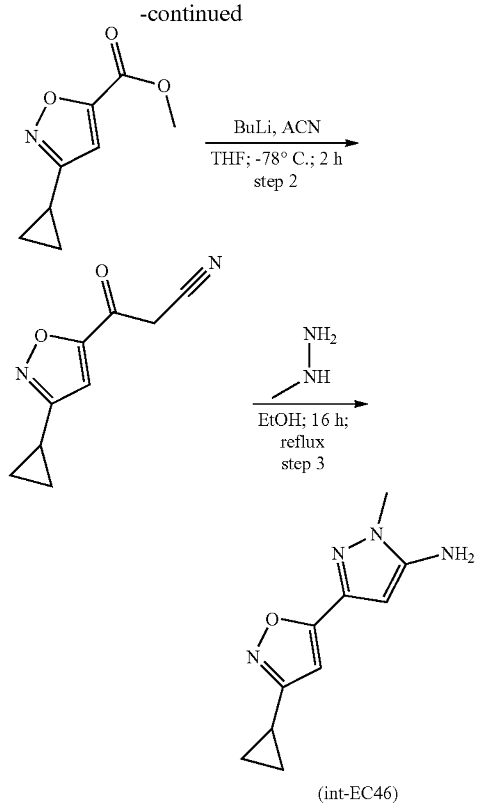

(int-EC46)

Step 1: A mixture of 3-cyclopropylisoxazole-5-carboxylic acid (1.0 g, 6.53 mmol) in 1.25 M HCl in MeOH (15 mL, 18.75 mmol) was heated in a microwave oven at 100° C. for 40 min. After cooling to rt, the solvent was removed and the residue was dissolved in MeOH and the solvent removed. After repeating this process for three times, methyl 3-cyclopropylisoxazole-5-carboxylate was obtained. LCMS (method b) m/z 168.1 $[M+H]^+$, $t_R$=0.84 min. $^1$H NMR (400 MHz, DMSO-$d_6$) δ ppm 7.09 (d, J=1.2 Hz, 1H), 3.87 (s, 3H), 2.16-2.00 (m, 1H), 1.11-0.99 (m, 2H), 0.90-0.77 (m, 2H).

Step 2: Acetonitrile (0.687 mL, 13.16) was added at −78° C. to 1.6 M solution of n-BuLi in hexane (8.23 mL, 13.16 mmol) in THF (25 mL). After stirring the reaction mixture at −78° C. for 20 min., solution of methyl 3-cyclopropylisoxazole-5-carboxylate (1.1 g, 6.58 mmol) in THF (25 mL) was added dropwise at −78° C. The reaction mixture was then stirred at −78° C. for 2 h before it was quenched by addition of 2N aq. HCl at −78° C. It was then treated with ethyl acetate and 2N HCl and the water layer was extracted with ethyl acetate. The combined organic layers were washed with brine, dried ($MgSO_4$) and concentrated to give 3-(3-cyclopropylisoxazol-5-yl)-3-oxopropanenitrile. LCMS (method b) m/z 175.1 $[M-H]^-$, $t_R$=0.73 min.

Step 3: A solution of 3-(3-cyclopropylisoxazol-5-yl)-3-oxopropanenitrile (1.2 g, 6.81 mmol) and methyl hydrazine (1.0 mL, 19.10 mmol) in EtOH (60 mL) was stirred at reflux for 16 h. After cooling to rt, the reaction mixture was concentrated and redissolved in EtOH. It was then evaporated to dryness. The crude product was purified by column chromatography (0-100% ethyl acetate containing 2% of (3.5 M $NH_3$ in methanol) in cyclohexane) to give 3-(3-cyclopropylisoxazol-5-yl)-1-methyl-1H-pyrazol-5-amine (int-EC46). LCMS (method b) m/z 205.1 $[M+H]^+$, $t_R$=0.65 min. $^1$H NMR (400 MHz, DMSO-$d_6$) δ ppm 6.32 (s, 1H), 5.64 (s, 1H), 5.44 (s, 2H), 3.57 (s, 3H), 2.05-1.92 (m, 1H), 1.06-0.96 (m, 2H), 0.85-0.75 (m, 2H).

Synthesis of 1-methyl-3-(6-(trifluoromethyl)pyridin-3-yl)-1H-pyrazol-5-amine (int-EC47)

(int-EC47)

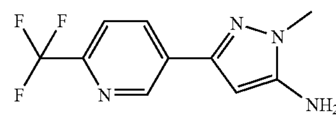

1-Methyl-3-(6-(trifluoromethyl)pyridin-3-yl)-1H-pyrazol-5-amine (int-EC47) was obtained using a method analogous to that described in step 2-3 for the synthesis of 3-(3-cyclopropylisoxazol-5-yl)-1-methyl-1H-pyrazol-5-amine (int-EC46) except 3-cyclopropylisoxazole-5-carboxylate (step 2) was replaced with methyl 6-(trifluoromethyl)nicotinate. LCMS (method b) m/z 243.1 $[M+H]^+$, $t_R$=0.75 min. $^1$H NMR (400 MHz, DMSO-da) δ ppm 9.04 (d, J=2.1 Hz, 1H), 8.26 (dd, J=8.4, 2.1 Hz, 1H), 7.84 (d, J=8.2 Hz, 1H), 5.90 (s, 1H), 5.46 (s, 2H), 3.61 (s, 3H).

Note that methyl 6-(trifluoromethyl)nicotinate was obtained using the following procedure: 2M solution of trimethylsilyldiazomethane in hexane (32.7 mL, 65.4 mmol) was added at 0° C. to a solution of 6-(trifluoromethyl) nicotinic acid (5.0 g, 26.2 mmol) in MeOH (200 mL). After stirring the reaction mixture at 0° C. for 1 h, the reaction mixture was concentrated, treated with water and extracted with ethyl acetate. The combined organic layers were washed with sat. $NaHCO_3$, dried ($MgSO_4$) and concentrated. The crude product was purified by column chromatography (0-50% ethyl acetate in cyclohexane) to give methyl 6-(trifluoromethyl)nicotinate. LCMS (method b) m/z 206.0 $[M+H]^+$, $t_R$=0.93 min. $^1$H NMR (400 MHz, DMSO-$d_6$) δ ppm 9.24 (d, J=2.1 Hz, 1H), 8.57 (dd, J=8.3, 1.7 Hz, 1H), 8.09 (d, J=8.2 Hz, 1H), 3.94 (s, 3H).

Synthesis of 4-chloro-2-(1-methyl-1H-pyrazol-3-yl) thiazol-5-amine (int-EC48)

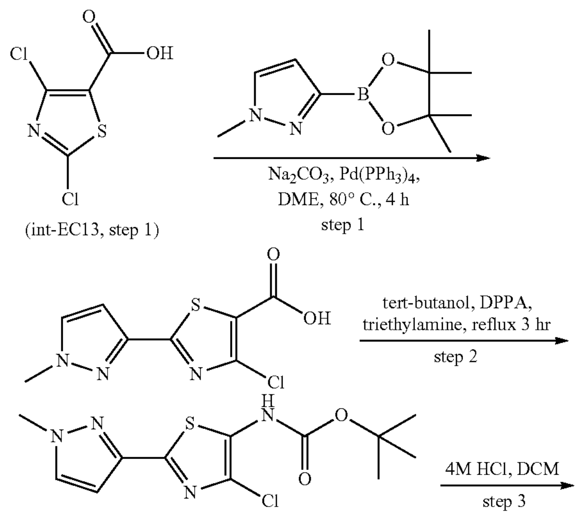

(int-EC13, step 1)

-continued

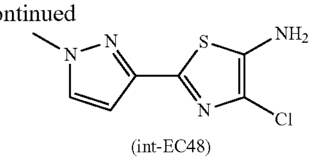

(int-EC48)

Step 1: A mixture of 1-methyl-3-(4,4,5,5-tetramethyl-1,3,2-dioxaborolan-2-yl)-1H-pyrazole (578 mg, 2.78 mmol), $Pd(PPh_3)_4$ (146 mg, 0.126 mmol), 2M $Na_2CO_3$ (4.4 mL, 8.8 mmol) and 2,4-dichlorothiazole-5-carboxylic acid (int-EC13, step 1, 500 mg, 2.52 mmol) in DME (13 mL) was heated to 80° C. for 5 h. After cooling to rt, the reaction mixture was treated with water and washed with ethyl acetate. The water phase was acidified with conc. HCl and the white precipitate was filtered off cold to give 4-chloro-2-(1-methyl-1H-pyrazol-3-yl)thiazole-5-carboxylic acid. LCMS (method b) m/z 243.9 $[M+H]^+$, $t_R$=0.52 min. $^1H$ NMR (400 MHz, DMSO-$d_6$) δ ppm 13.84 (s, 1H), 7.91 (d, J=2.4 Hz, 1H), 6.84 (d, J=2.4 Hz, 1H), 3.94 (s, 3H).

Step 2: DPPA (515 μL, 2.34 mmol) and triethylamine (261 μL, 1.87 mmol) were added at rt to a solution of 4-chloro-2-(1-methyl-1H-pyrazol-3-yl)thiazole-5-carboxylic acid (380 mg, 1.56 mmol) in tert-butanol (12 mL) and the reaction mixture was stirred at 95° C. for 3 h. After cooling to rt, the solvent was removed and the residue was treated with water and extracted with ethyl acetate. The combined organic layers were washed with brine, dried ($Na_2SO_4$) and concentrated. The crude product was purified by column chromatography (10-30% ethyl acetate in cyclohexane) to give tert-butyl (4-chloro-2-(1-methyl-1H-pyrazol-3-yl)thiazol-5-yl)carbamate. LCMS (method b) m/z 315.2 $[M+H]^+$, $t_R$=1.01 min. $^1H$ NMR (400 MHz, DMSO-$d_6$) δ ppm 10.22 (s, 1H) 7.83 (d, J=2.2 Hz, 1H) 6.68 (d, J=2.3 Hz, 1H) 3.90 (s, 3H) 1.49 (s, 9H).

Step 3: 4M HCl in dioxane (7.6 mL, 30.5 mmol) was added at rt to a solution of tert-butyl (4-chloro-2-(1-methyl-1H-pyrazol-3-yl)thiazol-5-yl)carbamate (400 mg, 1.27 mmol) in $CH_2Cl_2$ (25 mL). The reaction mixture was stirred at rt for 18 h before it was cooled to 0° C. The solid was filtered off, washed with $Et_2O$ and dried in high vacuum to give 4-chloro-2-(1-methyl-1H-pyrazol-3-yl)thiazol-5-amine (int-EC48). LCMS (method b) m/z 215.2 $[M+H]^+$, $t_R$=0.61 min. $^1H$ NMR (400 MHz, DMSO-$d_6$): δ ppm 7.75 (d, J=2.20 Hz, 1H) 6.55 (d, J=220 Hz, 1H) 6.37 (s, 3H) 3.85 (s, 3H).

Synthesis of 1-methyl-3-(5-methylpyridin-3-yl)-1H-pyrazol-5-amine (int-EC49)

(int-EC49)

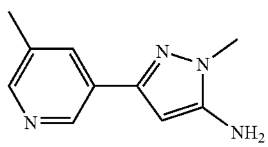

1-Methyl-3-(5-methylpyridin-3-yl)-1H-pyrazol-5-amine (int-EC49) was obtained using a method analogous to that described in step 2-3 for the synthesis of 3-(3-cyclopropylisoxazol-5-yl)-1-methyl-1H-pyrazol-5-amine (int-EC46) except in step 2 where 3-cyclopropylisoxazole-5-carboxylate was replaced with methyl 5-methylnicotinate. LCMS (method b) m/z 189.1 $[M+H]^+$, $t_R$=0.38 min. $^1H$ NMR (400 MHz, DMSO-$d_6$) δ ppm 8.65 (s, 1H), 8.26 (s, 1H), 7.82 (s, 1H), 5.75 (s, 1H), 5.34 (s, 2H), 3.57 (s, 3H), 2.30 (s, 3H).

Synthesis of N-(5-amino-1-methyl-1H-pyrazol-3-yl)-2,3-difluorobenzamide (int-EC50)

(int-EC50)

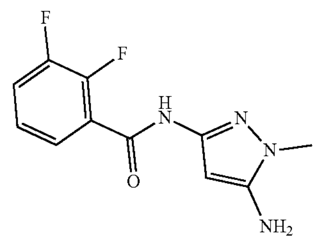

N-(5-amino-1-methyl-1H-pyrazol-3-yl)-2,3-difluorobenzamide (int-EC50) was obtained using an analogous method as that described for the synthesis of N-(5-amino-1-methyl-1H-pyrazol-3-yl)isobutyramide (int-EC38), except isobutyric acid (step 5) was replaced with 2,3-difluorobenzoic acid. LCMS (method b) m/z 253.1 $[M+H]^+$, $t_R$=0.58 min. $^1H$ NMR (400 MHz, DMSO-$d_6$) δ ppm 11.52 (s, 1H), 8.92 (d, J=5.7 Hz, 1H), 8.12-7.99 (m, 1H), 7.75-7.57 (m, 1H), 5.74 (s, 1H), 3.58 (s, 3H), 3.57 (s, 3H).

Synthesis of (S)-5-amino-N-(1-fluoropropan-2-yl)-1-methyl-1H-pyrazole-3-carboxamide (int-EC51)

(int-EC51)

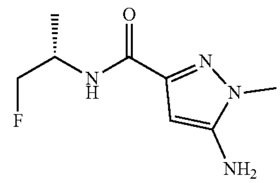

(S)-5-amino-N-(1-fluoropropan-2-yl)-1-methyl-1H-pyrazole-3-carboxamide (int-EC51) was obtained using an analogous method as that described for the synthesis of 5-amino-N-(2,2-difluoroethyl)-1-methyl-1H-pyrazole-3-carboxamide (int-EC40), except 2,2-difluoroethanamine was replaced with (S)-1-fluoropropan-2-amine (step 3). LCMS (method b) m/z 201.2 $[M+H]^+$, $t_R$=0.42 min. $^1H$ NMR (400 MHz, DMSO-$d_6$) δ ppm 7.77 (d, J=8.5 Hz, 1H), 5.74 (s, 1H), 5.16 (s, 3H), 4.53-4.10 (m, 3H), 3.58 (s, 3H), 1.12 (d, J=6.8 Hz, 3H).

Synthesis of 2-(5-fluoropyridin-3-yl)-4-methylthiazol-5-amine (int-EC52)

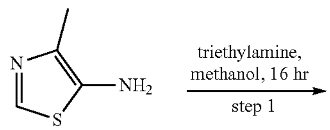

-continued

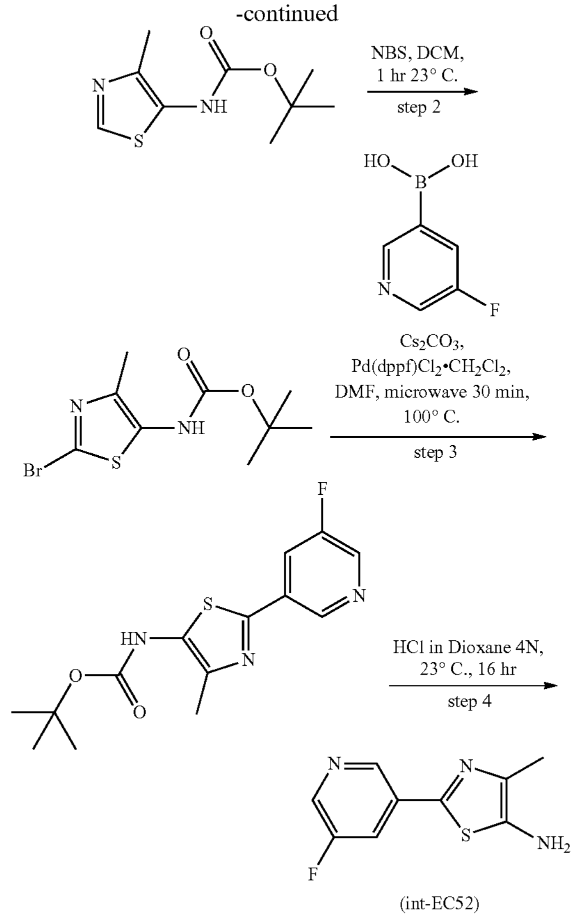

(int-EC52)

Step 1: A solution of di-tert-butyl dicarbonate (2.237 mL, 9.63 mmol) in methanol (20 mL) was added dropwise at 0° C. to a mixture of 4-methyl-1,3-thiazol-5 amine (1.0 g, 8.76 mmol) and triethylamine (3.66 mL, 26.3 mmol) in methanol (50 mL) and the reaction mixture was stirred at rt for 16 h. After removal of the solvent was removed, the residue was dissolved in $CH_2Cl_2$ and the solution was washed with water and sat. $NaHCO_3$, dried ($MgSO_4$) and concentrated. The crude product was purified by column chromatography (5-30% ethyl acetate in cyclohexane) to give tert-butyl (4-methylthiazol-5-yl)carbamate. LCMS (method b) m/z 215.1 $[M+H]^+$, $t_R$=0.81 min. $^1H$ NMR (400 MHz, DMSO-$d_6$) δ ppm 9.74 (s, 1H), 8.54 (s, 1H), 2.26 (s, 3H), 1.47 (s, 9H).

Step 2: NBS (0.640 g, 3.59 mmol) was added at rt to a solution of tert-butyl (4-methylthiazol-5-yl)carbamate (0.70 g, 3.27 mmol) in $CH_2Cl_2$ (35 mL) and the mixture was stirred at rt for 1 h. The reaction mixture was then concentrated and the residue was purified by column chromatography (5-20% ethyl acetate in cyclohexane) to give tert-butyl (2-bromo-4-methylthiazol-5-yl)carbamate. LCMS (method b) m/z 293.0 $[M+H]^+$, $t_R$=1.08 min. $^1H$ NMR (400 MHz, DMSO-$d_6$) δ ppm 10.23 (s, 1H), 2.24 (s, 3H), 1.47 (s, 9H).

Step 3: $PdCl_2$dppf (52.4 mg, 0.072 mmol) was added at rt to a degassed mixture of tert-butyl (2-bromo-4-methylthiazol-5-yl)carbamate (70 mg, 0.239 mmol), (5-fluoropyridin-3-yl)boronic acid (33.6 mg, 0.239 mmol) and cesium carbonate (389 mg, 1.194 mmol) in DMF (2.5 mL) and the mixture was then heated in a microwave oven at 100° C. for 30 min. After cooling to rt, the reaction mixture was diluted with ethyl acetate and filtered through a plug of Celite. The crude product was purified by preparative HPLC (Waters X-Bridge C18 OBD, 5 μm, 30*100 mm, Eluent A: $H_2O$+7.3 mM $NH_4OH$, B: $CH_3CN$+7.3 mM $NH_4OH$, Gradient: 20 to 99% B in 12.5 min hold 2.5 min, Flow 45 mL/min) to give tert-butyl (2-(5-fluoropyridin-3-yl)-4-methylthiazol-5-yl) carbamate. LCMS (method b) m/z 310.1 $[M+H]^+$, $t_R$=1.07 min. $^1H$ NMR (400 MHz, $CDCl_3$) δ ppm 8.97-8.92 (m, 1H), 8.50-8.44 (m, 1H), 8.21 (d, J=8.5 Hz, 1H), 6.80 (s, 1H), 2.44 (s, 3H), 1.56 (s, 9H).

Step 4: tert-Butyl (2-(5-fluoropyridin-3-yl)-4-methylthiazol-5-yl)carbamate (20 mg, 0.065 mmol) was treated with 4M HCl in dioxane (3 mL, 12 mmol) and the reaction mixture was stirred at rt for 16 h. The mixture was then concentrated to give 2-(5-fluoropyridin-3-yl)-4-methylthiazol-5-amine (int-EC52). LCMS (method b) m/z 210.0 $[M+H]^+$, $t_R$=0.67 min.

Synthesis of 1-methyl-3-(5-methylisoxazol-3-yl)-1H-pyrazol-5-amine (int-EC53)

(int-EC53)

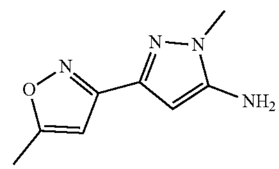

1-Methyl-3-(5-methylisoxazol-3-yl)-1H-pyrazol-5-amine (int-EC53) was obtained using an analogous method as that described in step 3 for the synthesis of 3-(3-cyclopropylisoxazol-5-yl)-1-methyl-1H-pyrazol-5-amine (int-EC46), except 3-(3-cyclopropylisoxazol-5-yl)-3-oxopropanenitrile was replaced with 3-(5-methylisoxazol-3-yl)-3-oxopropanenitrile. LCMS (method b) m/z 179.0 $[M+H]^+$, $t_R$=0.52 min. $^1H$ NMR (400 MHz, DMSO-$d_6$) δ ppm 6.38 (s, 1H), 5.64 (s, 1H), 5.37 (s, 2H), 3.57 (s, 3H), 2.40 (s, 3H).

Synthesis of 3-(5-ethylisoxazol-3-yl)-1-methyl-1H-pyrazol-5-amine (int-EC54)

(int-EC54)

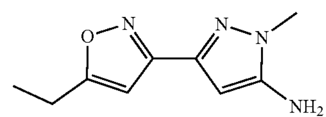

3-(5-Ethylisoxazol-3-yl)-1-methyl-1H-pyrazol-5-amine (int-EC54) was obtained using an analogous method as that described in steps 2-3 for the synthesis of 3-(3-cyclopropylisoxazol-5-yl)-1-methyl-1H-pyrazol-5-amine (int-EC46), except methyl 3-cyclopropylisoxazole-5-carboxylate (step 2) was replaced with ethyl 5-ethylisoxazole-3-carboxylate. LCMS (method b) m/z 193.1 $[M+H]^+$, $t_R$=0.64 min. $^1H$ NMR (400 MHz, DMSO-$d_6$) δ ppm 6.41 (t, J=0.9 Hz, 1H), 5.66 (s, 1H), 5.39 (s, 2H), 3.58 (s, 3H), 2.76 (qd, J=7.6, 0.9 Hz, 2H), 1.24 (t, J=7.6 Hz, 16H).

Synthesis of 1-ethyl-3-(6-(trifluoromethyl)pyridin-3-yl)-1H-pyrazol-5-amine (int-EC55)

(int-EC55)

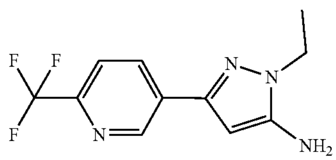

1-Ethyl-3-(6-(trifluoromethyl)pyridin-3-yl)-1H-pyrazol-5-amine (int-EC55) was obtained using an analogous method as that described in steps 2-3 for the synthesis of 3-(3-cyclopropylisoxazol-5-yl)-1-methyl-1H-pyrazol-5-amine (int-EC46), except methyl 3-cyclopropylisoxazole-5-carboxylate (step 2) was replaced with methyl 6-(trifluoromethyl)nicotinate and methyl hydrazine (step 3) was replaced with ethyl hydrazine. LCMS (method b) m/z 257.1 $[M+H]^+$, $t_R$=0.83 min. $^1H$ NMR (400 MHz, DMSO-$d_6$) δ ppm 9.03 (s, 1H), 8.26 (d, J=8.2 Hz, 1H), 7.84 (d, J=8.2 Hz, 1H), 5.89 (s, 1H), 5.44 (s, 2H), 3.97 (q, J=7.9, 7.2 Hz, 2H), 1.28 (t, J=7.0 Hz, 3H).

Note that methyl 6-(trifluoromethyl)nicotinate was obtained using the procedure described for the synthesis of 1-methyl-3-(6-(trifluoromethyl)pyridin-3-yl)-1H-pyrazol-5-amine (int-EC47).

Synthesis of 1-ethyl-3-(furan-2-yl)-1H-pyrazol-5-amine (int-EC56)

(int-EC56)

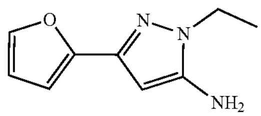

1-Ethyl-3-(furan-2-yl)-1H-pyrazol-5-amine (int-EC56) was obtained using an analogous method as that described in steps 2-3 for the synthesis of 3-(3-cyclopropylisoxazol-5-yl)-1-methyl-1H-pyrazol-5-amine (int-EC46), except methyl 3-cyclopropylisoxazole-5-carboxylate (step 2) was replaced with 3-(furan-2-yl)-3-oxopropanenitrile and methyl hydrazine (step 3) was replaced with ethyl hydrazine. LCMS (method b) m/z 178.1 $[M+H]^+$, $t_R$=0.59 min. $^1H$ NMR (400 MHz, DMSO-$d_6$) δ ppm 7.58 (s, 1H), 6.54-6.44 (m, 2H), 5.51 (s, 1H), 5.27 (s, 2H), 3.89 (q, J=7.2 Hz, 2H), 1.24 (t, J=7.1 Hz, 3H).

Synthesis of 3-(3-ethylisoxazol-5-yl)-1-methyl-1H-pyrazol-5-amine (int-EC57)

(int-EC57)

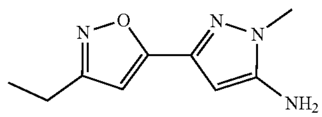

3-(3-Ethylisoxazol-5-yl)-1-methyl-1H-pyrazol-5-amine (int-EC57) was obtained using an analogous method as that described for the synthesis of 3-(3-cyclopropylisoxazol-5-yl)-1-methyl-1H-pyrazol-5-amine (int-EC46), except 3-cyclopropylisoxazole-5-carboxylic acid (step 1) was replaced with 3-ethylisoxazole-5-carboxylic acid. LCMS (method b) m/z 193.1 $[M+H]^+$, $t_R$=0.62 min. $^1H$ NMR (400 MHz, DMSO-$d_6$) δ ppm 6.50 (s, 1H), 5.67 (s, 1H), 5.44 (s, 2H), 3.58 (s, 3H), 2.62 (q, J=7.6 Hz, 2H), 1.20 (t, J=7.6 Hz, 3H).

Synthesis of 3-(5-fluoropyridin-2-yl)-1-methyl-1H-pyrazol-5-amine (int-EC58)

(int-EC58)

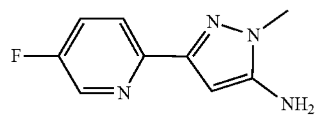

3-(5-Fluoropyridin-2-yl)-1-methyl-1H-pyrazol-5-amine (int-EC58) was obtained using an analogous method as that described for the synthesis of 3-(3-cyclopropylisoxazol-5-yl)-1-methyl-1H-pyrazol-5-amine (int-EC46), except 3-cyclopropylisoxazole-5-carboxylic acid (step 1) was replaced with 5-fluoropicolinic acid. LCMS (method b) m/z 193.1 $[M+H]^+$, $t_R$=0.54 min. $^1H$ NMR (400 MHz, DMSO-$d_3$) δ ppm 8.48 (d, J=2.9 Hz, 1H), 7.84 (dd, J=8.8, 4.7 Hz, 1H), 7.66 (td, J=8.8, 3.0 Hz, 1H), 5.82 (s, 1H), 5.32 (s, 2H), 3.58 (s, 3H).

Synthesis of 3-chloro-1-(6-(trifluoromethyl)pyridin-3-yl)-1H-pyrazol-4-amine (int-EC59)

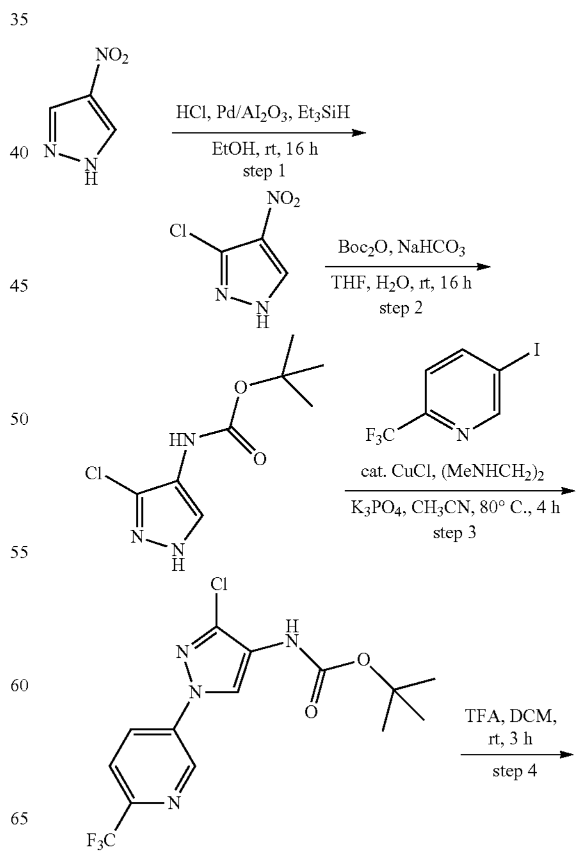

-continued

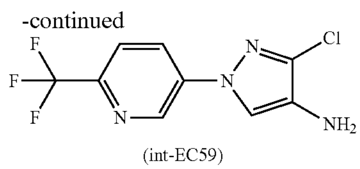

(int-EC59)

Step 1: Concentrated HCl (14.5 mL) was added at rt to a mixture of 4-nitro-1H-pyrazole (2.0 g, 17.7 mmol) in EtOH (24 mL) and while stirring the mixture was purged with argon for 10 min. Pd on alumina (113 mg) was then added, followed by the slow addition of triethylsilane (11.3 mL, 70.7 mmol). The mixture was then stirred at rt for 16 h. The mixture was then filtered through a plug of Celite and the biphasic mixture was separated. The lower phase was concentrated with the aid of acetonitrile being added to the mixture several times until a solid was obtained. Then, the solid was suspended in acetonitrile and filtered off. After washing with acetonitrile and drying in high vacuum, 3-chloro-1H-pyrazol-4-amine was obtained as an HCl salt. $^1$H NMR (400 MHz, DMSO-$d_6$) δ ppm 10.50 (s, 3H), 8.02 (s, 1H), 7.74 (s, 1H).

Step 2: $Boc_2O$ (3.74 g, 17.1 mmol) was added at rt to a mixture of 3-chloro-1H-pyrazol-4-amine (2.4 g, 15.6 mmol) and $NaHCO_3$ (2.88 g, 34.3 mmol) in THF (28 mL)/$H_2O$ (2.8 mL) and the mixture was stirred at rt for 16 h. The mixture was then treated with water and ethyl acetate and the water phase was extracted with ethyl acetate. The combined organic layers were washed with brine, dried ($Na_2SO_4$) and concentrated to give an oil. After treatment of with cyclohexane and short heating, a suspension was formed which was filtered off, washed with cyclohexane and dried to give tert-butyl (3-chloro-1H-pyrazol-4-yl)carbamate, LCMS (method b): m/z 218.2 $[M+H]^+$, $t_R$=0.75 min. 1H NMR (400 MHz, $CDCl_3$) δ (ppm) 7.89 (s, 1H), 7.64 (s, 1H), 6.25 (s, 1H), 1.42 (s, 9H)

Step 3: tert-Butyl (3-chloro-1H-pyrazol-4-yl)carbamate (408 mg, 1.5 mmol), 5-iodo-2-(trifluoromethyl)pyridine (491 mg, 1.8 mmol), $K_3PO_4$ (637 mg, 3 mmol) and CuCl (30 mg, 0.3 mmol) in dry acetonitrile (6 nL) was treated with N,N dimethylethylenediamine (331 mg, 3.75 mmol) and the mixture was heated at 75° C. for 1.5 h. After cooling to rt, the mixture was filtered through a plug of Celite and washed with acetonitrile. The filtrate was then concentrated, redissolved in acetonitrile (10 mL) and treated with water (20 mL) to obtain a solid which was filtered off and washed with water. The solid was then dissolved in ethyl acetate and washed with brine, dried ($Na_2SO_4$) and concentrated. The crude product was purified by column chromatography (10-20% ethyl acetate in cyclohexane) to give tert-butyl (3-chloro-1-(6-(trifluoromethyl)pyridin-3-yl)-1H-pyrazol-4-yl)carbamate LCMS (method b) m/z 363.1 $[M+H]^+$, $t_R$=1.23 min. $^1$H NMR (400 MHz, $CDCl_3$) δ ppm 9.05 (s, 1H), 8.42 (s, 1H), 8.14 (d, J=8.4 Hz, 1H), 7.76 (d, J=8.6 Hz, 1H), 6.38 (s, 1H), 1.55 (s, 9H).

Step 4: tert-Butyl (3-chloro-1-(6-(trifluoromethyl)pyridin-3-yl)-1H-pyrazol-4-yl)carbamate (330 mg, 0.91 mmol) in $CH_2Cl_2$ (0.91 mL) was treated with TFA (0.91 mL, 11.8 mmol) and the mixture was stirred at rt for 3 h. The reaction mixture was then diluted with $CH_2Cl_2$ and treated with sat. $NaHCO_3$. The water phase was extracted with $CH_2Cl_2$ and the combined organic layers were washed with brine, dried ($Na_2SO_4$) and concentrated to give 3-chloro-1-(6-(trifluoromethyl)pyridin-3-yl)-1H-pyrazol-4-amine (int-EC59). LCMS (method b) m/z 263.1 $[M+H]^+$, $t_R$=0.90 min. $^1$H NMR (400 MHz, DMSO-$d_6$) δ ppm 9.12 (d, J=2.6 Hz, 1H), 8.31 (dd, J=8.7, 2.6 Hz, 1H), 7.99 (s, 1H), 7.97 (d, J=8.8 Hz, 1H), 4.56 (s, 2H).

Synthesis of N-(5-amino-1-methyl-1H-pyrazol-3-yl)pivalamide (int-EC60)

(int-EC60)

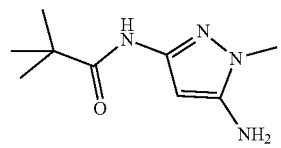

N-(5-Amino-1-methyl-1H-pyrazol-3-yl)pivalamide (int-EC60) was obtained using an analogous method as that described for the synthesis of N-(5-amino-1-methyl-1H-pyrazol-3-yl)isobutyramide (int-EC38), except isobutyric acid (step 5) was replaced with pivalic acid. LCMS (method b) m/z 197.2 $[M+H]^+$, $t_R$=0.48 min. $^1$H NMR (400 MHz, DMSO-$d_7$) δ ppm 10.88 (s, 1H), 5.60 (s, 1H), 3.57 (s, 3H), 3.56 (s, 3H), 1.22 (s, 9H).

Synthesis of 1-methyl-3-(3-methylisoxazol-5-yl)-1H-pyrazol-5-amine (int-EC61)

(int-EC61)

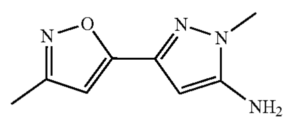

1-Methyl-3-(3-methylisoxazol-5-yl)-1H-pyrazol-5-amine (int-EC61) was obtained using an analogous method as that described in steps 2-3 for the synthesis of 3-(3-cyclopropylisoxazol-5-yl)-1-methyl-1H-pyrazol-5-amine (int-EC46), except methyl 3-cyclopropylisoxazole-5-carboxylate (step 2) was replaced with methyl 3-methylisoxazole-5-carboxylate. LCMS (method b) m/z 179.1 $[M+H]^+$, $t_R$=0.51 min. H NMR (400 MHz, DMSO-$d_6$) δ ppm 6.46 (s, 1H), 5.69 (s, 1H), 3.59 (s, 3H), 2.24 (s, 3H). ($NH_2$ not seen).

Synthesis of 5-amino-N-isopropylthiazole-2-carboxamide (int-EC62)

(int-EC62)

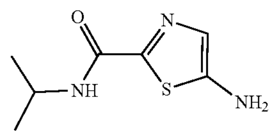

5-amino-N-isopropylthiazole-2-carboxamide (int-EC62) was obtained using an analogous method as that described for the synthesis of 5-amino-N-(2,2-difluoroethyl)-1-methyl-1H-pyrazole-3-carboxamide (int-EC40), except 5-((tert-butoxycarbonyl)amino)-1-methyl-1H-pyrazole-3-carboxylic acid was replaced with 5-((tert-butoxycarbonyl)amino)thiazole-2-carboxylic acid and 2,2-difluoroethanamine was replaced with propan-2-amine. LCMS (method b) m/z 186.1 $[M+H]^+$, $t_R$=0.54 min.

Synthesis of 3-methyl-1-(6-(trifluoromethyl)pyridin-3-yl)-1H-pyrazol-4-amine (int-EC63)

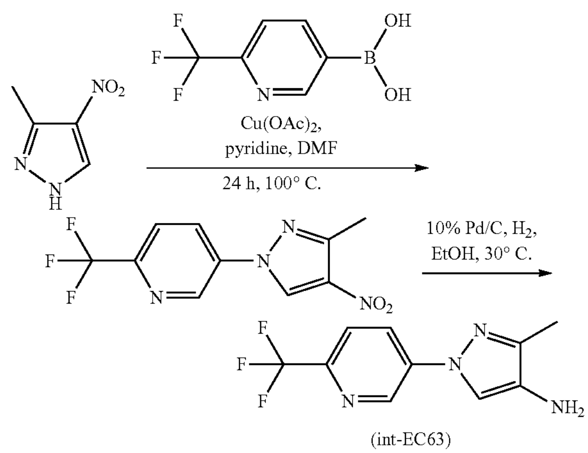

(int-EC63)

Step 1: To a solution of 3-methyl-4-nitro-1H-pyrazole (1.0 g, 7.87 mmol) in DMF (100 mL) was added in (6-(trifluoromethyl)pyridin-3-yl)boronic acid (2.253 g, 11.80 mmol), $Cu(OAc)_2$ (0.471 g, 2.36 mmol) and pyridine (0.255 mL, 3.15 mmol) and the solution was stirred under oxygen atmosphere at 100° C. for 24 h. After cooling to rt, the DMF was evaporated and the residue was diluted in ethyl acetate and extracted with $H_2O$. The aqueous layer was extracted again with ethyl acetate and the combined organic layers were dried and evaporated to dryness to give crude product which was purified by column chromatography (0-60% ethyl acetate in cyclohexane) to give 5-(3-methyl-4-nitro-1H-pyrazol-1-yl)-2-(trifluoromethyl)pyridine. LCMS (method b) m/z 273.0 $[M+H]^+$, $t_R$=1.08 min. $^1H$ NMR (400 MHz, DMSO-$d_6$) δ ppm 9.82 (s, 1H), 9.37 (d, J=2.6 Hz, 1H), 8.60 (dd, J=8.5, 2.6 Hz, 1H), 8.14 (d, J=8.9 Hz, 1H), 2.57 (s, 3H).

Step 2: A solution of 5-(3-methyl-4-nitro-1H-pyrazol-1-yl)-2-(trifluoromethyl)pyridine (1.12 g, 4.11 mmol) in ethanol (100 mL) was hydrogenated using H cube (10% Pd/C, 1 atm, 30° C.). The solution was then concentrated and the crude product was dissolved in $CH_2Cl_2$ and washed with 2N HCl. The water layer was made basic with 2N NaOH and extracted 3-times with $CH_2Cl_2$. The combined organic layers were concentrated to give 3-methyl-1-(6-(trifluoromethyl)pyridin-3-yl)-1H-pyrazol-4-amine (int-EC63). LCMS (method b) m/z 243.1 $[M+H]^+$, $t_R$=0.76 min. $^1H$ NMR (400 MHz, DMSO-$d_6$) δ ppm 9.08 (d, J=2.6 Hz, 1H), 8.23 (dd, J=8.7, 2.6 Hz, 1H), 7.91 (d, J=8.7 Hz, 1H), 7.79 (s, 1H), 4.32 (s, 2H), 2.18 (s, 3H).

Synthesis of 1-methyl-3-(pyridin-2-yl)-1H-pyrazol-5-amine (int-EC64)

(int-EC64)

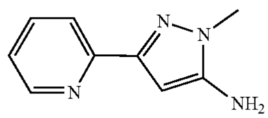

1-methyl-3-(pyridin-2-yl)-1H-pyrazol-5-amine (int-EC64) was obtained using an analogous method as that described in step 3 for the synthesis of 3-(3-cyclopropylisoxazol-5-yl)-1-methyl-1H-pyrazol-5-amine (int-EC46), except 3-(3-cyclopropylisoxazol-5-yl)-3-oxopropanenitrile was replaced with 3-oxo-3-(pyridin-2-yl)propanenitrile. LCMS (method b) m/z 175.1 $[M+H]^+$, $t_R$=0.36 min. $^1H$ NMR (400 MHz, DMSO-$d_6$) δ ppm 8.49 (d, J=4.5 Hz, 1H), 7.80 (d, J=7.9 Hz, 1H), 7.72 (t, J=7.6 Hz, 1H), 7.24-7.16 (m, 1H), 5.86 (s, 1H), 5.28 (s, 2H), 3.59 (s, 3H).

Synthesis of 4-chloro-2-(1-(oxetan-3-yl)-1H-pyrazol-4-yl)thiazol-5-amine (int-EC65)

(int-EC65)

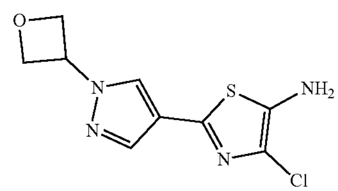

1-methyl-3-(pyridin-2-yl)-1H-pyrazol-5-amine (int-EC64) was obtained using an analogous method as that described or the synthesis of 4-chloro-2-(1-methyl-1H-pyrazol-3-yl)thiazol-5-amine (int-EC48), except 1-methyl-3-(4,4,5,5-tetramethyl-1,3,2-dioxaborolan-2-yl)-1H-pyrazole (step 2) was replaced with 1-(oxetan-3-yl)-4-(4,4,5,5-tetramethyl-1,3,2-dioxaborolan-2-yl)-1H-pyrazole. LCMS (method b) m/z 257.0 $[M+H]^+$, $t_R$=0.56 min. $^1H$ NMR (400 MHz, DMSO-$d_6$) δ ppm 8.31 (s, 1H), 7.89 (s, 1H), 5.68 (s, 2H), 5.60-5.50 (m, 1H), 4.92-4.88 (m, 4H).

Synthesis of 1-cyclopropyl-3-(furan-2-yl)-1H-pyrazol-5-amine (int-EC66)

(int-EC66)

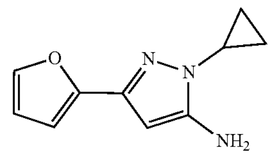

1-Cyclopropyl-3-(furan-2-yl)-1H-pyrazol-5-amine (int-EC66) was obtained using an analogous method as that described in step 3 for the synthesis of 3-(3-cyclopropylisoxazol-5-yl)-1-methyl-1H-pyrazol-5-amine (int-EC46), except 3-(3-cyclopropylisoxazol-5-yl)-3-oxopropanenitrile was replaced with 3-(furan-2-yl)-3-oxopropanenitrile and methyl hydrazine was replaced with cyclopropylhydrazine. LCMS (method b) m/z 190.1 $[M+H]^+$, $t_R$=0.64 min. $^1H$ NMR (400 MHz, DMSO-$d_6$) δ ppm 7.58 (d, J=1.7 Hz, 1H), 6.50 (d, J=3.3 Hz, 1H), 6.47 (dd, J=3.3, 1.8 Hz, 1H), 5.49 (s, 1H), 5.35 (s, 2H), 3.27-3.16 (m, 1H), 0.99-0.86 (m, 4H).

Synthesis of 3-(6-methoxypyridin-3-yl)-1-methyl-1H-pyrazol-5-amine (int-EC67)

(int-EC67)

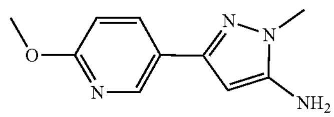

3-(6-Methoxypyridin-3-yl)-1-methyl-1H-pyrazol-5-amine (int-EC67) was obtained using an analogous method as that described in steps 2-3 for the synthesis of 3-(3-cyclopropylisoxazol-5-yl)-1-methyl-1H-pyrazol-5-amine (int-EC46), except methyl 3-cyclopropylisoxazole-5-carboxylate was replaced with methyl 6-methoxynicotinate. LCMS (method b) m/z 205.1 $[M+H]^+$, $t_R$=0.57 min. $^1H$ NMR (400 MHz, DMSO-$d_3$) δ ppm 8.41 (d, J=2.2 Hz, 1H), 7.94 (dd, J=8.6, 2.3 Hz, 1H), 6.79 (d, J=8.6 Hz, 1H), 5.66 (s, 1H), 5.29 (s, 2H), 3.85 (s, 3H), 3.54 (s, 3H).

Synthesis of 1-methyl-3-(5-(trifluoromethyl)pyridin-3-yl)-1H-pyrazol-5-amine (int-EC68)

(int-EC68)

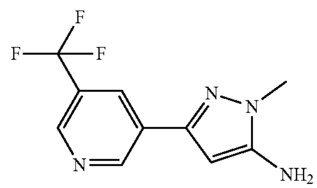

1-Methyl-3-(5-(trifluoromethyl)pyridin-3-yl)-1H-pyrazol-5-amine (int-EC68) was obtained using an analogous method as that described in steps 2-3 for the synthesis of 3-(3-cyclopropylisoxazol-5-yl)-1-methyl-1H-pyrazol-5-amine (int-EC46), except methyl 3-cyclopropylisoxazole-5-carboxylate was replaced with methyl 5-(trifluoromethyl) nicotinate. LCMS (method b) m/z 243.1 $[M+H]^+$, $t_R$=0.74 min. $^1H$ NMR (400 MHz, DMSO-d) δ ppm 9.15 (s, 1H), 8.81 (s, 1H), 8.30 (s, 1H), 5.95 (s, 1H), 5.44 (s, 2H), 3.60 (s, 3H).

Synthesis of 4-chloro-2-(1-(2-methoxyethyl)-1H-pyrazol-4-yl)thiazol-5-amine (int-EC69)

(int-EC69)

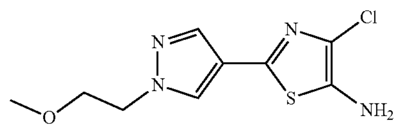

4-Chloro-2-(1-(2-methoxyethyl)-1H-pyrazol-4-yl)thiazol-5-amine (int-EC69) was obtained using an analogous method as that described or the synthesis of 4-chloro-2-(1-methyl-1H-pyrazol-3-yl)thiazol-5-amine (int-EC48), except 1-methyl-3-(4,4,5,5-tetramethyl-1,3,2-dioxaborolan-2-yl)-1H-pyrazole (step 2) was replaced with 1-(2-methoxyethyl)-4-(4,4,5,5-tetramethyl-1,3,2-dioxaborolan-2-yl)-1H-pyrazole. LCMS (method b) m/z 259.0 $[M+H]^+$, $t_R$=0.62 min. $^1H$ NMR (400 MHz, DMSO-$d_6$) δ ppm 8.11 (s, 1H), 7.74 (s, 1H), 5.11 (s, 3H), 4.26 (t, J=5.3 Hz, 2H), 3.69 (t, J=5.3 Hz, 3H), 3.23 (s, 3H).

Synthesis of 1-ethyl-3-(3-methylisoxazol-5-yl)-1H-pyrazol-5-amine (int-EC70)

(int-EC70)

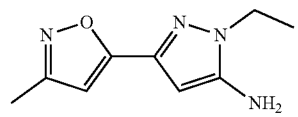

1-Ethyl-3-(3-methylisoxazol-5-yl)-1H-pyrazol-5-amine (int-EC70) was obtained using an analogous method as that described in steps 2-3 for the synthesis of 3-(3-cyclopropylisoxazol-5-yl)-1-methyl-1H-pyrazol-5-amine (int-EC46), except methyl 3-cyclopropylisoxazole-5-carboxylate (step 2) was replaced with methyl 3-methylisoxazole-5-carboxylate and methyl hydrazine (step 3) was replaced with ethyl hydrazine. LCMS (method b) m/z 193.1 $[M+H]^+$, $t_R$=0.58 min. $^1H$ NMR (400 MHz, DMSO-$d_6$) δ ppm 6.44 (s, 1H), 5.66 (s, 1H), 5.44 (s, 2H), 3.94 (q, J=7.2 Hz, 2H), 2.23 (s, 3H), 1.25 (t, J=7.2 Hz, 3H).

Synthesis of 5-amino-N-cyclopropyl-1-methyl-1H-pyrazole-3-carboxamide (int-EC71)

(int-EC71)

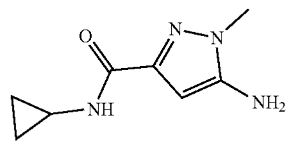

5-Amino-N-cyclopropyl-1-methyl-1H-pyrazole-3-carboxamide (int-EC71) was obtained using an analogous method as that described for the synthesis of 5-amino-N-(2,2-difluoroethyl)-1-methyl-1H-pyrazole-3-carboxamide (int-EC40), except 2,2-difluoroethanamine was replaced with cyclopropylamine. LCMS (method b) m/z 181.2 $[M+H]^+$, $t_R$=0.38 min. $^1H$ NMR (400 MHz, DMSO-$d_6$) δ ppm 7.97 (d, J=4.4 Hz, 1H), 5.76 (s, 1H), 3.57 (s, 3H), 2.81-2.70 (m, 1H), 0.69-0.45 (m, 4H). ($NH_3^+$ not observed).

Synthesis of 4-chloro-2-(1-(difluoromethyl)-1H-pyrazol-4-yl)thiazol-5-amine (int-EC72)

(int-EC72)

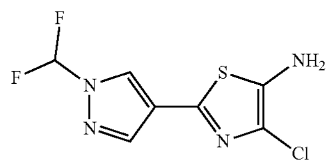

4-Chloro-2-(1-(difluoromethyl)-1H-pyrazol-4-yl)thiazol-5-amine (int-EC72) was obtained using an analogous method as that described or the synthesis of 4-chloro-2-(1- methyl-1H-pyrazol-3-yl)thiazol-5-amine (int-EC48), except 1-methyl-3-(4,4,5,5-tetramethyl-1,3,2-dioxaborolan-2-yl)-1H-pyrazole (step 2) was replaced with 1-(difluoromethyl)-4-(4,4,5,5-tetramethyl-1,3,2-dioxaborolan-2-yl)-1H-pyrazole. LCMS (method b) m/z 251.1 $[M+H]^+$, $t_R$=0.73 min. $^1H$ NMR (400 MHz, DMSO-$d_6$) δ ppm 8.67 (s, 1H), 8.11 (s, 1H), 7.81 (t, J=58.9 Hz, 1H). ($NH_3^+$ hidden in water peak).

Synthesis of 1-methyl-3-(6-methylpyridin-3-yl)-1H-pyrazol-5-amine (int-EC73)

(int-EC73)

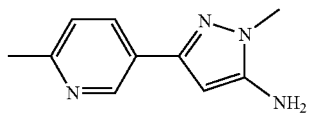

1-Methyl-3-(6-methylpyridin-3-yl)-1H-pyrazol-5-amine (int-EC73) was obtained using an analogous method as that described in steps 2-3 for the synthesis of 3-(3-cyclopropylisoxazol-5-yl)-1-methyl-1H-pyrazol-5-amine (int-EC46), except methyl 3-cyclopropylisoxazole-5-carboxylate was replaced with methyl 6-methylnicotinate. LCMS (method b) m/z 189.1 $[M+H]^+$, $t_R$=0.35 min. $^1H$ NMR (400 MHz, $CDCl_3$) δ ppm 8.79 (s, 1H), 8.16 (d, J=8.2 Hz, 1H), 7.30 (d, J=8.2 Hz, 1H), 5.89 (s, 1H), 3.73 (s, 3H), 3.65 (s, 2H), 2.69 (s, 3H).

Synthesis of methyl 5-amino-1-methyl-1H-pyrazole-3-carboxylate (int-EC74)

(int-EC74)

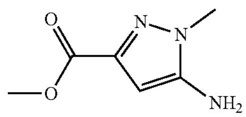

Methyl 5-amino-1-methyl-1H-pyrazole-3-carboxylate (int-EC74) was obtained using an analogous method as that described for the synthesis of 5-amino-4-chloro-N-isopropylthiazole-2-carboxamide (int-EC39), except 4-chloro-2-(isopropylcarbamoyl)thiazole-5-carboxylic acid was replaced with 3-(methoxycarbonyl)-1-methyl-1H-pyrazole-5-carboxylic acid. LCMS (method b) m/z 156.2 $[M+H]^+$, $t_R$=0.36 min. $^1H$ NMR (400 MHz, DMSO-$d_6$) δ ppm 6.89 (s, 3H), 5.74 (s, 1H), 3.72 (s, 3H), 3.59 (s, 3H).

Synthesis of 4-chloro-2-(6-(trifluoromethyl)pyridin-3-yl)thiazol-5-amine (int-EC75)

(int-EC75)

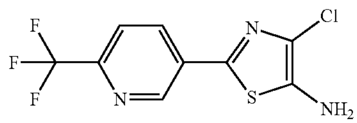

4-Chloro-2-(6-(trifluoromethyl)pyridin-3-yl)thiazol-5-amine (int-EC75) was obtained using an analogous method as that described for the synthesis of 5-amino-4-chloro-N-isopropylthiazole-2-carboxamide (int-EC39), except 4-chloro-2-(isopropylcarbamoyl)thiazole-5-carboxylic acid (int-EC9) was replaced with 4-chloro-2-(6-(trifluoromethyl)pyridin-3-yl)thiazole-5-carboxylic acid (int-EC6). LCMS (method b) m/z 280.0 $[M+H]^+$, $t_R$=1.00 min. $^1H$ NMR (400 MHz, DMSO-$d_7$) δ ppm 9.04 (d, J=2.3 Hz, 1H), 8.27 (dd, J=8.3, 2.2 Hz, 1H), 7.90 (d, J=8.3 Hz, 1H), 6.51 (s, 2H).

The table below lists the amine type EC intermediates which were purchased.

| Intermediate Code | Compound Structure | Compound Name | Source |
|---|---|---|---|
| Int-EC76 | 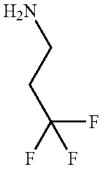 | 3,3,3-trifluoropropan-1-amine | ABCR (AB231459) |
| Int-EC77 | 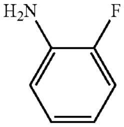 | 2-fluoroaniline | ABCR (AB103830) |
| Int-EC78 | 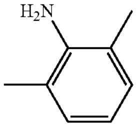 | 2,6-dimethylaniline | ABCR (AB116158) |

Synthesis of Example Compounds

Example 1: $N^2$,4-dimethyl-N—((R)-2-methyl 3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide (1)

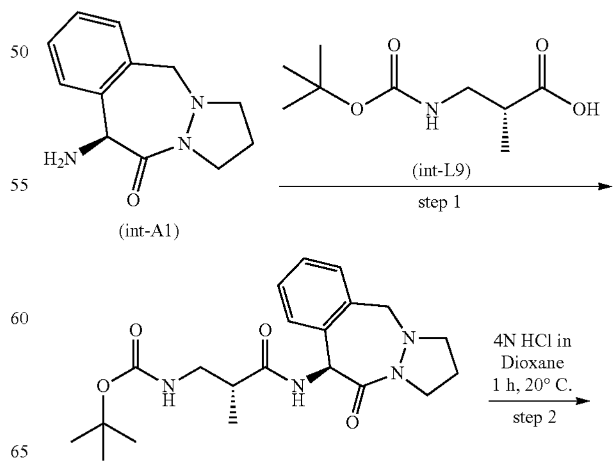

-continued

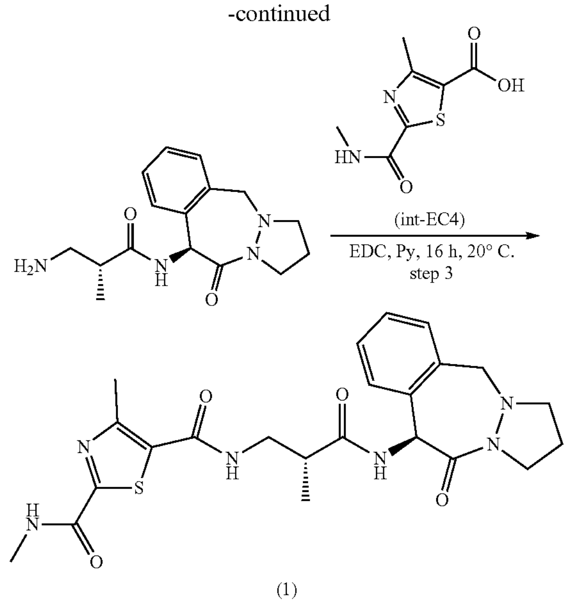

(1)

Step 1: To a solution of (S)-10-amino-2,3,5,10-tetrahydro-1H,11H-benzo[d]pyrazolo[1,2-a][1,2]diazepin-11-one (int-A1) (5.0 g, 11.12 mmol) in $CH_3CN$ (50 mL), were added (R)-3-((tert-butoxycarbonyl)amino)-2-methylpropanoic acid (int-L9) (2.26 g, 11.12 mmol), DIPEA (5.83 mL, 33.4 mmol) and TOTU (3.65 g, 11.12 mmol) and the reaction mixture was stirred at rt for 16 h. The reaction mixture was then concentrated and the crude product was dissolved in ethyl acetate and washed with 1N HCl and sat. $NaHCO_3$, dried ($MgSO_4$) and concentrated to provide an oil which was treated with cold $Et_2O$ to crystalize the product. The obtained precipitate was collected by filtration and dried in vacuum to give tert-butyl ((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)carbamate. LCMS (method a) m/z 403.1 $[M+H]^+$, $t_R$=0.92 min. $^1H$ NMR (400 MHz, DMSO-$d_6$) δ ppm: 8.21 (d, J=8.8 Hz, 1H), 7.29 (d, J=7.9 Hz, 1H), 7.23 (t, J=7.4 Hz, 1H), 7.15 (t, J=7.6 Hz, 1H), 7.06 (d, J=7.6 Hz, 1H), 6.80 (d, J=4.0 Hz, 1H), 6.70 (d, J=8.7 Hz, 1H), 4.24 (s, 2H), 3.62-3.43 (m, 2H), 3.31-3.22 (m, 1H), 3.21-3.08 (m, 2H), 3.00-2.91 (m, 1H), 2.89-2.79 (m, 1H), 2.42-2.27 (m, 1H), 2.16-2.07 (m, 1H), 1.40 (s, 9H), 1.01 (d, J=6.7 Hz, 3H).

Step 2: tert-Butyl ((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)carbamate (4.92 g, 11.0 mmol) was dissolved in 4N HCl (50 mL) and the reaction mixture was stirred at rt for 1 h. The reaction mixture was concentrated and then $CH_3CN/Et_2O$ was added. The resulting precipitate was filtered off, washed with cold $Et_2O$ and dried under vacuum to give (R)-3-amino-2-methyl-N—((S)-11-oxo-2,3,10,11-tetrahydro-1H,5H-benzo[d]pyrazolo[1,2-a][1,2]diazepin-10-yl)propanamide. LCMS (method a) m/z 303 $[M+H]^+$, $t_R$=0.41 min. $^1H$ NMR (400 MHz, DMSO-$d_6$) δ ppm: 8.74 (d, J=9.2 Hz, 1H), 7.79 (s, 3H), 7.31 (d, J=7.7 Hz, 1H), 7.24 (t, J=7.0 Hz, 1H), 7.18 (t, J=7.0 Hz, 1H), 7.07 (d, J=7.5 Hz, 1H), 6.77 (d, J=9.1 Hz, 1H), 4.25 (s, 2H), 3.56-3.49 (m, 2H), 3.33-3.24 (m, 1H), 3.22-3.14 (m, 1H). 3.11-2.98 (m, 2H), 2.94-2.79 (m, 1H), 2.43-2.30 (m, 1H), 2.18-2.03 (m, 1H), 1.20 (d, J=6.5 Hz, 3H).

Step 3: 4-Methyl-2-(methylcarbamoyl)thiazole-5-carboxylic acid (int-EC4) (10 mg, 0.04 mmol) and EDC (14.71 mg, 0.077 mmol) were added to a solution of (R)-3-amino-2-methyl-N—((S)-11-oxo-2,3,10,11-tetrahydro-1H,5H-benzo[d]pyrazolo[1,2-a][1,2]diazepin-10-yl)propanamide (13 mg, 0.038 mmol) in pyridine (2 mL) and the mixture was stirred at rt for 16 h. Ethyl acetate was added to the reaction mixture and the organic phase was washed with sat. $NaHCO_3$, dried ($MgSO_4$) and concentrated. The crude product was purified by preparative HPLC (Waters SunFire Prep C18 OBD 5 μm, 30*100 mm, Flow: 40 mL/min, $CH_3CN$: 5 min to 5%, 25 min to 60%) to yield $N^2$,4-dimethyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide (1). LCMS (method b) m/z 485.2 $[M+H]^+$, $t_R$=0.73 min. $^1H$ NMR (400 MHz, DMSO-$d_6$) δ ppm: 8.84 (q, J=4.0 Hz, 1H), 8.40 (t, J=5.6 Hz, 1H), 8.36 (d, J=8.9 Hz, 1H), 7.23 (d, J=7.9 Hz, 1H), 7.19 (t, J=7.5 Hz, 1H), 7.05 (d, J=7.6 Hz, 1H), 6.92 (t, J=7.6 Hz, 1H), 6.73 (d, J=8.8 Hz, 1H), 4.24 (s, 2H), 3.63-3.40 (m, 3H), 3.29-3.24 (m, 1H), 3.23-3.14 (m, 1H), 3.13-3.01 (m, 1H), 2.80 (d, J=4.8 Hz, 3H), 2.59 (s, 3H), 2.43-2.26 (m, 2H), 2.17-2.03 (m, 1H), 1.10 (d, J=6.9 Hz, 3H).

Alternatively, the resulting product was triturated in MTBE (or acetonitrile) and the suspension was filtered to obtain the solid. The solid was then dried under vacuum to afford compound of example 1 in a crystalline form.

Example 2: N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-4-methylisoxazole-5-carboxamide (2)

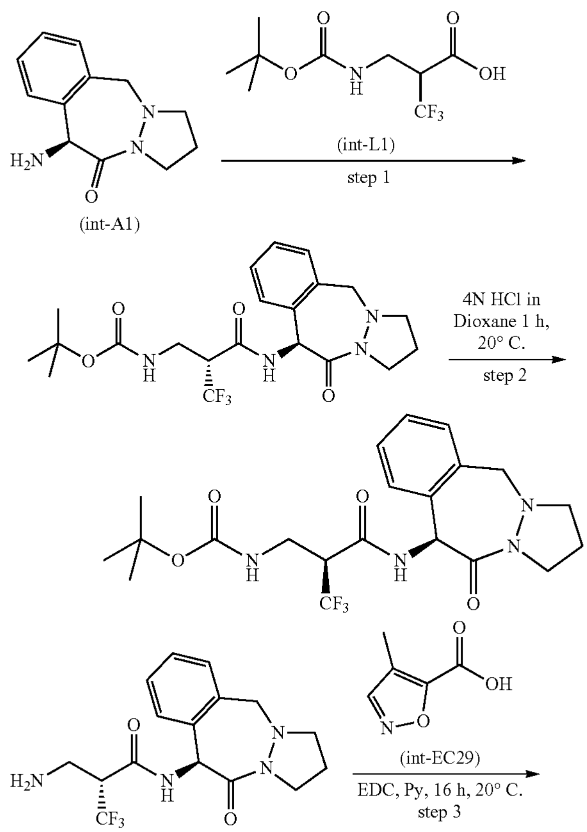

-continued

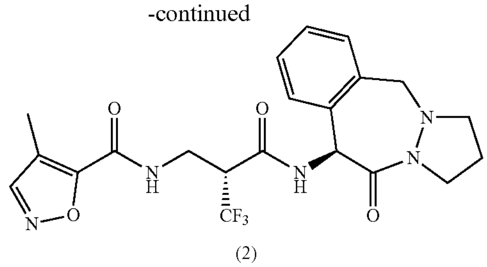

(2)

Step 1. To a mixture of (S)-10-Amino-2,3-dihydrobenzo[d]pyrazolo[1,2-a][1,2]diazepine-5,11(1H,10H)-dione (550 mg, 2.1 mmol) in $CH_3CN$ (10 mL) was added 2-(((tert-butoxycarbonyl)amino)methyl)-3,3,3-trifluoropropanoic acid (int-L1) (528 mg, 2.1 mmol), TOTU (674 mg, 2.1 mmol) and DIPEA (1.1 mL, 6.2 mol) and the mixture was stirred at rt for 3 d. The reaction mixture was concentrated, dissolved in ethyl acetate and washed with 1N HCl and with sat. $NaHCO_3$ solution, dried ($MgSO_4$) and concentrated to give a mixture of stereoisomers. The crude was purified by flash chromatography (0-30% ethyl acetate in cyclohexane) to give the desired isomer tert-butyl ((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)carbamate. LCMS (condition a) m/z 471.2 $[M+H]^+$, $t_R$=0.99 min.; $^1H$ NMR (400 MHz, DMSO-$d_6$) δ ppm 9.44 (d, J=7.7 Hz, 1H), 7.79 (d, J=7.6 Hz, 1H), 7.60-7.47 (m, 2H), 7.36 (d, J=7.8 Hz, 1H), 7.08 (t, J=5.3 Hz, 1H), 5.95 (d, J=7.8 Hz, 1H), 4.33-4.06 (m, 3H), 3.69-3.57 (m, 1H), 3.39-3.32 (m, 2H), 3.27-3.17 (m, 1H), 2.18-2.07 (m, 2H), 1.42 (s, 9H).

Step 2. A mixture of tert-butyl ((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)carbamate (360 mg, 0.8 mmol) in 4M HCl in dioxane (10 mL, 40 mmol) was stirred at rt for 1 h. The reaction mixture was then concentrated and treated with $CH_3CN$ and $Et_2O$. The precipitate was filtered off, washed with cold $Et_2O$ and dried in vacuum to give (R)-2-(aminomethyl)-N—((S)-5,11-dioxo-2,3,10,11-tetrahydro-1H,5H-benzo[d]pyrazolo[1,2-a][1,2]diazepin-10-yl)-3,3,3-trifluoropropanamide as an HCl salt which was used without further purification in the next step. LCMS (condition a) m/z 371.2 $[M+H]^+$, $t_R$=0.35 min. $^1H$ NMR (400 MHz, DMSO-$d_6$) δ ppm: 9.74 (d, J=8.2 Hz, 1H), 8.15 (s, 3H), 7.80 (d, J=7.7 Hz, 1H), 7.62 (t, J=7.6 Hz, 1H), 7.53-7.45 (m, 2H), 6.01 (d, J=8.0 Hz, 1H), 4.34-4.16 (m, 2H), 4.11-3.97 (m, 1H), 3.73-3.58 (m, 1H), 3.32-3.18 (m, 3H), 2.23-2.05 (m, 2H).

Step 3. 4-Methylisoxazole-5-carboxylic acid (int-EC29) (80 mg, 0.20 mmol) and EDC (75 mg, 0.39 mmol) were added at rt to a mixture of (R)-2-(aminomethyl)-N—((S)-5,11-dioxo-2,3,10,11-tetrahydro-1H,5H-benzo[d]pyrazolo[1,2-a][1,2]diazepin-10-yl)-3,3,3-trifluoropropanamide (50 mg, 0.39 mmol) in pyridine (2 mL) and the mixture was stirred at rt for 16 h. The reaction mixture was then treated with ethyl acetate and washed with sat. $NH_4Cl$ solution, dried ($MgSO_4$) and concentrated. The crude product was purified by preparative HPLC to yield N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-4-methylisoxazole-5-carboxamide (2). HPLC (condition a) m/z 480.2 $[M+H]^+$, $t_R$=0.78 min. $^1H$ NMR (400 MHz, DMSO-$d_6$) δ ppm: 9.47 (d, J=7.7 Hz, 1H), 9.05 (t, J=5.7 Hz, 1H), 8.70 (s, 1H), 7.76 (d, J=7.7 Hz, 1H), 7.43 (t, J=5.2 Hz, 1H), 7.27-7.18 (m, 2H), 5.96 (d, J=7.6 Hz, 1H), 4.42-4.17 (m, 2H), 4.11-3.99 (m, 1H), 3.74-3.57 (m, 3H), 3.26-3.14 (m, 1H), 2.25 (s, 3H), 2.20-2.08 (m, 2H).

Table 1 shows additional example compounds (Examples 3-61) which were prepared using methods analogous to those described in Example 1 or Example 2. The appropriate intermediates used in each step are listed, along with the coupling conditions for step 3.

TABLE 1

| Example No. | Compound Structure | Compound Name | Reaction Parameters | Analytics |
|---|---|---|---|---|
| 3 | 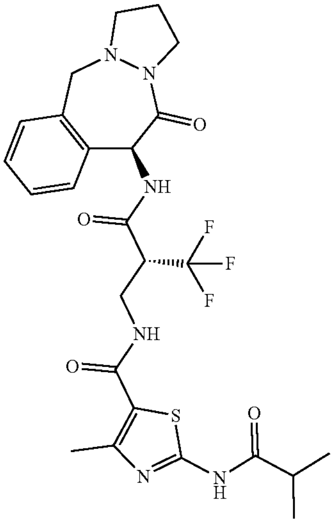 [SMILES: Cc1nc(NC(=O)C(C)C)sc1C(=O)NC[C@H](C(=O)N[C@@H]1C(=O)N2CCCN2Cc2ccccc21)C(F)(F)F] | 2-Isobutyramido-4-methyl-N-((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide | Step 1: int-A1 and int-L1<br>Step 3: int-EC1; EDC, pyridine | m/z 567.3 $[M + H]^+$, $t_R$ = 0.90 min (LCMS method a), $^1H$ NMR (400 MHz, DMSO-$d_6$) δ ppm: 12.24 (s, 1H). 9.06 (d. J = 8.8 Hz, 1H), 8.16 (t, J = 5.5 Hz, 1H), 7.18 - 7.11 (m, 2H), 7.04 (d, J = 7.6 Hz, 1H), 6.87 (t, J = 7.6 Hz, 1H), 6.76 (d, J = 8.7 Hz, 1H), 4.31 - 4.17 (m, 3H), 3.77 - 3.46 (m, 4H), 3.20 - 3.13 (m, 2H), 2.80 - 2.69 (m, 1H), 2.48 (s. 3H), 2.40 - 2.26 (m, 1H), 2.20 - 2.01 (m, 1H), 1.12 (dd, J = 6.9, 1.7 Hz, 6H). |

TABLE 1-continued

| Example No. | Compound Structure | Compound Name | Reaction Parameters | Analytics |
|---|---|---|---|---|
| 4 | 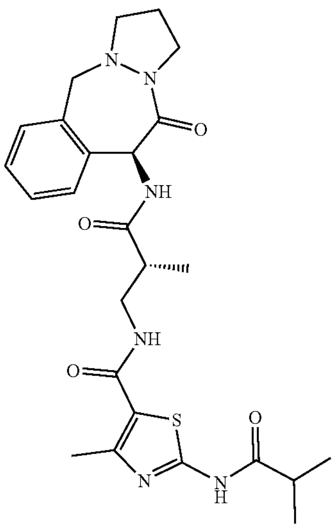 [SMILES: Cc1nc(NC(=O)C(C)C)sc1C(=O)NC[C@@H](C)C(=O)N[C@@H]1C(=O)N2CCCN2Cc2ccccc21] | 2-Isobutyramido-4-methyl-N-((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-5-carboxamide | Step 1: int-A1 and Int-L9 Step 3: int-EC1; EDC, pyridine | m/z 513.2 [M + H]$^+$, $t_R$ = 0.81 min (LCMS method a), $^1$H NMR (400 MHz, DMSO-$d_6$) δ ppm: 12.20 (9, 1H), 8.31 (d, J = 8.8 Hz, 1H), 7.84 (t, J = 5.4 Hz, 1H), 7.21 (d. J = 7.9 Hz, 1H), 7.14 (t, J = 7.4 Hz, 1H), 7.03 (d. J = 7.6 Hz, 1H), 6.88 (t, J = 7.6 Hz, 1H), 6.71 (d, J = 8.7 Hz, 1H), 4.23 (s, 2H), 3.63 - 3.42 (m, 3H), 3.28 - 3.22 (m, 1H), 3.21 - 3.13 (m, 2H), 3.11 - 3.00 (m, 1H), 2.77 - 2.67 (m, 1H), 2.47 (s, 3H), 2.41 - 2.26 (m, 1H), 2.11 (d, J = 10.2 Hz, 1H), 1.11 (dd, J = 6.8, 2.4 Hz, 6H), 1.08 (d, J = 6.9 Hz, 3H). |
| 5 | 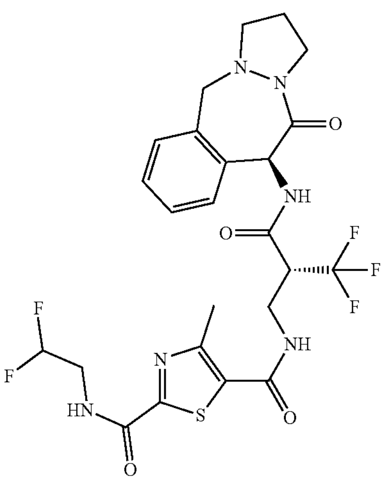 [SMILES: Cc1nc(C(=O)NCC(F)F)sc1C(=O)NC[C@H](C(=O)N[C@@H]1C(=O)N2CCCN2Cc2ccccc21)C(F)(F)F] | $N^2$-(2,2-Difluoroethyl)-4-methyl-$N^5$-((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide | Step 1: int-A1 and int-L1 Step 3: int-EC3; EDC, pyridine | m/z 589.2 [M + H]$^+$, $t_R$ = 0.93 min (LC/MS condition a), $^1$H NMR (400 MHz, DMSO-$d_6$) δ 9.22 (t, J = 6.2 Hz, 1H), 9.17 (d, J = 9.0 Hz, 1H), 8.84 (t, J = 5.6 Hz, 1H), 7.22 - 7.13 (m, 2H), 7.06 (d, J = 7.5 Hz, 1H), 6.88 (t, J = 7.7 Hz, 1H), 6.79 (d, J = 8.9 Hz, 1H), 6.15 (tt, J = 55.9, 4.2 Hz, 1H), 4.30 - 4.24 (m, 1H), 4.24 (s, 2H), 3.77 - 3.60 (m, 4H), 3.59 - 3.46 (m, 2H), 3.30 - 3.25 (m, 1H), 3.21 - 3.12 (m, 1H), 2.62 (s, 3H), 2.41 - 2.27 (m, 1H), 2.17 - 2.02 (m, 1H). |
| 6 | 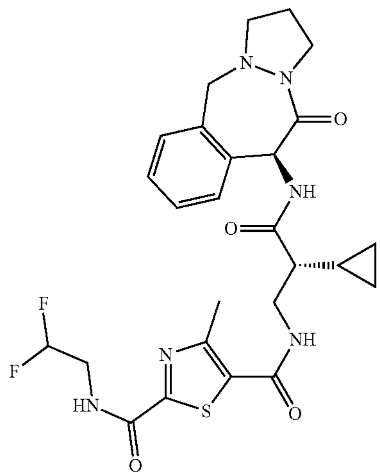 [SMILES: Cc1nc(C(=O)NCC(F)F)sc1C(=O)NC[C@H](C(=O)N[C@@H]1C(=O)N2CCCN2Cc2ccccc21)C1CC1] | $N^5$-((R)-2-Cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-(2,2-difluoroethyl)-4-methylthiazole-2,5-dicarboxamide | Step 1: int-A1 and int-L2 Step 3: int-EC3; EDC, pyridine | m/z 561.2 [M + H]$^+$, $t_R$ = 0.90 min (LC/MS condition a), $^1$H NMR (400 MHz, DMSO-$d_6$) δ 9.19 (t, J = 4.6 Hz, 1H), 8.48 (t, J = 5.1 Hz, 1H), 8.31 (d, J = 8.8 Hz, 1H), 7.26 - 7.13 (m, 2H), 7.04 (d, J = 7.6 Hz, 1H), 6.91 (t, J = 7.5 Hz, 1H), 6.74 (d, J = 8.4 Hz, 1H), 6.14 (tt, J = 56.4, 3.9 Hz, 1H), 4.23 (s, 2H), 3.75 - 3.60 (m, 2H), 3.58 - 3.44 (m, 4H), 3.30 - 3.25 (m, 1H), 3.23 - 3.12 (m, 1H), 2.59 (s, 3H), 2.34 (t, J = 8.4 Hz, 2H), 2.18 - 1.99 (m, 1H), 1.03 - 0.79 (m, 1H), 0.63 - 0.48 (m, 1H), 0.48 - 0.35 (m, 2H), 0.34 - 0.21 (m, 1H). |

TABLE 1-continued

| Example No. | Compound Structure | Compound Name | Reaction Parameters | Analytics |
|---|---|---|---|---|
| 7 | 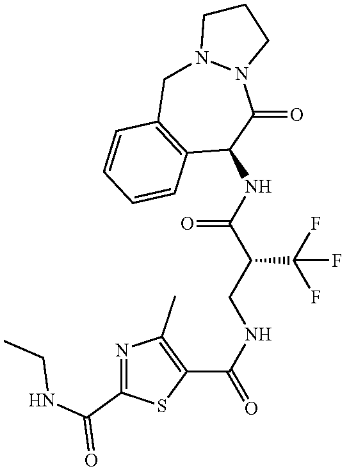 [SMILES: CCNC(=O)c1nc(C)c(C(=O)NC[C@H](C(=O)N[C@@H]2C(=O)N3CCCN3Cc3ccccc32)C(F)(F)F)s1] | $N^2$-Ethyl-4-methyl-$N^5$-((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide | Step 1: int-A1 and int-L1 Step 3: int-EC2; EDC, pyridine | m/z 553.2 $[M + H]^+$, $t_R$ = 0.91 min (LCMS method b), $^1H$ NMR (400 MHz, DMSO-$d_6$) δ 9.14 (d, 1H), 8.93 (s, 1H), 8.77 (s, 1H), 7.15 (s, 2H), 7.05 (s,1H), 6.87 (m, 1H), 6.79 (m, 1H), 4.22 (s, 3H), 3.67 (m, 6H), 3.26 (m,3H), 3.13 (m, 1H), 2.29 (s, 3H), 2.35 (m, 1H), 2.10 (m, 1H), 1.11 (s, 3H) |
| 8 | 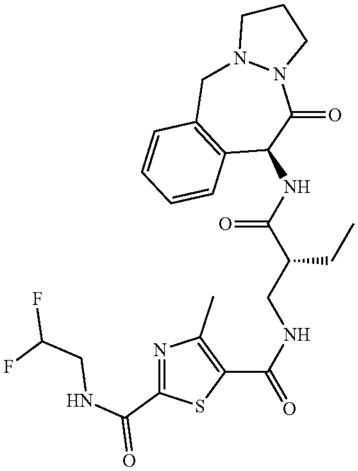 [SMILES: CC[C@H](CNC(=O)c1sc(C(=O)NCC(F)F)nc1C)C(=O)N[C@@H]1C(=O)N2CCCN2Cc2ccccc21] | $N^2$-(2,2-Difluoroethyl)-4-methyl-$N^5$-((R)-2-(((S)-11-oxo-2,3,10,11-tetrahydro-1H,5H-benzo[d]pyrazolo[1,2-a][1,2]diazepin-10-yl)carbamoyl)butyl) thiazole-2,5-dicarboxamide | Step 1: int-A1 and Int-L3 Step 3: int-EC3; EDC, pyridine | m/z 549.2 $[M + H]^+$, $t_R$ = 0.87 min (LCMS condition a), $^1H$ NMR (400 MHz, DMSO-$d_6$) δ 9.27 - 9.10 (m, 1H), 8.48 - 8.33 (m, 2H), 7.23 (d, J = 8.0 Hz, 1H), 7.17 (t, J = 7.4 Hz, 1H), 7.04 (d, J = 7.7 Hz, 1H), 6.89 (t, J = 7.6 Hz, 1H), 6.75 (d, J = 8.8 Hz, 1H), 6.34 - 5.94 (m, 1H), 4.23 (s, 2H), 3.73 - 3.60 (m, 1H), 3.58 - 3.35 (m, 4H), 3.29 - 3.23 (m, 1H), 3.22 - 3.10 (m, 2H), 2.98 - 2.85 (m, 1H), 2.60 (s, 3H), 2.41 - 2.25 (m, 1H), 2.16 - 2.04 (m, 1H), 1.59 - 1.42 (m, 2H), 0.90 (t, J = 7.4 Hz, 3H). |
| 9 | 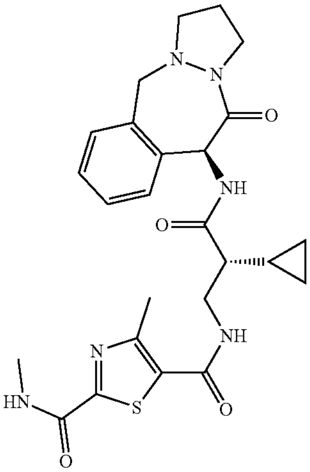 [SMILES: CNC(=O)c1nc(C)c(C(=O)NC[C@H](C(=O)N[C@@H]2C(=O)N3CCCN3Cc3ccccc32)C2CC2)s1] | $N^5$-((R)-2-Cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$,4-dimethylthiazole-2,5-dicarboxamide | Step 1: int-A1 and int-L2 Step 3: int-EC4; EDC, pyridine | m/z 511.2 $[M + H]^+$, $t_R$ = 0.79 min (LCMS method b), $^1H$ NMR (400 MHz, DMSO-$d_6$) δ 8.91 - 8.78 (m, 1H), 8.42 (t, J = 5.5 Hz, 1H), 8.29 (d, J = 8.8 Hz, 1H), 7.23 - 7.13 (m, 2H), 7.04 (d, J = 7.9 Hz, 1H), 6.91 (t, J = 7.3 Hz, 1H), 6.74 (d, J = 8.8 Hz, 1H), 4.23 (s, 2H), 3.56 - 3.52 (m, 4H), 3.35 - 3.25 (m, 1H), 3.22 - 3.11 (m, 1H), 2.79 (d, J = 4.7 Hz, 3H), 2.57 (s, 3H), 2.37 - 2.27 (m, 2H), 2.18 - 2.04 (m, 1H), 0.94 - 0.84 (m, 1H), 0.59 - 0.48 (m, 1H), 0.46 - 0.35 (m, 2H), 0.30 - 0.18 (m, 1H). |

TABLE 1-continued

| Example No. | Compound Structure | Compound Name | Reaction Parameters | Analytics |
|---|---|---|---|---|
| 10 | 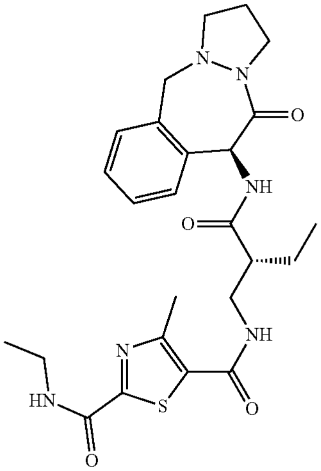 [SMILES: CCNC(=O)c1nc(C)c(C(=O)NC[C@@H](CC)C(=O)N[C@@H]2C(=O)N3CCCN3Cc3ccccc32)s1] | $N^2$-Ethyl-4-methyl-$N^5$-((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide | Step 1: int-A1 and Int-L3 Step 3: int-EC2; EDC, pyridine | m/z 513.3 $[M + H]^+$, $t_R$ = 0.85 min (LCMS method b), $^1H$ NMR (400 MHz, DMSO-$d_6$) δ 8.91 (t, J = 6.0 Hz, 1H), 8.41 - 8.31 (m, 2H), 7.23 (d, J = 7.9 Hz, 1H), 7.17 (t, J = 7.4 Hz, 1H), 7.04 (d, J = 7.7 Hz, 1H), 6.89 (t, J = 7.6 Hz, 1H), 6.75 (d, J = 8.8 Hz, 1H), 4.23 (s, 2H), 3.49 - 3.41 (m, 2H), 3.38 - 3.21 (m, 5H), 3.17 (ddd, J = 11.4, 7.5, 2.6 Hz, 1H), 2.95 - 2.85 (m, 1H), 2.58 (s, 3H), 2.35 (d, J = 11.3 Hz, 1H), 2.11 (d, J = 8.4 Hz, 1H), 1.60 - 1.40 (m, 2H), 1.11 (t, J = 7.1 Hz, 3H), 0.90 (t, J = 7.4 Hz, 3H). |
| 11 | 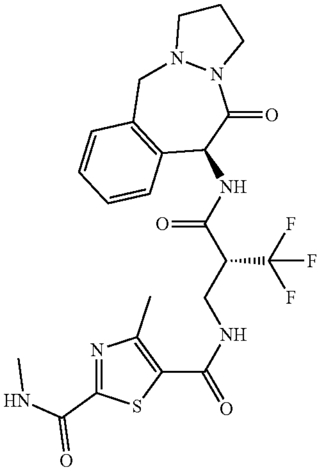 [SMILES: CNC(=O)c1nc(C)c(C(=O)NC[C@H](C(=O)N[C@@H]2C(=O)N3CCCN3Cc3ccccc32)C(F)(F)F)s1] | $N^2$,4-Dimethyl-$N^5$-((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide | Step 1: int-A1 and int-L1 Step 3: int-EC4; EDC, pyridine | m/z 539.2 $[M + H]^+$, $t_R$ = 0.85 min (LCMS method b), $^1H$ NMR (400 MHz, DMSO-$d_6$) δ 9.16 (d, J = 9.0 Hz, 1H), 8.91 - 8.84 (m, 1H), 8.81 - 8.73 (m, 1H), 7.23 - 7.11 (m, 2H), 7.05 (d, J = 7.7 Hz, 1H), 6.88 (t, J = 8.6 Hz, 1H), 6.79 (d, J = 8.9 Hz, 1H), 4.24 (s, 2H), 3.76 - 3.61 (m, 2H), 3.58 - 3.45 (m, 2H), 3.30 - 3.24 (m, 1H), 3.22 - 3.12 (m, 1H), 2.80 (d, J = 4.8 Hz, 3H), 2.60 (s, 3H), 2.41 - 2.27 (m, 2H), 2.17 - 2.00 (m, 1H). |
| 12 | 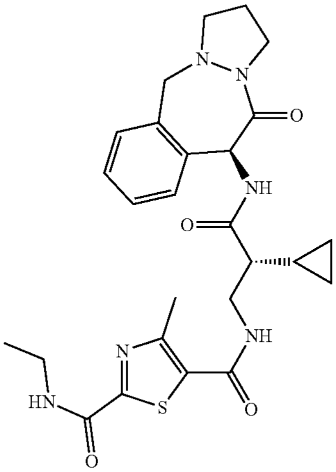 [SMILES: CCNC(=O)c1nc(C)c(C(=O)NC[C@H](C(=O)N[C@@H]2C(=O)N3CCCN3Cc3ccccc32)C2CC2)s1] | $N^5$-((R)-2-Cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-ethyl-4-methylthiazole-2,5-dicarboxamide | Step 1: int-A1 and int-L2 Step 3: int-EC2; EDC, pyridine | m/z 525.2 $[M + H]^+$, $t_R$ = 0.88 min (LCMS method b), $^1H$ NMR (400 MHz, DMSO-$d_6$) δ 8.89 (t, J = 6.0 Hz, 1H), 8.40 (t, J = 5.5 Hz, 1H), 8.28 (d, J = 9.0 Hz, 1H), 7.22 - 7.11 (m, 2H), 7.03 (d, J = 7.7 Hz, 1H), 6.90 (t, J = 7.6 Hz, 1H), 6.73 (d, J = 8.8 Hz, 1H), 4.22 (s, 2H), 3.60 - 3.41 (m, 4H), 3.28 - 3.20 (m, 3H), 3.19 - 3.12 (m, 1H), 2.56 (s, 3H), 2.36 - 2.27 (m, 2H), 2.15 - 2.06 (m, 1H), 1.10 (t, J = 7.2 Hz, 3H), 0.94 - 0.81 (m, 1H), 0.60 - 0.46 (m, 1H), 0.43 - 0.33 (m, 2H), 0.31 - 0.16 (m, 1H). |

TABLE 1-continued

| Example No. | Compound Structure | Compound Name | Reaction Parameters | Analytics |
|---|---|---|---|---|
| 13 | 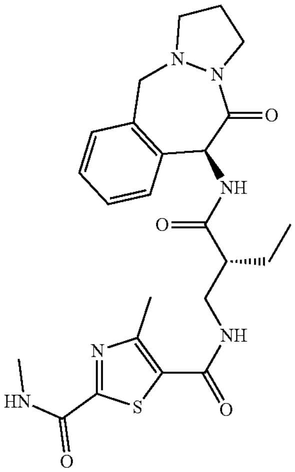 [SMILES: CC[C@H](CNC(=O)c1sc(C(=O)NC)nc1C)C(=O)N[C@@H]1C(=O)N2CCCN2Cc2ccccc21] | $N^2$,4-Dimethyl-$N^5$-((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide | Step 1: int-A1 and Int-L3 Step 3: int-EC4; EDC, pyridine | m/z 499.3 $[M + H]^+$, $t_R$ = 0.78 min (LCMS method b), $^1H$ NMR (400 MHz, DMSO-$d_6$) δ 8.88 - 8.81 (m, 1H), 8.41 - 8.33 (m, 2H), 7.23 (d, J = 7.9 Hz, 1H), 7.17 (t, J = 7.5 Hz, 1H), 7.04 (d, J = 7.5 Hz, 1H), 6.88 (t, J = 7.6 Hz, 1H), 6.75 (d, J = 8.9 Hz, 1H), 4.23 (s, 2H), 3.54 - 3.50 (m, 1H), 3.49 - 3.40 (m, 1H), 3.37 - 3.25 (m, 2H), 3.22 - 3.11 (m, 1H), 2.96 - 2.86 (m, 1H), 2.79 (d, J = 4.7 Hz, 3H), 2.58 (s, 3H), 2.43 - 2.28 (m, 2H), 2.15 - 2.02 (m, 1H), 1.58 - 1.41 (m, 2H), 0.90 (t, J = 7.4 Hz, 3H). |
| 14 | 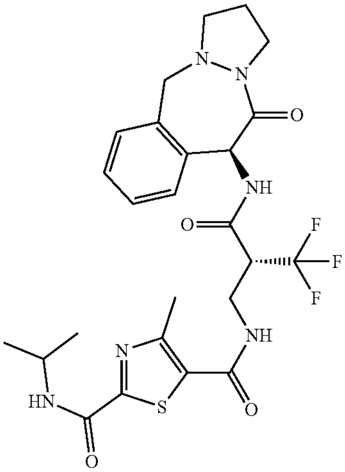 [SMILES: Cc1nc(C(=O)NC(C)C)sc1C(=O)NC[C@H](C(=O)N[C@@H]1C(=O)N2CCCN2Cc2ccccc21)C(F)(F)F] | $N^2$-Isopropyl-4-methyl-$N^5$-((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide | Step 1: int-A1 and int-L1 Step 3: int-EC5; EDC, pyridine | m/z 567.2 $[M + H]^+$, $t_R$ = 0.98 min (LCMS method b), $^1H$ NMR (400 MHz, DMSO-$d_6$) δ 9.16 (d, J = 8.9 Hz, 1H), 8.78 (t, J = 5.6 Hz, 1H), 8.71 (d, J = 8.4 Hz, 1H), 7.22 - 7.13 (m, 2H), 7.06 (d, J = 7.5 Hz, 1H), 6.89 (t, J = 7.6 Hz, 1H), 6.79 (d, J = 8.7 Hz, 1H), 4.24 (s, 2H), 4.15 - 4.03 (m, 1H), 3.76 - 3.60 (m, 2H), 3.58 - 3.48 (m, 2H), 3.27 (s, 2H), 3.22 - 3.10 (m, 1H), 2.61 (s, 3H), 2.37 (dd, J = 20.8, 10.4 Hz, 1H), 2.11 (s, 1H), 1.19 (d, J = 6.6 Hz, 6H). |
| 15 | 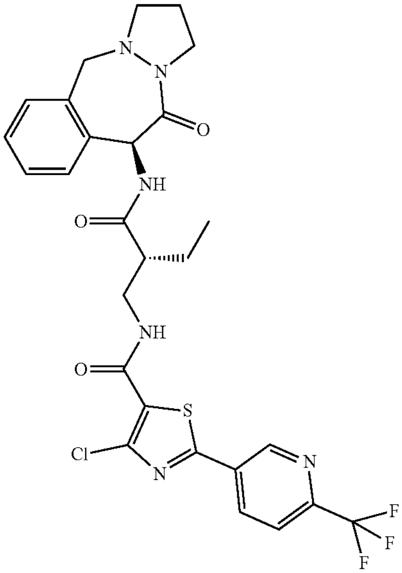 [SMILES: CC[C@H](CNC(=O)c1sc(-c2ccc(C(F)(F)F)nc2)nc1Cl)C(=O)N[C@@H]1C(=O)N2CCCN2Cc2ccccc21] | 4-Chloro-N-((R)-2-(((S)-11-oxo-2,3,10,11-tetrahydro-1H,5H-benzo[d]pyrazolo[1,2-a][1,2]diazepin-10-yl)carbamoyl)butyl)-2-(6-(trifluoromethyl)pyridin-3-yl)thiazole-5-carboxamide | Step 1: int-A1 and Int-L3 Step 3: int-EC6; EDC, pyridine | m/z 607.2 $[M + H]^+$, $t_R$ = 1.15 min (LCMS method b), $^1H$ NMR (400 MHz, DMSO-d6) δ 9.33 (s, 1H), 8.62 (d, J = 8.5 Hz, 1H), 8.53 (d, J = 8.9 Hz, 1H), 8.44 - 8.32 (m, 1H), 8.09 (d, J = 8.3 Hz, 1H), 7.33 - 7.13 (m, 2H), 7.12 - 6.93 (m, 2H), 6.77 (d, J = 9.8 Hz, 1H), 4.24 (s, 2H), 3.68 - 3.39 (m, 5H), 3.23 - 3.12 (m, 1H), 3.02 - 2.89 (m, 1H), 2.37 - 2.30 (m, 1H), 2.22 - 2.00 (m, 1H), 1.71 - 1.43 (m, 2H), 0.92 (t, J = 6.5 Hz, 3H). |

TABLE 1-continued

| Example No. | Compound Structure | Compound Name | Reaction Parameters | Analytics |
|---|---|---|---|---|
| 16 | 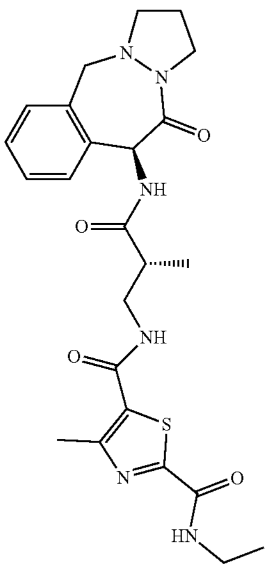 [SMILES: CCNC(=O)c1nc(C)c(C(=O)NC[C@@H](C)C(=O)N[C@@H]2C(=O)N3CCCN3Cc3ccccc32)s1] | $N^2$-Ethyl-4-methyl-$N^5$-((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide | Step 1: int-A1 and Int-L9 Step 3: int-EC2; EDC, pyridine | m/z 499.2 $[M + H]^+$, $t_R$ = 0.81 min (LCMS method b), $^1H$ NMR (400 MHz, DMSO-$d_6$) δ 8.90 (t, J = 6.0 Hz, 1H), 8.42 - 8.31 (m, 2H), 7.20 (d, J = 7.9 Hz, 1H), 7.16 (t, J = 7.6 Hz, 1H), 7.02 (d, J = 7.8 Hz, 1H), 6.89 (t, J = 7.5 Hz, 1H), 6.71 (d, J = 8.8 Hz, 1H), 4.22 (s, 2H), 3.55 - 3.51 (m, 2H), 3.31 - 3.20 (m, 5H), 3.20 - 3.11 (m, 1H), 3.10 - 2.99 (m, 1H), 2.57 (s, 3H), 2.41 - 2.27 (m, 1H), 2.13 - 2.03 (m, 1H), 1.15 - 1.04 (m, 6H). |
| 17 | 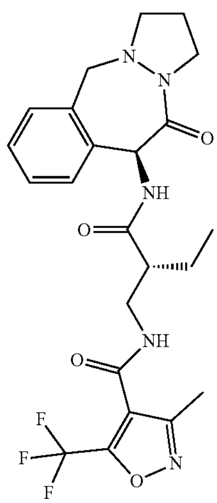 [SMILES: CC[C@H](CNC(=O)c1c(C)noc1C(F)(F)F)C(=O)N[C@@H]1C(=O)N2CCCN2Cc2ccccc21] | 3-Methyl-N-((R)-2-(((5)-11-oxo-2,3,10,11-tetrahydro-1H,5H-benzo[d]pyrazolo[1,2-a][1,2]diazepin-10-yl)carbamoyl)butyl)-5-(trifluoromethyl)isoxazole-4-carboxamide | Step 1: int-A1 and Int-L3 Step 3: int-EC20 replaced int-EC1; EDC, pyridine | m/z 494.4 $[M + H]^+$, $t_R$ = 0.99 min (LCMS method b), $^1H$ NMR (400 MHz, DMSO-$d_6$) δ 8.78 (t, J = 5.8 Hz, 1H), 8.49 (d, J = 9.2 Hz, 1H), 7.29 (d, J = 7.8 Hz, 1H), 7.22 (t, J = 7.4 Hz, 1H), 7.10 - 7.01 (m, 2H), 6.77 (d, J = 9.1 Hz, 1H), 4.24 (s, 2H), 3.57 - 3.47 (m, 2H), 3.47 - 3.34 (m, 2H), 3.33 - 3.24 (m, 1H), 3.21 - 3.13 (m, 1H), 2.92 - 2.82 (m, 1H), 2.41 - 2.30 (m, 1H), 2.28 (s, 3H), 2.15 - 2.04 (m, 1H), 1.62 - 1.47 (m, 2H), 0.91 (t, J = 7.4 Hz, 3H). |

TABLE 1-continued

| Example No. | Compound Structure | Compound Name | Reaction Parameters | Analytics |
|---|---|---|---|---|
| 18 | 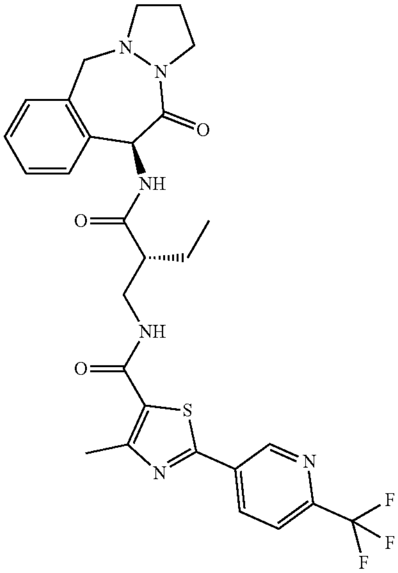 [SMILES: CC[C@H](CNC(=O)c1sc(-c2ccc(C(F)(F)F)nc2)nc1C)C(=O)N[C@@H]1C(=O)N2CCCN2Cc2ccccc21] | 4-Methyl-N-((R)-2-(((S)-11-oxo-2,3,10,11-tetrahydro-1H,5H-benzo[d]pyrazolo[1,2-a][1,2]diazepin-10-yl)carbamoyl)butyl)-2-(6-(trifluoromethyl)pyridin-3-yl)thiazole-5-carboxamide | Step 1: int-A1 and Int-L3 Step 3: int-EC7; EDC, pyridine | m/z 487.1 [M + H]$^+$, $t_R$ = 1.09 min (LCMS method b), $^1$H NMR (400 MHz, DMSO-$d_6$) δ 9.28 (d, J = 2.2 Hz, 1H), 8.55 (dd, J = 8.2, 2.2 Hz, 1H), 8.46 (d, J = 9.1 Hz, 1H), 8.35 (t, J = 5.6 Hz, 1H), 8.06 (d, J = 8.3 Hz, 1H), 7.26 (d, J = 7.9 Hz, 1H), 7.19 - 7.12 (m, 1H), 7.03 (d, J = 7.6 Hz, 1H), 6.92 (t, J = 7.6 Hz, 1H), 6.77 (d, J = 9.2 Hz, 1H), 4.23 (s, 2H), 3.58 - 3.44 (m, 3H), 3.43 - 3.34 (m, 1H), 3.30 - 3.24 (m, 1H), 3.22 - 3.13 (m, 1H), 3.00 - 2.89 (m, 1H), 2.63 (s, 3H), 2.38 - 2.27 (m, 1H), 2.17 - 2.02 (m, 1H), 1.62 - 1.45 (m, 2H), 0.91 (t, J = 7.4 Hz, 3H). |
| 19 | 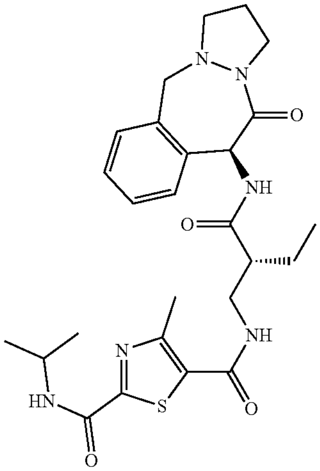 [SMILES: CC[C@H](CNC(=O)c1sc(C(=O)NC(C)C)nc1C)C(=O)N[C@@H]1C(=O)N2CCCN2Cc2ccccc21] | $N^2$-Isopropyl-4-methyl-$N^5$-((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide | Step 1: int-A1 and Int-L3 Step 3: int-EC5; EDC, pyridine | m/z 527.3 [M + H]$^+$, $t_R$ = 0.92 min (LCMS method b), $^1$H NMR (400 MHz, DMSO-$d_6$) δ 8.67 (d, J = 8.4 Hz, 1H), 8.43 - 8.31 (m, 2H), 7.23 (d, J = 7.9 Hz, 1H), 7.16 (d, J = 7.6 Hz, 1H), 7.04 (d, J = 7.7 Hz, 1H), 6.90 (t, J = 7.6 Hz, 1H), 6.75 (d, J = 9.0 Hz, 1H), 4.23 (s, 2H), 4.14 - 4.02 (m, 1H), 3.60 - 3.49 (m, 2H), 3.49 - 3.40 (m, 1H), 3.31 - 3.24 (m, 2H), 3.21 - 3.12 (m, 1H), 2.96 - 2.85 (m, 1H), 2.59 (s, 3H), 2.39 - 2.28 (m, 1H), 2.17 - 2.02 (m, 1H), 1.59 - 1.43 (m, 2H), 1.18 (d, J = 6.6 Hz, 6H), 0.90 (t, J = 7.4 Hz, 3H). |

TABLE 1-continued

| Example No. | Compound Structure | Compound Name | Reaction Parameters | Analytics |
|---|---|---|---|---|
| 20 | 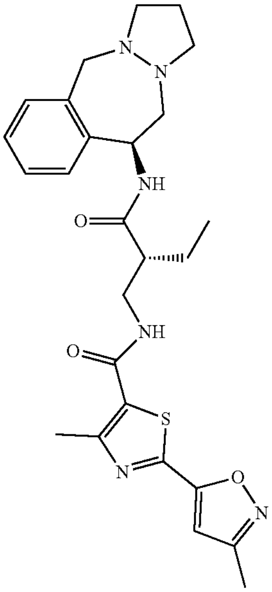 | 4-Methyl-2-(3-methylisoxazol-5-yl)-N-((R)-2-(((S)-11-oxo-2,3,10,11-tetrahydro-1H,5H-benzo[d]pyrazolo[1,2-a][1,2]diazepin-10-yl)carbamoyl)butyl) thiazole-5-carboxamide | Step 1: int-A1 and Int-L3 Step 3: int-EC8; EDC, pyridine | m/z 523.2 [M + H]$^+$, $t_R$ = 0.93 min (LCMS method b), $^1$H NMR (400 MHz, DMSO-$d_6$) δ 8.47 - 8.34 (m, 2H), 7.24 (d, J = 7.9 Hz, 1H), 7.16 (t, J = 7.4 Hz, 1H), 7.07 (s, 1H), 7.03 (d, J = 7.7 Hz, 1H), 6.88 (t, J = 7.6 Hz, 1H), 6.76 (d, J = 8.9 Hz, 1H), 4.23 (s, 2H), 3.59 - 3.41 (m, 3H), 3.41 - 3.33 (m, 1H), 3.30 - 3.24 (m, 2H), 3.22 - 3.12 (m, 1H), 2.98 - 2.86 (m, 1H), 2.60 (s, 3H), 2.33 (s, 3H), 2.16 - 2.03 (m, 1H), 1.60 - 1.44 (m, 2H), 0.91 (t, J = 7.4 Hz, 3H). |
| 21 | 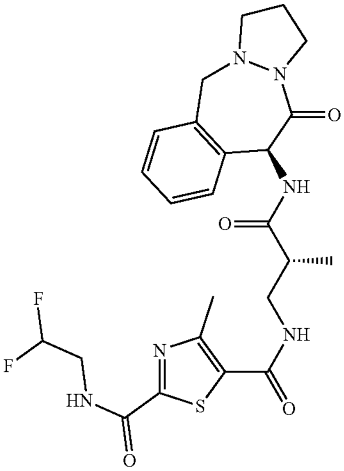 [SMILES: Cc1nc(C(=O)NCC(F)F)sc1C(=O)NC[C@@H](C)C(=O)N[C@@H]1C(=O)N2CCCN2Cc2ccccc21] | $N^2$-(2,2-Difluoroethyl)-4-methyl-$N^5$-((R)-2-methyl-3-oxo-3-(((S)-11-oxo-2,3,10,11-tetrahydro-1H,5H-benzo[d]pyrazolo[1,2-a][1,2]diazepin-10-yl)amino)propyl) thiazole-2,5-dicarboxamide | Step 1: int-A1 and Int-L9 Step 3: int-EC3; EDC, pyridine | m/z 535.2 [M + H]$^+$, $t_R$ = 0.83 min (LCMS condition a), $^1$H NMR (400 MHz, DMSO-$d_6$) δ 9.25 - 9.14 (m, 1H), 8.46 (t, J = 5.2 Hz, 1H), 8.39 (d, J = 8.8 Hz, 1H), 7.22 (d, J = 7.9 Hz, 1H), 7.17 (t, J = 7.4 Hz, 1H), 7.04 (d, J = 7.5 Hz, 1H), 6.91 (t, J = 7.6 Hz, 1H), 6.73 (d, J = 8.9 Hz, 1H), 6.14 (tt, J = 55.8, 4.0 Hz, 1H), 4.23 (s, 2H), 3.67 (t, J = 15.2 Hz, 2H), 3.57 - 3.39 (m, 3H), 3.28 - 3.25 (m, 1H), 3.24 - 3.12 (m, 2H), 3.12 - 3.00 (m, 1H), 2.60 (s, 3H), 2.41 - 2.27 (m, 1H), 2.17 - 2.03 (m, 1H), 1.09 (d, J = 6.9 Hz, 3H). |
| 22 | 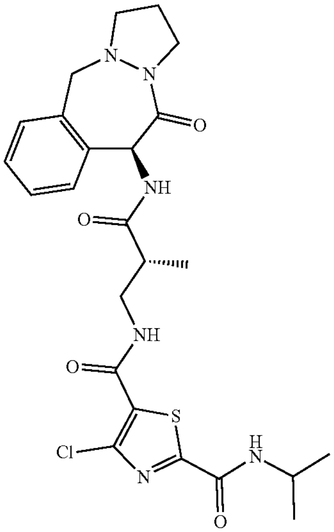 [SMILES: CC(C)NC(=O)c1nc(Cl)c(C(=O)NC[C@@H](C)C(=O)N[C@@H]2C(=O)N3CCCN3Cc3ccccc32)s1] | 4-Chloro-$N^2$-isopropyl-$N^5$-((R)-2-methyl-3-oxo-3-(((S)-11-oxo-2,3,10,11-tetrahydro-1H,5H-benzo[d]pyrazolo[1,2-a][1,2]diazepin-10-yl)amino)propyl) thiazole-2,5-dicarboxamide | Step 1: int-A1 and Int-L9 Step 3: int-EC9; EDC, pyridine | m/z 533.2 [M + H]$^+$, $t_R$ = 0.94 min (LCMS condition a), $^1$H NMR (400 MHz, DMSO-$d_6$) δ 8.93 (d, J = 8.3 Hz, 1H), 8.47 (t, J = 5.7 Hz, 1H), 8.44 (d, J = 9.0 Hz, 1H), 7.23 (d, J = 7.8 Hz, 1H), 7.19 (t, J = 7.5 Hz, 1H), 7.05 (d, J = 7.7 Hz, 1H), 7.01 (t, J = 7.7 Hz, 1H), 6.73 (d, J = 8.8 Hz, 1H), 4.24 (S, 2H), 4.13 - 4.00 (m, 1H), 3.63 - 3.43 (m, 3H), 3.41 - 3.31 (m, 1H), 3.22 - 3.13 (m, 1H), 3.12 - 3.01 (m, 1H), 2.43 - 2.28 (m, 2H), 2.15 - 2.04 (m, 1H), 1.18 (d, J = 6.6 Hz, 6H), 1.12 (d, J = 6.9 Hz, 3H). |

TABLE 1-continued

| Example No. | Compound Structure | Compound Name | Reaction Parameters | Analytics |
|---|---|---|---|---|
| 23 | 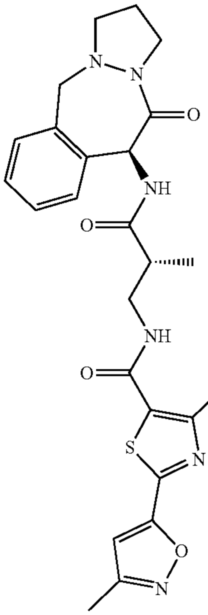 | 4-Methyl-N-((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)-2-(3-methylisoxazol-5-yl)thiazole-5-carboxamide | Step 1: int-A1 and Int-L9 Step 3: int-EC8; EDC, pyridine | m/z 509.4 $[M + H]^+$, $t_R$ = 0.88 min (LCMS condition a), $^1H$ NMR (400 MHz, DMSO-$d_6$) δ 8.46 - 8.36 (m, 2H), 7.22 (d, J = 7.9 Hz, 1H), 7.17 (t, J = 7.4 Hz, 1H), 7.08 (s, 1H), 7.04 (d, J = 7.7 Hz, 1H), 6.91 (t, J = 7.7 Hz, 1H), 6.73 (d, J = 8.9 Hz, 1H), 4.23 (s, 2H), 3.60 - 3.42 (m, 3H), 3.31 - 3.24 (m, 2H), 3.21 - 3.15 (m, 1H), 3.13 - 3.03 (m, 1H), 2.61 (s, 3H), 2.33 (s, 3H), 2.17 - 2.02 (m, 1H), 1.10 (d, J = 6.9 Hz, 3H). |
| 24 | 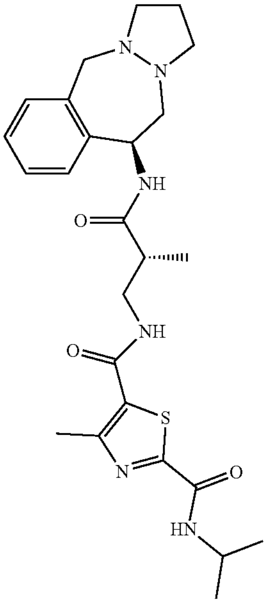 | $N^2$-Isopropyl-4-methyl-$N^5$-((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide | Step 1: int-A1 and Int-L9 Step 3: int-EC5; EDC, pyridine | m/z 513.3 $[M + H]^+$, $t_R$ = 0.88 min (LCMS method b), $^1H$ NMR (400 MHz, DMSO-$d_6$) δ 8.67 (d, J = 8.4 Hz, 1H), 8.46 - 8.33 (m, 2H), 7.22 (d, J = 7.7 Hz, 1H), 7.17 (t, J = 7.4 Hz, 1H), 7.04 (d, J = 7.7 Hz, 1H), 6.92 (t, J = 7.6 Hz, 1H), 6.72 (d, J = 8.8 Hz, 1H), 4.23 (s, 2H), 4.13 - 4.01 (m, 1H), 3.45 (dd, J = 8.6, 6.1 Hz, 2H), 3.34 - 3.22 (m, 3H), 3.17 (ddd, J = 10.9, 7.1, 2.6 Hz, 1H), 3.11 - 3.03 (m, 1H), 2.59 (s, 3H), 2.40 - 2.25 (m, 1H), 2.14 - 2.04 (m, 1H), 1.18 (d, J = 6.6 Hz, 6H), 1.09 (d, J = 7.0 Hz, 3H). |

TABLE 1-continued

| Example No. | Compound Structure | Compound Name | Reaction Parameters | Analytics |
|---|---|---|---|---|
| 25 | 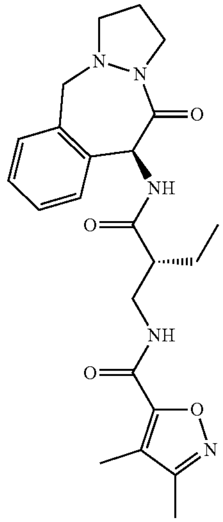 [SMILES: CC[C@H](CNC(=O)c1onc(C)c1C)C(=O)N[C@@H]1C(=O)N2CCCN2Cc2ccccc21] | 3,4-Dimethyl-N-((R)-2-(((S)-11-oxo-2,3,10,11-tetrahydro-1H,5H-benzo[d]pyrazolo[1,2-a][1,2]diazepin-10-yl)carbamoyl)butyl)isoxazole-5-carboxamide | Step 1: int-A1 and Int-L3 Step 3: int-EC21; T3P, DIPEA, $CH_2Cl_2$, 1 h 20° C. | m/z 440.2 $[M + H]^+$, $t_R$ = 0.80 min (LCMS method b), $^1H$ NMR (400 MHz, DMSO-$d_6$) δ 8.46 (d, J = 9.1 Hz, 1H), 7.90 (t, J = 5.6 Hz, 1H), 7.27 - 7.15 (m, 2H), 7.05 (d, J = 7.6 Hz, 1H), 6.96 (t, J = 7.6 Hz, 1H), 6.76 (d, J = 9.0 Hz, 1H), 4.23 (s, 2H), 3.58 - 3.46 (m, 2H), 3.39 (t, J = 6.2 Hz, 2H), 3.31 - 3.23 (m, 1H), 3.22 - 3.13 (m, 1H), 2.95 - 2.85 (m, 1H), 2.43 (s, 3H), 2.39 - 2.28 (m, 1H), 2.25 (s, 3H), 2.15 - 2.02 (m, 1H), 1.61 - 1.42 (m, 2H), 0.91 (t, J = 7.4 Hz, 3H). |
| 26 | 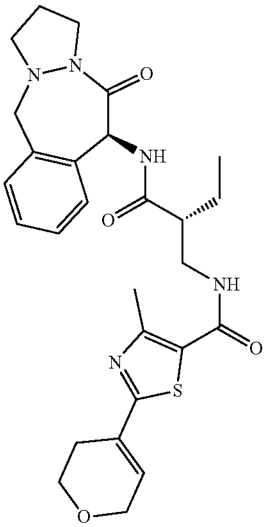 [SMILES: CC[C@H](CNC(=O)c1sc(C2=CCOCC2)nc1C)C(=O)N[C@@H]1C(=O)N2CCCN2Cc2ccccc21] | 2-(3,6-Dihydro-2H-pyran-4-yl)-4-methyl-N-((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide | Step 1: int-A1 and int-L3 Step 3: int-EC10; EDC, pyridine | m/z 524.3 $[M + H]^+$, $t_R$ = 0.87 min (LCMS method b), $^1H$ NMR (400 MHz, DMSO-$d_6$) δ 8.38 (d, J = 9.0 Hz, 1H), 8.08 (t, J = 5.5 Hz, 1H), 7.23 (d, J = 7.9 Hz, 1H), 7.18 (t, J = 7.4 Hz, 1H), 7.04 (d, J = 7.6 Hz, 1H), 6.87 (t, J = 7.3 Hz, 1H), 6.74 (d, J = 8.9 Hz, 1H), 6.71 - 6.67 (m, 1H), 4.32 - 4.18 (m, 4H), 3.80 (t, J = 5.4 Hz, 2H), 3.57 - 3.42 (m, 3H), 3.31 - 3.23 (m, 4H), 3.21 - 3.13 (m, 1H), 2.96 - 2.84 (m, 1H), 2.52 (s, 3H), 2.40 - 2.28 (m, 1H), 2.15 - 2.04 (m, 1H), 1.58 - 1.43 (m, 2H), 0.89 (t, J = 7.4 Hz, 3H). |

TABLE 1-continued

| Example No. | Compound Structure | Compound Name | Reaction Parameters | Analytics |
|---|---|---|---|---|
| 27 | 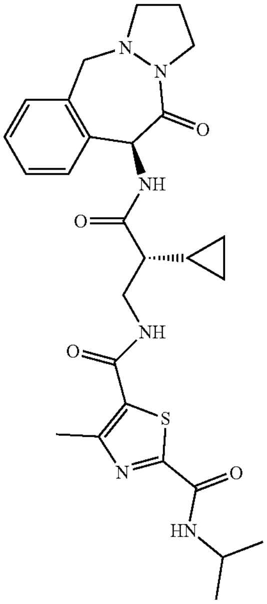 [SMILES: Cc1nc(C(=O)NC(C)C)sc1C(=O)NC[C@H](C(=O)N[C@@H]1C(=O)N2CCCN2Cc2ccccc21)C1CC1] | $N^5$-((R)-2-Cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-isopropyl-4-methylthiazole-2,5-dicarboxamide | Step 1: int-A1 and int-L2<br>Step 3: int-EC5; EDC, pyridine | m/z 539.3 $[M + H]^+$, $t_R$ = 0.95 min (LCMS method b), $^1H$ NMR (400 MHz, DMSO-$d_6$) δ 8.67 (d, J = 8.3 Hz, 1H), 8.41 (t, J = 5.6 Hz, 1H), 8.30 (d, J = 8.9 Hz, 1H), 7.25 - 7.13 (m, 2H), 7.04 (d, J = 7.5 Hz, 1H), 6.92 (t, J = 7.7 Hz, 1H), 6.74 (d, J = 8.8 Hz, 1H), 4.23 (s, 2H), 4.14 - 4.02 (m, 1H), 3.58 - 3.50 (m, 3H), 3.31 - 3.24 (m, 2H), 3.22 - 3.12 (m, 1H), 2.58 (s, 3H), 2.42 - 2.27 (m, 2H), 2.19 - 2.03 (m, 1H), 1.18 (d, J = 6.6 Hz, 6H), 0.95 - 0.83 (m, 1H), 0.59 - 0.48 (m, 1H), 0.47 - 0.36 (m, 2H), 0.30 - 0.20 (m, 1H). |
| 28 | 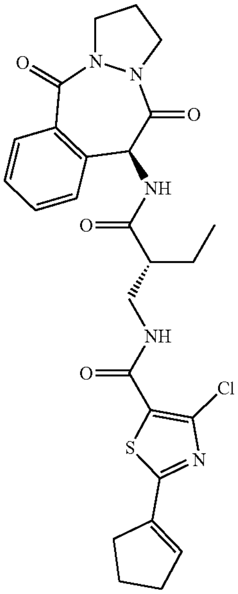 [SMILES: CC[C@H](CNC(=O)c1sc(C2=CCCC2)nc1Cl)C(=O)N[C@@H]1C(=O)N2CCCN2C(=O)c2ccccc21] | 4-Chloro-2-(cyclopent-1-en-1-yl)-N-((R)-2-(((S)-5,11-dioxo-2,3,10,11-tetrahydro-1H,5H-benzo[d]pyrazolo[1,2-a][1,2]diazepin-10-yl)carbamoyl)butyl)thiazole-5-carboxamide | Step 1: int-A1 and Int-L3<br>Step 3: int-EC11; EDC, pyridine | m/z 542.1 $[M + H]^+$, $t_R$ = 1.05 min (LCMS method b), $^1H$ NMR (400 MHz, DMSO-$d_6$) δ 8.91 (d, J = 8.2 Hz, 1H), 8.13 (t, J = 5.6 Hz, 1H), 7.77 (d, J = 7.3 Hz, 1H), 7.48 - 7.40 (m, 1H), 7.40 - 7.34 (m, 2H), 6.79 - 6.69 (m, 1H), 5.98 (d, J = 8.2 Hz, 1H), 4.36 - 4.21 (m, 1H), 4.07 - 3.99 (m, 1H), 3.68 - 3.57 (m, 1H), 3.54 - 3.45 (m, 1H), 3.25 - 3.20 (m, 2H), 3.02 - 2.93 (m, 1H), 2.73 - 2.65 (m, 2H), 2.59 - 2.53 (m, 2H), 2.20 - 2.08 (m, 2H), 2.05 - 1.91 (m, 2H), 1.62 - 1.43 (m, 2H), 0.93 (t, J = 7.4 Hz, 3H). |

TABLE 1-continued

| Example No. | Compound Structure | Compound Name | Reaction Parameters | Analytics |
|---|---|---|---|---|
| 29 | 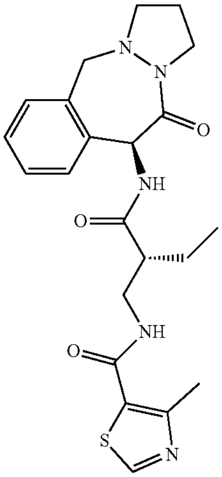 [SMILES: CC[C@H](CNC(=O)c1scnc1C)C(=O)N[C@@H]1C(=O)N2CCCN2Cc2ccccc21] | 4-Methyl-N-((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide | Step 1: int-A1 and Int-L3 Step 3:int-EC22; EDC, pyridine | m/z 442.2 $[M + H]^+$, $t_R$ = 0.73 min (LCMS method a), $^1H$ NMR (400 MHz, DMSO-$d_6$) δ 9.04 (s, 1H), 8.36 (d, J = 8.9 Hz, 1H), 8.15 (t, J = 5.3 Hz, 1H), 7.24 - 7.13 (m, 2H), 7.03 (d, J = 7.6 Hz, 1H), 6.83 (t, J = 7.6 Hz, 1H), 6.74 (d, J = 8.8 Hz, 1H), 4.23 (s, 2H), 3.50 - 3.42 (m, 3H), 3.35 - 3.24 (m, 2H), 3.21 - 3.12 (m, 1H), 2.96 - 2.87 (m, 1H), 2.56 (s, 3H), 2.42 - 2.27 (m, 1H), 2.15 - 2.02 (m, 1H), 1.58 - 1.42 (m, 2H), 0.89 (t, J = 7.4 Hz, 3H). |
| 30 | 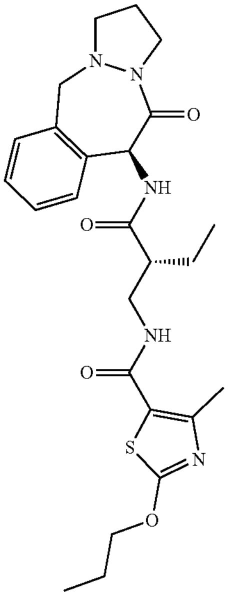 [SMILES: CCCOc1nc(C)c(C(=O)NC[C@@H](CC)C(=O)N[C@@H]2C(=O)N3CCCN3Cc3ccccc32)s1] | 4-Methyl-N-((R)-2-(((S)-11-oxo-2,3,10,11-tetrahydro-1H,5H-benzo[d]pyrazolo[1,2-a][1,2]diazepin-10-yl)carbamoyl)butyl)-2-propoxythiazole-5-carboxamide | Step 1: int-A1 and Int-L3 Step 3: int-EC23; EDC, pyridine | m/z 500.3 $[M + H]^+$, $t_R$ = 1.02 min (LCMS method b), $^1H$ NMR (400 MHz, DMSO-$d_6$) δ 8.35 (d, J = 8.9 Hz, 1H), 7.79 (t, J = 5.4 Hz, 1H), 7.24 - 7.14 (m, 2H), 7.04 (d, J = 7.6 Hz, 1H), 6.90 (t, J = 7.6 Hz, 1H), 6.73 (d, J = 8.8 Hz, 1H), 4.32 (t, J = 6.6 Hz, 2H), 4.23 (s, 2H), 3.61 - 3.47 (m, 2H), 3.48 - 3.37 (m, 1H), 3.30 - 3.24 (m, 2H), 3.22 - 3.12 (m, 1H), 2.93 - 2.81 (m, 1H), 2.40 (s, 3H), 2.37 - 2.27 (m, 1H), 2.15 - 2.00 (m, 1H), 1.81 - 1.67 (m, 2H), 1.58 - 1.40 (m, 2H), 0.94 (t, J = 7.4 Hz, 3H), 0.88 (t, J = 7.4 Hz, 3H). |
| 31 | 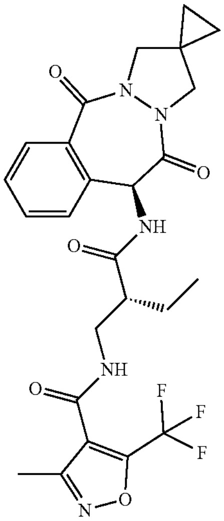 [SMILES: CC[C@H](CNC(=O)c1c(C)noc1C(F)(F)F)C(=O)N[C@@H]1C(=O)N2CC3(CC3)CN2C(=O)c2ccccc21] | N-((R)-2-(((S)-5,11-Dioxo-10,11-dihydro-1H,3H,5H-spiro[benzo[d]pyrazolo[1,2-a][1,2]diazepine-2,1'-cyclopropan]-10-yl)carbamoyl)butyl)-3-methyl-5-(trifluoromethyl)isoxazole-4-carboxamide | Step 1: int-C1 and Int-L3 Step 3: int-EC20; EDC, pyridine | m/z 534.2 $[M + H]^+$, $t_R$ = 1.00 min (LCMS method b), $^1H$ NMR (400 MHz, DMSO-$d_6$) δ 9.00 (d, J = 8.5 Hz, 1H), 8.75 (t, J = 5.6 Hz, 1H), 7.82 (d, J = 7.0 Hz, 1H), 7.57 - 7.42 (m, 3H), 6.07 (d, J = 8.4 Hz, 1H), 4.23 (d, J = 11.1 Hz, 1H), 3.92 (d, J = 10.8 Hz, 1H), 3.63 (d, J = 11.2 Hz, 1H), 3.52 - 3.33 (m, 2H), 3.30 - 3.24 (m, 1H), 2.97 - 2.84 (m, 1H), 2.24 (s, 3H), 1.63 - 1.51 (m, 2H), 0.95 (t, J = 7.4 Hz, 3H), 0.85 - 0.67 (m, 4H). |

TABLE 1-continued

| Example No. | Compound Structure | Compound Name | Reaction Parameters | Analytics |
|---|---|---|---|---|
| 32 | 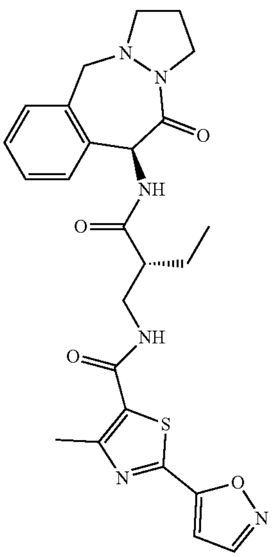 [SMILES: CC[C@H](CNC(=O)c1sc(-c2ccno2)nc1C)C(=O)N[C@@H]1C(=O)N2CCCN2Cc2ccccc21] | 2-(Isoxazol-5-yl)-4-methyl-N-((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide | Step 1: int-A1 and Int-L3 Step 3: Int-EC12; EDC, pyridine | m/z 509.3 $[M + H]^+$, $t_R$ = 0.87 min (LCMS method a), $^1H$ NMR (400 MHz, DMSO-$d_6$) δ 8.84 (d, J = 2.0 Hz, 1H), 8.44 (d, J = 9.6 Hz, 2H), 7.25 (d, J = 7.9 Hz, 1H), 7.22 (d, J = 2.0 Hz, 1H), 7.16 (t, J = 7.4 Hz, 1H), 7.03 (d, J = 7.7 Hz, 1H), 6.89 (t, J = 7.5 Hz, 1H), 6.76 (d, J = 9.1 Hz, 1H), 4.23 (s, 2H), 3.59 - 3.43 (m, 3H), 3.38 (d, J = 7.3 Hz, 1H), 3.26 (s, 1H), 3.22 - 3.12 (m, 1H), 2.99 - 2.87 (m, 1H), 2.61 (s, 3H), 2.40 - 2.30 (m, 1H), 2.18 - 2.03 (m, 1H), 1.63 - 1.43 (m, 2H), 0.91 (t, J = 7.4 Hz, 3H). |
| 33 | 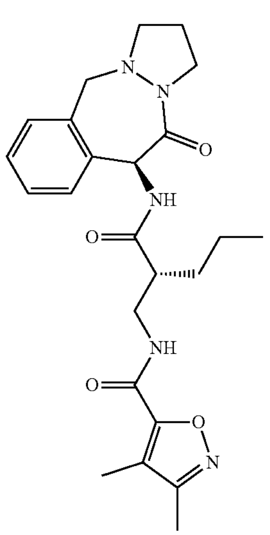 | 3,4-Dimethyl-N-((R)-2-(((S)-11-oxo-2,3,10,11-tetrahydro-1H,5H-benzo[d]pyrazolo[1,2-a][1,2]diazepin-10-yl)carbamoyl)pentyl)isoxazole-5-carboxamide | Step 1: int-A1 and int-L4 Step 3: Int-EC21; T3P, DIPEA, $CH_2Cl_2$, 4 d, 20° C. | m/z 534.2 $[M + H]^+$, $t_R$ = 1.00 min (LCMS method a), $^1H$ NMR (400 MHz, DMSO-$d_6$) δ 8.46 (d, J = 9.2 Hz, 1H), 7.90 (t, J = 5.6 Hz, 1H), 7.27 - 7.14 (m, 2H), 7.04 (d, J = 7.6 Hz, 1H), 6.93 (t, J = 7.5 Hz, 1H), 6.75 (d, J = 9.1 Hz, 1H), 4.23 (s, 2H), 3.51 - 3.49 (m, 2H), 3.41 - 3.35 (m, 2H), 3.31 - 3.24 (m, 1H), 3.22 - 3.12 (m, 1H), 3.03 - 2.91 (m, 1H), 2.43 (s, 3H), 2.39 - 2.28 (m, 1H), 2.25 (s, 3H), 2.15 - 2.03 (m, 1H), 1.57 - 1.47 (m, 1H), 1.43 - 1.27 (m, 3H), 0.89 (t, J = 7.2 Hz, 3H). |

TABLE 1-continued

| Example No. | Compound Structure | Compound Name | Reaction Parameters | Analytics |
|---|---|---|---|---|
| 34 | 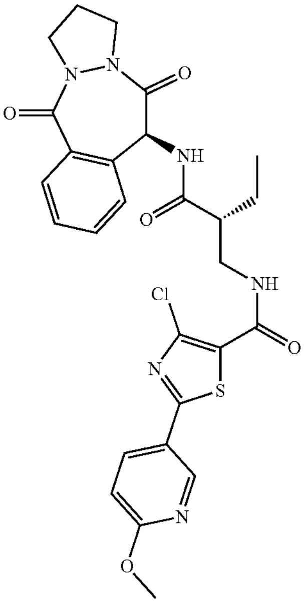 [SMILES: CC[C@H](CNC(=O)c1sc(-c2ccc(OC)nc2)nc1Cl)C(=O)N[C@@H]1C(=O)N2CCCN2C(=O)c2ccccc21] | 4-Chloro-N-((R)-2-(((S)-5,11-dioxo-2,3,10,11-tetrahydro-1H,5H-benzo[d]pyrazolo[1,2-a][1,2]diazepin-10-yl)carbamoyl)butyl)-2-(6-methoxypyridin-3-yl)thiazole-5-carboxamide | Step 1: int-B1 and Int-L3 Step 3: Int-EC13; EDC, pyridine | m/z 583.3 [M + H]$^+$, $t_R$ = 1.01 min (LCMS method b), $^1$H NMR (400 MHz, DMSO-$d_6$) δ 8.94 (d, J = 8.2 Hz, 1H), 8.84 - 8.74 (m, 1H), 8.25 - 8.17 (m, 2H), 7.83 - 7.73 (m, 1H), 7.48 - 7.34 (m, 3H), 6.99 (dd, J = 8.7, 0.7 Hz, 1H), 5.99 (d, J = 8.2 Hz, 1H), 4.37 - 4.20 (m, 1H), 4.12 - 4.00 (m, 1H), 3.94 (s, 3H), 3.69 - 3.58 (m, 1H), 3.58 - 3.48 (m, 1H), 3.46 - 3.37 (m, 1H), 3.26 - 3.14 (m, 1H), 3.05 - 2.94 (m, 1H), 2.21 - 2.04 (m, 2H), 1.66 - 1.46 (m, 2H), 0.94 (t, J = 7.4 Hz, 3H). |
| 35 | 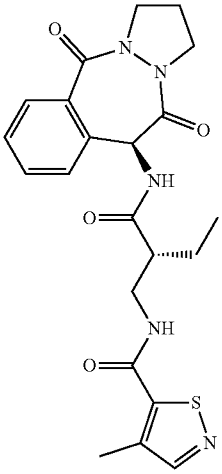 [SMILES: CC[C@H](CNC(=O)c1sncc1C)C(=O)N[C@@H]1C(=O)N2CCCN2C(=O)c2ccccc21] | N-((R)-2-(((S)-5,11-Dioxo-2,3,10,11-tetrahydro-1H,5H-benzo[d]pyrazolo[1,2-a][1,2]diazepin-10-yl)carbamoyl)butyl)-4-methylisothiazole-5-carboxamide | Step 1: int-B1 and Int-L3 Step 3: int-EC24; EDC, pyridine | m/z 456.4 [M + H]$^+$, $t_R$ = 0.75 min (LCMS method a), $^1$H NMR (400 MHz, DMSO-$d_6$) δ 8.86 (d, J = 8.2 Hz, 1H), 8.42 (s, 1H), 8.34 (t, J = 5.6 Hz, 1H), 7.76 (dd, J = 7.7, 1.4 Hz, 1H), 7.43 (t, J = 7.5 Hz, 1H), 7.35 (d, J = 7.7 Hz, 1H), 7.28 (td, J = 7.6, 1.4 Hz, 1H), 5.98 (d, J = 8.1 Hz, 1H), 4.35 - 4.21 (m, 1H), 4.11 - 3.98 (m, 1H), 3.69 - 3.57 (m, 1H), 3.38 - 3.32 (m, 2H), 3.27 - 3.15 (m, 1H), 3.04 - 2.91 (m, 1H), 2.33 (s, 3H), 2.20 - 2.09 (m, 2H), 1.62 - 1.42 (m, 2H), 0.93 (t, J = 7.4 Hz, 3H). |
| 36 | 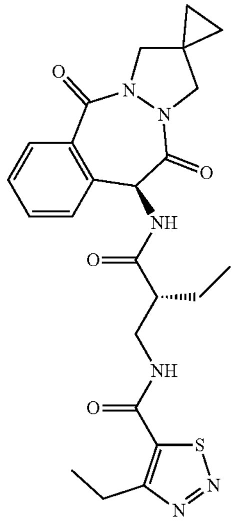 [SMILES: CCc1nnsc1C(=O)NC[C@@H](CC)C(=O)N[C@@H]1C(=O)N2CC3(CC3)CN2C(=O)c2ccccc21] | N-((R)-2-(((S)-5,11-Dioxo-10,11-dihydro-1H,3H,5H-spiro[benzo[d]pyrazolo[1,2-a][1,2]diazepine-2,1'-cyclopropan]-10-yl)carbamoyl)butyl)-4-ethyl-1,2,3-thiadiazole-5-carboxamide | Step 1: int-C1 and Int-L3 Step 3: int-EC25; EDC, pyridine | m/z 497.4 [M + H]$^+$, $t_R$ = 0.93 min (LCMS method a), $^1$H NMR (400 MHz, DMSO-$d_6$) δ 8.98 (d, J = 8.5 Hz, 1H), 8.86 (t, J = 5.5 Hz, 1H), 7.80 (dd, J = 7.9, 1.3 Hz, 1H), 7.45 (t, J = 7.3 Hz, 1H), 7.37 (d, J = 7.8 Hz, 1H), 7.33 - 7.27 (m, 1H), 6.06 (d, J = 8.4 Hz, 1H), 4.23 (d, J = 11.2 Hz, 1H), 3.91 (d, J = 10.8 Hz, 1H), 3.63 (d, J = 11.2 Hz, 1H), 3.49 - 3.40 (m, 1H), 3.38 - 3.33 (m, 1H), 3.30 - 3.25 (m, 1H), 3.14 (q, J = 7.5 Hz, 2H), 3.03 - 2.90 (m, 1H), 1.63 - 1.46 (m, 2H), 1.26 (t, J = 7.5 Hz, 3H), 0.94 (t, J = 7.4 Hz, 3H), 0.84 - 0.67 (m, 4H). |

TABLE 1-continued

| Example No. | Compound Structure | Compound Name | Reaction Parameters | Analytics |
|---|---|---|---|---|
| 37 | 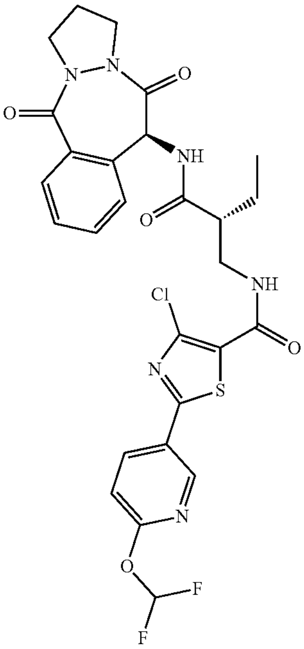 [SMILES: CC[C@H](CNC(=O)c1sc(-c2ccc(OC(F)F)nc2)nc1Cl)C(=O)N[C@@H]1C(=O)N2CCCN2C(=O)c2ccccc21] | 4-Chloro-2-(6-(difluoromethoxy)pyridin-3-yl)-N-((R)-2-(((S)-5,11-dioxo-2,3,10,11-tetrahydro-1H,5H-benzo[d]pyrazolo[1,2-a][1,2]diazepin-10-yl)carbamoyl)butyl)thiazole-5-carboxamide | Step 1: int-B1 and Int-L3<br>Step 3: Int-EC14; EDC, pyridine | m/z 619.3 $[M + H]^+$, $t_R$ = 1.08 min (LCMS method b), $^1H$ NMR (400 MHz, DMSO-$d_6$) δ 8.95 (d, J = 8.3 Hz, 1H), 8.86 (d, J = 2.5 Hz, 1H), 8.44 (dd, J = 8.7, 2.5 Hz, 1H), 8.25 (t, J = 5.7 Hz, 1H), 7.79 (t, J = 72.2 Hz, 1H), 7.78 - 7.74 (m, 1H), 7.46 - 7.35 (m, 3H), 7.27 (d, J = 8.7 Hz, 1H), 5.99 (d, J = 8.3 Hz, 1H), 4.35 - 4.20 (m, 1H), 4.14 - 3.96 (m, 1H), 3.69 - 3.58 (m, 1H), 3.57 - 3.48 (m, 1H), 3.45 - 3.37 (m, 1H), 3.26 - 3.18 (m, 1H), 3.06 - 2.92 (m, 1H), 2.24 - 2.06 (m, 2H), 1.66 - 1.47 (m, 2H), 0.94 (t, J = 7.4 Hz, 3H). |
| 38 | 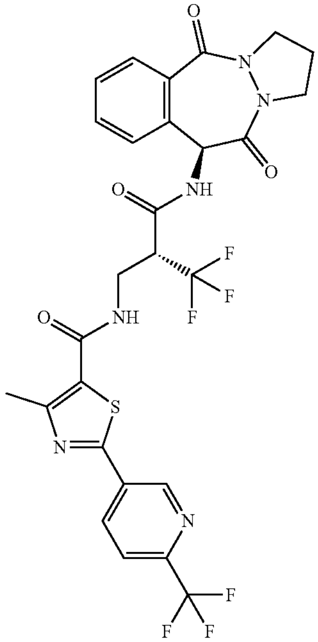 [SMILES: Cc1nc(-c2ccc(C(F)(F)F)nc2)sc1C(=O)NC[C@H](C(=O)N[C@@H]1C(=O)N2CCCN2C(=O)c2ccccc21)C(F)(F)F] | N-((R)-2-(((S)-5,11-Dioxo-2,3,10,11-tetrahydro-1H,5H-benzo[d]pyrazolo[1,2-a][1,2]diazepin-10-yl)carbamoyl)-3,3,3-trifluoropropyl)-4-methyl-2-(6-(trifluoromethyl)pyridin-3-yl)thiazole-5-carboxamide | Step 1: int-B1 and int-L1<br>Step 3: Int-EC7; EDC, pyridine | m/z 641.4 $[M + H]^+$, $t_R$ = 1.12 min (LCMS method b), $^1H$ NMR (400 MHz, DMSO-$d_6$) δ 9.59 (d, J = 8.2 Hz, 1H), 9.28 (s, 1H), 8.73 (t, J = 4.7 Hz, 1H), 8.56 (d, J = 9.2 Hz, 1H), 8.08 (d, J = 8.3 Hz, 1H), 7.76 (d, J = 7.7 Hz, 1H), 7.40 (t, J = 4.1 Hz, 1H), 7.31 - 7.21 (m, 2H), 6.00 (d, J = 8.0 Hz, 1H), 4.43 - 4.19 (m, 2H), 4.12 - 3.97 (m, 1H), 3.83 - 3.52 (m, 3H), 3.22 (q, J = 8.1 Hz, 1H), 2.62 (s, 3H), 2.24 - 2.01 (m, 2H). |

TABLE 1-continued

| Example No. | Compound Structure | Compound Name | Reaction Parameters | Analytics |
|---|---|---|---|---|
| 39 | 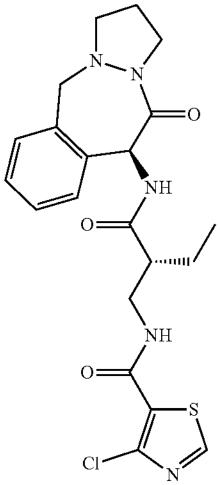 [SMILES: CC[C@H](CNC(=O)c1scnc1Cl)C(=O)N[C@@H]1C(=O)N2CCCN2Cc2ccccc21] | 4-Chloro-N-((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide | Step 1: int-A1 and Int-L3 Step 3: int-EC26 ; EDC, pyridine | m/z 462.1 $[M + H]^+$, $t_R$ = 0.81 min (LCMS method b), $^1H$ NMR (400 MHz, DMSO-$d_6$) δ 9.21 (s, 1H), 8.48 (d, J = 9.0 Hz, 1H), 8.27 (t, J = 5.5 Hz, 1H), 7.25 - 7.13 (m, 2H), 7.04 (d, J = 7.7 Hz, 1H), 6.92 (t, J = 7.6 Hz, 1H), 6.75 (d, J = 8.9 Hz, 1H), 4.23 (s, 2H), 3.58 - 3.46 (m, 3H), 3.42 - 3.37 (m, 1H), 3.29 - 3.24 (m, 1H), 3.21 - 3.11 (m, 1H), 2.98 - 2.87 (m, 1H), 2.39 - 2.28 (m, 1H), 2.16 - 2.03 (m, 1H), 1.63 - 1.42 (m, 2H), 0.90 (t, J = 7.4 Hz, 3H). |
| 40 | 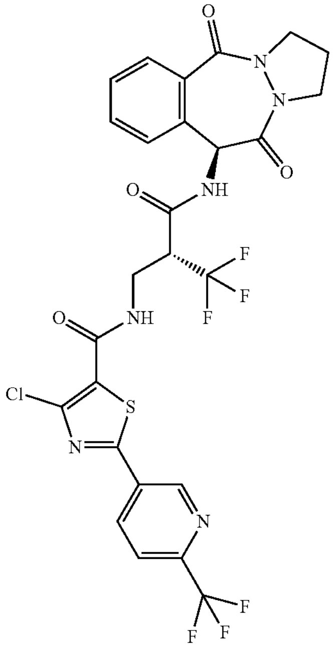 [SMILES: O=C(NC[C@H](C(=O)N[C@@H]1C(=O)N2CCCN2C(=O)c2ccccc21)C(F)(F)F)c1sc(-c2ccc(C(F)(F)F)nc2)nc1Cl] | 4-Chloro-N-((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-2-(6-(trifluoromethyl)pyridin-3-yl)thiazole-5-carboxamide | Step 1: int-B1 and int-L1 Step 3: Int-EC6; EDC, pyridine | m/z 661.1 $[M + H]^+$, $t_R$ = 1.17 min (LCMS method a), $^1H$ NMR (400 MHz, DMSO-$d_6$) δ 9.58 (d, J = 8.2 Hz, 1H), 9.33 (s, 1H), 8.71 (t, J = 5.9 Hz, 1H), 8.62 (d, J = 7.8 Hz, 1H), 8.10 (d, J = 8.1 Hz, 1H), 7.83 - 7.74 (m, 1H), 7.42 (t, J = 7.2 Hz, 1H), 7.38 - 7.25 (m, 2H), 5.99 (d, J = 8.3 Hz, 1H), 4.32 (d, J = 28.6 Hz, 2H), 4.14 - 3.95 (m, 1H), 3.83 - 3.70 (m, 2H), 3.69 - 3.56 (m, 1H), 2.25 - 2.08 (m, 3H). |

TABLE 1-continued

| Example No. | Compound Structure | Compound Name | Reaction Parameters | Analytics |
|---|---|---|---|---|
| 41 | 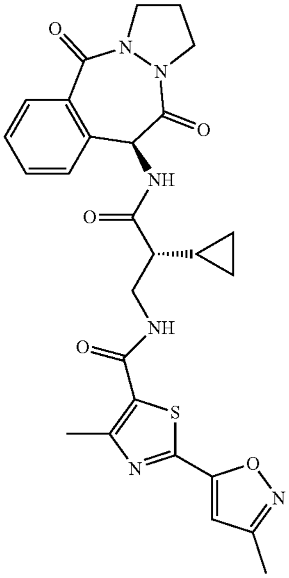 [SMILES: Cc1cc(-c2nc(C)c(C(=O)NC[C@H](C(=O)N[C@@H]3C(=O)N4CCCN4C(=O)c4ccccc43)C3CC3)s2)on1] | N-((R)-2-Cyclopropyl-3-(((S)-5,11-dioxo-2,3,10,11-tetrahydro-1H,5H-benzo[d]pyrazolo[1,2-a][1,2]diazepin-10-yl)amino)-3-oxopropyl)-4-methyl-2-(3-methylisoxazol-5-yl)thiazole-5-carboxamide | Step 1: int-B1 and int-L2 Step 3: Int-EC8; EDC, pyridine | m/z 549.4 $[M + H]^+$, $t_R$ = 0.92 min (LCMS method b), $^1H$ NMR (400 MHz, DMSO-$d_6$) δ 8.81 (d, J = 8.3 Hz, 1H), 8.45 (t, J = 5.5 Hz, 1H), 7.76 (dd, J = 7.6, 1.3 Hz, 1H), 7.40 (t, J = 7.2 Hz, 1H), 7.36 - 7.26 (m, 2H), 7.08 (s, 1H), 5.99 (d, J = 8.2 Hz, 1H), 4.34 - 4.23 (m, 1H), 4.11 - 3.99 (m, 1H), 3.72 - 3.58 (m, 1H), 3.56 - 3.46 (m, 2H), 3.25 - 3.17 (m, 1H), 2.57 (s, 3H), 2.44 - 2.35 (m, 1H), 2.33 (s, 3H), 2.22 - 2.03 (m, 2H), 1.00 - 0.81 (m, 1H), 0.62 - 0.53 (m, 1H), 0.51 - 0.37 (m, 2H), 0.34 - 0.23 (m, 1H). |
| 42 | 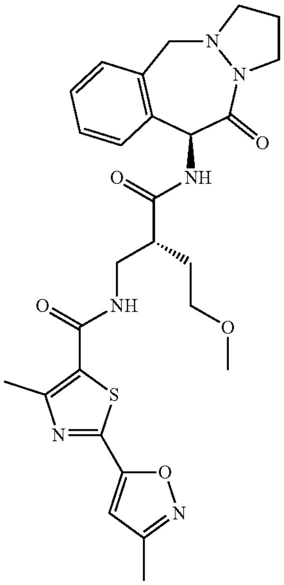 [SMILES: COCC[C@H](CNC(=O)c1sc(-c2cc(C)no2)nc1C)C(=O)N[C@@H]1C(=O)N2CCCN2Cc2ccccc21] | N-((R)-4-Methoxy-2-(((S)-11-oxo-2,3,10,11-tetrahydro-1H,5H-benzo[d]pyrazolo[1,2-a][1,2]diazepin-10-yl)carbamoyl)butyl)-4-methyl-2-(3-methylisoxazol-5-yl)thiazole-5-carboxamide | Step 1: int-A1 and int-L5 Step 3: Int-EC8; EDC, pyridine | m/z 553.4 $[M + H]^+$, $t_R$ = 0.90 min (LCMS method b), $^1H$ NMR (400 MHz, DMSO-$d_6$) δ 8.40 (t, J = 5.5 Hz, 1H), 8.34 (d, J = 8.9 Hz, 1H), 7.23 (d, J = 7.9 Hz, 1H), 7.15 (t, J = 7.5 Hz, 1H), 7.08 (s, 1H), 7.03 (d, J = 7.6 Hz, 1H), 6.85 (t, J = 7.5 Hz, 1H), 6.72 (d, J = 8.7 Hz, 1H), 4.23 (s, 2H), 3.59 - 3.45 (m, 3H), 3.41 - 3.34 (m, 2H), 3.31 - 3.25 (m, 2H), 3.24 (s, 3H), 3.21 - 3.13 (m, 1H), 3.12 - 3.03 (m, 1H), 2.61 (s, 3H), 2.37 (d, J = 11.7 Hz, 1H), 2.33 (s, 3H), 2.17 - 2.05 (m, 1H), 1.83 - 1.63 (m, 2H). |

TABLE 1-continued

| Example No. | Compound Structure | Compound Name | Reaction Parameters | Analytics |
|---|---|---|---|---|
| 43 | 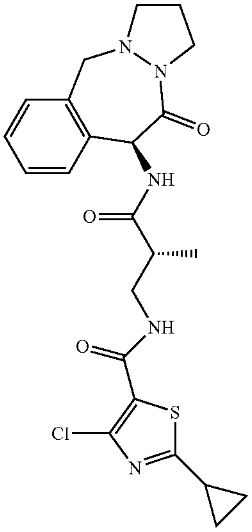 [SMILES: C[C@H](CNC(=O)c1sc(C2CC2)nc1Cl)C(=O)N[C@@H]1C(=O)N2CCCN2Cc2ccccc21] | 4-Chloro-2-cyclopropyl-N-((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-5-carboxamide | Step 1: int-A1 and Int-L9 Step 3: Int-EC15; EDC, pyridine | m/z 488.2 $[M + H]^+$, $t_R$ = 0.95 min (LCMS method a), $^1H$ NMR (400 MHz, DMSO-$d_6$) δ 8.45 (d, J = 9.0 Hz, 1H), 8.07 (t, J = 5.6 Hz, 1H), 7.19 (ddd, J = 6.8, 3.7, 2.4 Hz, 2H), 7.05 (dd, J = 7.9, 1.4 Hz, 1H), 6.94 (t, J = 7.3 Hz, 1H), 6.72 (d, J = 8.8 Hz, 1H), 4.23 (s, 2H), 3.56 - 3.46 (m, 3H), 3.38 - 3.22 (m, 2H), 3.21 - 3.12 (m, 1H), 3.11 - 3.02 (m, 1H), 2.47 - 2.40 (m, 1H), 2.40 - 2.24 (m, 1H), 2.17 - 2.01 (m, 1H), 1.25 - 1.14 (m, 2H), 1.10 (d, J = 6.9 Hz, 3H), 1.04 - 0.93 (m, 2H). |
| 44 | 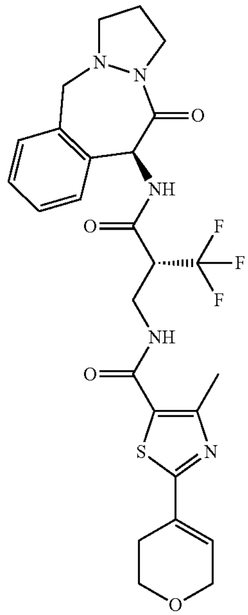 [SMILES: Cc1nc(C2=CCOCC2)sc1C(=O)NC[C@H](C(=O)N[C@@H]1C(=O)N2CCCN2Cc2ccccc21)C(F)(F)F] | 2-(3,6-Dihydro-2H-pyran-4-yl)-4-methyl-N-((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide | Step 1: int-A1 and int-L1 Step 3: Int-EC10; EDC, pyridine | m/z 564.2 $[M + H]^+$, $t_R$ = 0.94 min (LCMS method b), $^1H$ NMR (400 MHz, DMSO-$d_6$) δ 9.14 (d, J = 8.9 Hz, 1H), 8.48 (t, J = 5.5 Hz, 1H), 7.19 (t, J = 7.5 Hz, 1H), 7.15 (d, J = 8.0 Hz, 1H), 7.05 (d, J = 7.6 Hz, 1H), 6.88 - 6.74 (m, 2H), 6.73 - 6.67 (m, 1H), 4.28 - 4.19 (m, 5H), 3.81 (t, J = 5.4 Hz, 2H), 3.67 (t, J = 6.2 Hz, 2H), 3.58 - 3.46 (m, 2H), 3.31 - 3.24 (m, 3H), 3.22 - 3.12 (m, 1H), 2.54 (s, 3H), 2.40 - 2.29 (m, 1H), 2.18 - 2.02 (m, 1H). |

TABLE 1-continued

| Example No. | Compound Structure | Compound Name | Reaction Parameters | Analytics |
|---|---|---|---|---|
| 45 | 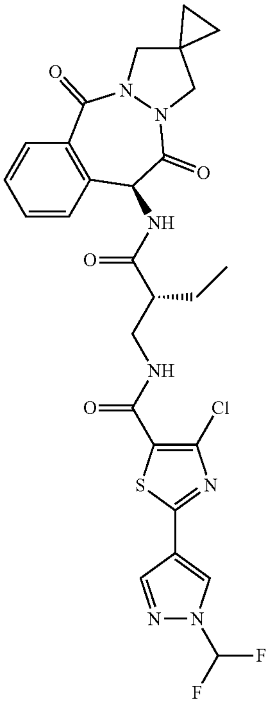 [SMILES: CC[C@H](CNC(=O)c1sc(-c2cnn(C(F)F)c2)nc1Cl)C(=O)N[C@@H]1C(=O)N2CC3(CC3)CN2C(=O)c2ccccc21] | 4-Chloro-2-(1-(difluoromethyl)-1H-pyrazol-4-yl)-N-((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl) thiazole-5-carboxamide | Step 1: int-C1 and Int-L3 Step 3: Int-EC16; EDC, pyridine | m/z 618.3 $[M + H]^+$, $t_R$ = 1.01 min (LCMS method b), $^1H$ NMR (400 MHz, DMSO-$d_6$) δ 9.04 (s, 1H), 8.99 (d, J = 8.3 Hz, 1H), 8.37 (s, 1H), 8.17 (t, J = 5.6 Hz, 1H), 7.88 (t, J = 58.7 Hz, 1H), 7.83 - 7.78 (m, 1H), 7.52 - 7.36 (m, 3H), 6.05 (d, J = 8.3 Hz, 1H), 4.23 (d, J = 11.1 Hz, 1H), 3.92 (d, J = 10.7 Hz, 1H), 3.64 (d, J = 11.1 Hz, 1H), 3.58 - 3.49 (m, 1H), 3.45 - 3.39 (m, 1H), 3.29 (d, J = 10.8 Hz, 1H), 3.07 - 2.94 (m, 1H), 1.66 - 1.48 (m, 2H), 0.95 (t, J = 7.4 Hz, 3H), 0.83 - 0.67 (m, 4H). |
| 46 | 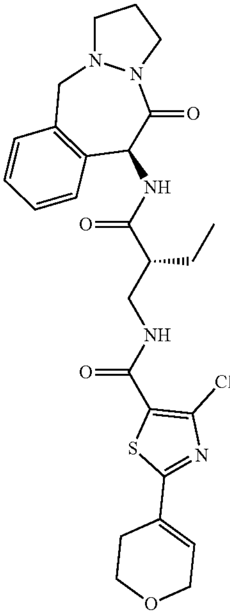 [SMILES: CC[C@H](CNC(=O)c1sc(C2=CCOCC2)nc1Cl)C(=O)N[C@@H]1C(=O)N2CCCN2Cc2ccccc21] | 4-Chloro-2-(3,6-dihydro-2H-pyran-4-yl)-N-((R)-2-(((S)-11-oxo-2,3,10,11-tetrahydro-1H,5H-benzo[d]pyrazolo[1,2-a][1,2]diazepin-10-yl)carbamoyl)butyl) thiazole-5-carboxamide | Step 1: int-A1 and Int-L3 Step 3: Int-EC17; EDC, pyridine | m/z 544.2 $[M + H]^+$, $t_R$ = 0.97 min (LCMS method b), $^1H$ NMR (400 MHz, DMSO-$d_6$) δ 8.50 (d, J = 9.1 Hz, 1H), 8.18 (t, J = 5.6 Hz, 1H), 7.23 (d, J = 7.9 Hz, 1H), 7.19 (t, J = 7.4 Hz, 1H), 7.05 (dd, J = 7.7, 1.4 Hz, 1H), 6.99 - 6.91 (m, 1H), 6.86 - 6.82 (m, 1H), 6.76 (d, J = 8.9 Hz, 1H), 4.30 - 4.25 (m, 2H), 4.24 (s, 2H), 3.80 (t, J = 5.4 Hz, 2H), 3.59 - 3.46 (m, 3H), 3.43 - 3.36 (m, 1H), 3.30 - 3.24 (m, 1H), 3.22 - 3.11 (m, 1H), 2.99 - 2.86 (m, 1H), 2.49 - 2.44 (m, 2H), 2.40 - 2.25 (m, 1H), 2.16 - 2.03 (m, 1H), 1.66 - 1.40 (m, 2H), 0.90 (t, J = 7.4 Hz, 3H). |

TABLE 1-continued

| Example No. | Compound Structure | Compound Name | Reaction Parameters | Analytics |
|---|---|---|---|---|
| 47 | 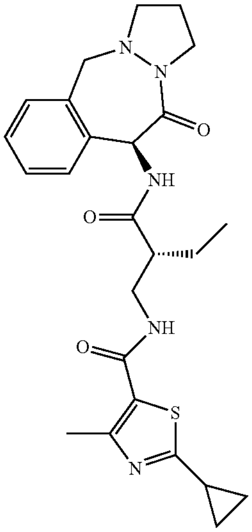 [SMILES: CC[C@H](CNC(=O)c1sc(C2CC2)nc1C)C(=O)N[C@@H]1C(=O)N2CCCN2Cc2ccccc21] | 2-Cyclopropyl-4-methyl-N-((R)-2-(((S)-11-oxo-2,3,10,11-tetrahydro-1H,5H-benzo[d]pyrazolo [1,2-a][1,2]diazepin-10-yl)carbamoyl)butyl) thiazole-5-carboxamide | Step 1: int-A1 and Int-L3 Step 3: 2int-EC27 ; EDC, pyridine | m/z 482.3 $[M + H]^+$, $t_R$ = 0.89 min (LCMS method a), $^1H$ NMR (400 MHz, DMSO-$d_6$) δ 8.35 (d, J = 8.9 Hz, 1H), 7.90 (t, J = 5.3 Hz, 1H), 7.25 - 7.13 (m, 2H), 7.04 (d, J = 7.6 Hz, 1H), 6.85 (t, J = 7.6 Hz, 1H), 6.73 (d, J = 8.8 Hz, 1H), 4.23 (s, 2H), 3.45 (ddd, J = 14.8, 11.4, 5.5 Hz, 3H), 3.33 - 3.23 (m, 2H), 3.21 - 3.11 (m, 1H), 2.94 - 2.77 (m, 1H), 2.45 (s, 3H), 2.40 - 2.26 (m, 2H), 2.16 - 2.03 (m, 1H), 1.58 - 1.39 (m, 2H), 1.18 - 1.08 (m, 2H), 0.97 - 0.91 (m, 2H), 0.88 (t, J = 7.4 Hz, 3H). |
| 48 | 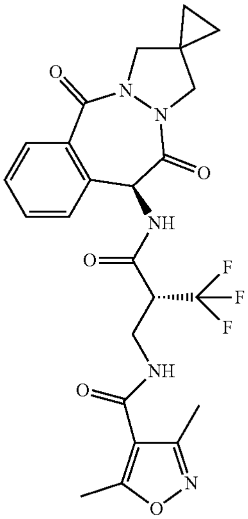 | N-((R)-2-(((S)-5,11-Dioxo-2,3,10,11-tetrahydro-1H,5H-benzo[d]pyrazolo [1,2-a][1,2]diazepin-10-yl)carbamoyl)-3,3,3-trifluoropropyl)-3,5-dimethylisoxazole-4-carboxamide | Step 1: int-B1 and int-L1 Step 3: int-EC28 ; EDC, pyridine | m/z 494.3 $[M + H]^+$, $t_R$ = 0.81 min (LCMS method a), $^1H$ NMR (400 MHz, DMSO-$d_6$) δ 9.57 (d, J = 8.1 Hz, 1H), 8.26 (t, J = 5.7 Hz, 1H), 7.78 (d, J = 7.7 Hz, 1H), 7.45 (t, J = 7.3 Hz, 1H), 7.33 - 7.23 (m, 2H), 6.00 (d, J = 8.0 Hz, 1H), 4.37 - 4.21 (m, 2H), 4.13 - 4.00 (m, 1H), 3.75 - 3.52 (m, 3H), 3.28 - 3.15 (m, 1H), 2.40 (s, 3H), 2.25 (s, 3H), 2.20 - 2.09 (m, 2H). |
| 49 | 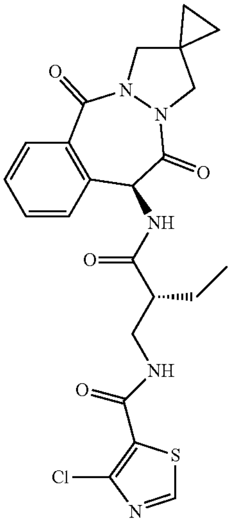 [SMILES: CC[C@H](CNC(=O)c1scnc1Cl)C(=O)N[C@@H]1C(=O)N2CC3(CC3)CN2C(=O)c2ccccc21] | 4-Chloro-N-((R)-2-(((S)-5,11-dioxo-10,11-dihydro-1H,3H,5H-spiro [benzo[d]pyrazolo[1,2-a][1,2]diazepine-2,1''-cyclopropan]-10-yl)carbamoyl)butyl) thiazole-5-carboxamide | Step 1: int-C1 and Int-L3 Step 3: int-EC26 replac; EDC, pyridine | m/z 502.2 $[M + H]^+$, $t_R$ = 0.87 min (LCMS method a), $^1H$ NMR (400 MHz, DMSO-$d_6$) δ 9.20 (s, 1H), 8.94 (d, J = 8.3 Hz, 1H), 8.25 (t, J = 5.6 Hz, 1H), 7.81 (d, J = 7.6 Hz, 1H), 7.51 - 7.41 (m, 1H), 7.40 - 7.35 (m, 2H), 6.04 (d, J = 8.2 Hz, 1H), 4.23 (d, J = 11.1 Hz, 1H), 3.91 (d, J = 10.7 Hz, 1H), 3.64 (d, J = 11.1 Hz, 1H), 3.42 - 3.35 (m, 2H), 3.29 (d, J = 10.7 Hz, 1H), 3.05 - 2.90 (m, 1H), 1.65 - 1.44 (m, 2H), 0.93 (t, J = 7.4 Hz, 3H), 0.85 - 0.65 (m, 4H). |

TABLE 1-continued

| Example No. | Compound Structure | Compound Name | Reaction Parameters | Analytics |
|---|---|---|---|---|
| 50 | 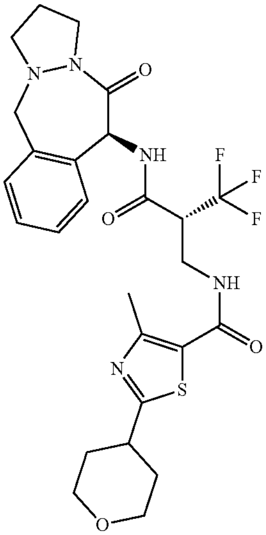 [SMILES: Cc1nc(C2CCOCC2)sc1C(=O)NC[C@H](C(=O)N[C@@H]1C(=O)N2CCCN2Cc2ccccc21)C(F)(F)F] | 4-Methyl-2-(tetrahydro-2H-pyran-4-yl)-N-((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide | Step 1: int-A1 and int-L1 Step 3: Int-EC18; EDC, pyridine | m/z 566.2 $[M + H]^+$, $t_R$ = 0.91 min (LCMS method b), $^1H$ NMR (400 MHz, $CDCl_3$) δ 7.43 (s, 1H), 7.18 - 7.08 (m, 1H), 7.03 - 6.93 (m, 2H), 6.86 - 6.70 (m, 2H), 6.52 (t, J = 5.4 Hz, 1H), 4.22 (s, 2H), 4.16 - 4.00 (m, 3H), 3.89 - 3.71 (m, 3H), 3.67 - 3.56 (m, 1H), 3.55 - 3.47 (m, 2H), 3.46 - 3.36 (m, 1H), 3.24 - 3.05 (m, 2H), 2.64 (s, 3H), 2.46 - 2.31 (m, 1H), 2.29 - 2.16 (m, 1H), 2.07 - 1.96 (m, 2H), 1.91 - 1.77 (m, 2H). |
| 51 | 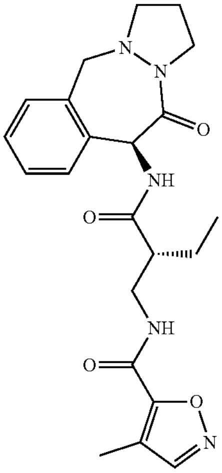 [SMILES: CC[C@H](CNC(=O)c1oncc1C)C(=O)N[C@@H]1C(=O)N2CCCN2Cc2ccccc21] | 4-Methyl-N-((R)-2-(((S)-11-oxo-2,3,10,11-tetrahydro-1H,5H-benzo[d]pyrazolo[1,2-a][1,2]diazepin-10-yl)carbamoyl)butyl)isoxazole-5-carboxamide | Step 1: int-A1 and Int-L3 Step 3: int-EC29 ; EDC, pyridine | m/z 426.1 $[M + H]^+$, $t_R$ = 0.79 min (LCMS method a), $^1H$ NMR (400 MHz, DMSO-$d_6$) δ 8.76 - 8.69 (m, 1H), 8.67 (s, 1H), 8.32 (d, J = 8.7 Hz, 1H), 7.19 (d, J = 8.0 Hz, 1H), 7.14 (t, J = 7.5 Hz, 1H), 7.02 (d, J = 7.5 Hz, 1H), 6.80 - 6.65 (m, 2H), 4.22 (s, 2H), 3.63 - 3.45 (m, 3H), 3.28 - 3.23 (m, 1H), 3.21 - 3.13 (m, 1H), 2.98 - 2.86 (m, 1H), 2.42 - 2.28 (m, 2H), 2.24 (s, 3H), 2.14 - 2.03 (m, 1H), 1.58 - 1.39 (m, 2H), 0.87 (t, J = 7.4 Hz, 3H). |
| 52 | 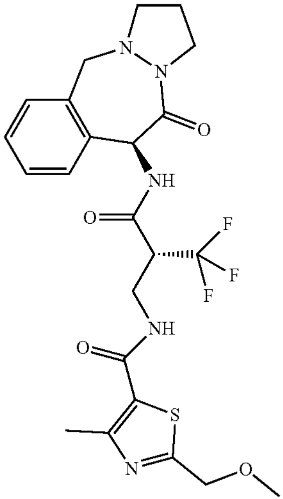 [SMILES: COCc1nc(C)c(C(=O)NC[C@H](C(=O)N[C@@H]2C(=O)N3CCCN3Cc3ccccc32)C(F)(F)F)s1] | 2-(Methoxymethyl)-4-methyl-N-((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide | Step 1: int-A1 and int-L1 Step 3: int-EC30; EDC, pyridine | m/z 526.3 $[M + H]^+$, $t_R$ = 0.89 min (LCMS method a), $^1H$ NMR (400 MHz, DMSO-$d_6$) δ 9.13 (d, J = 8.8 Hz, 1H), 8.48 (t, J = 5.5 Hz, 1H), 7.25 - 7.10 (m, 2H), 7.05 (d, J = 7.6 Hz, 1H), 6.84 (t, J = 7.4 Hz, 1H), 6.78 (d, J = 8.7 Hz, 1H), 4.69 (s, 2H), 4.30 - 4.25 (m, 1H), 4.23 (s, 2H), 3.72 - 3.61 (m, 2H), 3.59 - 3.49 (m, 2H), 3.41 (s, 3H), 3.32 - 3.26 (m, 1H), 3.22 - 3.11 (m, 1H), 2.54 (s, 3H), 2.40 - 2.28 (m, 1H), 2.17 - 2.08 (m, 1H). |

TABLE 1-continued

| Example No. | Compound Structure | Compound Name | Reaction Parameters | Analytics |
|---|---|---|---|---|
| 53 | 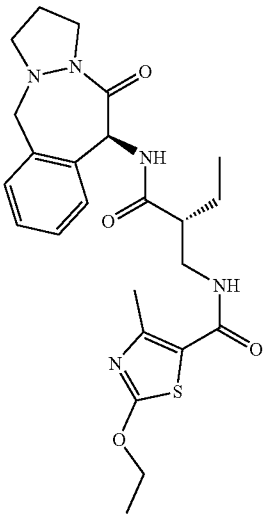 | 2-Ethoxy-4-methyl-N-((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide | Step 1: int-A1 and Int-L3 Step 3: int-EC31 ; EDC, pyridine | m/z 426.3 $[M + H]^+$, $t_R$ = 0.94 min (LCMS method b), $^1H$ NMR (400 MHz, DMSO-$d_6$) δ 8.35 (d, J = 8.9 Hz, 1H), 7.79 (t, J = 5.5 Hz, 1H), 7.24 - 7.15 (m, 2H), 7.04 (d, J = 7.2 Hz, 1H), 6.90 (t, J = 7.6 Hz, 1H), 6.73 (d, J = 8.8 Hz, 1H), 4.41 (q, J = 7.0 Hz, 2H), 4.23 (s, 2H), 3.59 - 3.48 (m, 2H), 3.48 - 3.38 (m, 1H), 3.30 - 3.24 (m, 2H), 3.20 - 3.13 (m, 1H), 2.92 - 2.84 (m, 1H), 2.40 (s, 3H), 2.36 - 2.27 (m, 1H), 2.14 - 2.02 (m, 1H), 1.57 - 1.39 (m, 2H), 1.35 (t, J = 7.0 Hz, 3H), 0.88 (t, J = 7.4 Hz, 3H). |
| 54 | 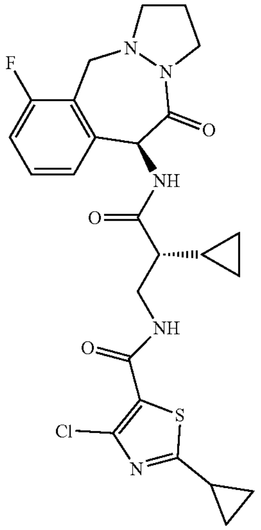 [SMILES: O=C(NC[C@H](C(=O)N[C@@H]1C(=O)N2CCCN2Cc2c(F)cccc21)C1CC1)c1sc(C2CC2)nc1Cl] | 4-Chloro-2-cyclopropyl-N-((R)-2-cyclopropyl-3-(((S)-6-fluoro-11-oxo-2,3,10,11-tetrahydro-1H,5H-benzo[d]pyrazolo[1,2-a][1,2]diazepin-10-yl)amino)-3-oxopropyl)thiazole-5-carboxamide | Step 1: int-A2 and int-L2 Step 3: Int-EC15; EDC, pyridine | m/z 532.3 $[M + H]^+$, $t_R$ = 1.14 min (LCMS method a), $^1H$ NMR (400 MHz, DMSO-$d_6$) δ 8.43 (d, J = 8.9 Hz, 1H), 8.08 (t, J = 5.7 Hz, 1H), 7.13 - 6.93 (m, 3H), 6.76 (d, J = 8.8 Hz, 1H), 4.17 (s, 2H), 3.64 - 3.60 (m, 2H), 3.36 - 3.20 (m, 3H), 2.48 - 2.27 (m, 4H), 2.19 - 2.03 (m, 1H), 1.23 - 1.14 (m, 2H), 1.05 - 0.96 (m, 2H), 0.94 - 0.82 (m, 1H), 0.58 - 0.49 (m, 1H), 0.48 - 0.35 (m, 2H), 0.29 - 0.19 (m, 1H). |
| 55 | 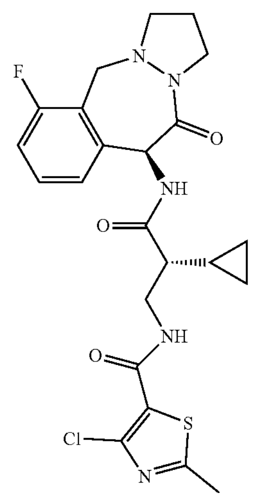 [SMILES: Cc1nc(Cl)c(C(=O)NC[C@H](C(=O)N[C@@H]2C(=O)N3CCCN3Cc3c(F)cccc32)C2CC2)s1] | 4-Chloro-N-((R)-2-cyclopropyl-3-(((S)-6-fluoro-11-oxo-2,3,10,11-tetrahydro-1H,5H-benzo[d]pyrazolo[1,2-a][1,2]diazepin-10-yl)amino)-3-oxopropyl)-2-methylthiazole-5-carboxamide | Step 1: int-A2 and int-L2 Step 3: Int-EC19; EDC, pyridine | m/z 506.3 $[M + H]^+$, $t_R$ = 1.01 min (LCMS method a), $^1H$ NMR (400 MHz, DMSO-$d_6$) δ 8.43 (d, J = 8.9 Hz, 1H), 8.14 (t, J = 5.6 Hz, 1H), 7.14 - 6.95 (m, 3H), 6.76 (d, J = 8.8 Hz, 1H), 4.17 (s, 2H), 3.60 - 3.47 (m, 4H), 3.37 - 3.21 (m, 2H), 2.66 (s, 3H), 2.45 - 2.28 (m, 2H), 2.17 - 2.03 (m, 1H), 0.95 - 0.82 (m, 1H), 0.58 - 0.49 (m, 1H), 0.48 - 0.36 (m, 2H), 0.30 - 0.20 (m, 1H). |

TABLE 1-continued

| Example No. | Compound Structure | Compound Name | Reaction Parameters | Analytics |
|---|---|---|---|---|
| 56 | 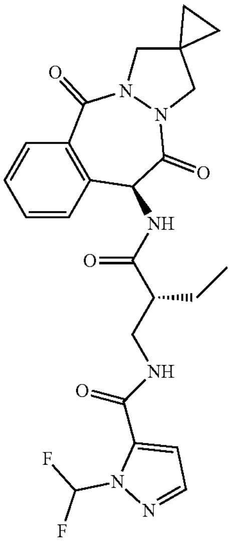 [SMILES: CC[C@H](CNC(=O)c1ccnn1C(F)F)C(=O)N[C@@H]1C(=O)N2CC3(CC3)CN2C(=O)c2ccccc21] | 1-(Difluoromethyl)-N-((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-1H-pyrazole-5-carboxamide | Step 1: int-C1 and Int-L3 Step 3: int-EC32 ; EDC, pyridine | m/z 501.3 $[M + H]^+$, $t_R$ = 0.90 min (LCMS method a), $^1H$ NMR (400 MHz, DMSO-$d_6$) δ 9.04 - 8.85 (m, 2H), 8.41 (t, J = 58.7 Hz, 1H), 7.98 - 7.88 (m, 1H), 7.78 (dd, J = 7.8, 1.4 Hz, 1H), 7.40 (t, J = 7.5 Hz, 1H), 7.20 (d, J = 7.9 Hz, 1H), 7.13 - 7.00 (m, 2H), 6.07 (d, J = 8.4 Hz, 1H), 4.22 (d, J = 11.1 Hz, 1H), 3.91 (d, J = 10.7 Hz, 1H), 3.63 (d, J = 11.1 Hz, 1H), 3.46 - 3.40 (m, 1H), 3.31 - 3.23 (m, 2H), 3.07 - 2.95 (m, 1H), 1.64 - 1.40 (m, 2H), 0.93 (t, J = 7.4 Hz, 3H), 0.84 - 0.67 (m, 4H). |
| 57 | 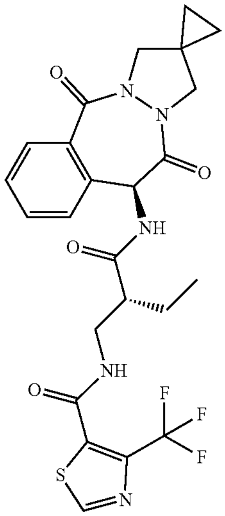 [SMILES: CC[C@H](CNC(=O)c1scnc1C(F)(F)F)C(=O)N[C@@H]1C(=O)N2CC3(CC3)CN2C(=O)c2ccccc21] | N-((R)-2-(((S)-5,11-Dioxo-10,11-dihydro-1H,3H,5H-spiro[benzo[d]pyrazolo[1,2-a][1,2]diazepine-2,1'-cyclopropan]-10-yl)carbamoyl)butyl)-4-(trifluoromethyl) thiazole-5-carboxamide | Step 1: int-C1 and Int-L3 Step 3: int-EC33 ; EDC, pyridine | m/z 536.2 $[M + H]^+$, $t_R$ = 0.92 min (LCMS method b), $^1H$ NMR (400 MHz, DMSO-$d_6$) δ 9.25 (s, 1H), 9.02 - 8.87 (m, 2H), 7.82 (dd, J = 7.6, 1.5 Hz, 1H), 7.55 (td, J = 7.5, 1.4 Hz, 1H), 7.51 - 7.40 (m, 2H), 6.05 (d, J = 8.2 Hz, 1H), 4.23 (d, J = 11.1 Hz, 1H), 4.01 - 3.86 (m, 1H), 3.64 (d, J = 11.1 Hz, 1H), 3.45 - 3.35 (m, 2H), 3.29 - 3.24 (m, 1H), 3.01 - 2.86 (m, 1H), 1.65 - 1.43 (m, 2H), 0.93 (t, J = 7.4 Hz, 3H), 0.84 - 0.66 (m, 4H). |
| 58 | 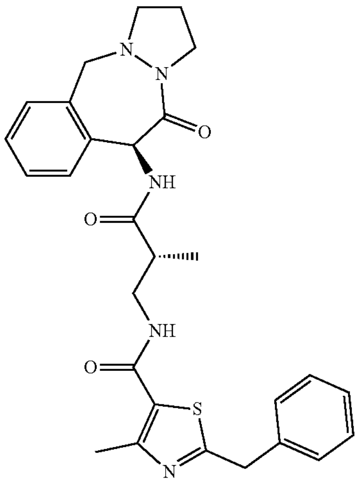 [SMILES: Cc1nc(Cc2ccccc2)sc1C(=O)NC[C@@H](C)C(=O)N[C@@H]1C(=O)N2CCCN2Cc2ccccc21] | 2-Benzyl-4-methyl-N-((R)-2-methyl-3-oxo-3-(((S)-11-oxo-2,3,10,11-tetrahydro-1H,5H-benzo[d]pyrazolo [1,2-a][1,2]diazepin-10-yl)amino)propyl) thiazole-5-carboxamide | Step 1: int-A1 and Int-L9 Step 3: int-EC34; T3P, DIPEA, $CH_2Cl_2$, 16 h, 20° C. | m/z 518.0 $[M + H]^+$, $t_R$ = 0.96 min (LCMS method a), $^1H$ NMR (400 MHz, DMSO-$d_6$) δ 8.30 (d, J = 8.9 Hz, 1H), 8.03 (t, J = 5.4 Hz, 1H), 7.38 - 7.32 (m, 4H), 7.30 - 7.23 (m, 1H), 7.15 - 7.08 (m, 2H), 7.02 (d, J = 7.6 Hz, 1H), 6.75 - 6.61 (m, 2H), 4.30 (s, 2H), 4.21 (s, 2H), 3.56 - 3.47 (m, 2H), 3.46 - 3.40 (m, 1H), 3.31 - 3.22 (m, 1H), 3.20 - 3.11 (m, 2H), 3.06 - 2.93 (m, 1H), 2.51 (s, 3H), 2.42 - 2.26 (m, 1H), 2.14 - 2.02 (m, 1H), 1.04 (d, J = 6.9 Hz, 3H). |

TABLE 1-continued

| Example No. | Compound Structure | Compound Name | Reaction Parameters | Analytics |
|---|---|---|---|---|
| 59 | 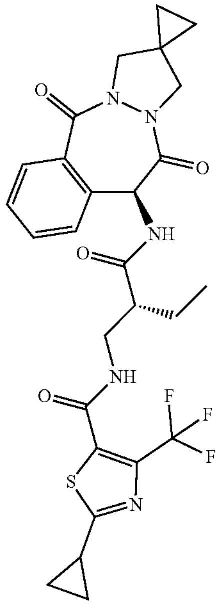 [SMILES: CC[C@H](CNC(=O)c1sc(C2CC2)nc1C(F)(F)F)C(=O)N[C@@H]1C(=O)N2CC3(CC3)CN2C(=O)c2ccccc21] | 2-Cyclopropyl-N-((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-4-(trifluoromethyl) thiazole-5-carboxamide | Step 1: int-C1 and Int-L3 Step 3: int-EC35; EDC, pyridine | m/z 576.2 [M + H]$^+$, $t_R$ = 1.04 min (LCMS method b), $^1$H NMR (400 MHz, DMSO-$d_6$) δ 8.93 (d, J = 8.4 Hz, 1H), 8.79 (t, J = 5.6 Hz, 1H), 7.82 (d, J = 8.9 Hz, 1H), 7.59 - 7.37 (m, 3H), 6.05 (d, J = 8.3 Hz, 1H), 4.23 (d, J = 11.2 Hz, 1H), 3.92 (d, J = 10.7 Hz, 1H), 3.63 (d, J = 11.2 Hz, 1H), 3.43 - 3.33 (m, 2H), 3.30 - 3.24 (m, 2H), 2.97 - 2.85 (m, 1H), 1.64 - 1.45 (m, 2H), 1.29 - 1.14 (m, 2H), 1.03 - 0.95 (m, 2H), 0.92 (t, J = 7.4 Hz, 3H), 0.83 - 0.65 (m, 4H). |
| 60 | 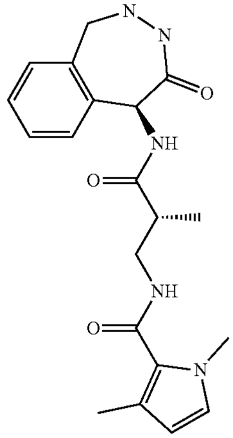 | 1,3-dimethyl-N-((R)-2-methyl-3-oxo-3-(((S)-11-oxo-2,3,10,11-tetrahydro-1H,5H-benzo[d]pyrazolo [1,2-a][1,2]diazepin-10-yl)amino)propyl)-1H-pyrrole-2-carboxamide | Step 1: int-A1 and Int-L9 Step 3: int-EC36 ; HATU, DIPEA, DMF 3 days at rt | m/z 424.3 [M + H]$^+$, $t_R$ = 0.86 min (LCMS method b) |
| 61 | 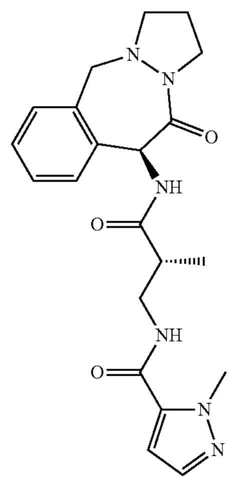 [SMILES: C[C@H](CNC(=O)c1ccnn1C)C(=O)N[C@@H]1C(=O)N2CCCN2Cc2ccccc21] | 1-methyl-N-((R)-2-methyl-3-oxo-3-(((S)-11-oxo-2,3,10,11-tetrahydro-1H,5H-benzo[d]pyrazolo [1,2-a][1,2]diazepin-10-yl)amino)propyl)-1H-pyrazole-5-carboxamide | Step 1: int-A1 and Int-L9 Step 3: int-EC37; HATU, DIPEA, DMF 16 h at rt | m/z 411.2 [M + H]$^+$, $t_R$ = 0.69 min (LCMS method b), $^1$H NMR (400 MHz, DMSO-$d_6$) δ 7.48 (d, J = 2.2 Hz, 1H), 7.23 - 7.14 (m, 2H), 7.10 (d, J = 8.0 Hz, 1H), 7.06 - 6.87 (m, 3H), 6.76 (d, J = 7.3 Hz, 1H), 6.56 (d, J = 2.2 Hz, 1H), 4.25 (s, 3H), 4.23 (s, 2H), 3.79 - 3.69 (m, 2H), 3.66 - 3.50 (m, 2H), 3.46 - 3.35 (m, 1H), 3.16 - 3.06 (m, 1H), 3.03 - 2.91 (m, 1H), 2.47 - 2.31 (m, 1H), 2.26 - 2.14 (m, 1H), 1.33 (d, J = 7.0 Hz, 3H). |

Example 62: (R)—$N^4$-(3-Isobutyramido-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide (62)

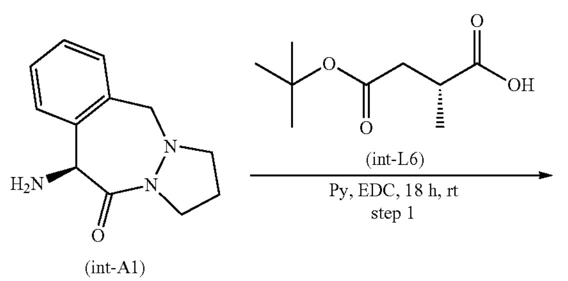

(int-A1)

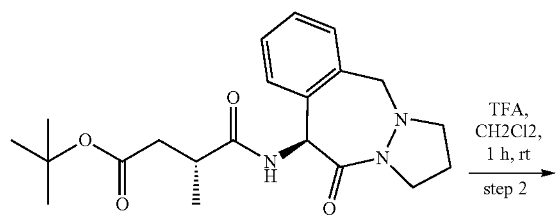

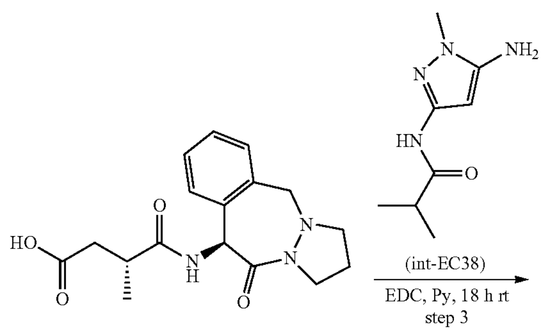

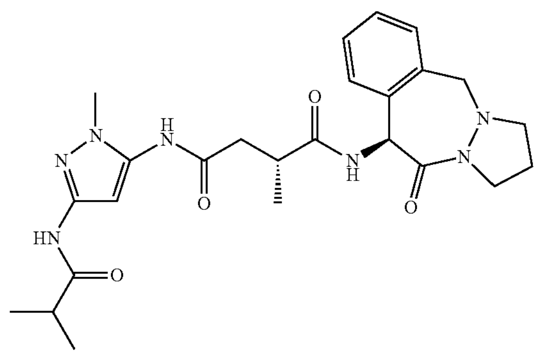

(62)

Step 1: EDC (19.17 g, 100 mmol) was added to a solution of (R)-4-(tert-butoxy)-2-methyl-4-oxobutanoic acid (int-L6) (9.41 g, 50.0 mmol) and (S)-10-amino-2,3,5,10-tetrahydro-1H,11H-benzo[d]pyrazolo[1,2-a][1,2]diazepin-11-one (int-A1) (22.48 g, 50.0 mmol) in pyridine (300 mL) and the reaction mixture was stirred at rt for 18 h. Solvent was then removed, the residue was dissolved in ethyl acetate and washed with cold 1M HCl. The aqueous layer was extracted with ethyl acetate. The organic layers were washed with sat. $NaHCO_3$ and brine, dried ($Na_2SO_4$) and concentrated. The resulting oil was crystallized with $Et_2O$ to give tert-butyl (R)-3-methyl-4-oxo-4-(((S)-11-oxo-2,3,10,11-tetrahydro-1H,5H-benzo[d]pyrazolo[1,2-a][1,2]diazepin-10-yl)amino) butanoate. LCMS (method b) m/z 388 $[M+H]^+$, $t_R$=0.99 min. $^1$H NMR (400 MHz, DMSO-$d_6$) δ ppm 8.33 (d, J=8.8 Hz, 1H), 7.37 (d, J=7.8 Hz, 1H), 7.21 (t, J=7.2 Hz, 1H), 7.13 (t, J=7.5 Hz, 1H), 7.05 (d, J=7.5 Hz, 1H), 6.67 (d, J=87 Hz, 1H), 4.23 (s, 2H), 3.48-3.59 (m, 2H), 3.23-3.29 (m, 1H), 3.06-3.22 (m, 2H), 2.53-2.61 (m, 1H), 2.33-2.41 (m, 1H), 2.26 (dd, J=16.3, 53 Hz, 1H), 2.03-2.17 (m, 1H), 1.38 (s, 9H), 1.08 (d, J=7.0 Hz, 3H).

Step 2: TFA (83 mL) was added to a solution of tert-butyl (R)-3-methyl-4-oxo-4-(((S)-11-oxo-2,3,10,11-tetrahydro-1H,5H-benzo[d]pyrazolo[1,2-a][1,2]diazepin-10-yl)amino) butanoate (16.67 g, 43 mmol) in $CH_2Cl_2$ (215 mL) and the mixture stirred at rt for 1 h. The reaction mixture was diluted with water, the organic layer was washed with water and the collected aqueous layers were extracted with $CH_2Cl_2$. The combined organic layers were dried ($Na_2SO_4$) and concentrated. The crude product was purified by column chromatography with ethyl acetate to give (R)-3-methyl-4-oxo-4-(((S)-11-oxo-2,3,10,11-tetrahydro-1H,5H-benzo[d]pyrazolo[1,2-a][1,2]diazepin-10-yl)amino)butanoic acid. LCMS (method b) m/z 332.2 $[M+H]^+$, $t_R$=0.62 min. $^1$H NMR (400 MHz, DMSO-$d_6$) δ ppm 12.09 (s, 1H), 834 (d, J=8.9 Hz, 1H), 7.41 (d, J=7.8 Hz, 1H), 7.21 (t, J=7.2 Hz, 1H), 7.14 (t, J=7.3 Hz, 1H), 7.04 (d, J=73 Hz, 1H), 6.68 (d, J=8.8 Hz, 1H). 4.23 (s, 2H), 3.47-3.59 (m. 2H). 3.24-3.30 (m. 1H), 3.07-3.22 (m, 2H), 2.59 (dd. J=16.6, 9.3 Hz, 1H), 2.31-2.41 (m, 1H), 2.27 (dd, J=16.8, 5.3 Hz, 1H), 2.03-2.15 (m, 1H), 1.09 (d, J=7.0 Hz, 3H).

Step 3: EDC (156 mg, 0.815 mmol) was added to a solution of (R)-3-methyl-4-oxo-4-(((S)-11-oxo-2,3,10,11-tetrahydro-1H,5H-benzo[d]pyrazolo[1,2-a][1,2]diazepin-10-yl)amino)butanoic acid (90 mg, 0.27 mmol), N-(5-amino-1-methyl-1H-pyrazol-3-yl)isobutyramide (int-EC38) (60 mg, 0.27 mmol) in pyridine (2.5 mL) and the mixture was stirred rt for 16 h. The reaction was quenched with water and extracted with ethyl acetate. The combined organic layers were washed with water and brine, dried ($Na_2SO_4$) and concentrated. The crude product was purified by SFC (Column: Reprospher PEI 100A, 250×30 mm, 5 μm; 36° C.: Eluent A: $CO_2$, Eluent B: 15-20% MeOH in 9.8 min; Flow: 100 mL/min; Pressure: 130 bar) to give (R)—$N^4$-(3-isobutyramido-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide (62). LCMS (method b) m/z 496.3 $[M+H]^+$, $t_R$=0.71 min. $^1$H-NMR (400 MHz, DMSO-$d_6$) δ ppm 10.12 (s, 1H), 9.88 (s, 1H), 8.32 (d, J=8.8 Hz, 1H), 7.33 (d, J=7.8 Hz, 1H), 7.18 (t, J=7.3 Hz, 1H), 7.11 (t, J=7.5 Hz, 1H), 7.06-6.99 (m, 1H), 6.68 (d, J=8.7 Hz, 1H), 6.45 (s, 1H), 4.23 (s, 2H), 3.61-3.49 (m, 2H), 3.47 (s, 3H), 3.28-3.22 (m, 1H), 3.19-3.12 (m, 2H), 2.75 (dd, J=15.3, 8.5 Hz, 1H), 2.62-2.53 (m, 1H), 2.45-2.30 (m, 2H), 2.10 (s, 1H), 1.14 (d, J=7.0 Hz, 3H), 1.05 (d, J=6.8 Hz, 6H).

Table 2 shows additional example compounds (Examples 63-105) which were prepared using a method analogous to that described in Example 62. The appropriate intermediates used in each step are listed, along with the coupling conditions for step 3.

TABLE 2

| Example No. | Compound Structure | Compound Name | Reaction Parameters | Analytics |
|---|---|---|---|---|
| 63 | 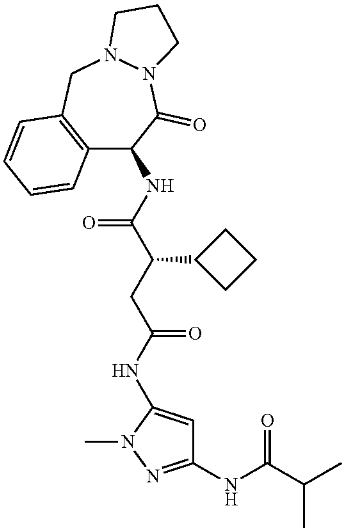 [SMILES: CC(C)C(=O)Nc1cc(NC(=O)C[C@H](C(=O)N[C@@H]2C(=O)N3CCCN3Cc3ccccc32)C2CCC2)n(C)n1] | (S)-2-Cyclobutyl-$N^4$-(3-isobutyramido-1-methyl-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L8 Step 3: int-EC38; EDC, pyridine | m/z 536.4 $[M + H]^+$, $t_R$ = 0.82 min (LCMS method b), $^1H$ NMR (400 MHz, DMSO-$d_6$) δ 10.11 (s, 1H), 9.86 (s, 1H), 8.19 (d, J = 8.8 Hz, 1H), 7.37 (d, J = 7.8 Hz, 1H), 7.16 (t, J = 7.4 Hz, 1H), 7.11 - 6.98 (m, 2H), 6.65 (d, J = 8.6 Hz, 1H), 6.45 (s, 1H), 4.22 (s, 2H), 3.64 - 3.47 (m, 2H), 3.43 (s, 3H), 3.28 - 3.22 (m, 1H), 3.21 - 3.08 (m, 2H), 2.70 - 2.53 (m, 2H), 2.44 - 2.30 (m, 3H), 2.16 - 1.94 (m, 3H), 1.90 - 1.69 (m, 4H), 1.05 (d, J = 6.7 Hz, 6H). |
| 64 | 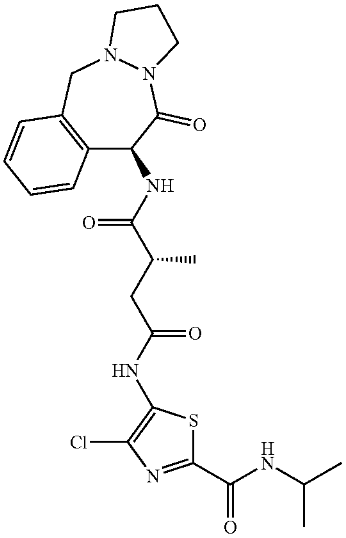 [SMILES: CC(C)NC(=O)c1nc(Cl)c(NC(=O)C[C@@H](C)C(=O)N[C@@H]2C(=O)N3CCCN3Cc3ccccc32)s1] | (R)-$N^4$-(4-Chloro-2-(isopropylcarbamoyl)thiazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC39; EDC, pyridine | m/z 533.2 $[M + H]^+$, $t_R$ = 0.94 min (LCMS method b), $^1H$ NMR (400 MHz, DMSO-$d_6$) δ 11.23 (s, 1H), 8.53 (d, J = 8.4 Hz, 1H), 8.38 (d, J = 8.8 Hz, 1H), 7.35 (d, J = 7.9 Hz, 1H), 7.19 (t, J = 7.4 Hz, 1H), 7.11 - 6.98 (m, 2H), 6.66 (d, J = 8.7 Hz, 1H), 4.22 (s, 2H), 4.12 - 3.99 (m, 1H), 3.54 (t, J = 8.1 Hz, 2H), 3.25 (d, J = 6.7 Hz, 2H), 3.22 - 3.11 (m, 1H), 2.97 (dd, J = 15.8, 9.2 Hz, 1H), 2.61 (dd, J = 15.8, 5.6 Hz, 1H), 2.38 - 2.30 (m, 1H), 2.18 - 2.02 (m, 1H), 1.16 (d, J = 6.6 Hz, 6H), 1.13 (d, J = 7.0 Hz, 3H). |

TABLE 2-continued

| Example No. | Compound Structure | Compound Name | Reaction Parameters | Analytics |
|---|---|---|---|---|
| 65 | 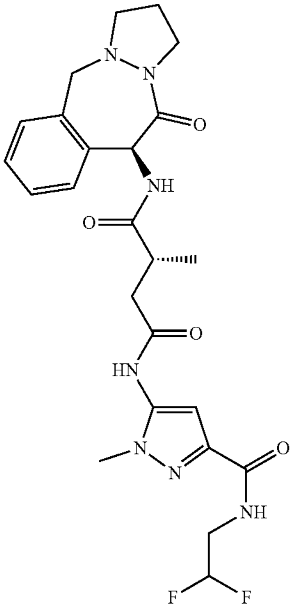 [SMILES: C[C@H](CC(=O)Nc1cc(C(=O)NCC(F)F)nn1C)C(=O)N[C@@H]1C(=O)N2CCCN2Cc2ccccc21] | (R)-$N^4$-(3-((2,2-difluoroethyl)carbamoyl)-1-methyl-1H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC40; EDC, pyridine | m/z 518.4 $[M + H]^+$, $t_R$ = 0.72 min (LCMS method b), $^1H$ NMR (400 MHz, $CDCl_3$) δ 9.25 (s, 1H), 7.34 (d, J = 7.6 Hz, 1H), 7.20 - 7.08 (m, 2H), 7.02 (t, J = 6.4 Hz, 1H), 6.98 - 6.89 (m, 2H), 6.70 (s, 1H), 6.67 (d, J = 7.6 Hz, 1H), 5.91 (tt, J = 56.1, 4.2 Hz, 1H), 4.18 (s, 2H), 3.85 - 3.65 (m, 3H), 3.64 - 3.53 (m, 1H), 3.41 (s, 3H), 3.38 - 3.31 (m, 1H), 3.26 - 3.14 (m, 1H), 3.13 - 3.03 (m, 1H), 2.96 - 2.82 (m, 1H), 2.62 - 2.49 (m, 1H), 2.45 - 2.29 (m, 1H), 2.25 - 2.09 (m, 1H), 1.33 (d, J = 7.1 Hz, 3H). |
| 66 | 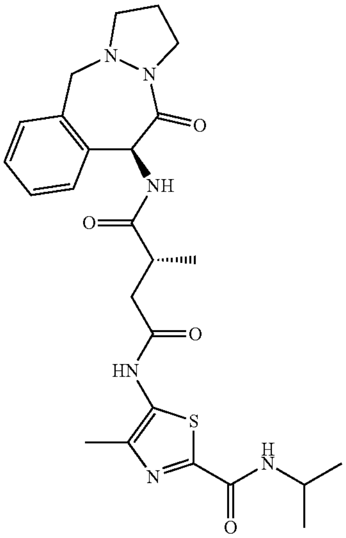 [SMILES: Cc1nc(C(=O)NC(C)C)sc1NC(=O)C[C@@H](C)C(=O)N[C@@H]1C(=O)N2CCCN2Cc2ccccc21] | (R)-$N^4$-(2-(Isopropylcarbamoyl)-4-methylthiazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC41; EDC, pyridine | m/z 513.3 $[M + H]^+$, $t_R$ = 0.89 min (LCMS method b), $^1H$ NMR (400 MHz, DMSO-$d_6$) δ 10.72 (s, 1H), 8.36 (d, J = 8.8 Hz, 1H), 8.19 (d, J = 8.4 Hz, 1H), 7.34 (d, J = 7.9 Hz, 1H), 7.18 (t, J = 7.4 Hz, 1H), 7.08 - 6.98 (m, 2H), 6.67 (d, J = 8.7 Hz, 1H), 4.22 (s, 2H), 4.13 - 3.98 (m, 1H), 3.60 - 3.47 (m, 2H), 3.31 (s, 1H), 3.28 - 3.21 (m, 1H), 3.21 - 3.10 (m, 1H), 2.89 (dd, J = 15.6, 9.0 Hz, 1H), 2.56 (dd, J = 15.6, 5.8 Hz, 1H), 2.40 (s, 3H), 2.37 - 2.29 (m, 1H), 2.16 - 2.01 (m, 1H), 1.16 (d, J = 6.6 Hz, 6H), 1.14 (d, J = 7.2 Hz, 3H). |

TABLE 2-continued

| Example No. | Compound Structure | Compound Name | Reaction Parameters | Analytics |
|---|---|---|---|---|
| 67 | 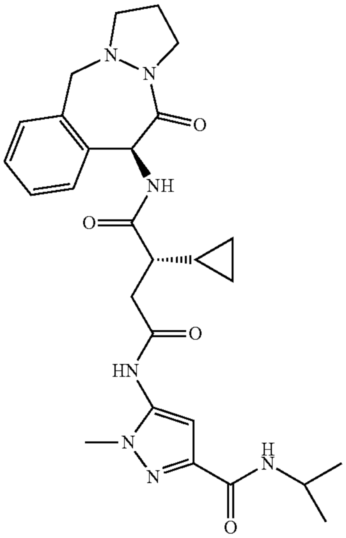 [SMILES: CC(C)NC(=O)c1cc(NC(=O)C[C@H](C(=O)N[C@@H]2C(=O)N3CCCN3Cc3ccccc32)C2CC2)n(C)n1] | (S)-2-Cyclopropyl-N[4]-(3-(isopropylcarbamoyl)-1-methyl-1H-pyrazol-5-yl)-N[1]-((S)-11-oxo-2,3,10,11-tetrahydro-1H,5H-benzo[d]pyrazolo[1,2-a][1,2]diazepin-10-yl)succinamide | Step 1: int-A1 and Int-L7 Step 3: int-EC42; EDC, pyridine | m/z 522.5 $[M + H]^+$, $t_R$ = 0.80 min (LCMS method b), $^1H$ NMR (400 MHz, DMSO-$d_6$) δ 10.07 (s, 1H), 8.19 (d, J = 8.6 Hz, 1H), 7.67 (d, J = 8.3 Hz, 1H), 7.35 (d, J = 8.0 Hz, 1H), 7.18 (t, J = 7.4 Hz, 1H), 7.08 - 6.98 (m, 2H), 6.68 (d, J = 8.5 Hz, 1H), 6.54 (s, 1H), 4.23 (s, 2H), 4.10 - 3.96 (m, 1H), 3.62 (s, 3H), 3.58 - 3.44 (m, 2H), 3.22 - 3.09 (m, 1H), 2.87 (dd, J = 15.1, 9.5 Hz, 1H), 2.69 - 2.53 (m, 2H), 2.41 - 2.26 (m, 2H), 2.18 - 2.03 (m, 1H), 1.13 (d, J = 6.6 Hz, 6H), 0.94 - 0.80 (m, 1H), 0.64 - 0.55 (m, 1H), 0.55 - 0.45 (m, 1H), 0.44 - 0.35 (m, 1H), 0.29 - 0.16 (m, 1H). |
| 68 | 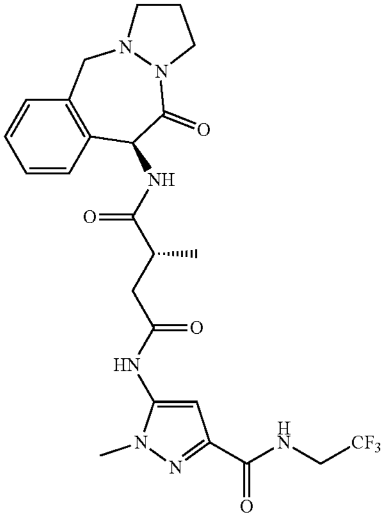 [SMILES: C[C@H](CC(=O)Nc1cc(C(=O)NCC(F)(F)F)nn1C)C(=O)N[C@@H]1C(=O)N2CCCN2Cc2ccccc21] | (R)-2-methyl-N[4]-(1-methyl-3-((2,2,2-trifluoroethyl)carbamoyl)-1H-pyrazol-5-yl)-N[1]-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC43; EDC, pyridine | m/z 536.5 $[M + H]^+$, $t_R$ = 0.78 min (LCMS method b), $^1H$ NMR (400 MHz, DMSO-$d_6$) δ 10.12 (s, 1H), 8.62 (t, J = 6.6 Hz, 1H), 8.35 (d, J = 8.8 Hz, 1H), 7.33 (d, J = 7.8 Hz, 1H), 7.19 (t, J = 7.4 Hz, 1H), 7.11 - 6.97 (m, 2H), 6.69 (d, J = 8.8 Hz, 1H), 6.63 (s, 1H), 4.23 (s, 2H), 4.06 - 3.90 (m, 2H), 3.67 (s, 3H), 3.58 - 3.45 (m, 2H), 3.28 - 3.22 (m, 2H), 3.20 - 3.12 (m, 1H), 2.78 (dd, J = 15.5, 8.9 Hz, 1H), 2.47 - 2.42 (m, 1H), 2.41 - 2.27 (m, 1H), 2.20 - 2.02 (m, 1H), 1.15 (d, J = 6.9 Hz, 3H). |
| 69 | 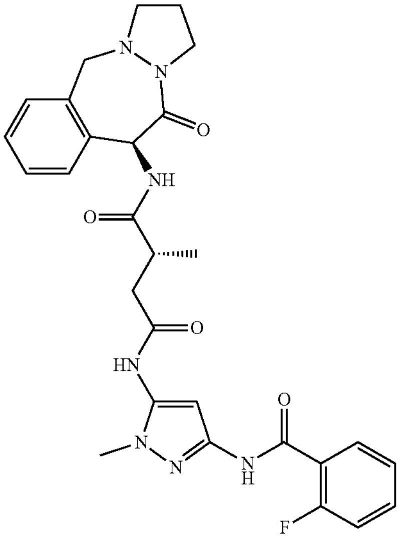 [SMILES: C[C@H](CC(=O)Nc1cc(NC(=O)c2ccccc2F)nn1C)C(=O)N[C@@H]1C(=O)N2CCCN2Cc2ccccc21] | (R)-N[4]-(3-(2-Fluorobenzamido)-1-methyl-1H-pyrazol-5-yl)-2-methyl-N[1]-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC44; EDC, pyridine | m/z 548.3 $[M + H]^+$, $t_R$ = 0.82 min (LCMS method b), $^1H$ NMR (400 MHz, DMSO-$d_6$) δ 10.62 (s, 1H), 9.97 (s, 1H), 8.33 (d, J = 8.8 Hz, 1H), 7.63 (t, J = 7.6 Hz, 1H), 7.54 (t, J = 7.0 Hz, 1H), 7.41 - 7.24 (m, 3H), 7.23 - 7.09 (m, 2H), 7.04 (d, J = 7.5 Hz, 1H), 6.69 (d, J = 8.7 Hz, 1H), 6.60 (s, 1H), 4.23 (s, 2H), 3.60 - 3.44 (m, 5H), 3.28 - 3.23 (m, 2H), 3.22 - 3.19 (m, 1H), 2.78 (dd, J = 15.5, 8.7 Hz, 1H), 2.44 - 2.31 (m, 2H), 2.19 - 2.00 (m, 1H), 1.15 (d, J = 6.9 Hz, 3H). |

TABLE 2-continued

| Example No. | Compound Structure | Compound Name | Reaction Parameters | Analytics |
|---|---|---|---|---|
| 70 | 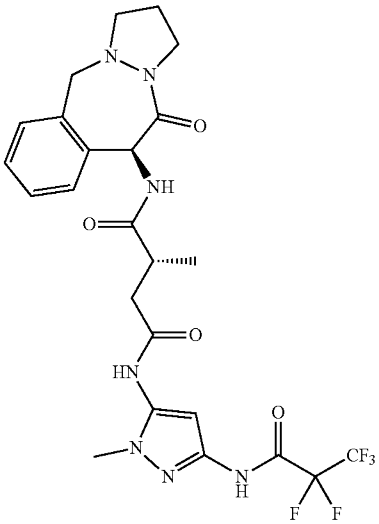 [SMILES: C[C@H](CC(=O)Nc1cc(NC(=O)C(F)(F)C(F)(F)F)nn1C)C(=O)N[C@@H]1C(=O)N2CCCN2Cc2ccccc21] | (R)-2-Methyl-$N^4$-(1-methyl-3-(2,2,3,3,3-pentafluoropropanamido)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC45; EDC, pyridine | m/z 572.3 $[M + H]^+$, $t_R$ = 0.89 min (LCMS method b), $^1H$ NMR (400 MHz, DMSO-$d_6$) δ 11.96 (s, 1H), 10.05 (s, 1H), 8.34 (d, J = 8.8 Hz, 1H), 7.34 (d, J = 7.8 Hz, 1H), 7.17 (t, J = 7.4 Hz, 1H), 7.09 (t, J = 7.5 Hz, 1H), 7.04 (d, J = 7.5 Hz, 1H), 6.68 (d, J = 8.7 Hz, 1H), 6.52 (s, 1H), 4.23 (s, 2H), 3.56 (s, 3H), 3.55 - 3.45 (m, 2H), 3.28 - 3.21 (m, 2H), 3.20 - 3.11 (m, 1H), 2.77 (dd, J = 15.4, 8.8 Hz, 1H), 2.47 - 2.42 (m, 1H), 2.38 - 2.28 (m, 1H), 2.15 - 2.02 (m, 1H), 1.14 (d, J = 7.0 Hz, 3H). |
| 71 | 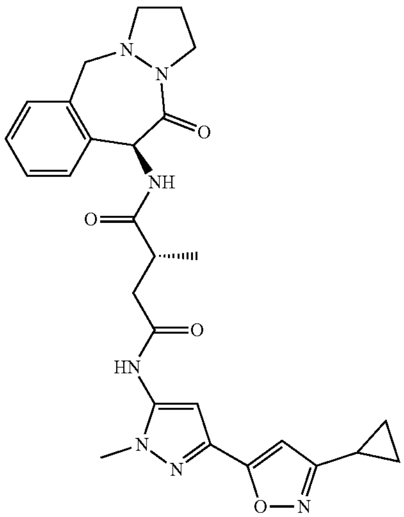 [SMILES: C[C@H](CC(=O)Nc1cc(-c2cc(C3CC3)no2)nn1C)C(=O)N[C@@H]1C(=O)N2CCCN2Cc2ccccc21] | (R)-$N^4$-(3-(3-Cyclopropylisoxazol-5-yl)-1-methyl-1H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC46; EDC, pyridine | m/z 518.2 $[M + H]^+$, $t_R$ = 0.89 min (LCMS method b), $^1H$ NMR (400 MHz, DMSO-$d_6$) δ 10.15 (s, 1H), 8.39 (d, J = 9.0 Hz, 1H), 7.34 (d, J = 7.8 Hz, 1H), 7.19 (t, J = 7.5 Hz, 1H), 7.11 - 6.98 (m, 2H), 6.69 (d, J = 8.9 Hz, 1H), 6.63 (s, 1H), 6.49 (s, 1H), 4.23 (s, 2H), 3.66 (s, 3H), 3.60 - 3.47 (m, 2H), 3.29 - 3.22 (m, 2H), 3.22 - 3.13 (m, 1H), 2.79 (dd, J = 15.4, 8.6 Hz, 1H), 2.34 - 2.31 (m, 2H), 2.12 - 1.98 (m, 2H), 1.15 (d, J = 7.0 Hz, 3H), 1.06 - 0.96 (m, 2H), 0.85 - 0.76 (m, 2H). |

TABLE 2-continued

| Example No. | Compound Structure | Compound Name | Reaction Parameters | Analytics |
|---|---|---|---|---|
| 72 | 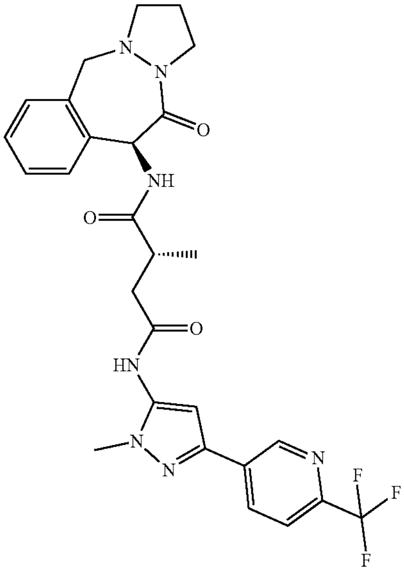 [SMILES: C[C@H](CC(=O)Nc1cc(-c2ccc(C(F)(F)F)nc2)nn1C)C(=O)N[C@@H]1C(=O)N2CCCN2Cc2ccccc21] | (R)-2-Methyl-$N^4$-(1-methyl-3-(6-(trifluoromethyl)pyridin-3-yl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC47; EDC, pyridine | m/z 556.3 $[M + H]^+$, $t_R$ = 0.96 min (LCMS method b), $^1H$ NMR (400 MHz, DMSO-$d_6$) δ 10.14 (s, 1H), 9.13 (d, J = 2.1 Hz, 1H), 8.43 (d, J = 9.0 Hz, 1H), 8.37 (dd, J = 8.1, 2.1 Hz, 1H), 7.92 (d, J = 8.2 Hz, 1H), 7.35 (d, J = 7.8 Hz, 1H), 7.19 (t, J = 7.4 Hz, 1H), 7.09 (t, J = 7.5 Hz, 1H), 7.04 (d, J = 7.6 Hz, 1H), 6.89 (s, 1H), 6.71 (d, J = 8.9 Hz, 1H), 4.23 (s, 2H), 3.68 (s, 3H), 3.58 - 3.49 (m, 2H), 3.31 - 3.22 (m, 2H), 3.21 - 3.11 (m, 1H), 2.80 (dd, J = 15.4, 8.7 Hz, 1H), 2.48 - 2.43 (m, 1H), 2.40 - 2.28 (m, 1H), 2.10 (s, 1H), 1.16 (d, J = 7.0 Hz, 3H). |
| 73 | 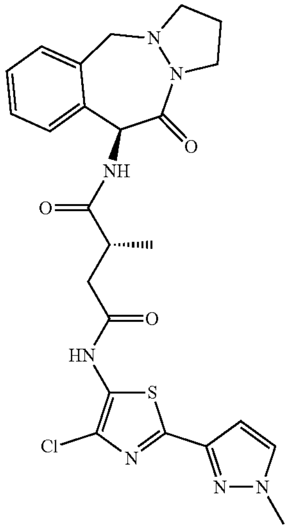 [SMILES: C[C@H](CC(=O)Nc1sc(-c2ccn(C)n2)nc1Cl)C(=O)N[C@@H]1C(=O)N2CCCN2Cc2ccccc21] | (R)-$N^4$-(4-Chloro-2-(1-methyl-1H-pyrazol-3-yl)thiazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC48; EDC, pyridine | m/z 528.2 $[M + H]^+$, $t_R$ = 0.86 min (LCMS method b), $^1H$ NMR (400 MHz, DMSO-$d_6$) δ 10.97 (s, 1H), 8.37 (d, J = 8.8 Hz, 1H), 7.83 (d, J = 2.3 Hz, 1H), 7.35 (d, J = 7.9 Hz, 1H), 7.19 (t, J = 7.4 Hz, 1H), 7.10 (t, J = 7.5 Hz, 1H), 7.04 (d, J = 7.6 Hz, 1H), 6.71 - 6.64 (m, 2H), 4.23 (s, 2H), 3.92 (s, 3H), 3.61 - 3.45 (m, 2H), 3.31 - 3.23 (m, 2H), 3.22 - 3.12 (m, 1H), 2.95 (dd, J = 15.6, 8.9 Hz, 1H), 2.59 (dd, J = 15.6, 5.9 Hz, 1H), 2.41 - 2.30 (m, 1H), 2.16 - 2.03 (m, 1H), 1.14 (d, J = 7.0 Hz, 3H). |

TABLE 2-continued

| Example No. | Compound Structure | Compound Name | Reaction Parameters | Analytics |
|---|---|---|---|---|
| 74 | 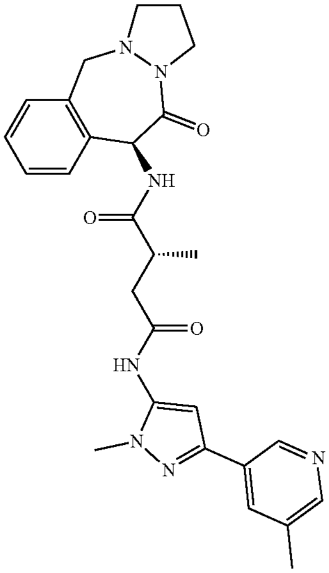 [SMILES: Cc1cncc(-c2cc(NC(=O)C[C@@H](C)C(=O)N[C@@H]3C(=O)N4CCCN4Cc4ccccc43)n(C)n2)c1] | (R)-2-Methyl-$N^4$-(1-methyl-3-(5-methylpyridin-3-yl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC49; EDC, pyridine | m/z 502.2 $[M + H]^+$, $t_R$ = 0.71 min (LCMS method b), $^1H$ NMR (400 MHz, DMSO-$d_6$) δ 10.07 (s, 1H), 8.74 (s, 1H), 8.42 (d, J = 9.0 Hz, 1H), 8.32 (s, 1H), 7.92 (s, 1H), 7.35 (d, J = 8.0 Hz, 1H), 7.19 (t, J = 7.4 Hz, 1H), 7.09 (t, J = 7.6 Hz, 1H), 7.04 (d, J = 7.7 Hz, 1H), 6.75 - 6.61 (m, 2H), 4.23 (s, 2H), 3.63 (s, 3H), 3.58 - 3.46 (m, 2H), 3.29 - 3.23 (m, 2H), 3.21 - 3.11 (m, 1H), 2.78 (dd, J = 15.3, 8.6 Hz, 1H), 2.47 - 2.41 (m, 1H), 2.40 - 2.34 (m, 1H), 2.33 (s, 3H), 2.16 - 1.97 (m, 1H), 1.15 (d, J = 6.9 Hz, 3H). |
| 75 | 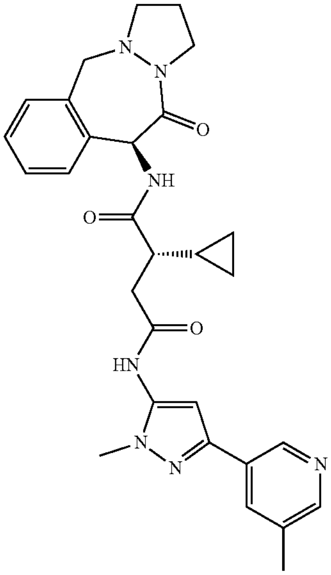 [SMILES: Cc1cncc(-c2cc(NC(=O)C[C@H](C(=O)N[C@@H]3C(=O)N4CCCN4Cc4ccccc43)C3CC3)n(C)n2)c1] | (S)-2 Cyclopropyl-$N^4$-(1-methyl-3-(5-methylpyridin-3-yl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L7 Step 3: int-EC49; EDC, pyridine | m/z 528.3 $[M + H]^+$, $t_R$ = 0.80 min (LCMS method b), $^1H$ NMR (400 MHz, DMSO-$d_6$) δ 10.07 (s, 1H), 8.74 (s, 1H), 8.33 (s, 1H), 8.24 (d, J = 8.7 Hz, 1H), 7.91 (s, 1H), 7.37 (d, J = 7.9 Hz, 1H), 7.18 (t, J = 7.4 Hz, 1H), 7.11 - 6.95 (m, 2H), 6.73 - 6.64 (m, 2H), 4.23 (s, 2H), 3.62 (s, 3H), 3.59 - 3.42 (m, 2H), 3.30 - 3.24 (m, 1H), 3.22 - 3.12 (m, 1H), 2.94 - 2.82 (m, 1H), 2.70 - 2.53 (m, 2H), 2.43 - 2.34 (m, 1H), 2.33 (s, 3H), 2.16 - 2.03 (m, 1H), 0.93 - 0.82 (m, 1H), 0.65 - 0.56 (m, 1H), 0.56 - 0.47 (m, 1H), 0.46 - 0.37 (m, 1H), 0.29 - 0.19 (m, 1H). |

TABLE 2-continued

| Example No. | Compound Structure | Compound Name | Reaction Parameters | Analytics |
|---|---|---|---|---|
| 76 | 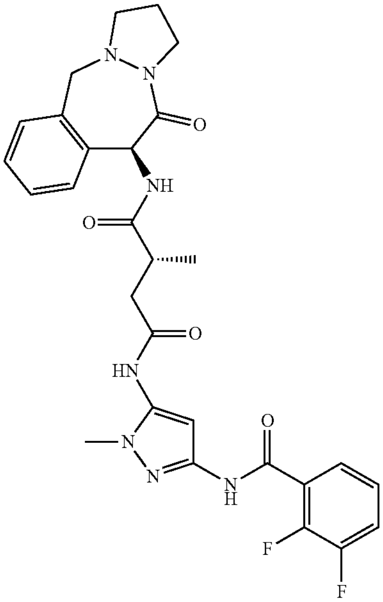 [SMILES: C[C@H](CC(=O)Nc1cc(NC(=O)c2cccc(F)c2F)nn1C)C(=O)N[C@@H]1C(=O)N2CCCN2Cc2ccccc21] | (R)-$N^4$-(3-(2,3-Difluorobenzamido)-1-methyl-1 H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC50; EDC, pyridine | m/z 566.3 $[M + H]^+$, $t_R$ = 0.84 min (LCMS method b), $^1H$ NMR (400 MHz, DMSO-$d_6$) δ 10.83 (s, 1H), 9.98 (s, 1H), 8.34 (d, J = 8.8 Hz, 1H), 7.65 - 7.50 (m, 1H), 7.43 (t, J = 6.9 Hz, 1H), 7.36 (d, J = 7.7 Hz, 1H), 7.33 - 7.25 (m, 1H), 7.22 - 7.09 (m, 2H), 7.04 (d, J = 7.4 Hz, 1H), 6.69 (d, J = 8.8 Hz, 1H), 6.60 (s, 1H), 4.23 (s, 2H), 3.61 - 3.47 (m, 5H), 3.29 - 3.22 (m, 2H), 3.20 - 3.11 (m, 1H), 2.78 (dd, J = 15.4, 8.7 Hz, 1H), 2.47 - 2.27 (m, 2H), 2.16 - 2.02 (m, 1H), 1.15 (d, J = 6.9 Hz, 3H). |
| 77 | 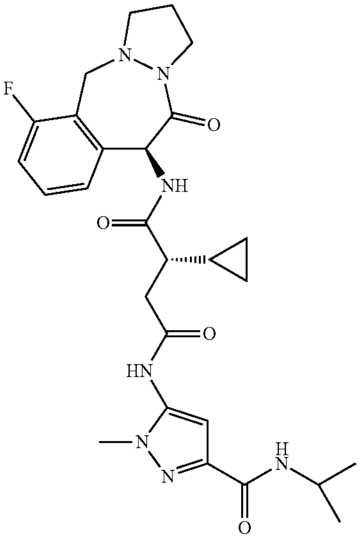 [SMILES: CC(C)NC(=O)c1cc(NC(=O)C[C@H](C(=O)N[C@@H]2C(=O)N3CCCN3Cc3c(F)cccc32)C2CC2)n(C)n1] | (S)-2-Cyclopropyl-$N^1$-((S)-6-fluoro-11-oxo-2,3,10,11-tetrahydro-1H,5H-benzo[d]pyrazolo[1,2-a][1,2]diazepin-10-yl)-$N^4$-(3-(isopropylcarbamoyl)-1-methyl-1H-pyrazol-5-yl)succinamide | Step 1: int-A2 and Int-L7 Step 3: int-EC42; EDC, pyridine | m/z 540.4 $[M + H]^+$, $t_R$ = 0.85 min (LCMS method b), $^1H$ NMR (400 MHz, DMSO-$d_6$) δ 10.07 (s, 1H), 8.29 (d, J = 8.7 Hz, 1H), 7.67 (d, J = 8.3 Hz, 1H), 7.23 (d, J = 7.5 Hz, 1H), 7.15 - 7.02 (m, 2H), 6.71 (d, J = 8.6 Hz, 1H), 6.53 (s, 1H), 4.17 (s, 2H), 4.10 - 3.98 (m, 1H), 3.61 (s, 3H), 3.59 - 3.51 (m, 2H), 3.28 - 3.23 (m, 1H), 2.87 (dd, J = 15.2, 9.6 Hz, 1H), 2.68 - 2.52 (m, 2H), 2.44 - 2.31 (m, 2H), 2.16 - 2.04 (m, 1H), 1.13 (d, J = 6.6 Hz, 6H), 0.92 - 0.80 (m, 1H), 0.63 - 0.55 (m, 1H), 0.54 - 0.45 (m, 1H), 0.45 - 0.35 (m, 1H), 0.27 - 0.16 (m, 1H). |

TABLE 2-continued

| Example No. | Compound Structure | Compound Name | Reaction Parameters | Analytics |
|---|---|---|---|---|
| 78 | 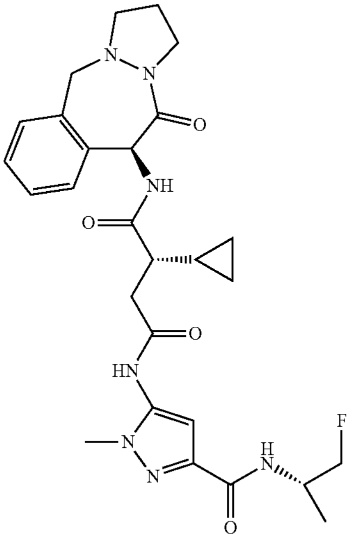 [SMILES: C[C@@H](CF)NC(=O)c1cc(NC(=O)C[C@H](C(=O)N[C@@H]2C(=O)N3CCCN3Cc3ccccc32)C2CC2)n(C)n1] | (S)-2-Cyclopropyl-$N^4$-(3-(((S)-1-fluoropropan-2-yl)carbamoyl)-1-methyl-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L7<br>Step 3: int-EC51; EDC, pyridine | m/z 540.4 $[M + H]^+$, $t_R$ = 0.79 min (LCMS method b), $^1H$ NMR (400 MHz, DMSO-$d_6$) δ 10.10 (s, 1H), 8.21 (d, J = 8.7 Hz, 1H), 7.92 (d, J = 8.4 Hz, 1H), 7.35 (d, J = 8.1 Hz, 1H), 7.18 (t, J = 7.4 Hz, 1H), 7.08 - 6.97 (m, 2H), 6.68 (d, J = 8.5 Hz, 1H), 6.57 (s, 1H), 4.51 - 4.25 (m, 3H), 4.23 (s, 2H), 3.63 (s, 3H), 3.59 - 3.48 (m, 2H), 3.22 - 3.11 (m, 1H), 2.87 (dd, J = 15.0, 9.6 Hz, 1H), 2.67 - 2.54 (m, 3H), 2.39 - 2.29 (m, 1H), 2.19 - 2.01 (m, 1H), 1.13 (d, J = 6.7 Hz, 3H), 0.93 - 0.80 (m, 1H), 0.67 - 0.54 (m, 1H), 0.55 - 0.45 (m, 1H), 0.44 - 0.35 (m, 1H), 0.28 - 0.17 (m, 1H). |
| 79 | 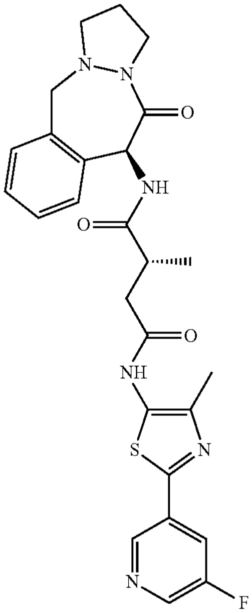 [SMILES: Cc1nc(-c2cncc(F)c2)sc1NC(=O)C[C@@H](C)C(=O)N[C@@H]1C(=O)N2CCCN2Cc2ccccc21] | (R)-$N^4$-(2-(5-fluoropyridin-3-yl)-4-methylthiazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6<br>Step 3: int-EC52; 1-methyl-1-H-imidazole MsCl, $CH_2Cl_2$, 20° C., 2 h | m/z 523.2 $[M + H]^+$, $t_R$ = 0.90 min (LCMS method b), $^1H$ NMR (400 MHz, DMSO-$d_6$) δ 10.77 (s, 1H), 8.90 (t, J = 1.7 Hz, 1H), 8.60 (d, J = 2.7 Hz, 1H), 8.43 (d, J = 8.9 Hz, 1H), 8.12 - 8.06 (m, 1H), 7.35 (d, J = 7.9 Hz, 1H), 7.18 (t, J = 7.4 Hz, 1H), 7.11 (t, J = 7.4 Hz, 1H), 7.02 (d, J = 7.4 Hz, 1H), 6.69 (d, J = 8.9 Hz, 1H), 4.22 (s, 2H), 3.58 - 3.46 (m, 2H), 3.31 - 3.22 (m, 2H), 3.21 - 3.12 (m, 1H), 2.89 (dd, J = 15.3, 8.9 Hz, 1H), 2.61 - 2.53 (m, 1H), 2.43 (s, 3H), 2.39 - 2.34 (m, 1H), 2.16 - 2.03 (m, 1H), 1.15 (d, J = 7.0 Hz, 3H). |

TABLE 2-continued

| Example No. | Compound Structure | Compound Name | Reaction Parameters | Analytics |
|---|---|---|---|---|
| 80 | 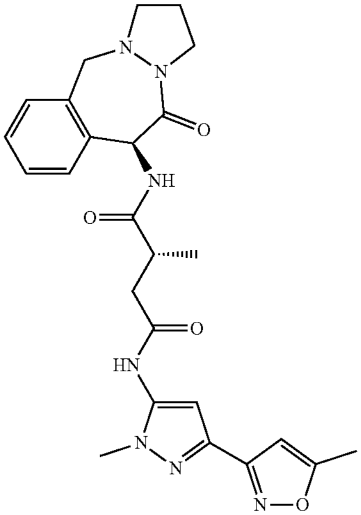 [SMILES: Cc1cc(-c2cc(NC(=O)C[C@@H](C)C(=O)N[C@@H]3C(=O)N4CCCN4Cc4ccccc43)n(C)n2)no1] | (R)-2-Methyl-$N^4$-(1-methyl-3-(5-methylisoxazol-3-yl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC53; EDC, pyridine | m/z 492.3 $[M + H]^+$, $t_R$ = 0.81 min (LCMS method b), $^1H$ NMR (400 MHz, DMSO-$d_6$) δ 10.12 (s, 1H), 8.38 (d, J = 8.9 Hz, 1H), 7.34 (d, J = 7.9 Hz, 1H), 7.19 (t, J = 7.4 Hz, 1H), 7.11 - 6.99 (m, 2H), 6.69 (d, J = 8.8 Hz, 1H), 6.61 (s, 1H), 6.49 (s, 1H), 4.23 (s, 2H), 3.66 (s, 3H), 3.60 - 3.44 (m, 2H), 3.30 - 3.24 (m, 2H), 3.21 - 3.10 (m, 1H), 2.79 (dd, J = 15.4, 8.8 Hz, 1H), 2.48 - 2.43 (m, 1H), 2.43 (s, 3H), 2.40 - 2.29 (m, 1H), 2.16 - 2.01 (m, 1H), 1.15 (d, J = 6.9 Hz, 3H). |
| 81 | 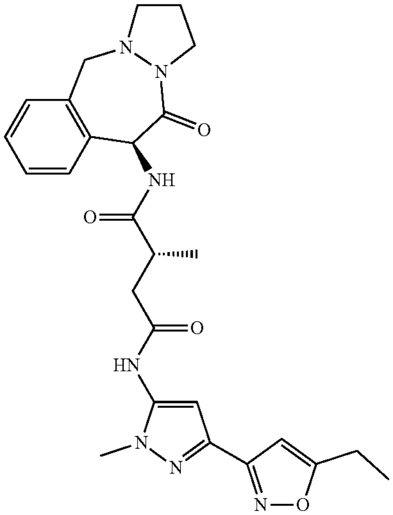 [SMILES: CCc1cc(-c2cc(NC(=O)C[C@@H](C)C(=O)N[C@@H]3C(=O)N4CCCN4Cc4ccccc43)n(C)n2)no1] | (R)-$N^4$-(3-(5-Ethylisoxazol-3-yl)-1-methyl-1H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC54; EDC, pyridine | m/z 506.3 $[M + H]^+$, $t_R$ = 0.89 min (LCMS method b), $^1H$ NMR (400 MHz, DMSO-$d_6$) δ 10.12 (s, 1H), 8.39 (d, J = 8.9 Hz, 1H), 7.34 (d, J = 7.9 Hz, 1H), 7.19 (t, J = 7.4 Hz, 1H), 7.11 - 7.00 (m, 2H), 6.69 (d, J = 8.8 Hz, 1H), 6.62 (s, 1H), 6.51 (s, 1H), 4.23 (s, 2H), 3.66 (s, 3H), 3.60 - 3.46 (m, 2H), 3.30 - 3.23 (m, 2H), 3.21 - 3.11 (m, 1H), 2.87 - 2.72 (m, 3H), 2.48 - 2.42 (m, 1H), 2.40 - 2.31 (m, 1H), 2.16 - 2.02 (m, 1H), 1.25 (t, J = 7.6 Hz, 3H), 1.15 (d, J = 7.0 Hz, 3H). |
| 82 | 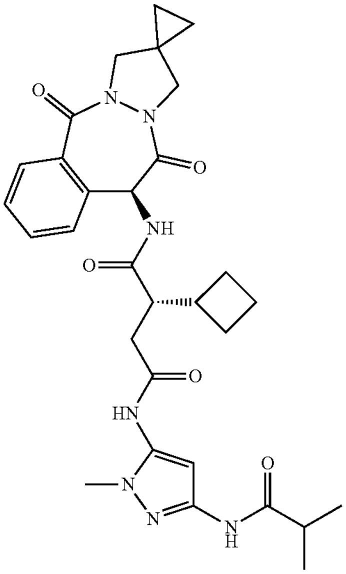 [SMILES: CC(C)C(=O)Nc1cc(NC(=O)C[C@H](C(=O)N[C@@H]2C(=O)N3CC4(CC4)CN3C(=O)c3ccccc32)C2CCC2)n(C)n1] | (S)-2-Cyclobutyl-$N^1$-((S)-5,11-dioxo-10,11-dihydro-1H,3H,5H-spiro[benzo[d]pyrazolo[1,2-a][1,2]diazepine-2,1'-cyclopropan]-10-yl)-$N^4$-(3-isobutyramido-1-methyl-1H-pyrazol-5-yl)succinamide | Step 1: int-C1 and Int-L8 Step 3: int-EC38; EDC, pyridine | m/z 576.4 $[M + H]^+$, $t_R$ = 0.88 min (LCMS method b), $^1H$ NMR (400 MHz, DMSO-$d_6$) δ 10.12 (s, 1H), 9.85 (s, 1H), 8.70 (d, J = 8.0 Hz, 1H), 7.79 (d, J = 7.6 Hz, 1H), 7.57 - 7.49 (m, 2H), 7.45 - 7.36 (m, 1H), 6.46 (s, 1H), 5.95 (d, J = 7.9 Hz, 1H), 4.22 (d, J = 11.2 Hz, 1H), 3.92 (d, J = 10.8 Hz, 1H), 3.63 (d, J = 11.1 Hz, 1H), 3.38 (s, 3H), 3.29 - 3.20 (m, 2H), 2.65 - 2.54 (m, 2H), 2.44 - 2.25 (m, 2H), 2.13 - 1.94 (m, 2H), 1.94 - 1.86 (m, 1H), 1.85 - 1.72 (m, 3H), 1.05 (d, J = 6.8 Hz, 6H), 0.84 - 0.69 (m, 4H). |

TABLE 2-continued

| Example No. | Compound Structure | Compound Name | Reaction Parameters | Analytics |
|---|---|---|---|---|
| 83 | 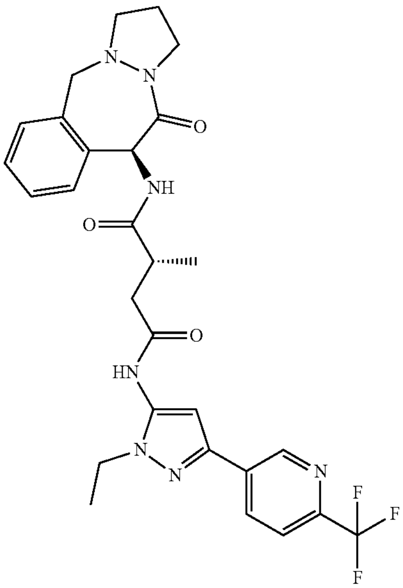 [SMILES: CCn1nc(-c2ccc(C(F)(F)F)nc2)cc1NC(=O)C[C@@H](C)C(=O)N[C@@H]1C(=O)N2CCCN2Cc2ccccc21] | (R)-$N^4$-(1-Ethyl-3-(6-(trifluoromethyl)pyridin-3-yl)-1H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC55; EDC, pyridine | m/z 570.2 $[M + H]^+$, $t_R$ = 1.03 min (LCMS method b), $^1H$ NMR (400 MHz, DMSO-$d_6$) δ 10.07 (s, 1H), 9.13 (s, 1H), 8.49 - 8.30 (m, 2H), 7.91 (d, J = 8.2 Hz, 1H), 7.35 (d, J = 7.9 Hz, 1H), 7.19 (t, J = 7.4 Hz, 1H), 7.09 (t, J = 7.6 Hz, 1H), 7.04 (d, J = 7.7 Hz, 1H), 6.88 (s, 1H), 6.71 (d, J = 8.9 Hz, 1H), 4.23 (s, 2H), 4.04 (q, J = 7.4 Hz, 2H), 3.59 - 3.46 (m, 2H), 3.30 - 3.22 (m, 2H), 3.21 - 3.10 (m, 1H), 2.81 (dd, J = 15.5, 8.6 Hz, 1H), 2.48 - 2.43 (m, 1H), 2.41 - 2.27 (m, 1H), 2.15 - 2.03 (m, 1H), 1.26 (t, J = 7.1 Hz, 3H), 1.16 (d, J = 6.9 Hz, 3H). |
| 84 | 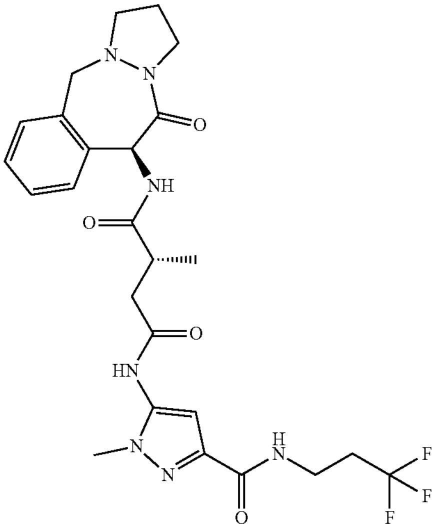 [SMILES: C[C@H](CC(=O)Nc1cc(C(=O)NCCC(F)(F)F)nn1C)C(=O)N[C@@H]1C(=O)N2CCCN2Cc2ccccc21] | (R)-2-Methyl-$N^4$-(1-methyl-3-((3,3,3-trifluoropropyl)carbamoyl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: Int-EC75; EDC, pyridine | m/z 550.3 $[M + H]^+$, $t_R$ = 0.81 min (LCMS method b), $^1H$ NMR (400 MHz, DMSO-$d_6$) δ 10.07 (s, 1H), 8.34 (d, J = 8.9 Hz, 1H), 8.22 (t, J = 6.0 Hz, 1H), 7.33 (d, J = 7.8 Hz, 1H), 7.19 (t, J = 7.4 Hz, 1H), 7.11 - 6.98 (m, 2H), 6.68 (d, J = 8.8 Hz, 1H), 6.56 (s, 1H), 4.23 (s, 2H), 3.64 (s, 3H), 3.58 - 3.49 (m, 2H), 3.48 - 3.40 (m, 2H), 3.28 - 3.21 (m, 2H), 3.20 - 3.12 (m, 1H), 2.77 (dd, J = 15.5, 8.7 Hz, 1H), 2.57 - 2.51 (m, 2H), 2.48 - 2.40 (m, 1H), 2.40 - 2.28 (m, 1H), 2.20 - 2.03 (m, 1H), 1.14 (d, J = 6.9 Hz, 3H). |

TABLE 2-continued

| Example No. | Compound Structure | Compound Name | Reaction Parameters | Analytics |
|---|---|---|---|---|
| 85 | 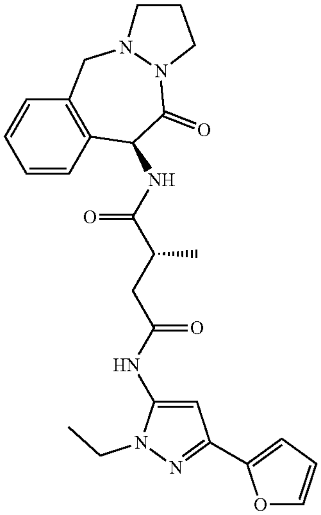 [SMILES: CCn1nc(-c2ccco2)cc1NC(=O)C[C@@H](C)C(=O)N[C@@H]1C(=O)N2CCCN2Cc2ccccc21] | (R)-N4-(1-Ethyl-3-(furan-2-yl)-1H-pyrazol-5-yl)-2-methyl-N1-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC56; EDC, pyridine | m/z 491.4 $[M + H]^+$, $t_R$ = 0.87 min (LCMS method b), $^1H$ NMR (400 MHz, DMSO-$d_6$) δ 9.98 (s, 1H), 8.38 (d, J = 8.9 Hz, 1H), 7.66 (d, J = 2.3 Hz, 1H), 7.34 (d, J = 7.9 Hz, 1H), 7.19 (t, J = 7.4 Hz, 1H), 7.12 - 6.99 (m, 2H), 6.70 (d, J = 8.8 Hz, 1H), 6.64 (d, J = 3.3 Hz, 1H), 6.53 (dd, J = 3.4, 1.8 Hz, 1H), 6.46 (s, 1H), 4.23 (s, 2H), 3.98 (q, J = 7.3, 6.7 Hz, 2H), 3.59 - 3.48 (m, 2H), 3.29 - 3.22 (m, 2H), 3.21 - 3.12 (m, 1H), 2.78 (dd, J = 15.3, 8.6 Hz, 1H), 2.47 - 2.41 (m, 1H), 2.37 - 2.31 (m, 1H), 2.16 - 2.03 (m, 1H), 1.21 (t, J = 7.1 Hz, 3H), 1.15 (d, J = 6.9 Hz, 3H). |
| 86 | 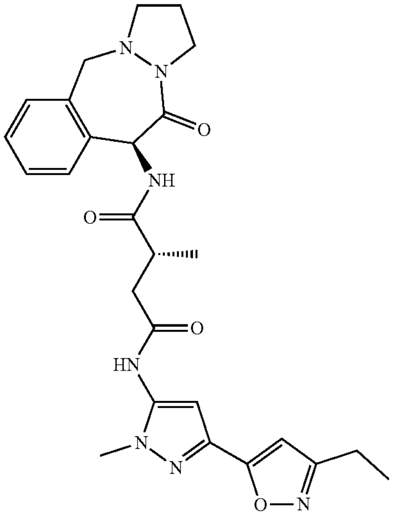 [SMILES: CCc1cc(-c2cc(NC(=O)C[C@@H](C)C(=O)N[C@@H]3C(=O)N4CCCN4Cc4ccccc43)n(C)n2)on1] | (R)-NA-(3-(3-Ethylisoxazol-5-yl)-1-methyl-1H-pyrazol-5-yl)-2-methyl-N1-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC57; EDC, pyridine | m/z 506.3 $[M + H]^+$, $t_R$ = 0.87 min (LCMS method b), $^1H$ NMR (400 MHz, DMSO-$d_6$) δ 10.16 (d, 1H), 8.40 (d, J = 8.9 Hz, 1H), 7.34 (d, J = 7.9 Hz, 1H), 7.19 (t, J = 7.4 Hz, 1H), 7.15 - 7.01 (m, 2H), 6.70 (d, J = 8.8 Hz, 1H), 6.66 (s, 1H), 6.65 (s, 1H), 4.23 (s, 2H), 3.67 (s, 3H), 3.59 - 3.45 (m, 2H), 3.31 - 3.24 (m, 2H), 3.22 - 3.10 (m, 1H), 2.79 (dd, J = 15.5, 8.8 Hz, 1H), 2.65 (q, J = 7.6 Hz, 2H), 2.48 - 2.44 (m, 1H), 2.37 - 2.28 (m, 1H), 2.16 - 2.03 (m, 1H), 1.22 (t, J = 7.6 Hz, 3H), 1.15 (d, J = 7.0 Hz, 3H). |
| 87 | 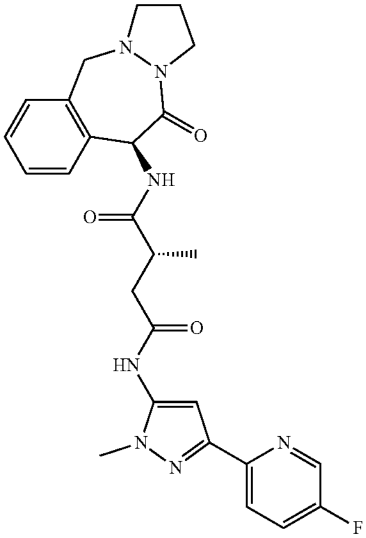 [SMILES: C[C@H](CC(=O)Nc1cc(-c2ccc(F)cn2)nn1C)C(=O)N[C@@H]1C(=O)N2CCCN2Cc2ccccc21] | (R)-N4-(3-(5-Fluoropyridin-2-yl)-1-methyl-1H-pyrazol-5-yl)-2-methyl-N1-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC58; EDC, pyridine | m/z 506.3 $[M + H]^+$, $t_R$ = 0.82 min (LCMS method b), $^1H$ NMR (400 MHz, DMSO-$d_6$) δ 10.08 (s, 1H), 8.55 (d, J = 3.0 Hz, 1H), 8.39 (d, J = 8.8 Hz, 1H), 7.92 (dd, J = 8.8, 4.6 Hz, 1H), 7.79 - 7.68 (m, 1H), 7.35 (d, J = 7.9 Hz, 1H), 7.19 (t, J = 7.4 Hz, 1H), 7.09 (t, J = 7.6 Hz, 1H), 7.04 (d, J = 7.6 Hz, 1H), 6.73 (s, 1H), 6.70 (d, J = 8.8 Hz, 1H), 4.23 (s, 2H), 3.66 (s, 3H), 3.58 - 3.47 (m, 2H), 3.30 - 3.22 (m, 2H), 3.20 - 3.10 (m, 1H), 2.79 (dd, J = 15.3, 8.8 Hz, 1H), 2.48 - 2.42 (m, 1H), 2.36 - 2.28 (m, 1H), 2.15 - 2.02 (m, 1H), 1.15 (d, J = 6.9 Hz, 3H). |

TABLE 2-continued

| Example No. | Compound Structure | Compound Name | Reaction Parameters | Analytics |
|---|---|---|---|---|
| 88 | 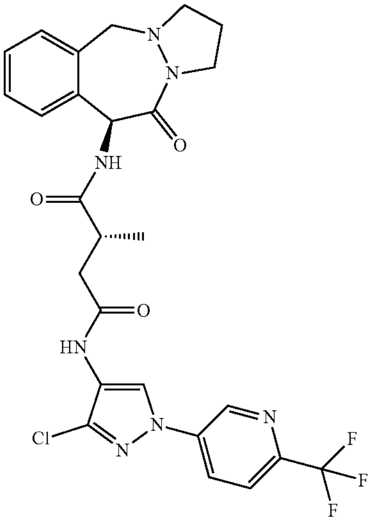 [SMILES: C[C@H](CC(=O)Nc1cn(-c2ccc(C(F)(F)F)nc2)nc1Cl)C(=O)N[C@@H]1C(=O)N2CCCN2Cc2ccccc21] | (R)-$N^4$-(3-Chloro-1-(6-(trifluoromethyl)pyridin-3-yl)-1H-pyrazol-4-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC59; EDC, pyridine | m/z 576.3 $[M + H]^+$, $t_R$ = 1.05 min (LCMS method b), $^1H$ NMR (400 MHz, DMSO-$d_6$) δ 9.92 (s, 1H), 9.25 (d, J = 2.5 Hz, 1H), 9.00 (s, 1H), 8.47 (d, J = 8.6 Hz, 1H), 8.35 (d, J = 9.0 Hz, 1H), 8.04 (d, J = 8.7 Hz, 1H), 7.35 (d, J = 7.9 Hz, 1H), 7.25 - 7.07 (m, 2H), 7.03 (d, J = 7.5 Hz, 1H), 6.70 (d, J = 8.8 Hz, 1H), 4.23 (s, 2H), 3.59 - 3.47 (m, 2H), 3.24 - 3.10 (m, 3H), 2.85 (dd, J = 15.1, 7.9 Hz, 1H), 2.41 - 2.29 (m, 2H), 2.19 - 2.00 (m, 1H), 1.15 (d, J = 6.9 Hz, 3H). |
| 89 | 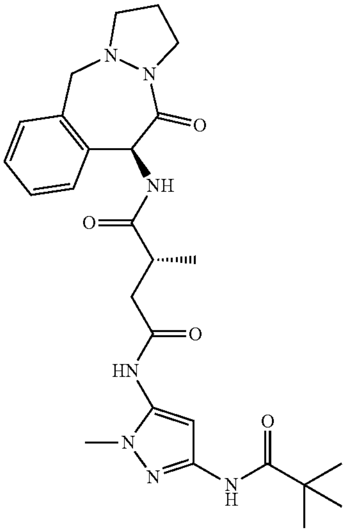 [SMILES: C[C@H](CC(=O)Nc1cc(NC(=O)C(C)(C)C)nn1C)C(=O)N[C@@H]1C(=O)N2CCCN2Cc2ccccc21] | (R)-2-Methyl-$N^4$-(1-methyl-3-pivalamido-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC60; EDC, pyridine | m/z 510.4 $[M + H]^+$, $t_R$ = 0.78 min (LCMS method b), $^1H$ NMR (400 MHz, DMSO-$d_6$) δ 9.89 (s, 1H), 9.66 (s, 1H), 8.32 (d, J = 8.8 Hz, 1H), 7.33 (d, J =7.8 Hz, 1H), 7.18 (t, J = 7.3 Hz, 1H), 7.11 (t, J = 7.6 Hz, 1H), 7.04 (d, J = 6.4 Hz, 1H), 6.68 (d, J = 8.7 Hz, 1H), 6.42 (s, 1H), 4.23 (s, 2H), 3.59 - 3.50 (m, 2H), 3.48 (s, 3H), 3.28 - 3.21 (m, 2H), 3.21 - 3.11 (m, 1H), 2.75 (dd, J = 15.3, 8.6 Hz, 1H), 2.46 - 2.31 (m, 2H), 2.20 - 2.03 (m, 1H), 1.18 (s, 9H), 1.14 (d, J = 7.0 Hz, 3H). |
| 90 | 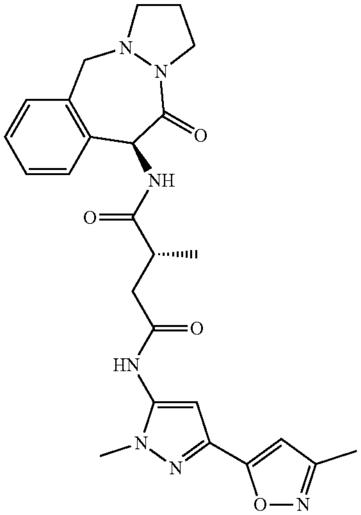 [SMILES: Cc1cc(-c2cc(NC(=O)C[C@@H](C)C(=O)N[C@@H]3C(=O)N4CCCN4Cc4ccccc43)n(C)n2)on1] | (R)-2-Methyl-$N^4$.(1-methyl-3-(3-methylisoxazol-5-yl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC61; EDC, pyridine | m/z 492.3 $[M + H]^+$, $t_R$ = 0.80 min (LCMS method b), $^1H$ NMR (400 MHz, DMSO-$d_6$) δ 10.15 (s, 1H), 8.40 (d, J = 8.9 Hz, 1H), 7.34 (d, J = 7.9 Hz, 1H), 7.19 (t, J = 7.4 Hz, 1H), 7.11 - 6.99 (m, 2H), 6.70 (d, J = 8.9 Hz, 1H), 6.65 (s, 1H), 6.59 (s, 1H), 4.23 (s, 2H), 3.67 (s, 3H), 3.59 - 3.46 (m, 2H), 3.30 - 3.22 (m, 2H), 3.21 - 3.10 (m, 1H), 2.79 (dd, J = 15.4, 8.8 Hz, 1H), 2.47 - 2.44 (m, 1H), 2.40 - 2.34 (m, 1H), 2.26 (s, 3H), 2.16 - 2.03 (m, 1H), 1.15 (d, J = 7.0 Hz, 3H). |

TABLE 2-continued

| Example No. | Compound Structure | Compound Name | Reaction Parameters | Analytics |
|---|---|---|---|---|
| 91 | 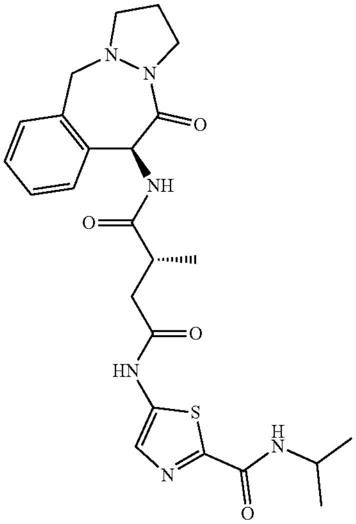 [SMILES: CC(C)NC(=O)c1ncc(NC(=O)C[C@@H](C)C(=O)N[C@@H]2C(=O)N3CCCN3Cc3ccccc32)s1] | (R)-$N^4$-(2-(Isopropylcarbamoyl)thiazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC62; EDC, pyridine | m/z 499.2 $[M + H]^+$, $t_R$ = 0.82 min (LCMS method b), $^1H$ NMR (400 MHz, DMSO-$d_6$) δ 11.62 (s, 1H), 8.37 (d, J = 8.8 Hz, 1H), 8.29 (d, J = 8.4 Hz, 1H), 7.54 (s, 1H), 7.32 (d, J = 8.1 Hz, 1H), 7.18 (t, J = 7.4 Hz, 1H), 7.07 - 6.98 (m, 2H), 6.66 (d, J = 8.7 Hz, 1H), 4.22 (s, 2H), 4.13 - 4.00 (m, 1H), 3.58 - 3.46 (m, 2H), 3.35 - 3.31 (m, 1H), 3.28 - 3.22 (m, 1H), 3.20 - 3.12 (m, 1H), 2.77 (dd, J = 15.5, 9.3 Hz, 1H), 2.55 - 2.51 (m, 1H), 2.39 - 2.28 (m, 1H), 2.14 - 2.00 (m, 1H), 1.17 (d, J = 6.6 Hz, 6H), 1.14 (d, J = 7.0 Hz, 3H). |
| 92 | 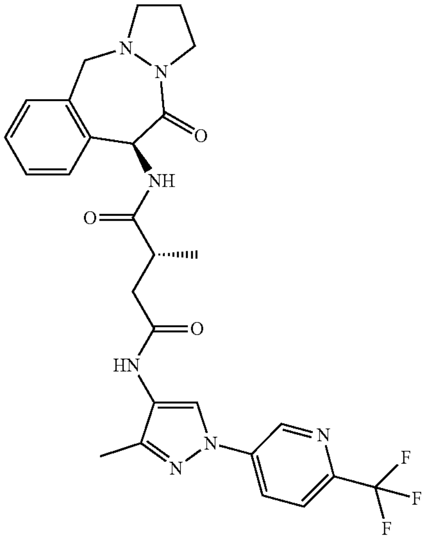 [SMILES: Cc1nn(-c2ccc(C(F)(F)F)nc2)cc1NC(=O)C[C@@H](C)C(=O)N[C@@H]1C(=O)N2CCCN2Cc2ccccc21] | (R)-2-Methyl-$N^4$-(3-methyl-1-(6-(trifluoromethyl)pyridin-3-yl)-1H-pyrazol-4-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC63; 1-methyl-1-H-imidazole MsCl, $CH_2Cl_2$, 23° C., 16 h | m/z 556.2 $[M + H]^+$, $t_R$ = 1.00 min (LCMS method b), $^1H$ NMR (400 MHz, DMSO-$d_6$) δ 9.71 (s, 1H), 9.21 (s, 1H), 8.82 (d, J = 1.7 Hz, 1H), 8.45 - 8.30 (m, 2H), 7.98 (d, J = 8.6 Hz, 1H), 7.35 (d, J = 7.9 Hz, 1H), 7.17 (t, J = 7.4 Hz, 1H), 7.08 (t, J = 7.5 Hz, 1H), 7.02 (d, J = 7.6 Hz, 1H), 6.70 (d, J = 8.9 Hz, 1H), 4.22 (s, 2H), 3.59 - 3.45 (m, 2H), 3.31 - 3.22 (m, 2H), 3.21 - 3.09 (m, 1H), 2.79 (dd, J = 15.2, 8.1 Hz, 1H), 2.48 - 2.41 (m, 1H), 2.39 - 2.30 (m, 1H), 2.26 (s, 3H), 2.18 - 2.01 (m, 1H), 1.15 (d, J = 6.7 Hz, 3H). |

TABLE 2-continued

| Example No. | Compound Structure | Compound Name | Reaction Parameters | Analytics |
|---|---|---|---|---|
| 93 | 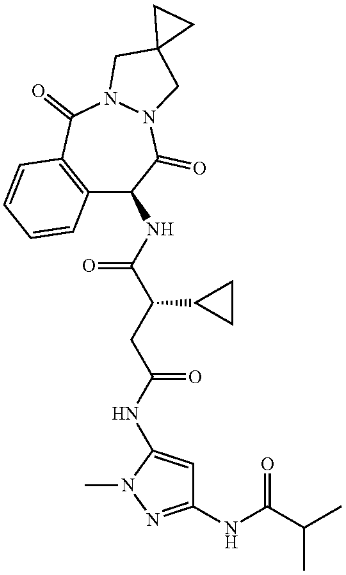 [SMILES: CC(C)C(=O)Nc1cc(NC(=O)C[C@H](C(=O)N[C@@H]2C(=O)N3CC4(CC4)CN3C(=O)c3ccccc32)C2CC2)n(C)n1] | (S)-2-Cyclopropyl-$N^1$-((S)-5,11-dioxo-10,11-dihydro-1H,3H,5H-spiro[benzo[d]pyrazolo[1,2-a][1,2]diazepine-2,1'-cyclopropan]-10-yl)-$N^4$-(3-isobutyramido-1-methyl-1H-pyrazol-5-yl)succinamide | Step 1: int-C1 and Int-L7<br>Step 3: int-EC38; EDC, pyridine | m/z 562.4 $[M + H]^+$, $t_R$ = 0.81 min (LCMS method b), $^1H$ NMR (400 MHz, DMSO-$d_6$) δ 10.13 (s, 1H), 9.88 (s, 1H), 8.67 (d, J = 7.8 Hz, 1H), 7.79 (d, J = 7.6 Hz, 1H), 7.57 - 7.44 (m, 2H), 7.41 (t, J = 7.3 Hz, 1H), 6.46 (s, 1H), 5.96 (d, J = 7.8 Hz, 1H), 4.23 (d, J = 11.1 Hz, 1H), 3.94 (d, J = 10.7 Hz, 1H), 3.65 (d, J = 11.1 Hz, 1H), 3.40 (s, 3H), 3.33 - 3.30 (m, 1H), 2.91 - 2.73 (m, 1H), 2.65 - 2.53 (m, 3H), 1.05 (d, J = 6.9 Hz, 6H), 0.94 - 0.84 (m, 1H), 0.83 - 0.69 (m, 4H), 0.67 - 0.58 (m, 1H), 0.55 - 0.47 (m, 1H), 0.47 - 0.37 (m, 1H), 0.30 - 0.18 (m, 1H). |
| 94 | 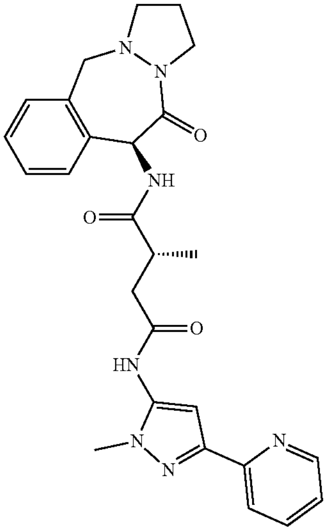 [SMILES: C[C@H](CC(=O)Nc1cc(-c2ccccn2)nn1C)C(=O)N[C@@H]1C(=O)N2CCCN2Cc2ccccc21] | (R)-2-Methyl-$N^4$-(1-methyl-3-(pyridin-2-yl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6<br>Step 3: int-EC64v | m/z 488.3 $[M + H]^+$, $t_R$ = 0.74 min (LCMS method b), $^1H$ NMR (400 MHz, DMSO-$d_6$) δ 10.06 (s, 1H), 8.62 - 8.51 (m, 1H), 8.37 (d, J = 8.8 Hz, 1H), 7.87 (d, J = 8.0 Hz, 1H), 7.79 (t, J = 7.6 Hz, 1H), 7.35 (d, J = 7.9 Hz, 1H), 7.31 - 7.24 (m, 1H), 7.18 (t, J = 7.5 Hz, 1H), 7.10 (t, J = 7.5 Hz, 1H), 7.04 (d, J = 7.6 Hz, 1H), 6.76 (s, 1H), 6.70 (d, J = 8.7 Hz, 1H), 4.23 (s, 2H), 3.66 (s, 3H), 3.58 - 3.48 (m, 2H), 3.29 - 3.23 (m, 2H), 3.20 - 3.10 (m, 1H), 2.79 (dd, J = 15.3, 8.8 Hz, 1H), 2.47 - 2.42 (m, 1H), 2.39 - 2.33 (m, 1H), 2.15 - 2.01 (m, 1H), 1.15 (d, J = 6.9 Hz, 3H). |

TABLE 2-continued

| Example No. | Compound Structure | Compound Name | Reaction Parameters | Analytics |
|---|---|---|---|---|
| 95 | 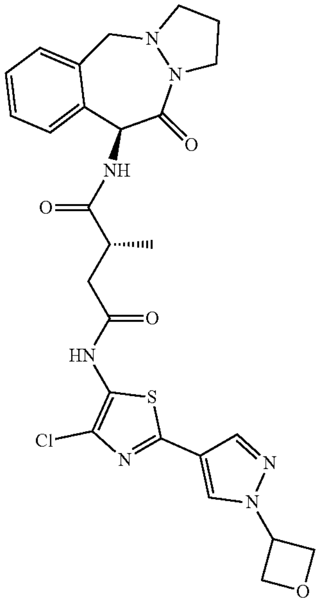 [SMILES: C[C@H](CC(=O)Nc1sc(-c2cnn(C3COC3)c2)nc1Cl)C(=O)N[C@@H]1C(=O)N2CCCN2Cc2ccccc21] | (R)-$N^4$-(4-Chloro-2-(1-(oxetan-3-yl)-1H-pyrazol-4-yl)thiazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC65; EDC, pyridine | m/z 570.2 $[M + H]^+$, $t_R$ = 0.81 min (LCMS method b), $^1H$ NMR (400 MHz, DMSO-$d_6$) δ 10.95 (s, 1H), 8.49 (s, 1H), 8.36 (d, J = 8.8 Hz, 1H), 8.05 (s, 1H), 7.34 (d, J = 7.9 Hz, 1H), 7.19 (t, J = 7.4 Hz, 1H), 7.11 (t, J = 7.5 Hz, 1H), 7.03 (d, J = 7.5 Hz, 1H), 6.68 (d, J = 8.7 Hz, 1H), 5.76 - 5.55 (m, 1H), 5.00 - 4.87 (m, 4H), 4.22 (s, 2H), 3.61 - 3.45 (m, 2H), 3.29 - 3.21 (m, 2H), 3.20 - 3.10 (m, 1H), 2.94 (dd, J = 15.6, 8.9 Hz, 1H), 2.57 (dd, J = 15.7, 6.1 Hz, 1H), 2.41 - 2.26 (m, 1H), 2.15 - 2.00 (m, 1H), 1.13 (d, J = 7.0 Hz, 3H). |
| 96 | 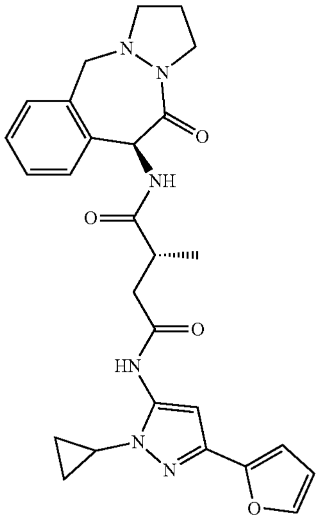 [SMILES: C[C@H](CC(=O)Nc1cc(-c2ccco2)nn1C1CC1)C(=O)N[C@@H]1C(=O)N2CCCN2Cc2ccccc21] | (R)-$N^4$-(1-Cyclopropyl-3-(furan-2-yl)-1H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC66; EDC, pyridine | m/z 503.3 $[M + H]^+$, $t_R$ = 0.91 min (LCMS method b), $^1H$ NMR (400 MHz, DMSO-$d_6$) δ 10.05 (s, 1H), 8.39 (d, J = 9.0 Hz, 1H), 7.66 (d, J = 1.8 Hz, 1H), 7.34 (d, J = 7.9 Hz, 1H), 7.19 (t, J = 7.4 Hz, 1H), 7.11 - 7.00 (m, 2H), 6.71 (d, J = 8.8 Hz, 1H), 6.64 (d, J = 3.3 Hz, 1H), 6.53 (dd, J = 3.4, 1.8 Hz, 1H), 6.49 (s, 1H), 4.23 (s, 2H), 3.58 - 3.49 (m, 2H), 3.48 - 3.39 (m, 1H), 3.30 - 3.24 (m, 2H), 3.21 - 3.12 (m, 1H), 2.83 (dd, J = 15.4, 8.6 Hz, 1H), 2.42 - 2.29 (m, 2H), 2.16 - 2.03 (m, 1H), 1.16 (d, J = 6.9 Hz, 3H), 0.99 - 0.80 (m, 4H). |

TABLE 2-continued

| Example No. | Compound Structure | Compound Name | Reaction Parameters | Analytics |
|---|---|---|---|---|
| 97 | 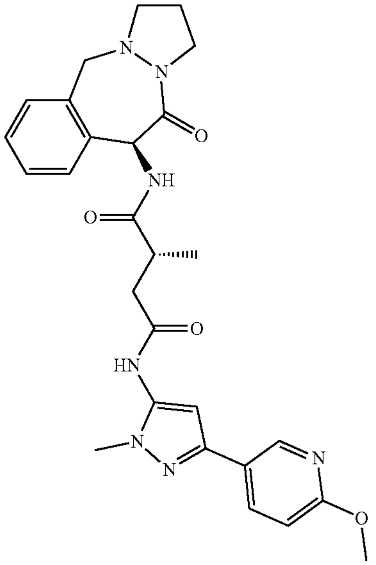 [SMILES: COc1ccc(-c2cc(NC(=O)C[C@@H](C)C(=O)N[C@@H]3C(=O)N4CCCN4Cc4ccccc43)n(C)n2)cn1] | (R)-$N^4$-(3-(6-Methoxypyridin-3-yl)-1-methyl-1H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC67; EDC, pyridine | m/z 518.3 $[M + H]^+$, $t_R$ = 0.84 min (LCMS method b), $^1H$ NMR (400 MHz, DMSO-$d_6$) δ 10.05 (s, 1H), 8.53 (s, 1H), 8.43 (d, J = 9.0 Hz, 1H), 8.03 (dd, J = 8.7, 2.2 Hz, 1H), 7.37 (d, J = 7.9 Hz, 1H), 7.21 (t, J = 7.5 Hz, 1H), 7.11 (t, J = 7.6 Hz, 1H), 7.05 (d, J = 7.7 Hz, 1H), 6.86 (d, J = 8.5 Hz, 1H), 6.72 (d, J = 8.8 Hz, 1H), 6.63 (d, J = 1.7 Hz, 1H), 4.25 (s, 2H), 3.88 (s, 3H), 3.63 (s, 3H), 3.58 - 3.49 (m, 2H), 3.33 - 3.23 (m, 2H), 3.24 - 3.13 (m, 1H), 2.80 (dd, J = 15.4, 8.7 Hz, 1H), 2.49 - 2.43 (m, 1H), 2.40 - 2.29 (m, 1H), 2.18 - 2.04 (m, 1H), 1.17 (d, J = 6.9 Hz, 3H). |
| 98 | 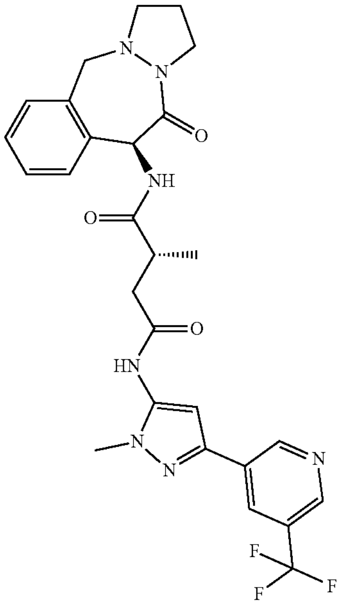 [SMILES: C[C@H](CC(=O)Nc1cc(-c2cncc(C(F)(F)F)c2)nn1C)C(=O)N[C@@H]1C(=O)N2CCCN2Cc2ccccc21] | (R)-2-Methyl-$N^4$-(1-methyl-3-(5-(trifluoromethyl)pyridin-3-yl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC68; EDC, pyridine | m/z 556.2 $[M + H]^+$, $t_R$ = 0.96 min (LCMS method b), $^1H$ NMR (400 MHz, DMSO-$d_6$) δ 10.12 (s, 1H), 9.26 (s, 1H), 8.88 (s, 1H), 8.49 - 8.36 (m, 2H), 7.36 (d, J = 7.9 Hz, 1H), 7.18 (t, J = 7.4 Hz, 1H), 7.09 (t, J = 7.5 Hz, 1H), 7.04 (d, J = 7.6 Hz, 1H), 6.92 (s, 1H), 6.71 (d, J = 8.9 Hz, 1H), 4.23 (s, 2H), 3.67 (s, 3H), 3.59 - 3.47 (m, 2H), 3.30 - 3.23 (m, 2H), 3.21 - 3.10 (m, 1H), 2.80 (dd, J = 15.3, 8.7 Hz, 1H), 2.48 - 2.43 (m, 1H), 2.40 - 2.28 (m, 1H), 2.18 - 2.03 (m, 1H), 1.16 (d, J = 7.0 Hz, 3H). |

TABLE 2-continued

| Example No. | Compound Structure | Compound Name | Reaction Parameters | Analytics |
| --- | --- | --- | --- | --- |
| 99 | 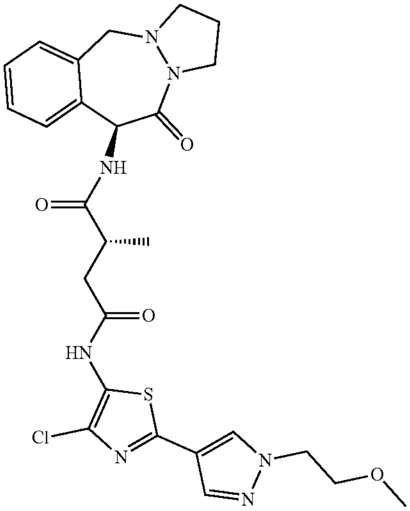 [SMILES: COCCn1cc(-c2nc(Cl)c(NC(=O)C[C@@H](C)C(=O)N[C@@H]3C(=O)N4CCCN4Cc4ccccc43)s2)cn1] | (R)-$N^4$-(4-Chloro-2-(1-(2-methoxyethyl)-1H-pyrazol-4-yl)thiazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6<br>Step 3: int-EC69; EDC, pyridine | m/z 572.2 $[M + H]^+$, $t_R$ = 0.85 min (LCMS method b), $^1H$ NMR (400 MHz, DMSO-$d_6$) δ 10.92 (s, 1H), 8.36 (d, J = 8.8 Hz, 1H), 8.30 - 8.26 (m, 1H), 7.90 (d, J = 0.7 Hz, 1H), 7.34 (d, J = 7.8 Hz, 1H), 7.19 (t, J = 7.3 Hz, 1H), 7.11 (t, J = 7.5 Hz, 1H), 7.03 (d, J = 7.5 Hz, 1H), 6.68 (d, J = 8.7 Hz, 1H), 4.30 (t, J = 5.3 Hz, 2H), 4.22 (s, 2H), 3.72 (t, J = 5.3 Hz, 2H), 3.59 - 3.48 (m, 2H), 3.30 - 3.25 (m, 2H), 3.24 (s, 3H), 3.20 - 3.11 (m, 1H), 2.93 (dd, J = 15.6, 8.9 Hz, 1H), 2.57 (dd, J = 15.4, 5.7 Hz, 1H), 2.41 - 2.26 (m, 1H), 2.16 - 2.02 (m, 1H), 1.13 (d, J = 6.9 Hz, 3H). |
| 100 | 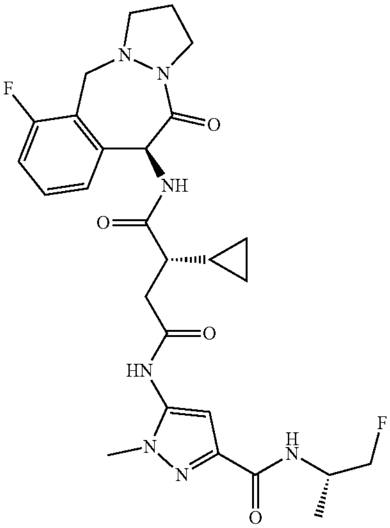 [SMILES: C[C@@H](CF)NC(=O)c1cc(NC(=O)C[C@H](C(=O)N[C@@H]2C(=O)N3CCCN3Cc3c(F)cccc32)C2CC2)n(C)n1] | (S)-2-Cyclopropyl-$N^1$-((S)-6-fluoro-11-oxo-2,3,10,11-tetrahydro-1H,5H-benzo[d]pyrazolo[1,2-a][1,2]diazepin-10-yl)-$N^4$-(3-(((S)-1-fluoropropan-2-yl)carbamoyl)-1-methyl-1H-pyrazol-5-yl)succinamide | Step 1: int-A2 and Int-L7<br>Step 3: int-EC51; EDC, pyridine | m/z 558.4 $[M + H]^+$, $t_R$ = 0.83 min (LCMS method b), $^1H$ NMR (400 MHz, DMSO-$d_6$) δ 10.10 (s, 1H), 8.31 (d, J = 8.7 Hz, 1H), 7.92 (d, J = 8.5 Hz, 1H), 7.23 (d, J = 7.4 Hz, 1H), 7.14 - 7.03 (m, 2H), 6.71 (d, J = 8.4 Hz, 1H), 6.56 (s, 1H), 4.51 - 4.21 (m, 3H), 4.17 (s, 2H), 3.63 (s, 3H), 3.59 - 3.51 (m, 2H), 3.29 - 3.22 (m, 1H), 2.87 (dd, J = 15.2, 9.7 Hz, 1H), 2.68 - 2.52 (m, 3H), 2.44 - 2.29 (m, 1H), 2.16 - 2.05 (m, 1H), 1.13 (d, J = 6.7 Hz, 3H), 0.94 - 0.77 (m, 1H), 0.64 - 0.55 (m, 1H), 0.53 - 0.45 (m, 1H), 0.44 - 0.35 (m, 1H), 0.26 - 0.17 (m, 1H). |
| 101 | 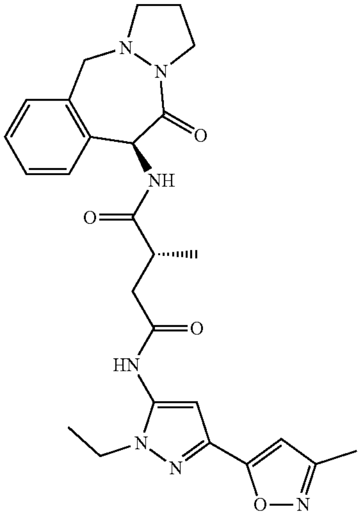 [SMILES: CCn1nc(-c2cc(C)no2)cc1NC(=O)C[C@@H](C)C(=O)N[C@@H]1C(=O)N2CCCN2Cc2ccccc21] | (R)-$N^4$-(1-Ethyl-3-(3-methylisoxazol-5-yl)-1H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6<br>Step 3: int-EC70; EDC, pyridine | m/z 506.3 $[M + H]^+$, $t_R$ = 0.85 min (LCMS method b), $^1H$ NMR (400 MHz, DMSO-$d_6$) δ 10.11 (s, 1H), 8.40 (d, J = 8.9 Hz, 1H), 7.34 (d, J = 7.9 Hz, 1H), 7.19 (t, J = 7.4 Hz, 1H), 7.12 - 6.97 (m, 2H), 6.70 (d, J = 8.8 Hz, 1H), 6.65 (s, 1H), 6.60 (s, 1H), 4.23 (s, 2H), 4.04 (q, J = 7.4 Hz, 2H), 3.61 - 3.44 (m, 2H), 3.30 - 3.22 (m, 2H), 3.21 - 3.13 (m, 1H), 2.79 (dd, J = 15.4, 8.7 Hz, 1H), 2.48 - 2.43 (m, 1H), 2.40 - 2.29 (m, 1H), 2.26 (s, 3H), 2.15 - 2.03 (m, 1H), 1.23 (t, J = 7.2 Hz, 3H), 1.15 (d, J = 7.0 Hz, 3H). |

TABLE 2-continued

| Example No. | Compound Structure | Compound Name | Reaction Parameters | Analytics |
|---|---|---|---|---|
| 102 | 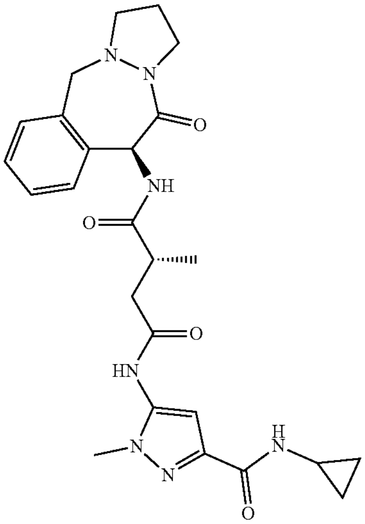 [SMILES: C[C@H](CC(=O)Nc1cc(C(=O)NC2CC2)nn1C)C(=O)N[C@@H]1C(=O)N2CCCN2Cc2ccccc21] | (R)-N[4]-(3-(Cyclopropylcarbamoyl)-1-methyl-1H-pyrazol-5-yl)-2-methyl-N[1]-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC71; EDC, pyridine | m/z 494.4 $[M + H]^+$, $t_R$ = 0.74 min (LCMS method b), $^1H$ NMR (400 MHz, DMSO-$d_6$) δ 10.05 (s, 1H), 8.34 (d, J = 8.9 Hz, 1H), 8.01 (d, J = 4.6 Hz, 1H), 7.33 (d, J = 7.9 Hz, 1H), 7.19 (t, J = 7.4 Hz, 1H), 7.10 - 6.99 (m, 2H), 6.68 (d, J = 8.8 Hz, 1H), 6.55 (s, 1H), 4.23 (s, 2H), 3.62 (s, 3H), 3.57 - 3.48 (m, 2H), 3.28 - 3.20 (m, 2H), 3.20 - 3.11 (m, 1H), 2.83 - 2.72 (m, 2H), 2.46 - 2.29 (m, 2H), 2.19 - 2.01 (m, 1H), 1.14 (d, J = 6.9 Hz, 3H), 0.68 - 0.51 (m, 4H). |
| 103 | 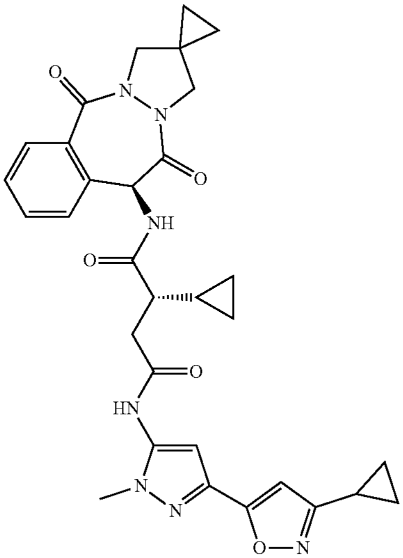 [SMILES: Cn1nc(-c2cc(C3CC3)no2)cc1NC(=O)C[C@H](C(=O)N[C@@H]1C(=O)N2CC3(CC3)CN2C(=O)c2ccccc21)C1CC1] | (S)-2-Cyclopropyl-N[4]-(3-(3-cyclopropylisoxazol-5-yl)-1-methyl-1H-pyrazol-5-yl)-N[1]-((S)-5,11-dioxo-10,11-dihydro-1H,3H,5H-spiro[benzo[d]pyrazolo[1,2-a][1,2]diazepine-2,1''-cyclopropan]-10-yl)succinamide | Step 1: int-C1 and Int-L7 Step 3: int-EC46; EDC, pyridine | m/z 584.3 $[M + H]^+$, $t_R$ = 0.98 min (LCMS method b), $^1H$ NMR (400 MHz, DMSO-$d_6$) δ 10.15 (s, 1H), 8.74 (d, J = 7.9 Hz, 1H), 7.87 - 7.75 (m, 1H), 7.52 - 7.47 (m, 1H), 7.45 - 7.40 (m, 2H), 6.60 (s, 1H), 6.49 (s, 1H), 5.97 (d, J = 7.9 Hz, 1H), 4.22 (d, J = 11.1 Hz, 1H), 3.94 (d, J = 10.7 Hz, 1H), 3.65 (d, J = 11.1 Hz, 1H), 3.59 (s, 3H), 3.30 - 3.24 (m, 1H), 2.92 - 2.80 (m, 1H), 2.70 - 2.63 (m, 2H), 2.08 - 1.95 (m, 1H), 1.08 - 0.96 (m, 2H), 0.94 - 0.85 (m, 1H), 0.84 - 0.78 (m, 5H), 0.74 - 0.69 (m, 1H), 0.68 - 0.59 (m, 1H), 0.57 - 0.49 (m, 1H), 0.47 - 0.38 (m, 1H), 0.29 - 0.18 (m, 1H). |

TABLE 2-continued

| Example No. | Compound Structure | Compound Name | Reaction Parameters | Analytics |
|---|---|---|---|---|
| 104 | 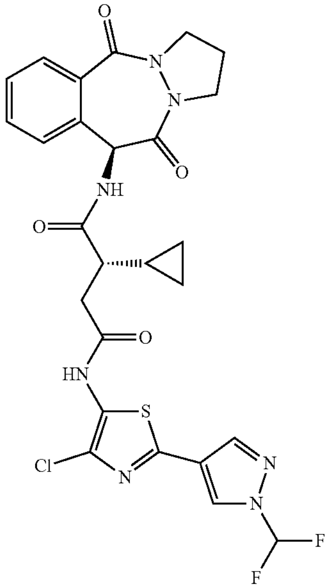 [SMILES: O=C(C[C@H](C(=O)N[C@@H]1C(=O)N2CCCN2C(=O)c2ccccc21)C1CC1)Nc1sc(-c2cnn(C(F)F)c2)nc1Cl] | (S)-$N^4$-(4-Chloro-2-(1-(difluoromethyl)-1H-pyrazol-4-yl)thiazol-5-yl)-2-cyclopropyl-$N^1$-((S)-5,11-dioxo-2,3,10,11-tetrahydro-1H,5H-benzo[d]pyrazolo[1,2-a][1,2]diazepin-10-yl)succinamide | Step 1: int-B1 and Int-L7 Step 3: int-EC72; EDC, pyridine | m/z 604.2 $[M + H]^+$, $t_R$ = 0.94 min (LCMS method b), $^1H$ NMR (400 MHz, DMSO-$d_6$) δ 11.04 (s, 1H), 8.88 (s, 1H), 8.68 (d, J = 7.8 Hz, 1H), 8.28 (s, 1H), 7.86 (t, J = 58.9 Hz, 1H), 7.74 (d, J = 7.7 Hz, 1H), 7.56 - 7.46 (m, 2H), 7.41 (t, J = 7.3 Hz, 1H), 5.88 (d, J = 7.7 Hz, 1H), 4.33 - 4.20 (m, 1H), 4.14 - 3.99 (m, 1H), 3.72 - 3.55 (m, 1H), 3.27 - 3.19 (m, 1H), 3.02 (dd, J = 15.7, 9.8 Hz, 1H), 2.75 (dd, J = 15.6, 5.1 Hz, 1H), 2.69 - 2.58 (m, 1H), 2.23 - 2.06 (m, 2H), 0.96 - 0.80 (m, 1H), 0.68 - 0.58 (m, 1H), 0.55 - 0.37 (m, 2H), 0.29 - 0.16 (m, 1H). |
| 105 | 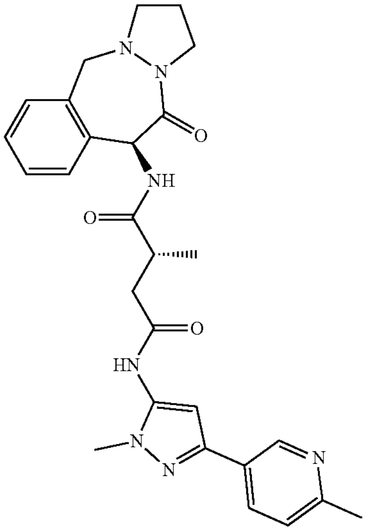 [SMILES: Cc1ccc(-c2cc(NC(=O)C[C@@H](C)C(=O)N[C@@H]3C(=O)N4CCCN4Cc4ccccc43)n(C)n2)cn1] | (R)-2-Methyl-$N^4$-(1-methyl-3-(6-methylpyridin-3-yl)-1H-pyrazol-5-yl)-$N^1$-((S)-11-oxo-2,3,10,11-tetrahydro-1H,5H-benzo[d]pyrazolo[1,2-a][1,2]diazepin-10-yl)succinamide | Step 1: int-A1 and Int-L6 Step 3: int-EC73; 1-methyl-1-H-imidazole MsCl, $CH_2Cl_2$, 20° C., 2 h | m/z 502.3 $[M + H]^+$, $t_R$ = 0.66 min (LCMS method b), $^1H$ NMR (400 MHz, DMSO-$d_6$) δ 10.06 (s, 1H), 8.80 (s, 1H), 8.42 (d, J = 8.9 Hz, 1H), 8.02 - 7.89 (m, 1H), 7.36 (d, J = 7.9 Hz, 1H), 7.27 (d, J = 8.0 Hz, 1H), 7.19 (t, J = 7.5 Hz, 1H), 7.09 (t, J = 7.7 Hz, 1H), 7.04 (d, J = 7.7 Hz, 1H), 6.70 (d, J = 9.0 Hz, 1H), 6.68 (s, 1H), 4.23 (s, 2H), 3.63 (S, 3H), 3.56 - 3.47 (m, 2H), 3.30 - 3.23 (m, 2H), 3.22 - 3.14 (m, 1H), 2.78 (dd, J = 15.4, 8.7 Hz, 1H), 2.47 (s, 3H), 2.46 - 2.42 (m, 1H), 2.39 - 2.27 (m, 1H), 2.19 - 1.99 (m, 1H), 1.15 (d, J = 6.9 Hz, 3H). |

TABLE 2-continued

| Example No. | Compound Structure | Compound Name | Reaction Parameters | Analytics |
|---|---|---|---|---|
| 106 | 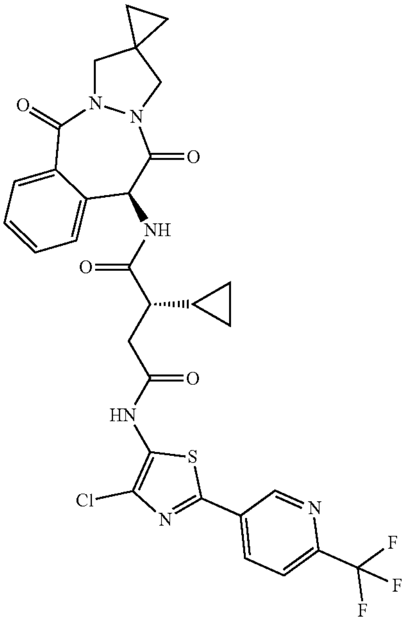 [SMILES: O=C(C[C@H](C(=O)N[C@@H]1C(=O)N2CC3(CC3)CN2C(=O)c2ccccc21)C1CC1)Nc1sc(-c2ccc(C(F)(F)F)nc2)nc1Cl] | (S)-$N^4$-(4-Chloro-2-(6-(trifluoromethyl)pyridin-3-yl)thiazol-5-yl)-2-cyclopropyl-$N^1$-((S)-5,11-dioxo-10,11-dihydro-1H,3H,5H-spiro[benzo[d]pyrazolo[1,2-a][1,2]diazepine-2,1'-cyclopropan]-10-yl)succinamide | Step 1: int-B1 and Int-L7<br>Step 3: int-EC72; EDC, pyridine | m/z 659.3 $[M + H]^+$, $t_R$ = 1.18 min (LCMS method b), $^1H$ NMR (400 MHz, DMSO-$d_6$) δ 11.31 (s, 1H), 9.25 (d, J = 2.2 Hz, 1H), 8.78 (d, J = 7.9 Hz, 1H), 8.56 - 8.47 (m, 1H), 8.02 (d, J = 8.3 Hz, 1H), 7.78 (dd, J = 7.7, 1.3 Hz, 1H), 7.61 - 7.51 (m, 2H), 7.42 (td, J = 7.0, 6.4, 1.4 Hz, 1H), 5.96 (d, J = 7.8 Hz, 1H), 4.22 (d, J = 11.1 Hz, 1H), 3.94 (d, J = 10.7 Hz, 1H), 3.65 (d, J = 11.1 Hz, 1H), 3.29 - 3.24 (m, 1H), 3.07 (dd, J = 15.8, 9.9 Hz, 1H), 2.80 (dd, J = 15.8, 5.0 Hz, 1H), 2.72 - 2.62 (m, 1H), 0.97 - 0.84 (m, 1H), 0.83 - 0.76 (m, 3H), 0.75 - 0.69 (m, 1H), 0.68 - 0.59 (m, 1H), 0.56 - 0.38 (m, 2H), 0.29 - 0.19 (m, 1H). |
| 107 | 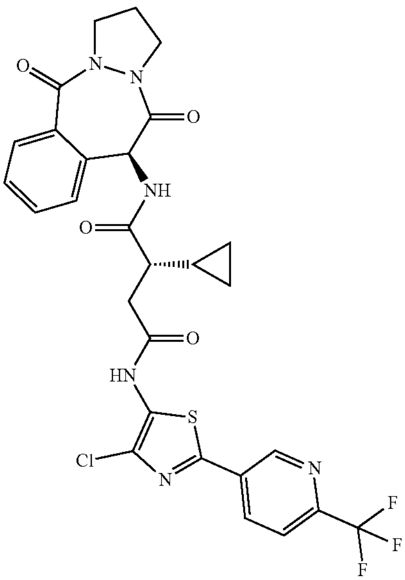 [SMILES: O=C(C[C@H](C(=O)N[C@@H]1C(=O)N2CCCN2C(=O)c2ccccc21)C1CC1)Nc1sc(-c2ccc(C(F)(F)F)nc2)nc1Cl] | (S)-$N^4$-(4-Chloro-2-(6-(trifluoromethyl)pyridin-3-yl)thiazol-5-yl)-2-cyclopropyl-$N^1$-((S)-5,11-dioxo-2,3,10,11-tetrahydro-1H,5H-benzo[d]pyrazolo[1,2-a][1,2]diazepin-10-yl)succinamide | Step 1: Int-B1, Int-L7<br>Step 3: int-EC75<br>Isolated as a crystal: slurry in water at 50° C. then 10° C., isolated by filtration of the white suspension | m/z 633.2 $[M + H]^+$, $t_R$ = 1.12 min (LCMS method b), $^1H$ NMR (400 MHz, DMSO-$d_6$) δ 11.31 (s, 1H), 9.24 (d, J = 2.2 Hz, 1H), 8.73 (d, J = 7.8 Hz, 1H), 8.51 (dd, J = 8.3, 2.2 Hz, 1H), 8.01 (d, J = 8.3 Hz, 1H), 7.74 (dd, J = 7.6, 1.4 Hz, 1H), 7.61 - 7.47 (m, 2H), 7.41 (td, J = 7.3, 1.6 Hz, 1H), 5.89 (d, J = 7.7 Hz, 1H), 4.34 - 4.21 (m, 1H), 4.15 - 4.02 (m, 1H), 3.69 - 3.57 (m, 1H), 3.28 - 3.17 (m, 1H), 3.07 (dd, J = 15.8, 9.9 Hz, 1H), 2.80 (dd, J = 15.8, 5.0 Hz, 1H), 2.72 - 2.61 (m, 1H), 2.24 - 2.04 (m, 2H), 0.95 - 0.82 (m, 1H), 0.69-0.59 (m, 1H), 0.56 - 0.48 (m, 1H), 0.47 - 0.37 (m, 1H), 0.30 - 0.20 (m, 1H). |

TABLE 2-continued

| Example No. | Compound Structure | Compound Name | Reaction Parameters | Analytics |
|---|---|---|---|---|
| 108 | 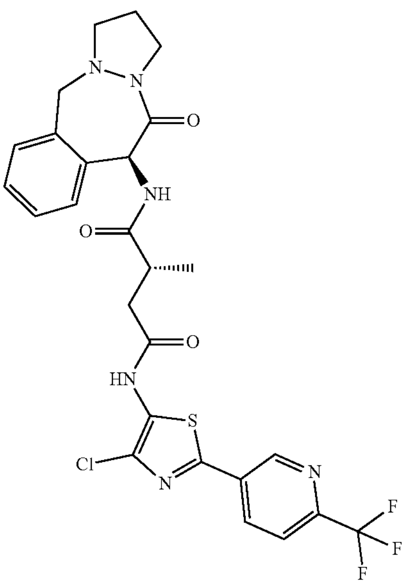 [SMILES: C[C@H](CC(=O)Nc1sc(-c2ccc(C(F)(F)F)nc2)nc1Cl)C(=O)N[C@@H]1C(=O)N2CCCN2Cc2ccccc21] | (R)-$N^4$-(4-Chloro-2-(6-(trifluoromethyl)pyridin-3-yl)thiazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 1: Int-A1, Int-L6 Step 3: int-EC75 Isolated as a crystal (recrystalize from EtOH:$H_20$ (1:1)) | m/z 593.3 $[M + H]^+$, $t_R$ = 1.12 min (LCMS method b), $^1H$ NMR (400 MHz, DMSO-$d_6$) δ 11.33 (s, 1H), 9.24 (s, 1H), 8.51 (d, J = 8.3 Hz, 1H), 8.43 (d, J = 8.9 Hz, 1H), 8.01 (d, J = 8.4 Hz, 1H), 7.37 (d, J = 7.6 Hz, 1H), 7.25 - 7.09 (m, 2H), 7.03 (d, J = 7.3 Hz, 1H), 6.69 (d, J = 8.8 Hz, 1H), 4.23 (s, 2H), 3.65 - 3.47 (m, 2H), 3.32 - 3.22 (m, 2H), 3.22 - 3.11 (m, 1H), 3.01 (dd, J = 15.8, 9.0 Hz, 1H), 2.64 (dd, J = 15.8, 5.8 Hz, 1H), 2.43 - 2.29 (m, 1H), 2.18 - 1.99 (m, 1H), 1.16 (d, J = 7.0 Hz, 3H). |

Example 109: (R)—$N^4$-(3-((2-fluorophenyl)carbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide (109)

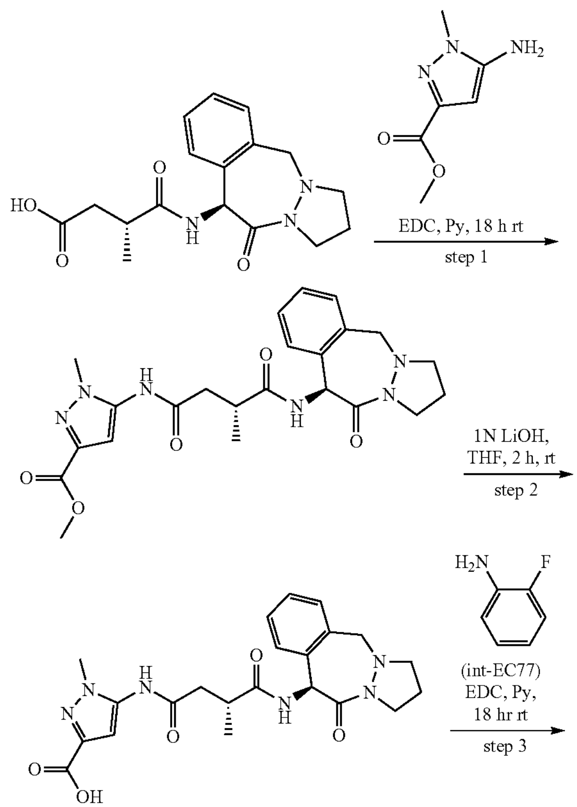

-continued

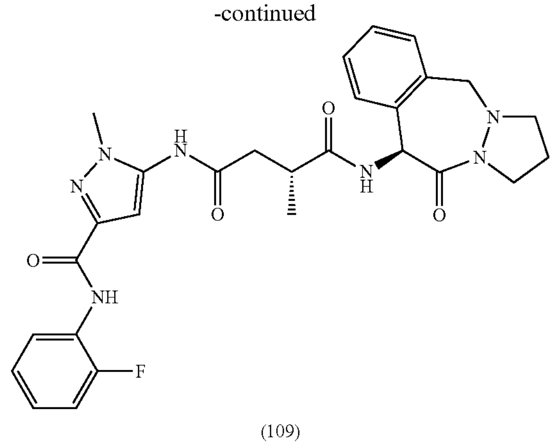

(109)

Step 1: EDC (1.15 g, (6.04 mmol) was added to a solution of (R)-3-methyl-4-oxo-4-(((S)-11-oxo-2,3,10,11-tetrahydro-1H,5H-benzo[d]pyrazolo[1,2-a][1,2]diazepin-10-yl)amino) butanoic acid (see step 2 of Example 62), (1.0 g, 3.02 mmol), methyl 5-amino-1-methyl-1H-pyrazole-3-carboxylate hydrochloride (714 mg, 3.17 mmol) and pyridine (1.2 mL, 15.09 mmol) in acetonitrile (30 mL) and the mixture was stirred at rt for 18 h. The reaction was treated with sat. $NaHCO_3$ and extracted with ethyl acetate. The combined organic layers were washed with water and brine, dried ($Na_2SO_4$) and concentrated to give methyl 1-methyl-5-((R)-3-methyl-4-oxo-4-(((S)-11-oxo-2,3,10,11-tetrahydro-1H, 5H-benzo[d]pyrazolo[1,2-a][1,2]diazepin-10-yl)amino)butanamido)-1H-pyrazole-3-carboxylate. LCMS (method b) m/z 469.2 $[M+H]^+$, $t_R$=0.71 min. $^1H$ NMR (400 MHz, DMSO-$d_6$) δ ppm 10.14 (s, 1H), 8.35 (d, J=8.9 Hz, 1H), 7.33 (d, J=7.8 Hz, 1H), 7.20 (t, J=7.4 Hz, 1H), 7.11-7.01 (m, 2H), 6.74-6.60 (m, 2H), 4.23 (s, 2H), 3.78 (s, 3H), 3.67 (s, 3H), 3.56-3.49 (m, 2H), 3.29-3.22 (m, 2H), 3.20-3.11 (m, 1H), 2.77 (dd, J=15.3, 8.9 Hz, 1H), 2.47-2.41 (m, 1H), 2.39-2.31 (m, 1H), 2.14-2.08 (m, 1H), 1.14 (d, J=6.9 Hz, 3H).

Step 2: 1 M LiOH in $H_2O$ (15 mL, 15 mmol) was added to a mixture of methyl 1-methyl-5-((R)-3-methyl-4-oxo-4-(((S)-11-oxo-2,3,10,11-tetrahydro-1H,5H-benzo[d]pyrazolo[1,2-a][1,2]diazepin-10-yl)amino)butanamido)-1H-pyrazole-3-carboxylate in THF (20 mL) and the mixture stirred at 0° C. for 2 h. The mixture was acidified with 2N HCl to pH 3 under ice cooling and the mixture was extracted with ethyl acetate. The organic layers were dried ($Na_2SO_4$) and concentrated. The crude product was purified by column chromatography (reverse phase column eluted with 10% to 40% $H_2O$ in $CH_3CN$) to give 1-methyl-5-((R)-3-methyl-4-oxo-4-(((S)-11-oxo-2,3,10,11-tetrahydro-1H,5H-benzo[d]pyrazolo[1,2-a][1,2]diazepin-10-yl)amino)butanamido)-1H-pyrazole-3-carboxylic acid. LCMS (method b) m/z 455.2 $[M+H]^+$, $t_R$=0.59 min. $^1H$ NMR (400 MHz, DMSO-$d_6$) δ ppm 12.55 (s, 1H), 10.09 (s, 1H), 8.34 (d, J=8.8 Hz, 1H), 7.33 (d, J=7.8 Hz, 1H), 7.19 (t, J=7.4 Hz, 1H), 7.10-6.98 (m, 2H), 6.68 (d, J=8.7 Hz, 1H), 6.61 (s, 1H), 4.23 (s, 2H), 3.66 (s, 3H), 3.59-3.47 (m, 2H), 3.28-3.23 (m, 2H), 3.21-3.18 (m, 1H), 2.77 (dd, J=15.4, 8.8 Hz, 1H), 2.48-2.42 (m, 1H), 2.39-2.26 (m, 1H), 2.16-2.00 (m, 1H), 1.14 (d, J=6.9 Hz, 3H).

Step 3: EDC (70 mg, 0.363 mmol) was added to a solution of 1-methyl-5-((R)-3-methyl-4-oxo-4-(((S)-11-oxo-2,3,10,11-tetrahydro-1H,5H-benzo[d]pyrazolo[1,2-a][1,2]diazepin-10-yl)amino)butanamido)-1H-pyrazole-3-carboxylic acid (55 mg, 0.121 mmol) and 2-fluoroaniline (int-EC77) (14 μl, 0.133 mmol) in pyridine (1.2 mL) and the mixture stirred at rt for 18 h. The reaction was treated with sat. $NaHCO_3$ and extracted with ethyl acetate. The combined organic layers were washed with water and brine, dried ($Na_2SO_4$) and concentrated. The crude product was dissolved in methanol, the precipitate was filtered off cold and dried on high vacuum to give (R)—$N^4$-(3-((2-fluorophenyl)carbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide (109). LCMS (method b) m/z 548.3 $[M+H]^+$, $t_R$=0.92 min; $^1H$ NMR (400 MHz, DMSO-$d_6$) δ ppm 10.17 (s, 1H), 9.47 (s, 1H), 8.36 (d, J=8.9 Hz, 1H), 7.98-7.78 (m, 1H), 7.35 (d, J=7.9 Hz, 1H), 7.33-7.24 (m, 1H), 7.24-7.15 (m, 3H), 7.12-7.01 (m, 2H), 6.72 (s, 1H), 6.69 (d, J=8.8 Hz, 1H), 4.23 (s, 2H), 3.72 (s, 3H), 3.61-3.45 (m, 2H), 3.29-3.22 (m, 2H), 3.22-3.18 (m, 1H), 2.80 (dd, J=15.4, 8.8 Hz, 1H), 2.48-2.43 (m, 1H), 2.42-2.27 (m, 1H), 2.18-2.03 (m, 1H), 1.16 (d, J=7.0 Hz, 3H).

Table 3 shows additional example compounds (Example 107) which was prepared using a method analogous to that described in Example 109. The appropriate intermediates used in each step are listed, along with the coupling conditions for step 3.

TABLE 3

| Example No. | Compound Structure | Compound Name | Reaction Parameters | Analytics |
|---|---|---|---|---|
| 110 | 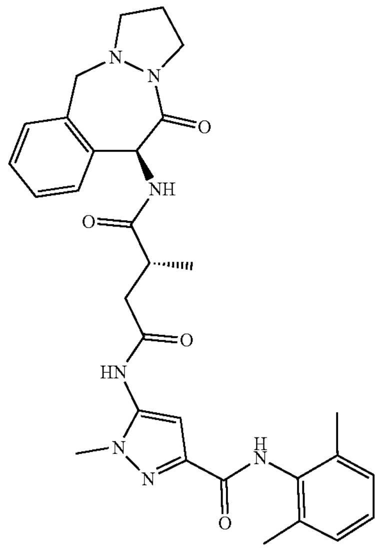 [SMILES: Cc1cccc(C)c1NC(=O)c1cc(NC(=O)C[C@@H](C)C(=O)N[C@@H]2C(=O)N3CCCN3Cc3ccccc32)n(C)n1] | (R)-$N^4$-(3-((2,6-dimethylphenyl)carbamoyl)-1-methyl-1H-pyrazol-5-yl)-2-methyl-$N^1$-((S)-11-oxo-2,3,10,11-tetrahydro-1H,5H-benzo[d]pyrazolo[1,2-a][1,2]diazepin-10-yl)succinamide | Step 3: int-EC78 | m/z 558.2 $[M + H]^+$, $t_R$ = 0.89 min (LCMS method b), $^1H$ NMR (400 MHz, DMSO-$d_6$) δ 10.12 (s, 1H), 9.44 (s, 1H), 8.36 (d, J = 8.9 Hz, 1H), 7.34 (d, J = 7.9 Hz, 1H), 7.18 (t, J = 7.4 Hz, 1H), 7.07 (d, J = 12.9 Hz, 5H), 6.70 (d, J = 8.9 Hz, 1H), 6.67 (s, 1H), 4.23 (s, 2H), 3.70 (s, 3H), 3.61 − 3.46 (m, 2H), 3.29 − 3.23 (m, 2H), 3.21 − 3.18 (m, 1H), 2.79 (dd, J = 15.3, 8.8 Hz, 1H), 2.48 − 2.44 (m, 1H), 2.39 − 2.26 (m, 1H), 2.15 (s, 6H), 2.13 − 2.04 (m, 1H), 1.16 (d, J = 7.0 Hz, 3H). |

Example 111: (R)-3-(1H-benzo[d]imidazol-2-yl)-2-methyl-N—((S)-11-oxo-2,3,10,11-tetrahydro-1H,5H-benzo[d]pyrazolo[1,2-a][1,2]diazepin-10-yl)propanamide (111)

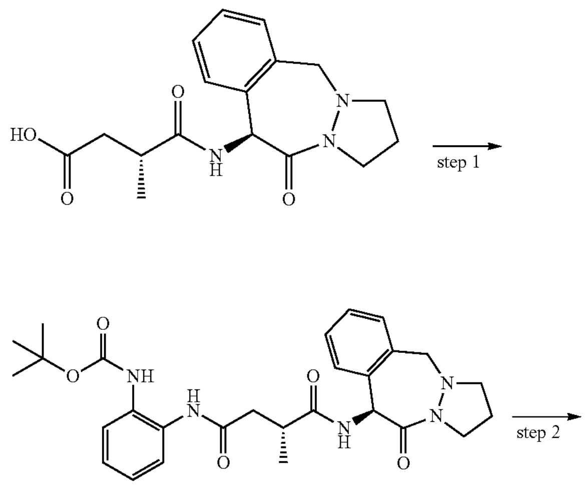

-continued

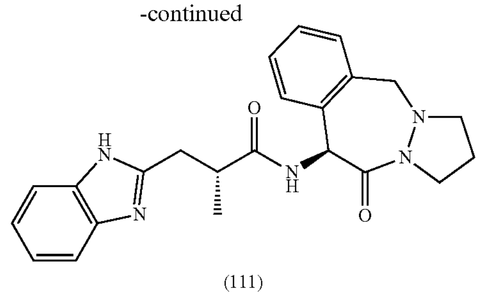

(111)

Step 1: To a solution of (R)-3-methyl-4-oxo-4-(((S)-11-oxo-2,3,10,11-tetrahydro-1H,5H-benzo[d]pyrazolo[1,2-a][1,2]diazepin-10-yl)amino)butanoic acid (see step 2 of Example 62) (20 mg, 0.060 mmol) in DMF (1 mL) were added DIPEA (0.032 mL, 0.18 mmol) and HATU (23 mg, 0.060 mmol). The reaction mixture was stirred for 30 min, until tert-butyl 2-aminophenylcarbamate (12.6 mg, 0.060 mmol) was added. The reaction mixture was purified by preparative HPLC-MS (Waters, column X-Bridge $C_{18}$ ODB 5 μm 30*100 mm, flow 45 mL/min, water/ACN: 5→99% ACN in 12.5 min, 7.3 mM $NH_3$) to give tert-butyl 2-((R)-3-methyl-4-oxo-4-((S)-11-oxo-1,2,3,5,10,11-hexahydrobenzo[d]pyrazolo[1,2-a][1,2]diazepin-10-ylamino)butanamido)phenylcarbamate. HPLC (method a) m/z 522 $[M+H]^+$, $t_R$=2.14 min. $^1$H NMR (400 MHz, MeOD) δ ppm: 7.61 (d, 1H), 7.39 (m, 2H), 7.23-7.01 (m, 5H), 6.83 (s, 1H), 4.30 (dd, 2H), 3.68 (m, 3H), 3.40 (m, 1H), 3.27 (m, 1H), 2.88 (dd, 1H), 2.61 (dd, 1H), 2.47 (m, 1H), 2.22 (m, 1H), 1.49 (s, 9H), 1.34 (d, 3H).

Step 2: Tert-butyl 2-((R)-3-methyl-4-oxo-4-((S)-11-oxo-1,2,3,5,10,11-hexahydrobenzo[d]pyrazolo[1,2-a][1,2]diazepin-10-ylamino)butanamido)phenylcarbamate (101 mg, 0.19 mmol) was dissolved in a 1.25 M HCl solution in MeOH (3 mL, 3.8 mmol). The sample was heated to 150° C. for 30 min in a microwave. The reaction mixture was concentrated under vacuum and coevaporated three times with a 7N $NH_3$ solution in MeOH. The reaction mixture was purified by preparative HPLC-MS (column X-Bridge $C_{18}$ ODB 5 um 30*100 mm, flow 45 mL/min, water/ACN: 5→99% ACN in 12.5 min, 7.3 mM $NH_3$) to give (R)-3-(1H-benzo[d]imidazol-2-yl)-2-methyl-N—((S)-11-oxo-2,3,10,11-tetrahydro-1H,5H-benzo[d]pyrazolo[1,2-a][1,2]diazepin-10-yl)propanamide (111). HPLC (method a) m/z 404.3 $[M+H]^+$, $t_R$=1.47 min (HPLC condition a), $^1$H NMR (400 MHz, $CDCl_3$) δ ppm: 7.74 (brs, 1H), 7.27 (m, 3H), 7.11 (m, 2H), 6.98 (d, 1H), 6.78-6.59 (m, 3H), 4.23 (s, 2H, 3.78 (m, 2H), 3.64 (m, 1H), 3.42-3.23 (m, 4H), 3.13 (m, 1H), 2.41 (m, 1H), 2.23 (m, 1H), 1.45 (d, 3H).

Table 4 shows additional example compounds (Examples 112 to 119) which were prepared using a method analogous to that described in Example 111. The appropriate intermediates used in each step are listed, along with the coupling conditions for step 4.

TABLE 4

| Example No. | Compound Structure | Compound Name | Reaction Parameters | Analytics |
|---|---|---|---|---|
| 112 | 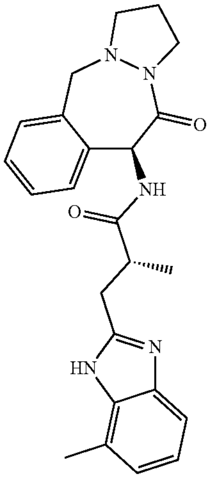 [SMILES: Cc1cccc2nc(C[C@@H](C)C(=O)N[C@@H]3C(=O)N4CCCN4Cc4ccccc43)[nH]c12] | (R)-2-methyl-3-(7-methyl-1H-benzo[d]imidazol-2-yl)-N-((S)-11-oxo-2,3,10,11-tetrahydro-1H,5H-benzo[d]pyrazolo[1,2-a][1,2]diazepin-10-yl) propanamide | 1.25 M HCl in MeOH, 80° C., 20 min, microwave tert-butyl 2-aminophenyl carbamate was replaced with 3-methylbenzene-1,2-diamine | m/z 418.2 [M + H]+, $t_R$ = 0.69 min (LCMS method b), $^1$H NMR (400 MHz, DMSO-d6) δ 12.05 (s, 1H), 8.20 (m, 1H), 7.40-7.22 (dd, 1H), 7.05 (m, 2H), 6.95 (m, 2H), 6.88-6.68 (dd, 1H), 6.64 (m, 1H), 6.48 (dt, 1H), 4.18 (s, 2H), 3.62-3.45 (m, 5H), 3.15 (m, 2H), 2.90 (m, 1H), 2.46 (s, 3H), 2.10 (m, 1H), 1.20 (d, 3H). |

TABLE 4-continued

| Example No. | Compound Structure | Compound Name | Reaction Parameters | Analytics |
|---|---|---|---|---|
| 113 | 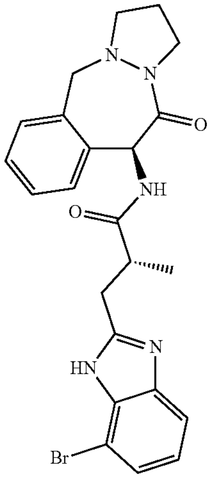 [SMILES: C[C@H](Cc1nc2cccc(Br)c2[nH]1)C(=O)N[C@@H]1C(=O)N2CCCN2Cc2ccccc21] | (R)-3-(7-bromo-1H-benzo[d]imidazol-2-yl)-2-methyl-N-((S)-11-oxo-2,3,10,11-tetrahydro-1H,5H-benzo[d]pyrazolo[1,2-a][1,2]diazepin-10-yl)propanamide | 1.25 M HCl in MeOH, 80° C., 10 min, microwave tert-butyl 2-aminophenyl carbamate was replaced with 3-bromobenzene-1,2-diamine | m/z 482.1 [M + H]$^+$, $t_R$ = 0.85 min (LCMS method b), $^1$H NMR (400 MHz, DMSO-d6) δ 8.26 (d, 1H), 7.47 (m, 1H), 7.36 (d, 1H), 7.08 (m, 2H), 6.97 (d, 1H), 6.76 (m, 1H), 6.64 (d, 1H), 6.56 (m, 1H), 4.18 (s, 2H), 3.53 (m, 3H), 3.17 (m, 3H), 2.92 (dd, 1H), 2.09 (m, 2H), 1.12 (d, 3H). |
| 114 | 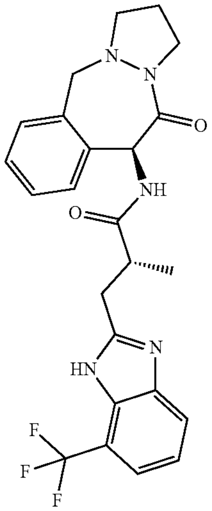 [SMILES: C[C@H](Cc1nc2cccc(C(F)(F)F)c2[nH]1)C(=O)N[C@@H]1C(=O)N2CCCN2Cc2ccccc21] | (R)-2-methyl-N-((S)-11-oxo-2,3,10,11-tetrahydro-1H,5H-benzo[d]pyrazolo[1,2-a][1,2]diazepin-10-yl)-3-(7-(trifluoromethyl)-1H-benzo[d]imidazol-2-yl)propanamide | 1.25 M HCl in MeOH, 100° C., 15 min, microwave tert-butyl 2-aminophenyl carbamate was replaced with 3-(trifluoromethyl) benzene-1,2-diamine | m/z 472.3 [M + H]$^+$, $t_R$ = 0.93 min (LCMS method b), $^1$H NMR (400 MHz, DMSO-d6) δ 12.63 (m, 1H), 8.26 (m, 1H), 7.91-7.72 (dd, 1H), 7.50 (m, 1H), 7.33 (m, 1H), 7.09-6.95 (m, 2H), 6.64 (m, 2H), 6.39 (m, 1H), 4.18 (s, 2H), 3.53 (m, 4H), 3.18 (m, 3H), 2.97 (m, 1H), 2.08 (m, 1H), 1.21 (d, 3H). |
| 115 | 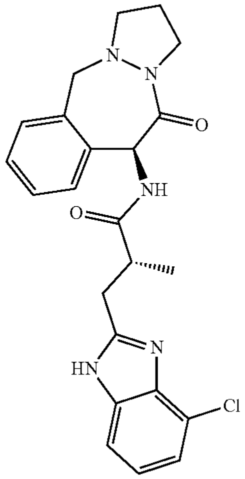 [SMILES: C[C@H](Cc1nc2c(Cl)cccc2[nH]1)C(=O)N[C@@H]1C(=O)N2CCCN2Cc2ccccc21] | (R)-3-(4-chloro-1H-benzo[d]imidazol-2-yl)-2-methyl-N-((S)-11-oxo-2,3,10,11-tetrahydro-1H,5H-benzo[d]pyrazolo[1,2-a][1,2]diazepin-10-yl)propanamide | 1.25 M HCl in MeOH, 100° C., 5 min, microwave tert-butyl 2-aminophenyl carbamate was replaced with 4-chlorobenzene-1,2-diamine | m/z 438.2 [M + H]$^+$, $t_R$ = 0.82 min (LCMS method b), $^1$H NMR (400 MHz, DMSO-d6) δ 12.5 (s, 1H), 8.27 (m, 1H), 7.40 (d, 1H), 7.24 (m, 1H), 7.16 (dd, 1H), 7.06 (t, 1H), 8.97 (d, 1H), 6.72 (d, 1H), 6.63 (d, 1H), 6.49 (t, 1H), 4.18 (s, 2H), 3.53 (m, 2H), 3.34 (m, 2H), 3.26 (m, 1H), 3.16 (m, 1H), 2.92 (m, 1H), 2.34 (m, 1H), 2.10 (m, 1H), 1.12 (d, 3H). |

TABLE 4-continued

| Example No. | Compound Structure | Compound Name | Reaction Parameters | Analytics |
|---|---|---|---|---|
| 116 | 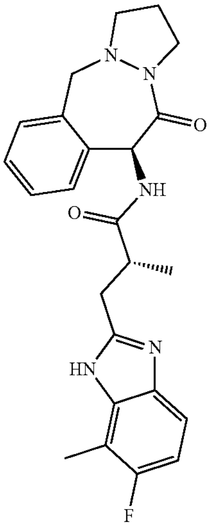 [SMILES: Cc1c(F)ccc2nc(C[C@@H](C)C(=O)N[C@@H]3C(=O)N4CCCN4Cc4ccccc43)[nH]c12] | (R)-3-(6-fluoro-7-methyl-1H-benzo[d]imidazol-2-yl)-2-methyl-N-((S)-11-oxo-2,3,10,11-tetrahydro-1H,5H-benzo[d]pyrazolo[1,2-a][1,2]diazepin-10-yl)propanamide | 1.25 M HCl in MeOH, 60° C., 10 min, microwave tert-butyl 2-aminophenyl carbamate was replaced with 4-fluoro-3-methylbenzene-1,2-diamine | m/z 436.3 $[M + H]^+$, $t^R$ = 2.81 min (HPLC method b), $^1H$ NMR (400 MHz, DMSO-d6 + TFA) δ 8.61 (d, 1H), 7.64 (m, 1H), 7.39 (t, 1H), 7.08 (t, 1H), 6.98 (d, 1H), 6.49 (d, 1H), 6.44 (m, 1H), 4.18 (s, 2H), 3.52 (m, 3H), 3.32 (m, 3H), 3.14 (m, 1H), 2.47 (s, 3H), 2.34 (m, 1H), 2.08 (m, 1H), 1.30 (d, 3H). |
| 117 | 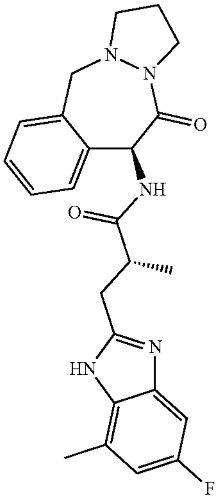 [SMILES: Cc1cc(F)cc2nc(C[C@@H](C)C(=O)N[C@@H]3C(=O)N4CCCN4Cc4ccccc43)[nH]c12] | (R)-3-(5-fluoro-7-methyl-1H-benzo[d]imidazol-2-yl)-2-methyl-N-((S)-11-oxo-2,3,10,11-tetrahydro-1H,5H-benzo[d]pyrazolo[1,2-a][1,2]diazepin-10-yl)propanamide | 1.25 M HCl in MeOH, 60° C., 10 min, microwave | m/z 436.2 $[M + H]^+$, $t_R$ = 2.81 min (HPLC method b), 1H NMR (400 MHz, DMSO-d6) δ ppm: 12.23 (d, 1H), 8.29 (t, 1H), 7.30 (m, 1H), 7.09 (m, 1H), 6.97 (m, 2H), 6.80 (m, 1H), 6.64 (m, 1H), 6.45 (m, 1H), 4.19 (s, 2H), 3.53 (m, 3H), 3.20 (m, 3H), 3.12 (m, 1H), 2.45 (s, 3H), 2.34 (m, 1H), 2.09 (m, 1H), 1.30 (d, 3H). |
| 118 | 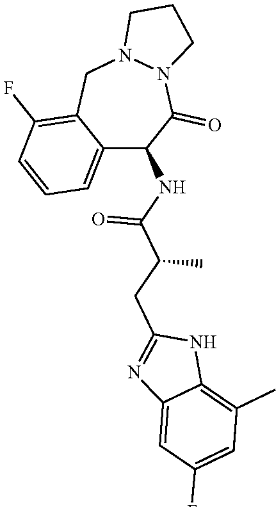 | (R)-N-((S)-6-fluoro-11-oxo-2,3,10,11-tetrahydro-1 H,5H-benzo[d]pyrazolo[1,2-a][1,2]diazepin-10-yl)-3-(5-fluoro-7-methyl-1H-benzo[d]imidazol-2-yl)-2-methylpropanamide | 1.25M HCl in MeOH; microwave, 100° C., 5 min. tert-butyl 2-aminophenyl carbamate was replaced with 5-fluoro-3-methylbenzene-1,2-diamine Intermediate prepared by Example 62: replace int-A1 with int-A2 | m/z 454.2 $[M + H]^+$, $t_R$ = 0.83 min (HPLC method b), $^1H$ NMR (400 MHz, $CDCl_3$) δ ppm: 8.34 (d, 1 H), 7.00 (d, 2 H), 6.83 (d, 1 H), 6.64 (d, 3 H), 4.11 (br. s., 2 H), 3.53 (dd, 3 H), 3.19 − 3.30 (m, 2 H), 3.17 (d, 1 H), 2.86 (dd, 1 H), 2.44 (br. s., 3 H), 2.00 − 2.15 (m, 1 H), 1.18 (d, 3 H). |

TABLE 4-continued

| Example No. | Compound Structure | Compound Name | Reaction Parameters | Analytics |
|---|---|---|---|---|
| 119 | 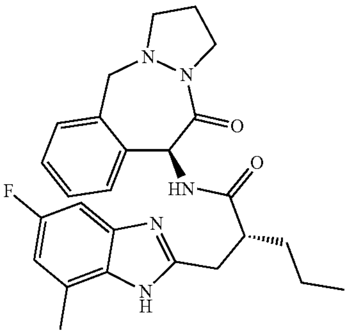 [SMILES: CCC[C@H](Cc1nc2cc(F)cc(C)c2[nH]1)C(=O)N[C@@H]1C(=O)N2CCCN2Cc2ccccc21] | (R)-2-((5-fluoro-7-methyl-1H-benzo[d]imidazol-2-yl)methyl)-N-((S)-11-oxo-2,3,10,11-tetrahydro-1H,5H-benzo[d]pyrazolo [1,2-a][1,2]diazepin-10-yl)pentanamide | 1.25 M HCl in MeOH, 80° C., 10 min, microwave tert-butyl 2-aminophenyl carbamate was replaced with 5-fluoro-3-methylbenzene-1,2-diamine Intermediate prepared by Example 62: replace int-L6 with int-L3 | m/z 464.2 [M + H]+, $t_R$ = 1.74 min (HPLC method a), $^1$H NMR (400 MHz, DMSO-d6) δ ppm: 12.21 (d, 1H), 8.16 (d, 1H), 7.16 (d, 1H), 7.06 (m, 1H), 6.96 (d, 1H), 6.83 (t, 1H), 6.63 (t, 1H), 6.53 (d, 1H), 6.31 (m, 1H), 4.17 (s, 2H), 3.52 (m, 2H), 3.40 (m, 1H), 3.26 (m, 1H), 3.10 (m, 2H), 2.94 (m, 1H), 2.45 (s, 3H), 2.33 (m, 1H), 2.09 (m, 1H), 1.61 (m, 1H), 1.49 (m, 1H), 1.34 (m, 2H), 0.92 (t, 3H). |

Biological Assays

Abbreviations

DC Dendritic Cell(s)
DNP 2,4-dinitrophenyl
Gal4 Regulatory protein GAL4, YPL248C
FCM Flow Cytometry
KLH keyhole limpet hemacyanin
$IC_{50}$ Concentration yielding 50% of maximum inhibition
IgG Immunoglobulin G
NT Amino terminal
PAGE Polyacrilamide gel electrophoresis
PBS Phosphate buffer saline
RGA reporter gene assay
RT room temperature
SDS sodium dodecylsulfate
Sppl2a signal peptide protease like 2a
TL Translocation assay
TNF Tumor necrosis factor Sppl2a RGA (Reporter Gene Assay):

Sppl2a is an intramembrane aspartyl protease with similarities to presenilin, the active subunit of the γ-secretase complex. The assay is based on the coupling of the proteolytic degradation of a membrane bound synthetic substrate (VP16-Gal4 fusion protein with the N-terminal domain of TNF alpha), which migrates to the nucleus upon cleavage, with the Gal4 driven expression of luciferase. Inhibition of Sppl2a results in a reduction of nuclear VP16-Gal4 activator and therefore in a reduction of the production of luciferase. The luciferase dependent-luminescence is plotted against the concentrations of compound to generate a dose response curve, which allows the calculation of the $IC_{50}$ value.

DNA vectors encoding human Sppl2a, NT-TNF-VP16-Gal4 and a Gal4-luciferase reporter were transiently transfected in HEK293 cells. In a typical experiment 5 µg plasmid for SPPL2a, 10 µg plasmid encoding the reporter Gal4-luciferase and 20 µg plasmid encoding the substrate NT-TF-VP16-Gal4 were mixed together. The DNA mixture was combined with 107 µl FuGENE® (Promega), 735 µl Opti-MEM® (Life Technologies) and incubated for 5 minutes at RT. To this mixture 20 mL of concentrated HEK293 cells were added and thoroughly mixed. The cell suspension was distributed to a white solid 384 well plate. Within 5 hours, 50 nl of compound in DMSO was stamped into the wells via pintool. The plate was incubated for 24 h at 37° C., 5% $CO_2$ in a humidified incubator, before the addition of 25 µl Bright Glo. After incubation at RT for 5 min, the plate was transferred to a luminometer and the luminescence was measured. The $IC_{50}$ was determined by plotting compound concentration vs. normalized luminescence values.

γ-secretase RGA (Reporter Gene Assay):

Presenilins are the active subunits of γ-secretase complex; a membrane bound protease that cleaves numerous type I transmembrane substrates. The current assay has been developed to monitor the γ-secretase activity toward Notch, an important modulator of immune cells development. The assay is based on the coupling of the proteolytic degradation of a membrane bound synthetic substrate, a VP16-Gal4 fusion protein with Notch1, which migrates to the nucleus upon cleavage, where it activates Gal4 driven expression of luciferase. Inhibitors of γ-secretase will result in a reduction of nuclear VP16-Gal4 activator and therefore in a reduction of the production of luciferase. The luciferase dependent-luminescence is plotted against the concentrations of compound to generate a dose response curve, which allows the calculation of the $IC_{50}$ value.

DNA vectors encoding human Notch1-VP16-Gal4 and a Gal4-luciferase reporter were transiently transfected in HEK293 cells, which express γ-secretase components endogenously. In a typical experiment 10 µg plasmid encoding the reporter Gal4-luciferase and 20 µg plasmid encoding the substrate Notch1-VP16-Gal4 were mixed together. The DNA mixture was combined with 107 µl FuGENE® (Promega), 735 µl Opti-MEM® (Life Technologies) and incubated for 5 minutes at RT. To this mixture 20 mL of concentrated HEK293 cells were added and thoroughly mixed. The cell suspension was distributed to a white solid 384 well plate. Within hours, 50 nl of compound in DMSO was stamped into the wells via pintool. The plate was incubated for 24 h at 37° C., 5% $CO_2$ in a humidified incubator, before the addition of 25 µl Bright Glo. After incubation at room temperature for 5 min, the plate was transferred to a luminometer and the luminescence was measured. The $IC_{50}$ was determined by plotting compound concentration vs. normalized luminescence values.

Sppl2a TL Assay:

SPPL2a, TL in U-2 OS Cells. Stable U-2 OS cell lines expressing human SPPL2a constitutively and a EGFP-labeled TNFα(aa1-76) NTF substrate under a doxycycline-regulated promoter were used for the imaging assays. Cells were seeded at 3000 cells/30 µL/384-well in DMEM/GlutaMax™-I (Invitrogen) supplemented with tetracycline-free 10% FBS (Amimed) and incubated at 37° C., 5% $CO_2$ for 3-4 h. Subsequently, 3.3 µL of inhibitors, prediluted in doxycycline-containing medium for 11-point concentration-response curves, were added to each well using a CyBi well liquid handling device (Cybio AG, Jena, Germany) to result in final inhibitor concentrations ranging from 100 µM to 1 nM (final DMSO concentration 0.9% (v/v)) and 5 µg/mL doxycycline). The cells were incubated with inhibitor at 37° C., 5% $CO_2$ for 24 h. Thereafter cell were fixed in 4% PFA/PBS and in parallel, nuclei were stained with Hoechst (Invitrogen) 1:5000 in PBS for 30 min. The plates were imaged using a Cellomics ArrayScan VTI HCS reader with 10×/0.3NA objective (Thermo Fisher Scientific, USA). Six images per well were acquired. Images for the EGFP signal (Ex395, Em509) and the Hoechst nuclear dye (Ex350, Em425) were acquired simultaneously with image analysis using the "Nuclear Translocation" assay algorithm of the Cellomics ArrayScan software. Nuclei were detected based on the Hoechst staining, the nuclear mask was transferred to the EGFP channel, and a 4 pixel wide cytoplasm ring region was defined around the nucleus. The intensity of the EGFP signal was measured both in the nuclear and in the cytoplasm ring region of each individual cell (in general 800-1000 individual cells were analyzed per well), and the difference of the average nuclear versus average cytoplasmic intensity of the EGFP signal was calculated ("CircRingAvgIntenDiffCh2"="CircAvgIntenCh2"−"RingAvgIntenCh2"). Additionally the number of cells were acquired (feature termed "ValidCellCount") and used to calculate cell toxicity (CC50). Percent inhibition was calculated relative to the positive (0.5 µM LY-411,575=100% inhibition) and negative (DMSO=0% inhibition) controls. The $IC_{50}$ value was calculated from the plot of percentage of inhibition vs inhibitor concentration using nonlinear regression analysis software, e.g., Origin (OriginLab Corp.).

CD74/p8 Mouse Whole Blood Assay: Flow Cytometry Format

Mouse whole blood Balb/c mice (sodium citrate) was ordered by Bioreclamation LLC; USA. The blood was used the next day upon receipt (stored at 4° C.). 100 µL blood were transferred in 96 well format plate, where compounds, an 11 point dilutions down from 30 µM, to be tested were previously deposited. The plate was incubated for 5 h in the incubator at 37° C., 5% $CO_2$ under continuous motion. After the incubation the blood was diluted with RBC Lysis Buffer (Amined; Cat. Nr 3-13F00-H or BD; Cat. Nr 555899). The solution was mixed by pipetting and incubated 10 min in the 37° C. incubator. The white blood cells were sedimented for 3 min at 2000 rpm. After removing the supernatant the cell pellet was resuspended and washed twice in RCB Buffer and kept≈ 5 min at room temperature, followed by a centrifugation for 2 min at 2000 rpm. The cell pellet was then resuspend in D-PBS and centrifuged twice. Finally, the cells were taken up in of D-PBS/0.5% inactivated fetal bovine serum/2 mM EDTA. The cell suspension was treated with Live/Dead fixable stain (Life Technologies, >470 nm version), B cells were identified by surface staining with an anti-B220 antibody coupled to APC fluorofor. After staining, the cells were extensively washed with PBS. The cells were permeabilized and fixed in FACS lysing buffer; (BD; #349202, dil 1:10 in water) and labelled with an anti CD74, FITC labelled antibody, washed once more with diluted FACS lysing buffer and spin down. The cell pellet was washed with D-PBS/0.5% inactivated fetal bovine serum/2 mM EDTA and PBS prior to the analysis in a flow cytometer. The compound concentrations were plotted against the intensity (medium fluorescence intensity) of the CD74 signal on the gated life B cell and $IC_{50}$ were determined by fitting data for a 11 concentrations dose response.

Biological Data:

The compounds described herein were evaluated using the assays described above. Table 5 lists the corresponding $IC_{50}$ (µM) values obtained for each example compound described above.

TABLE 5

| Example No. | SPPL2a TL $IC_{50}$ (µM) | SPPL2a RGA $IC_{50}$ (µM) | g-secretase RGA $IC_{50}$ (µM) | Sppl2a CD74 whole blood $IC_{50}$ (µM) |
|---|---|---|---|---|
| 1 | 0.024 | 0.029 | >10 | 0.358 |
| 2 | 0.45 | 0.180 | >10 | nd |
| 3 | 0.0005 | 0.003 | >10 | 0.100 |
| 4 | 0.001 | 0.012 | >10 | 0.100 |
| 5 | 0.002 | 0.002 | >10 | 0.225 |
| 6 | 0.002 | 0.002 | >10 | 1.564 |
| 7 | 0.003 | 0.002 | >10 | 0.120 |
| 8 | 0.003 | 0.004 | >10 | 2.433 |
| 9 | 0.003 | 0.004 | >10 | 0.157 |
| 10 | 0.004 | 0.005 | >10 | 0.289 |
| 11 | 0.004 | 0.003 | >10 | 0.095 |
| 12 | 0.005 | 0.004 | >10 | 0.280 |
| 13 | 0.006 | 0.008 | >10 | 0.161 |
| 14 | 0.007 | 0.003 | >10 | 0.269 |
| 15 | 0.011 | 0.008 | >10 | nd |
| 16 | 0.011 | 0.008 | >10 | 0.659 |
| 17 | 0.011 | 0.005 | >10 | 2.354 |
| 18 | 0.012 | 0.003 | >10 | nd |
| 19 | 0.012 | 0.006 | >10 | 0.819 |
| 20 | 0.012 | 0.220 | >10 | nd |
| 21 | 0.013 | 0.007 | >10 | 5.939 |
| 22 | 0.014 | 0.012 | >10 | 3.000 |
| 23 | 0.016 | 0.021 | >10 | 0.992 |
| 24 | 0.021 | 0.033 | >10 | 1.655 |
| 25 | 0.024 | 0.009 | >10 | 0.420 |
| 26 | 0.025 | 0.101 | >10 | 2.233 |
| 27 | 0.026 | 0.005 | >10 | 0.947 |
| 28 | 0.028 | 0.088 | >10 | nd |
| 29 | 0.029 | 0.084 | >10 | nd |
| 30 | 0.029 | 0.016 | >10 | nd |
| 31 | 0.033 | 0.022 | >10 | nd |
| 32 | 0.037 | 0.010 | >10 | 0.174 |
| 33 | 0.037 | 0.007 | >10 | nd |
| 34 | 0.043 | 0.050 | >10 | nd |
| 35 | 0.045 | 0.034 | >10 | nd |
| 36 | 0.045 | 0.034 | >10 | nd |
| 37 | 0.053 | 0.032 | >10 | nd |
| 38 | 0.054 | 0.043 | >10 | nd |
| 39 | 0.054 | 0.024 | >10 | nd |
| 40 | 0.057 | 0.042 | >10 | nd |
| 41 | 0.059 | 0.037 | >10 | nd |
| 42 | 0.062 | 0.027 | >10 | 0.847 |
| 43 | 0.063 | 0.104 | >10 | 1.737 |
| 44 | 0.067 | 0.027 | >10 | nd |
| 45 | 0.078 | 0.086 | >10 | 2.514 |
| 46 | 0.079 | 0.054 | >10 | 2.683 |
| 47 | 0.083 | 0.041 | >10 | 0.741 |
| 48 | 0.085 | 0.022 | >10 | nd |
| 49 | 0.091 | 0.089 | >10 | nd |
| 50 | 0.097 | 0.090 | >10 | 1.395 |
| 51 | 0.099 | 0.052 | >10 | nd |
| 52 | 0.118 | 0.030 | 9.7 | 0.148 |
| 53 | 0.125 | 0.022 | >10 | 0.279 |
| 54 | 0.129 | 0.048 | >10 | nd |
| 55 | 0.163 | 0.152 | >10 | nd |
| 56 | 0.191 | 0.101 | >10 | nd |
| 57 | 0.332 | 0.148 | >10 | nd |
| 58 | 0.373 | 0.194 | >10 | nd |
| 59 | 0.555 | 0.661 | >10 | nd |
| 60 | 0.580 | 0.277 | >10 | nd |
| 61 | 0.686 | 0.691 | >10 | nd |
| 62 | 0.0003 | 0.057 | >10 | 0.317 |
| 63 | 0.0006 | 0.011 | >10 | 0.343 |
| 64 | 0.001 | 0.003 | 8.1 | 0.230 |
| 65 | 0.001 | 0.014 | >10 | 0.519 |
| 66 | 0.002 | 0.002 | 8.1 | 0.136 |

TABLE 5-continued

| Example No. | SPPL2a TL $IC_{50}$ (μM) | SPPL2a RGA $IC_{50}$ (μM) | g-secretase RGA $IC_{50}$ (μM) | Sppl2a CD74 whole blood $IC_{50}$ (μM) |
|---|---|---|---|---|
| 67 | 0.002 | 0.005 | >10 | nd |
| 68 | 0.003 | 0.034 | >10 | 0.329 |
| 69 | 0.003 | 0.009 | >10 | 1.242 |
| 70 | 0.004 | 0.013 | >10 | nd |
| 71 | 0.004 | 0.004 | >10 | nd |
| 72 | 0.004 | 0.009 | >10 | nd |
| 73 | 0.004 | 0.025 | >10 | nd |
| 74 | 0.004 | 0.013 | >10 | nd |
| 75 | 0.005 | 0.004 | >10 | nd |
| 76 | 0.005 | 0.007 | >10 | 1.690 |
| 77 | 0.006 | 0.005 | >10 | 0.250 |
| 78 | 0.006 | 0.043 | >10 | nd |
| 79 | 0.007 | 0.010 | >10 | nd |
| 80 | 0.007 | 0.008 | >10 | 0.910 |
| 81 | 0.008 | 0.005 | >10 | nd |
| 82 | 0.009 | 0.036 | >10 | 1.873 |
| 83 | 0.009 | 0.006 | >10 | nd |
| 84 | 0.009 | 0.040 | >10 | nd |
| 85 | 0.010 | 0.022 | >10 | 0.203 |
| 86 | 0.010 | 0.004 | >10 | nd |
| 87 | 0.010 | 0.010 | >10 | nd |
| 88 | 0.010 | 0.007 | >10 | nd |
| 89 | 0.011 | 0.060 | >10 | 0.649 |
| 90 | 0.011 | 0.011 | >10 | 0.635 |
| 91 | 0.011 | 0.024 | >10 | 0.500 |
| 92 | 0.012 | 0.011 | >10 | nd |
| 93 | 0.012 | 0.168 | >10 | 1.129 |
| 94 | 0.012 | 0.034 | >10 | 2.540 |
| 95 | 0.012 | 0.023 | >10 | nd |
| 96 | 0.012 | 0.028 | >10 | nd |
| 97 | 0.013 | 0.015 | >10 | nd |
| 98 | 0.014 | 0.008 | >10 | nd |
| 99 | 0.014 | 0.050 | >10 | 0.892 |
| 100 | 0.015 | 0.028 | >10 | 0.272 |
| 101 | 0.015 | 0.007 | >10 | 0.473 |
| 102 | 0.017 | 0.123 | >10 | 1.519 |
| 103 | 0.017 | 0.013 | >10 | 1.247 |
| 104 | 0.017 | 0.017 | >10 | nd |
| 105 | 0.018 | 0.023 | >10 | nd |
| 106 | 0.010 | 0.008 | 1.6 | nd |
| 107 | 0.015 | 0.011 | 3.5 | nd |
| 108 | 0.003 | 0.003 | 3.7 | nd |
| 109 | 0.002 | 0.003 | >10 | 10.000 |
| 110 | 0.015 | 0.020 | >10 | nd |
| 111 | 0.666 | 0.077 | 2.661 | nd |
| 112 | 0.139 | 0.028 | 1.584 | nd |
| 113 | 0.180 | 0.042 | 2.105 | nd |
| 114 | 0.548 | 0.063 | 1.255 | nd |
| 115 | 3.974 | 0.228 | 0.956 | nd |
| 116 | 0.116 | 0.013 | 0.398 | nd |
| 117 | 0.140 | 0.021 | 0.979 | nd |
| 118 | 0.116 | 0.019 | 2.610 | nd |
| 119 | 0.185 | 0.019 | 0.756 | nd |

nd indicates not determined.

The invention claimed is:

1. A compound of Formula (I) or a pharmaceutically acceptable salt or stereoisomer thereof, (I)

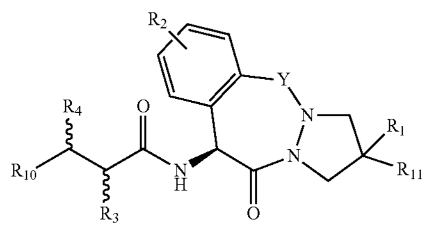

wherein:

Y is $CH_2$ or C═O;

$R_1$ is H, $C_1$-$C_6$alkyl or halogen;

$R_2$ is H or halogen;

$R_3$ is H, $C_1$-$C_6$alkyl, $C_1$-$C_6$haloalkyl, $C_3$-$C_6$cycloalkyl, $C_1$-$C_6$alkyl-phenyl or $C_1$-$C_6$alkyl substituted with $C_1$-$C_6$alkoxy;

$R_4$ is H, $C_1$-$C_6$alkyl or $C_1$-$C_6$alkyl-phenyl;

$R_{10}$ is —NHC(═O)$R_5$ or —C(═O)NH$R_5$;

$R_5$ is a 5-membered heteroaryl having 1, 2 or 3 heteroatoms as ring members each independently selected from N, O and S, wherein the 5-membered heteroaryl is unsubstituted or the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;

vi) $C_1$-$C_6$haloalkyl;

vii) —NHC(═O) $C_1$-$C_6$alkyl, wherein the $C_1$-$C_6$alkyl is optionally substituted by $C_1$-$C_6$alkoxy;

viii) —NHC(═O)—$C_1$-$C_6$haloalkyl;

ix) —NHC(═O)—$C_3$-$C_6$cycloalkyl;

x) —C(═O)NH—$C_1$-$C_6$alkyl, wherein the $C_1$-$C_6$alkyl is optionally substituted by $C_1$-$C_6$alkoxy;

xi) —C(═O)NH—$C_1$-$C_6$haloalkyl;

xii) —C(═O)NH—$C_3$-$C_6$cycloalkyl xiii) —NHC(═O) phenyl, wherein the phenyl is optionally substituted with one or more substituents independently selected from halogen and $C_1$-$C_6$alkyl;

xiv) —C(═O)NHphenyl, wherein the phenyl is optionally substituted with one or more substituents independently selected from halogen and $C_1$-$C_6$alkyl;

xv) $C_1$-$C_6$alkoxy or $C_1$-$C_6$haloalkoxy;

xvi) phenyloxy optionally substituted with one or more halogen;

xvii) phenyl optionally substituted by one or more substituents independently selected from halogen, —CN, $C_1$-$C_6$alkyl, $C_1$-$C_6$alkoxy, $C_1$-$C_6$haloakoxy and $C_1$-$C_6$haloalkyl;

xviii) a 4 to 6-member heterocyclyl optionally substituted with oxo, —C(═O)O$C_1$-$C_6$alkyl or —C(═O)O$C_1$-$C_6$cycloalkyl;

xix) a 5 or 6 membered heteroaryl having 1 or 2 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by —OH, $C_1$-$C_6$alkoxy or a 4 to 6-member heterocyclyl optionally substituted with oxo; and xx) a 9 or 10 membered bicyclic heteroaryl having 1 to 4 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by $C_1$-$C_6$alkoxy; and $R_{11}$ is H, $C_1$-$C_6$alkyl or halogen; or $R_1$ and $R_{11}$ together with the carbon atom to which they are attached, may form a 3 to 6 membered carbocyclic ring.

2. The compound of claim 1, or a pharmaceutically acceptable salt or stereoisomer thereof, having a structure of Formula (II)

(II)

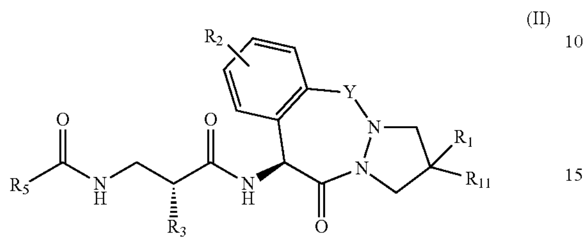

wherein:

Y is $CH_2$ or C═O;

$R_1$ is H, $C_1$-$C_6$alkyl or halogen;

$R_2$ is H or halogen;

$R_3$ is H, $C_1$-$C_6$alkyl, $C_1$-$C_6$haloalkyl, $C_3$-$C_6$cycloalkyl, $C_1$-$C_6$alkyl-phenyl or $C_1$-$C_6$alkyl substituted with $C_1$-$C_6$alkoxy;

$R_4$ is H, $C_1$-$C_6$alkyl or $C_1$-$C_6$alkyl-phenyl;

$R_{10}$ is —NHC(═O)$R_5$ or —C(═O)NH$R_5$;

$R_5$ is a 5-membered heteroaryl having 1, 2 or 3 heteroatoms as ring members each independently selected from N, O and S, wherein the 5-membered heteroaryl is unsubstituted or the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;

vi) $C_1$-$C_6$haloalkyl;

vii) —NHC(═O) $C_1$-$C_6$alkyl, wherein the $C_1$-$C_6$alkyl is optionally substituted by $C_1$-$C_6$alkoxy;

viii) —NHC(═O)—$C_1$-$C_6$haloalkyl;

ix) —NHC(═O)—$C_3$-$C_6$cycloalkyl;

x) —C(═O)NH—$C_1$-$C_6$alkyl, wherein the $C_1$-$C_6$alkyl is optionally substituted by $C_1$-$C_6$alkoxy;

xi) —C(═O)NH—$C_1$-$C_6$haloalkyl;

xii) —C(═O)NH—$C_3$-$C_6$cycloalkyl xiii) —NHC(═O) phenyl, wherein the phenyl is optionally substituted with one or more substituents independently selected from halogen and $C_1$-$C_6$alkyl;

xiv) —C(═O)NHphenyl, wherein the phenyl is optionally substituted with one or more substituents independently selected from halogen and $C_1$-$C_6$alkyl;

xv) $C_1$-$C_6$alkoxy or $C_1$-$C_6$haloalkoxy;

xvi) phenyloxy optionally substituted with one or more halogen;

xvii) phenyl optionally substituted by one or more substituents independently selected from halogen, —CN, $C_1$-$C_6$alkyl, $C_1$-$C_6$alkoxy, $C_1$-$C_6$haloakoxy and $C_1$-$C_6$haloalkyl;

xviii) a 4 to 6-member heterocyclyl optionally substituted with oxo, —C(═O)O$C_1$-$C_6$alkyl or —C(═O)O$C_1$-$C_6$cycloalkyl;

xix) a 5 or 6 membered heteroaryl having 1 or 2 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by —OH, $C_1$-$C_6$alkoxy or a 4 to 6-member heterocyclyl optionally substituted with oxo; and xx) a 9 or 10 membered bicyclic heteroaryl having 1 to 4 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by $C_1$-$C_6$alkoxy;

$R_{11}$ is H, $C_1$-$C_6$alkyl or halogen; or $R_1$ and $R_{11}$ together with the carbon atom to which they are attached, may form a 3 to 6 membered carbocyclic ring.

3. The compound of claim 1, or a pharmaceutically acceptable salt thereof, having a structure of Formula (IIA), Formula (IIB), Formula (IIC) or Formula (IID):

(IIA)

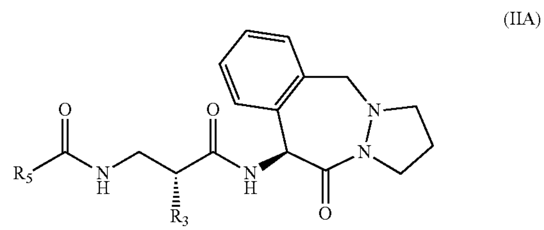

(IIB)

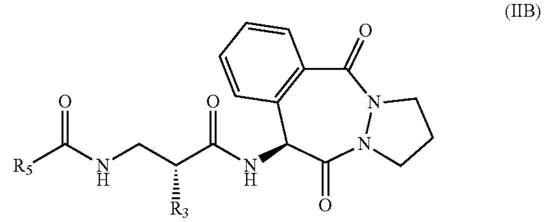

(IIC)

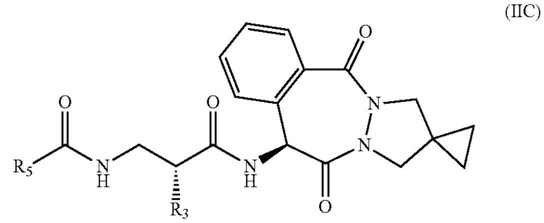

(IID)

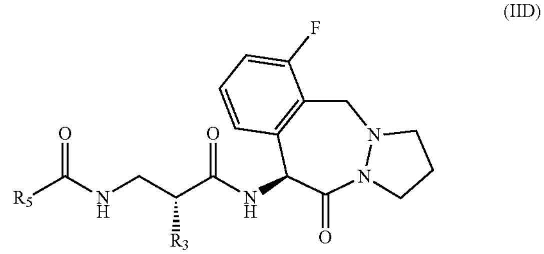

wherein $R_3$ is H, $C_1$-$C_6$alkyl, $C_1$-$C_6$haloalkyl, $C_3$-$C_6$cycloalkyl, $C_1$-$C_6$alkyl-phenyl or $C_1$-$C_6$alkyl substituted with $C_1$-$C_6$alkoxy;

$R_5$ is a 5-membered heteroaryl having 1, 2 or 3 heteroatoms as ring members each independently selected from N, O and S, wherein the 5-membered heteroaryl is unsubstituted or the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;

vi) $C_1$-$C_6$haloalkyl;

vii) —NHC(═O) $C_1$-$C_6$alkyl, wherein the $C_1$-$C_6$alkyl is optionally substituted by $C_1$-$C_6$alkoxy;

viii) —NHC(═O)—$C_1$-$C_6$haloalkyl;

ix) —NHC(═O)—$C_3$-$C_6$cycloalkyl;

x) —C(═O)NH—$C_1$-$C_6$alkyl, wherein the $C_1$-$C_6$alkyl is optionally substituted by $C_1$-$C_6$alkoxy;

xi) —C(═O)NH—$C_1$-$C_6$haloalkyl;

xii) —C(═O)NH—$C_3$-$C_6$cycloalkyl xiii) —NHC(═O) phenyl, wherein the phenyl is optionally substituted with one or more substituents independently selected from halogen and $C_1$-$C_6$alkyl;

xiv) —C(═O)NHphenyl, wherein the phenyl is optionally substituted with one or more substituents independently selected from halogen and $C_1$-$C_6$alkyl;

xv) $C_1$-$C_6$alkoxy or $C_1$-$C_6$haloalkoxy;

xvi) phenyloxy optionally substituted with one or more halogen;

xvii) phenyl optionally substituted by one or more substituents independently selected from halogen, —CN, $C_1$-$C_6$alkyl, $C_1$-$C_6$alkoxy, $C_1$-$C_6$haloakoxy and $C_1$-$C_6$haloalkyl;

xviii) a 4 to 6-member heterocyclyl optionally substituted with oxo, —C(═O)O$C_1$-$C_6$alkyl or —C(═O)O$C_1$-$C_6$cycloalkyl;

xix) a 5 or 6 membered heteroaryl having 1 or 2 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by —OH, $C_1$-$C_6$alkoxy or a 4 to 6-member heterocyclyl optionally substituted with oxo; and xx) a 9 or 10 membered bicyclic heteroaryl having 1 to 4 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by $C_1$-$C_6$alkoxy.

4. The compound of claim 1, or a pharmaceutically acceptable salt thereof, having a structure of Formula (III)

(III)

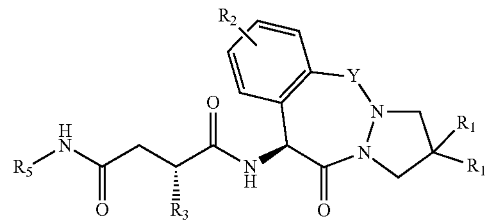

wherein:

Y is $CH_2$ or C═O;

$R_1$ is H, $C_1$-$C_6$alkyl or halogen;

$R_2$ is H or halogen;

$R_3$ is H, $C_1$-$C_6$alkyl, $C_1$-$C_6$haloalkyl, $C_3$-$C_6$cycloalkyl, $C_1$-$C_6$alkyl-phenyl or $C_1$-$C_6$alkyl substituted with $C_1$-$C_6$alkoxy;

$R_5$ is a 5-membered heteroaryl having 1, 2 or 3 heteroatoms as ring members each independently selected from N, O and S, wherein the 5-membered heteroaryl is unsubstituted or the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;

vi) $C_1$-$C_6$haloalkyl;

vii) —NHC(═O) $C_1$-$C_6$alkyl, wherein the $C_1$-$C_6$alkyl is optionally substituted by $C_1$-$C_6$alkoxy;

viii) —NHC(═O)—$C_1$-$C_6$haloalkyl;

ix) —NHC(═O)—$C_3$-$C_6$cycloalkyl;

x) —C(═O)NH—$C_1$-$C_6$alkyl, wherein the $C_1$-$C_6$alkyl is optionally substituted by $C_1$-$C_6$alkoxy;

xi) —C(═O)NH—$C_1$-$C_6$haloalkyl;

xii) —C(═O)NH—$C_3$-$C_6$cycloalkyl xiii) —NHC(═O) phenyl, wherein the phenyl is optionally substituted with one or more substituents independently selected from halogen and $C_1$-$C_6$alkyl;

xiv) —C(═O)NHphenyl, wherein the phenyl is optionally substituted with one or more substituents independently selected from halogen and $C_1$-$C_6$alkyl;

xv) $C_1$-$C_6$alkoxy or $C_1$-$C_6$haloalkoxy;

xvi) phenyloxy optionally substituted with one or more halogen;

xvii) phenyl optionally substituted by one or more substituents independently selected from halogen, —CN, $C_1$-$C_6$alkyl, $C_1$-$C_6$alkoxy, $C_1$-$C_6$haloalkoxy and $C_1$-$C_6$haloalkyl;

xviii) a 4 to 6-member heterocyclyl optionally substituted with oxo, —C(═O)O$C_1$-$C_6$alkyl or —C(═O)O$C_1$-$C_6$cycloalkyl;

xix) a 5 or 6 membered heteroaryl having 1 or 2 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by —OH, $C_1$-$C_6$alkoxy or a 4 to 6-member heterocyclyl optionally substituted with oxo; and xx) a 9 or 10 membered bicyclic heteroaryl having 1 to 4 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by $C_1$-$C_6$alkoxy; and $R_{11}$ is H, $C_1$-$C_6$alkyl or halogen; or $R_1$ and $R_{11}$ together with the carbon atom to which they are attached, may form a 3 to 6 membered carbocyclic ring.

5. The compound of claim 1, or a pharmaceutically acceptable salt thereof, having a structure of Formula (IIIA), Formula (IIIB), Formula (IIIC) or Formula (IIID):

(IIIA)

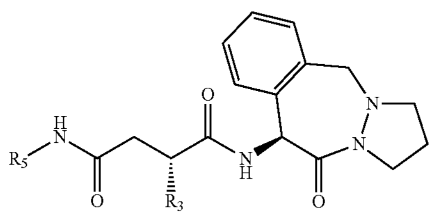

(IIIB)

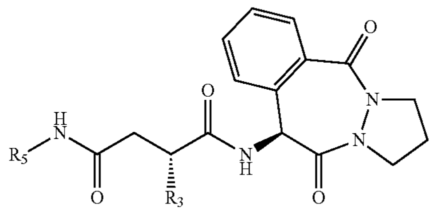

(IIIC)

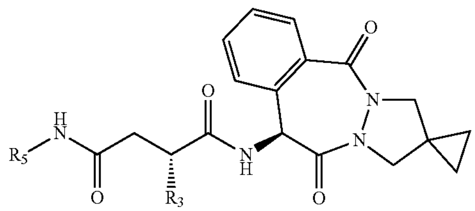

(IIID)

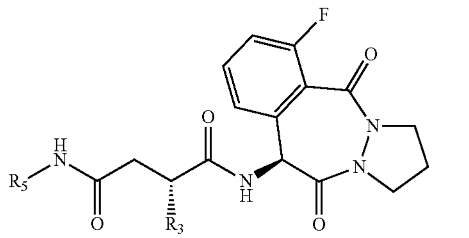

wherein $R_3$ is H, $C_1$-$C_6$alkyl, $C_1$-$C_6$haloalkyl, $C_3$-$C_6$cycloalkyl, $C_1$-$C_6$alkyl-phenyl or $C_1$-$C_6$alkyl substituted with $C_1$-$C_6$alkoxy;

$R_5$ is a 5-membered heteroaryl having 1, 2 or 3 heteroatoms as ring members each independently selected from N, O and S, wherein the 5-membered heteroaryl is unsubstituted or the 5-membered heteroaryl is substituted with one or more substituents independently selected from:

i) halogen;

ii) amino;

iii) $C_3$-$C_6$cycloalkyl optionally substituted by one or more halogen;

iv) $C_3$-$C_6$cycloalkenyl;

v) $C_1$-$C_6$alkyl optionally substituted by $C_1$-$C_6$alkoxy, $C_3$-$C_6$cycloalkyl or phenyl;

vi) $C_1$-$C_6$haloalkyl;

vii) —NHC(═O) $C_1$-$C_6$alkyl, wherein the $C_1$-$C_6$alkyl is optionally substituted by $C_1$-$C_6$alkoxy;

viii) —NHC(═O)—$C_1$-$C_6$haloalkyl;

ix) —NHC(═O)—$C_3$-$C_6$cycloalkyl;

x) —C(═O)NH—$C_1$-$C_6$alkyl, wherein the $C_1$-$C_6$alkyl is optionally substituted by $C_1$-$C_6$alkoxy;

xi) —C(═O)NH—$C_1$-$C_6$haloalkyl;

xii) —C(═O)NH—$C_3$-$C_6$cycloalkyl xiii) —NHC(═O) phenyl, wherein the phenyl is optionally substituted with one or more substituents independently selected from halogen and $C_1$-$C_6$alkyl;

xiv) —C(═O)NHphenyl, wherein the phenyl is optionally substituted with one or more substituents independently selected from halogen and $C_1$-$C_6$alkyl;

xv) $C_1$-$C_6$alkoxy or $C_1$-$C_6$haloalkoxy;

xvi) phenyloxy optionally substituted with one or more halogen;

xvii) phenyl optionally substituted by one or more substituents independently selected from halogen, —CN, $C_1$-$C_6$alkyl, $C_1$-$C_6$alkoxy, $C_1$-$C_6$haloalkoxy and $C_1$-$C_6$haloalkyl;

xviii) a 4 to 6-member heterocyclyl optionally substituted with oxo, —C(═O)O$C_1$-$C_6$alkyl or —C(═O)O$C_1$-$C_6$cycloalkyl;

xix) a 5 or 6 membered heteroaryl having 1 or 2 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by —OH, $C_1$-$C_6$alkoxy or a 4 to 6-member heterocyclyl optionally substituted with oxo; and xx) a 9 or 10 membered bicyclic heteroaryl having 1 to 4 heteroatoms as ring members each independently selected from N, O and S, wherein the heteroaryl is unsubstituted or the heteroaryl is substituted by one or more substituents independently selected from halogen, $C_1$-$C_6$haloalkyl, $C_1$-$C_6$haloalkoxy, $C_1$-$C_6$alkoxy, 4 to 6-member heterocyclyl, $C_3$-$C_6$cycloalkyl, $C_3$-$C_6$cycloalkenyl and $C_1$-$C_6$alkyl optionally substituted by $C_1$-$C_6$alkoxy.

6. The compound of claim 1, or a pharmaceutically acceptable salt or stereoisomer thereof, wherein $R_3$ is methyl, ethyl, propyl, iso-propyl, $CF_3$, —$CH_2$-phenyl, cyclopropyl, cyclobutyl or —$CH_2CH_2OCH_3$.

7. The compound of claim 1, or a pharmaceutically acceptable salt or stereoisomer thereof, wherein $R_5$ is

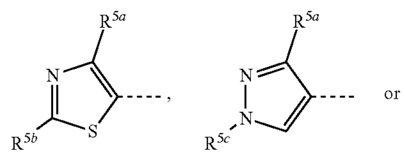

-continued

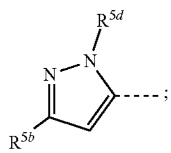

wherein $R^{5a}$ is $C_1$-$C_6$alkyl, $C_1$-$C_6$haloalkyl or halogen;

$R^{5b}$ is —C(O)—NH—$C_1$-$C_6$alkyl, —C(O)NH—$C_1$-$C_6$haloalkyl, —C(O)NHphenyl, —NHC(═O)$C_1$-$C_6$alkyl, $C_1$-$C_6$alkoxy, $C_1$-$C_6$haloalkoxy, $C_3$-$C_6$cycloalkyl, $C_3$-$C_6$cycloalkenyl, 4- to 6-membered heterocyclyl, 5- or 6-membered ring heteroaryl; wherein heteroaryl is optionally substituted with halogen, $C_1$-$C_6$alkyl, $C_1$-$C_6$haloalkyl, $C_1$-$C_6$alkoxy, $C_1$-$C_6$haloakoxy or $C_3$-$C_6$cycloalkyl; and wherein heterocyclyl is optionally substituted with oxo, —C(O)O—$C_1$-$C_6$alkyl or —C(O)O—$C_3$-$C_6$cycloalkyl; and wherein —C(O)NHphenyl is optionally substituted with halogen or $C_1$-$C_6$alkyl;

$R^{5c}$ is 5- or 6-membered ring heteroaryl optionally substituted with halogen, $C_1$-$C_6$alkyl, $C_1$-$C_6$haloalkyl, $C_1$-$C_6$alkoxy, $C_1$-$C_6$haloakoxy or $C_3$-$C_6$cycloalkyl; and $R^{5d}$ is $C_1$-$C_6$alkyl or $C_1$-$C_6$haloalkyl.

8. The compound of claim 1, or a pharmaceutically acceptable salt or stereoisomer thereof, wherein $R_5$ is:

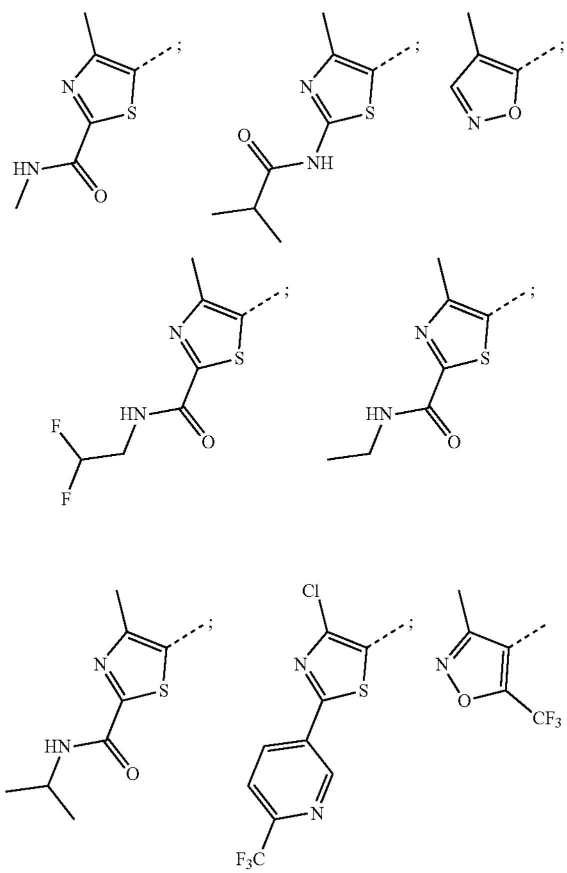

-continued

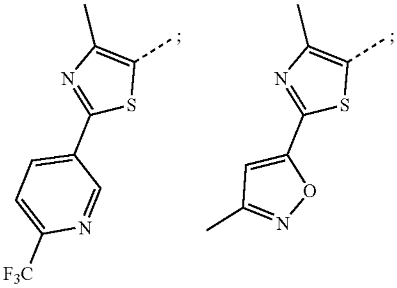

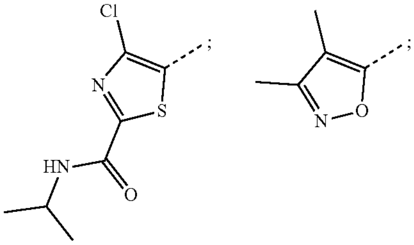

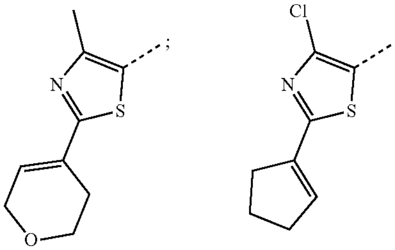

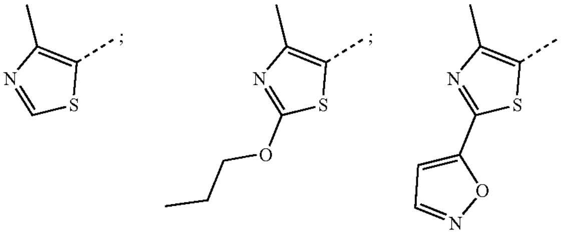

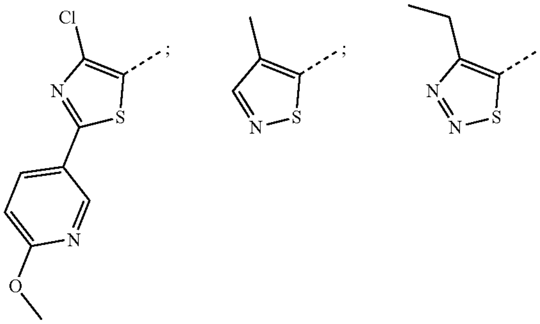

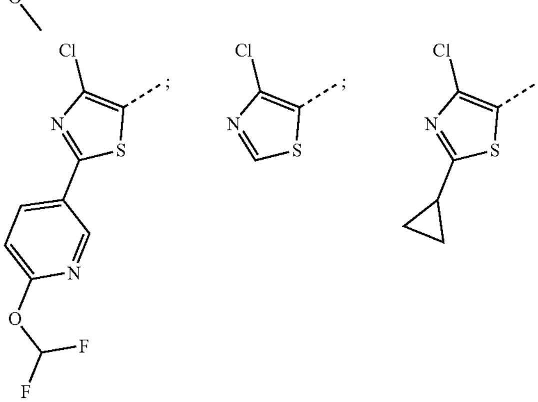

-continued
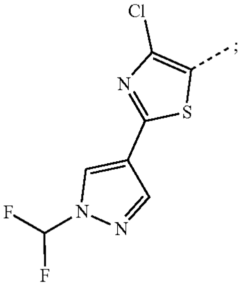
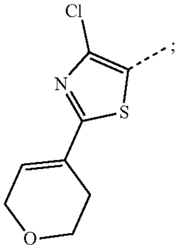
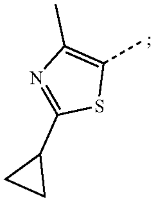
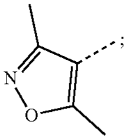
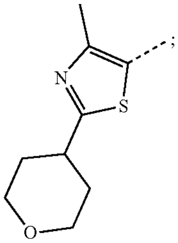
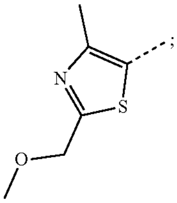
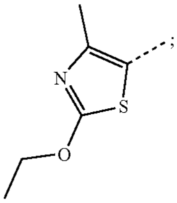
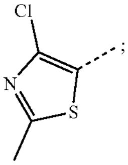
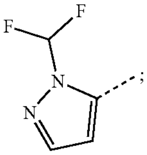
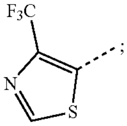
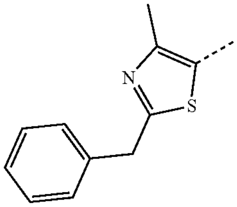
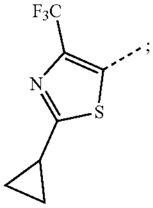
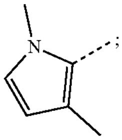
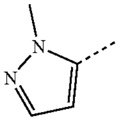
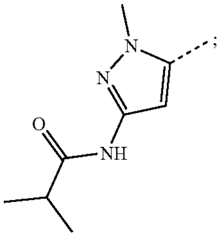
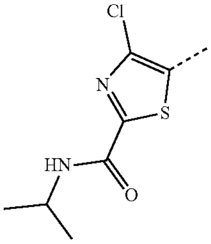
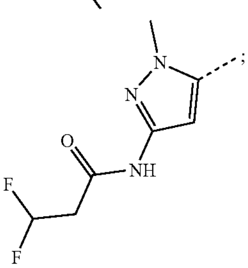
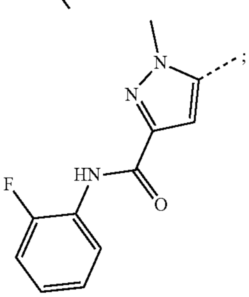
-continued
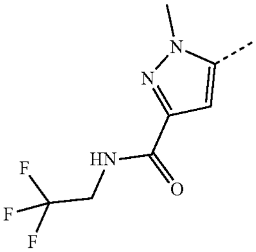
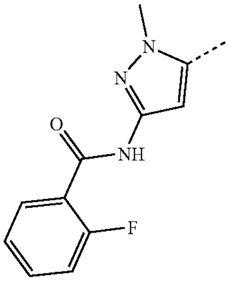
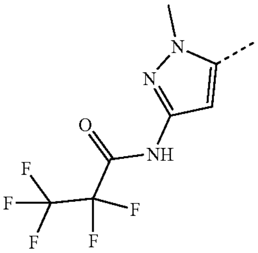
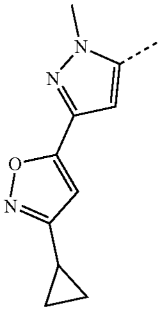
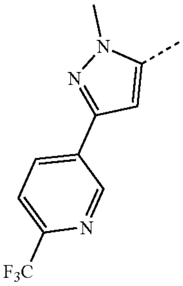
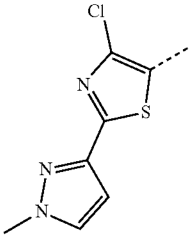
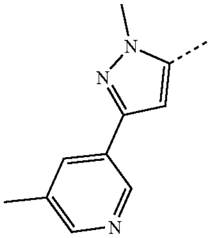
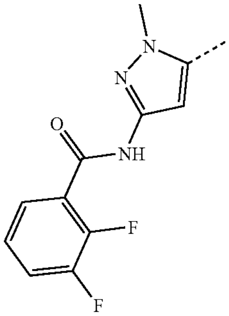
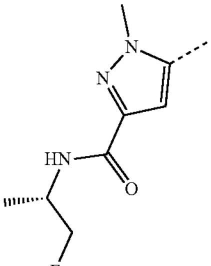
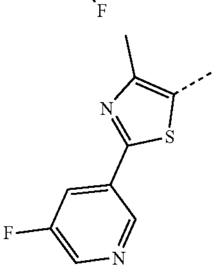

-continued
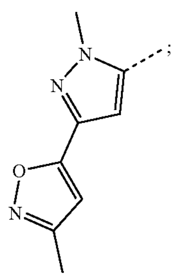
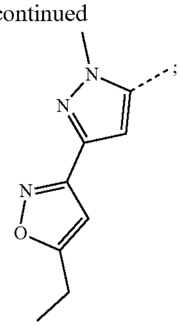
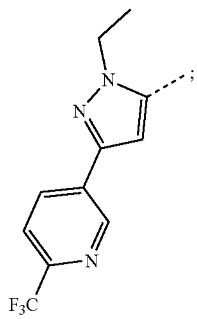
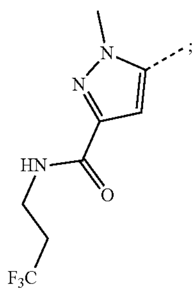
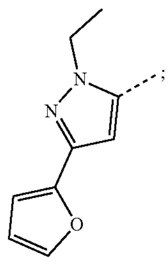
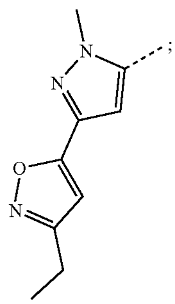
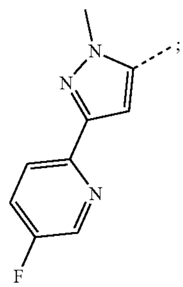
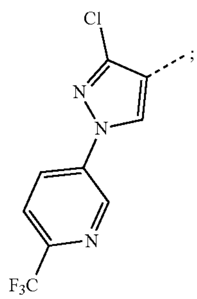
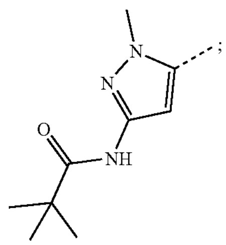
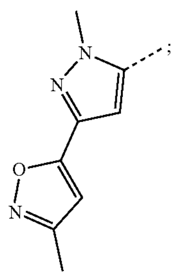
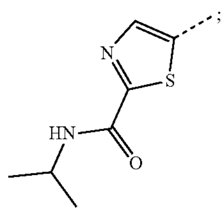
-continued
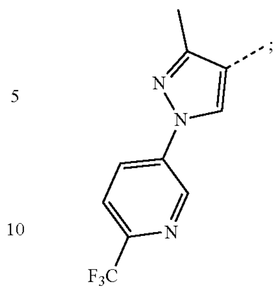
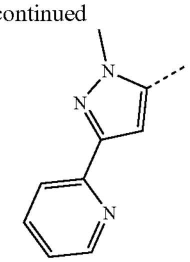
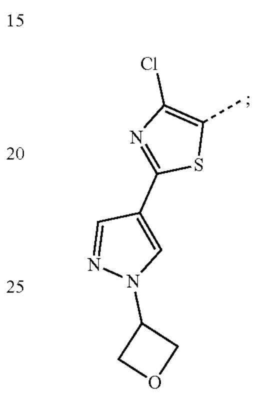
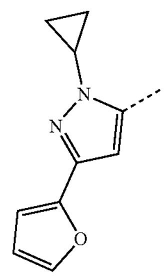
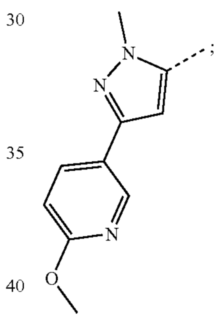
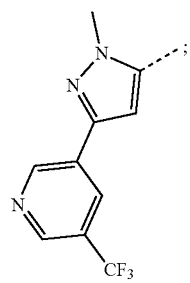
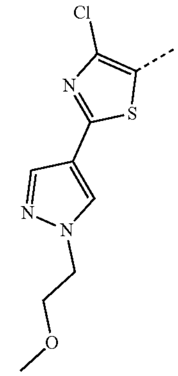
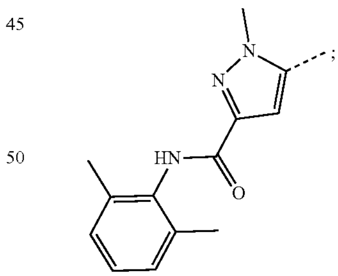
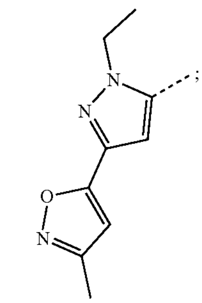
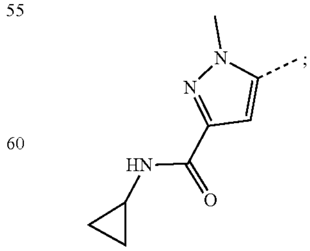
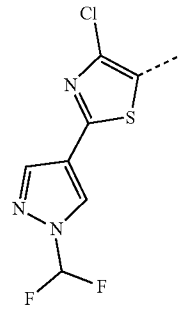

-continued
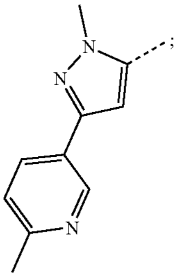
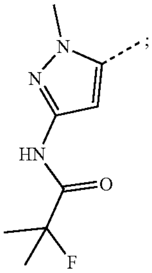
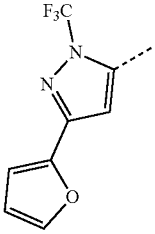
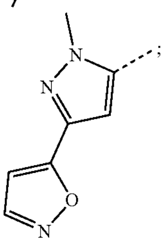
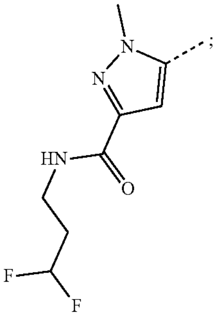
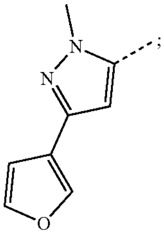
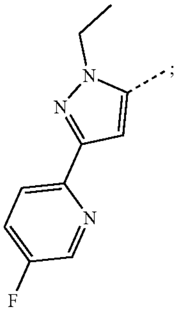
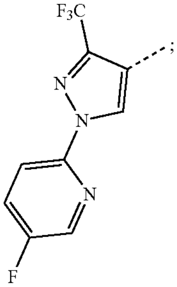
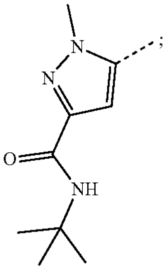
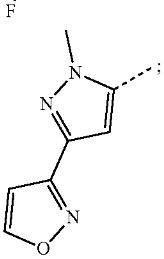
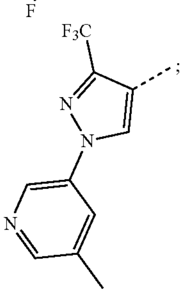
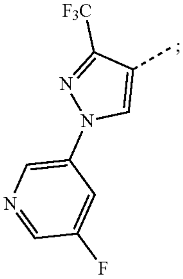
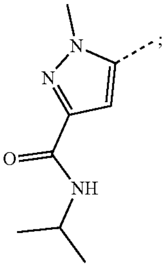
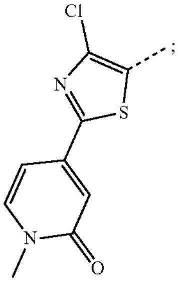
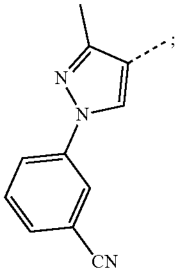
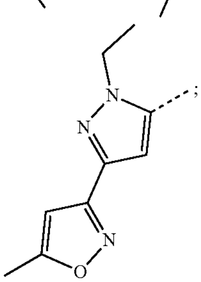
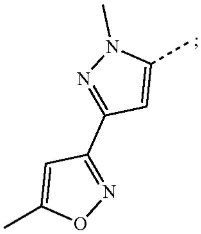
-continued
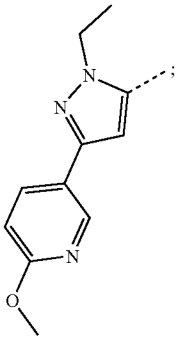
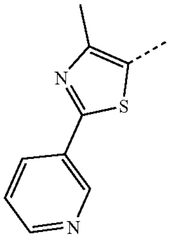
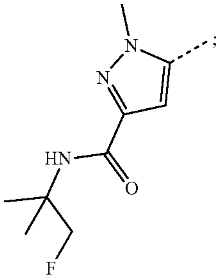
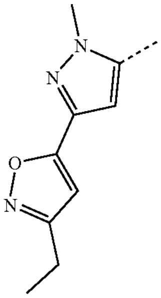
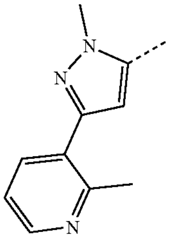
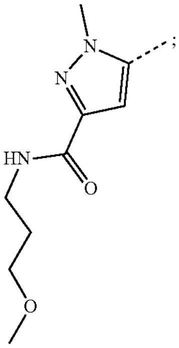
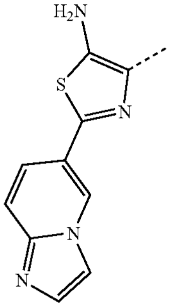
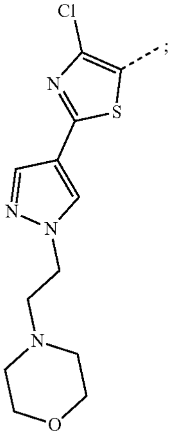
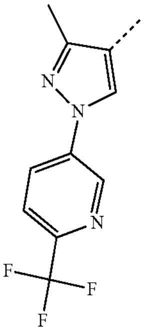
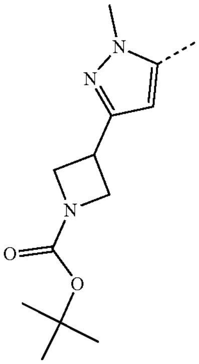

-continued
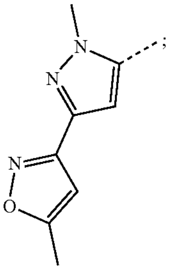
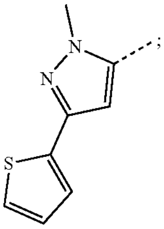
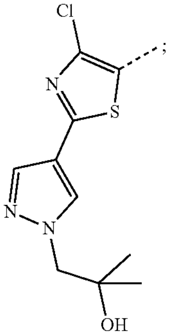
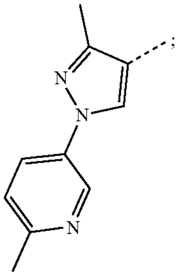
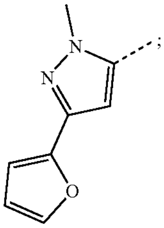
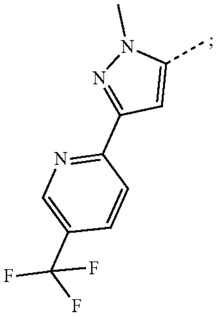
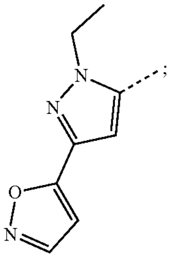
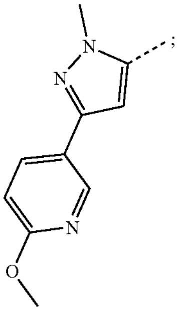
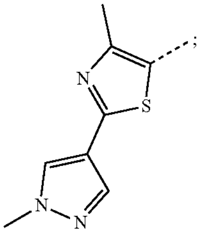
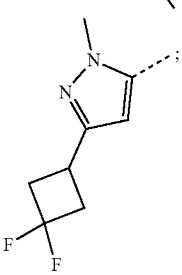
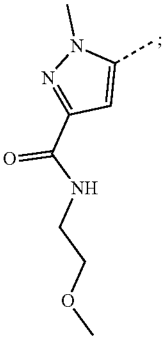
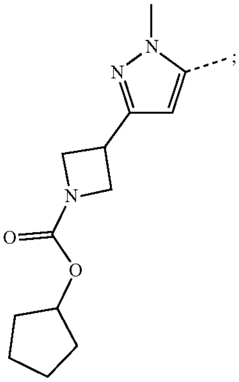
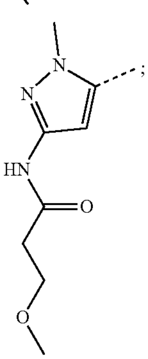
-continued
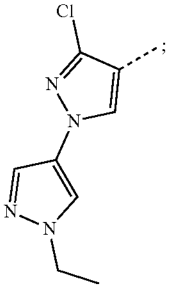
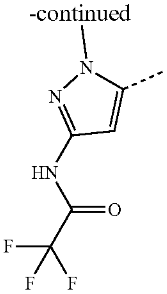
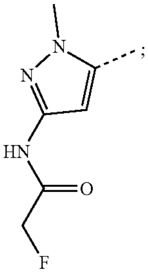
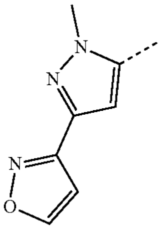
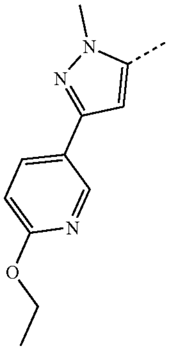
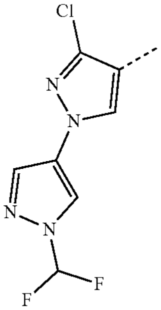
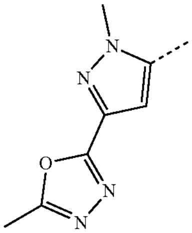
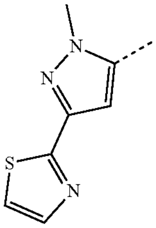
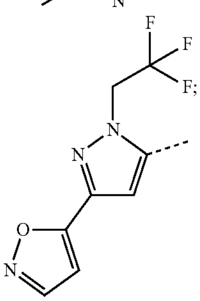
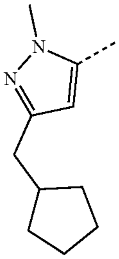
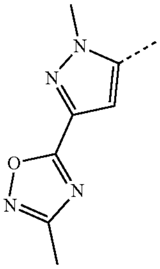
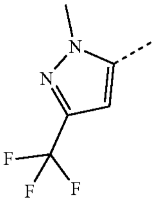
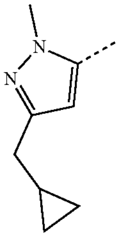
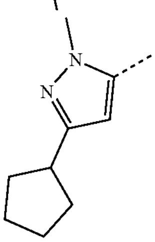
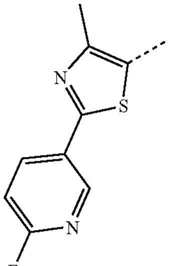
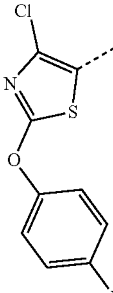
or -continued

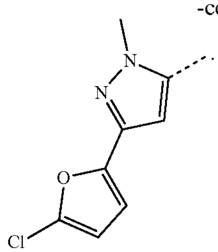

9. The compound of claim 1 selected from:

$N^2$,4-dimethyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-4-methylisoxazole-5-carboxamide;

2-isobutyramido-4-methyl-N—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide;

2-isobutyramido-4-methyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-5-carboxamide;

$N^2$-(2,2-difluoroethyl)-4-methyl-$N^5$—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide;

$N^5$—((R)-2-cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-(2,2-difluoroethyl)-4-methylthiazole-2,5-dicarboxamide;

$N^2$-ethyl-4-methyl-$N^5$—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide;

$N^2$-(2,2-difluoroethyl)-4-methyl-$N^5$—((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide;

$N^5$—((R)-2-cyclopropyl-3-oxo-3-(((S)-11-oxo-2,3,10,11-tetrahydro-1H,5H-benzo[d]pyrazolo[1,2-a][1,2]diazepin-10-yl)amino)propyl)-N2,4-dimethylthiazole-2,5-dicarboxamide;

$N^2$-ethyl-4-methyl-$N^5$—((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide;

$N^2$,4-dimethyl-$N^5$—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide;

$N^5$—((R)-2-cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-ethyl-4-methylthiazole-2,5-dicarboxamide;

$N^2$,4-dimethyl-$N^5$—((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide;

$N^2$-isopropyl-4-methyl-$N^5$—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-2,5-dicarboxamide;

4-chloro-N—((R)-2-(((S)-11-oxo-2,3,10,11-tetrahydro-1H,5H-benzo[d]pyrazolo[1,2-a][1,2]diazepin-10-yl)carbamoyl)butyl)-2-(6-(trifluoromethyl)pyridin-3-yl)thiazole-5-carboxamide;

$N^2$-ethyl-4-methyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

3-methyl-N—((R)-2-(((S)-11-oxo-2,3,10,11-tetrahydro-1H,5H-benzo[d]pyrazolo[1,2-a][1,2]diazepin-10-yl)carbamoyl)butyl)-5-(trifluoromethyl)isoxazole-4-carboxamide;

4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)-2-(6-(trifluoromethyl)pyridin-3-yl)thiazole-5-carboxamide;

$N^2$-isopropyl-4-methyl-$N^5$—((R)-2-(((S)-11-oxo-2,3,10,11-tetrahydro-1H,5H-benzo[d]pyrazolo[1,2-a][1,2]diazepin-10-yl)carbamoyl)butyl)thiazole-2,5-dicarboxamide;

4-methyl-2-(3-methylisoxazol-5-yl)-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

$N^2$-(2,2-difluoroethyl)-4-methyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

4-chloro-$N^2$-isopropyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

4-methyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)-2-(3-methylisoxazol-5-yl)thiazole-5-carboxamide;

$N^2$-isopropyl-4-methyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide;

3,4-dimethyl-N—((R)-2-(((S)-11-oxo-2,3,10,11-tetrahydro-1H,5H-benzo[d]pyrazolo[1,2-a][1,2]diazepin-10-yl)carbamoyl)butyl)isoxazole-5-carboxamide;

2-(3,6-dihydro-2H-pyran-4-yl)-4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

$N^5$—((R)-2-cyclopropyl-3-oxo-3-(((S)-11-oxo-2,3,10,11-tetrahydro-1H,5H-benzo[d]pyrazolo[1,2-a][1,2]diazepin-10-yl)amino)propyl)-$N^2$-isopropyl-4-methylthiazole-2,5-dicarboxamide;

4-chloro-2-(cyclopent-1-en-1-yl)-N—((R)-2-(((S)-5,11-dioxo-2,3,10,11-tetrahydro-1H,5H-benzo[d]pyrazolo[1,2-a][1,2]diazepin-10-yl)carbamoyl)butyl)thiazole-5-carboxamide;

4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)-2-propoxythiazole-5-carboxamide;

N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-3-methyl-5-(trifluoromethyl)isoxazole-4-carboxamide;

2-(isoxazol-5-yl)-4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

3,4-dimethyl-N—((R)-2-(((S)-11-oxo-2,3,10,11-tetrahydro-1H,5H-benzo[d]pyrazolo[1,2-a][1,2]diazepin-10-yl)carbamoyl)pentyl)isoxazole-5-carboxamide;

4-chloro-N—((R)-2-(((S)-5,11-dioxo-2,3,10,11-tetrahydro-1H,5H-benzo[d]pyrazolo[1,2-a][1,2]diazepin-10-yl)carbamoyl)butyl)-2-(6-methoxypyridin-3-yl)thiazole-5-carboxamide;

N—((R)-2-(((S)-5,11-dioxo-2,3,10,11-tetrahydro-1H,5H-benzo[d]pyrazolo[1,2-a][1,2]diazepin-10-yl)carbamoyl)butyl)-4-methylisothiazole-5-carboxamide;

N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-4-ethyl-1,2,3-thiadiazole-5-carboxamide;

4-chloro-2-(6-(difluoromethoxy)pyridin-3-yl)-N—((R)-2-(((S)-5,11-dioxo-2,3,10,11-tetrahydro-1H,5H-benzo[d]pyrazolo[1,2-a][1,2]diazepin-10-yl)carbamoyl)butyl)thiazole-5-carboxamide;

N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-4-methyl-2-(6-(trifluoromethyl)pyridin-3-yl)thiazole-5-carboxamide;

4-chloro-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

4-chloro-N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-2-(6-(trifluoromethyl)pyridin-3-yl)thiazole-5-carboxamide;

N—((R)-2-cyclopropyl-3-(((S)-5,11-dioxo-2,3,10,11-tetrahydro-1H,5H-benzo[d]pyrazolo[1,2-a][1,2]diazepin-10-yl)amino)-3-oxopropyl)-4-methyl-2-(3-methylisoxazol-5-yl)thiazole-5-carboxamide;

N—((R)-4-methoxy-2-(((S)-11-oxo-2,3,10,11-tetrahydro-1H,5H-benzo[d]pyrazolo[1,2-a][1,2]diazepin-10-yl)carbamoyl)butyl)-4-methyl-2-(3-methylisoxazol-5-yl)thiazole-5-carboxamide;

4-chloro-2-cyclopropyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-5-carboxamide;

2-(3,6-dihydro-2H-pyran-4-yl)-4-methyl-N—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide;

4-chloro-2-(1-(difluoromethyl)-1H-pyrazol-4-yl)-N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)thiazole-5-carboxamide;

4-chloro-2-(3,6-dihydro-2H-pyran-4-yl)-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

2-cyclopropyl-4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

N—((R)-2-(((S)-5,11-dioxo-2,3,10,11-tetrahydro-1H,5H-benzo[d]pyrazolo[1,2-a][1,2]diazepin-10-yl)carbamoyl)-3,3,3-trifluoropropyl)-3,5-dimethylisoxazole-4-carboxamide;

4-chloro-N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)thiazole-5-carboxamide;

4-methyl-2-(tetrahydro-2H-pyran-4-yl)-N—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide;

4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)isoxazole-5-carboxamide;

2-(methoxymethyl)-4-methyl-N—((R)-3,3,3-trifluoro-2-(((S)-11-oxo-2,3,10,11-tetrahydro-1H,5H-benzo[d]pyrazolo[1,2-a][1,2]diazepin-10-yl)carbamoyl)propyl)thiazole-5-carboxamide;

2-ethoxy-4-methyl-N—((R)-2-(((S)-11-oxo-2,3,10,11-tetrahydro-1H,5H-benzo[d]pyrazolo[1,2-a][1,2]diazepin-10-yl)carbamoyl)butyl)thiazole-5-carboxamide;

4-chloro-2-cyclopropyl-N—((R)-2-cyclopropyl-3-(((S)-6-fluoro-11-oxo-2,3,10,11-tetrahydro-1H,5H-benzo[d]pyrazolo[1,2-a][1,2]diazepin-10-yl)amino)-3-oxopropyl)thiazole-5-carboxamide;

4-chloro-N—((R)-2-cyclopropyl-3-(((S)-6-fluoro-11-oxo-2,3,10,11-tetrahydro-1H,5H-benzo[d]pyrazolo[1,2-a][1,2]diazepin-10-yl)amino)-3-oxopropyl)-2-methylthiazole-5-carboxamide;

1-(difluoromethyl)-N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-1H-pyrazole-5-carboxamide;

N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-4-(trifluoromethyl)thiazole-5-carboxamide;

2-benzyl-4-methyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-5-carboxamide;

2-cyclopropyl-N—((R)-2-(((S)-5,11-dioxo-10,11-dihydro-1H,3H,5H-spiro[benzo[d]pyrazolo[1,2-a][1,2]diazepine-2,1'-cyclopropan]-10-yl)carbamoyl)butyl)-4-(trifluoromethyl)thiazole-5-carboxamide;

1,3-dimethyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)-1H-pyrrole-2-carboxamide;

1-methyl-N—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)-1H-pyrazole-5-carboxamide;

(R)—$N^4$-(3-isobutyramido-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclobutyl-$N^4$-(3-isobutyramido-1-methyl-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(4-chloro-2-(isopropylcarbamoyl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-((2,2-difluoroethyl)carbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(2-(isopropylcarbamoyl)-4-methylthiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^4$-(3-(isopropylcarbamoyl)-1-methyl-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-((2,2,2-trifluoroethyl)carbamoyl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(2-fluorobenzamido)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl) succinamide;

(R)-2-methyl-$N^4$-(1-methyl-3-(2,2,3,3,3-pentafluoropropanamido)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(3-cyclopropylisoxazol-5-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(6-(trifluoromethyl)pyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(4-chloro-2-(1-methyl-1H-pyrazol-3-yl)thiazol-5-yl)-2-methyl-$N^1$—((S)-11-oxo-2,3,10,11-tetrahydro-1H,5H-benzo[d]pyrazolo[1,2-a][1,2]diazepin-10-yl) succinamide;

(R)-2-methyl-$N^4$-(1-methyl-3-(5-methylpyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^4$-(1-methyl-3-(5-methylpyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(2,3-difluorobenzamido)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^1$—((S)-6-fluoro-11-oxo-2,3,10,11-tetrahydro-1H,5H-benzo[d]pyrazolo[1,2-a][1,2]diazepin-10-yl)-$N^4$-(3-(isopropylcarbamoyl)-1-methyl-1H-pyrazol-5-yl)succinamide;

(S)-2-cyclopropyl-$N^4$-(3-(((S)-1-fluoropropan-2-yl)carbamoyl)-1-methyl-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(2-(5-fluoropyridin-3-yl)-4-methylthiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(5-methylisoxazol-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(5-ethylisoxazol-3-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl) succinamide;

(S)-2-cyclobutyl-$N^1$—((S)-5,11-dioxo-10,11-dihydro-1H,3H,5H-spiro[benzo[d]pyrazolo[1,2-a][1,2]diazepine-2,1'-cyclopropan]-10-yl)-$N^4$-(3-isobutyramido-1-methyl-1H-pyrazol-5-yl)succinamide;

(R)—$N^4$-(1-ethyl-3-(6-(trifluoromethyl)pyridin-3-yl)-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-((3,3,3-trifluoropropyl)carbamoyl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(1-ethyl-3-(furan-2-yl)-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-(3-ethylisoxazol-5-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl) succinamide;

(R)—$N^4$-(3-(5-fluoropyridin-2-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl) succinamide;

(R)—$N^4$-(3-chloro-1-(6-(trifluoromethyl)pyridin-3-yl)-1H-pyrazol-4-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-pivalamido-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(3-methylisoxazol-5-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(2-(isopropylcarbamoyl)thiazol-5-yl)-2-methyl-$N^1$—((S)-11-oxo-2,3,10,11-tetrahydro-1H,5H-benzo [d]pyrazolo[1,2-a][1,2]diazepin-10-yl)succinamide;

(R)-2-methyl-$N^4$-(3-methyl-1-(6-(trifluoromethyl)pyridin-3-yl)-1H-pyrazol-4-yl)-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^1$—((S)-5,11-dioxo-10,11-dihydro-1H,3H,5H-spiro[benzo[d]pyrazolo[1,2-a][1,2]diazepine-2,1'-cyclopropan]-10-yl)-$N^4$-(3-isobutyramido-1-methyl-1H-pyrazol-5-yl)succinamide;

(R)-2-methyl-$N^4$-(1-methyl-3-(pyridin-2-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(4-chloro-2-(1-(oxetan-3-yl)-1H-pyrazol-4-yl) thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(1-cyclopropyl-3-(furan-2-yl)-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl) succinamide;

(R)—$N^4$-(3-(6-methoxypyridin-3-yl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)-2-methyl-$N^4$-(1-methyl-3-(5-(trifluoromethyl)pyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(R)—$N^4$-(4-chloro-2-(1-(2-methoxyethyl)-1H-pyrazol-4-yl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^1$—((S)-6-fluoro-11-oxo-2,3,10,11-tetrahydro-1H,5H-benzo[d]pyrazolo[1,2-a][1,2]diazepin-10-yl)-$N^4$-(3-(((S)-1-fluoropropan-2-yl)carbamoyl)-1-methyl-1H-pyrazol-5-yl)succinamide;

(R)—$N^4$-(1-ethyl-3-(3-methylisoxazol-5-yl)-1H-pyrazol-5-yl)-2-methyl-$N^1$—((S)-1 1-oxo-2,3,10,11-tetrahydro-1H,5H-benzo[d]pyrazolo[1,2-a][1,2]diazepin-10-yl)succinamide;

(R)—$N^4$-(3-(cyclopropylcarbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(S)-2-cyclopropyl-$N^4$-(3-(3-cyclopropylisoxazol-5-yl)-1-methyl-1H-pyrazol-5-yl)-$N^1$—((S)-5,11-dioxo-10,11-dihydro-1H,3H,5H-spiro[benzo[d]pyrazolo[1,2-a][1,2]diazepine-2,1'-cyclopropan]-10-yl)succinamide;

(S)—$N^4$-(4-chloro-2-(1-(difluoromethyl)-1H-pyrazol-4-yl)thiazol-5-yl)-2-cyclopropyl-$N^1$—((S)-5,11-dioxo-2,3,10,11-tetrahydro-1H,5H-benzo[d]pyrazolo[1,2-a][1,2]diazepin-10-yl)succinamide;

(R)-2-methyl-$N^4$-(1-methyl-3-(6-methylpyridin-3-yl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide;

(S)—$N^4$-(4-chloro-2-(6-(trifluoromethyl)pyridin-3-yl)thiazol-5-yl)-2-cyclopropyl-$N^1$—((S)-5,11-dioxo-10,11-dihydro-1H,3H,5H-spiro[benzo[d]pyrazolo[1,2-a][1,2]diazepine-2,1'-cyclopropan]-10-yl)succinamide;

(S)—$N^4$-(4-chloro-2-(6-(trifluoromethyl)pyridin-3-yl)thiazol-5-yl)-2-cyclopropyl-$N^1$—((S)-5,11-dioxo-2,3,10,11-tetrahydro-1H,5H-benzo[d]pyrazolo[1,2-a][1,2]diazepin-10-yl)succinamide;

(R)—$N^4$-(4-chloro-2-(6-(trifluoromethyl)pyridin-3-yl)thiazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

(R)—$N^4$-(3-((2-fluorophenyl)carbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide; and (R)—$N^4$-(3-((2,6-dimethylphenyl)carbamoyl)-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide;

or a pharmaceutically acceptable salt thereof.

10. A pharmaceutical composition comprising a therapeutically effective amount of a compound according to claim 1, or a pharmaceutically acceptable salt or stereoisomer thereof, and one or more pharmaceutically acceptable carriers.

11. A combination comprising a therapeutically effective amount of a compound according to claim 1, or a pharmaceutically acceptable salt or stereoisomer thereof, and at least one other drug substance.

12. A method of treating a disease or disorder mediated by Sppl2a activity in a subject, wherein the method comprises administering to the subject a therapeutically effective amount of a compound according to claim 1, or a pharmaceutically acceptable salt or stereoisomer thereof.

13. The method according to claim 12, wherein the disease or disorder mediated by Sppl2a activity is selected from pemphigus vulgaris, pemphigus foliaceus, Sjogren's disease, systemic lupus erythematosus (SLE), rheumatoid arthritis (RA), lupus nephritis, systemic sclerosis, multiple sclerosis (MS), autoimmune hepatitis, uveitis, pemphigus vulgaris, pemphigus foliaceus, myasthenia gravis, Hashimoto thyroiditis, thrombocytopenia purpura, myocarditis, atopic dermatitis, Goodpasture syndrome or type I diabetes.

14. The method according to claim 12, wherein the disease or disorder mediated by Sppl2a activity is acute and chronic graft versus host disease (GvHD); or the prevention of rejection in clinical/surgical transplantation procedures of solid organs or cell populations.

15. The method according to claim 12, wherein the disease or disorder mediated by Sppl2a activity is a lymphoma.

16. The compound according to claim 1, wherein the compound of Formula I is $N^2$,4-dimethyl-$N^5$—((R)-2-methyl-3-oxo-3-(((S)-11-oxo-2,3,10,11-tetrahydro-1H,5H-benzo[d]pyrazolo[1,2-a][1,2]diazepin-10-yl)amino)propyl)thiazole-2,5-dicarboxamide, or a pharmaceutically acceptable salt thereof.

17. The compound according to claim 1, wherein the compound of Formula I is (R)—$N^4$-(3-Isobutyramido-1-methyl-1H-pyrazol-5-yl)-2-methyl-$N^1$—((S)-11-oxo-2,3,10,11-tetrahydro-1H,5H-benzo[d]pyrazolo[1,2-a][1,2]diazepin-10-yl)succinamide, or a pharmaceutically acceptable salt thereof.

18. The compound according to claim 1, wherein the compound of Formula I is (R)-2-methyl-$N^4$-(1-methyl-3-((2,2,2-trifluoroethyl)carbamoyl)-1H-pyrazol-5-yl)-$N^1$—((S)-11-oxo-2,3,10,11-tetrahydro-1H,5H-benzo[d]pyrazolo[1,2-a][1,2]diazepin-10-yl)succinamide, or a pharmaceutically acceptable salt thereof.

* * * * *